United States Patent
Stemmer

(12) 
(10) Patent No.: US 6,180,406 B1
(45) Date of Patent: *Jan. 30, 2001

(54) METHODS FOR GENERATING POLYNUCLEOTIDES HAVING DESIRED CHARACTERISTICS BY ITERATIVE SELECTION AND RECOMBINATION

(75) Inventor: Willem P.C. Stemmer, Los Gatos, CA (US)

(73) Assignee: Maxygen, Inc., Redwood City, CA (US)

(*) Notice: Under 35 U.S.C. 154(b), the term of this patent shall be extended for 0 days.

This patent is subject to a terminal disclaimer.

(21) Appl. No.: 09/099,015

(22) Filed: Jun. 17, 1998

Related U.S. Application Data

(62) Division of application No. 08/621,859, filed on Mar. 25, 1996, which is a continuation-in-part of application No. 08/564,955, filed on Nov. 30, 1995, now Pat. No. 5,811,238, and a continuation-in-part of application No. 08/537,874, filed as application No. PCT/US95/02126 on Feb. 17, 1995, now Pat. No. 5,830,721, which is a continuation-in-part of application No. 08/198,431, filed on Feb. 17, 1994, now Pat. No. 5,605,793.

(51) Int. Cl.⁷ .............................. C12N 15/00; C12Q 1/68; C12P 19/34; C07H 21/02
(52) U.S. Cl. ............................ 435/440; 435/6; 435/91.2; 536/23.1; 536/24.3; 935/76; 935/77; 935/78
(58) Field of Search .......................... 435/6, 91.2, 172.3, 435/440; 536/23.1, 24.3

(56) References Cited

U.S. PATENT DOCUMENTS

| | | |
|---|---|---|
| 4,683,202 | 7/1987 | Mullis . |
| 4,800,159 | 1/1989 | Mullis et al. . |
| 4,965,188 | 10/1990 | Mullis et al. . |
| 4,994,368 | 2/1991 | Goodman et al. . |
| 4,994,379 | 2/1991 | Chang . |
| 5,023,171 | 6/1991 | Ho et al. . |
| 5,043,272 | 8/1991 | Hartley . |
| 5,093,257 | 3/1992 | Gray . |
| 5,176,995 | 1/1993 | Sninsky et al. . |
| 5,187,083 | 2/1993 | Mullis . |
| 5,223,408 | 6/1993 | Goeddel et al. . |
| 5,234,824 | 8/1993 | Mullis . |
| 5,264,563 | 11/1993 | Huse . |
| 5,279,952 | 1/1994 | Wu . |
| 5,316,935 | 5/1994 | Arnold et al. . |
| 5,356,801 | 10/1994 | Rambosek et al. . |
| 5,360,728 | 11/1994 | Prasher . |
| 5,418,149 | 5/1995 | Gelfand et al. . |
| 5,422,266 | 6/1995 | Cormier et al. . |
| 5,489,523 | 2/1996 | Mathur . |
| 5,502,167 | 3/1996 | Waldmann et al. . |
| 5,512,463 * | 4/1996 | Stemmer ........................ 435/91.2 |
| 5,514,568 * | 5/1996 | Stemmer ........................ 435/91.2 |
| 5,521,077 | 5/1996 | Khosla et al. . |
| 5,523,388 | 6/1996 | Huse . |
| 5,541,309 | 7/1996 | Prasher . |
| 5,556,750 | 9/1996 | Modrich et al. . |
| 5,556,772 | 9/1996 | Sorge et al. . |
| 5,605,793 | 2/1997 | Stemmer . |
| 5,629,179 | 5/1997 | Mierendorf et al. . |
| 5,652,116 | 7/1997 | Grandi et al. . |
| 5,679,522 | 10/1997 | Modrich et al. . |
| 5,698,426 | 12/1997 | Huse . |
| 5,714,316 | 2/1998 | Weiner et al. . |

(List continued on next page.)

FOREIGN PATENT DOCUMENTS

| | | |
|---|---|---|
| 0 252 666 | 1/1988 | (EP) . |
| 552 266 | 7/1993 | (EP) . |
| 544 809 B1 | 12/1998 | (EP) . |
| 563 296 B1 | 3/1999 | (EP) . |
| WO 90/07576 | 7/1990 | (WO) . |
| WO 90/14430 | 11/1990 | (WO) . |
| WO90/14424 | 11/1990 | (WO) . |
| WO 91/01087 | 2/1991 | (WO) . |
| WO 91/06570 | 5/1991 | (WO) . |
| WO 91/07506 | 5/1991 | (WO) . |
| WO 91/15581 | 10/1991 | (WO) . |
| WO 91/16427 | 10/1991 | (WO) . |
| WO 92/06176 | 4/1992 | (WO) . |
| WO 92/07075 | 4/1992 | (WO) . |
| WO 92/18645 | 10/1992 | (WO) . |
| WO9218645 * | 10/1992 | (WO) . |
| WO 93/02191 | 2/1993 | (WO) . |
| WO 93/06213 | 4/1993 | (WO) . |
| WO 93/11237 | 6/1993 | (WO) . |
| WO 93/15208 | 8/1993 | (WO) . |
| WO 93/16192 | 8/1993 | (WO) . |
| WO 93/18141 | 9/1993 | (WO) . |
| WO 93/25237 | 12/1993 | (WO) . |
| WO 94/03596 | 2/1994 | (WO) . |
| WO 94/09817 | 5/1994 | (WO) . |
| WO 94/11496 | 5/1994 | (WO) . |
| WO 94/13804 | 6/1994 | (WO) . |
| WO 95/17413 | 6/1995 | (WO) . |
| WO 95/22625 | 8/1995 | (WO) . |

(List continued on next page.)

OTHER PUBLICATIONS

Arkin et al., "An Algorithm for Protein Engineering: Simulations of Recursive Ensemble Mutagenesis" *Proc. Natl. Acad. Sci. USA*, 89(16):7811–7815 (1992).

(List continued on next page.)

*Primary Examiner*—W. Gary Jones
*Assistant Examiner*—Ethan Whisenant
(74) *Attorney, Agent, or Firm*—Joe Liebeschuetz; Norman Kruse

(57) ABSTRACT

A method for DNA reassembly after random fragmentation, and its application to mutagenesis of nucleic acid sequences by in vitro or in vivo recombination is described. In particular, a method for the production of nucleic acid fragments or polynucleotides encoding mutant proteins is described. The present invention also relates to a method of repeated cycles of mutagenesis, shuffling and selection which allow for the directed molecular evolution in vitro or in vivo of proteins.

69 Claims, 37 Drawing Sheets

U.S. PATENT DOCUMENTS

| | | |
|---|---|---|
| 5,723,323 | 3/1998 | Kauffman et al. . |
| 5,756,316 | 5/1998 | Schellenberger . |
| 5,763,192 | 6/1998 | Kauffman et al. . |
| 5,770,434 | 6/1998 | Huse . |
| 5,773,267 | 6/1998 | Jacobs et al. . |
| 5,783,431 | 7/1998 | Peterson et al. . |
| 5,795,747 * | 8/1998 | Henco et al. ............... 435/91.1 |
| 5,808,022 | 9/1998 | Huse . |
| 5,811,238 | 9/1998 | Stemmer et al. . |
| 5,814,476 | 9/1998 | Kauffman et al. . |
| 5,817,483 | 10/1998 | Kauffman et al. . |
| 5,824,469 | 10/1998 | Horwitz et al. . |
| 5,824,485 | 10/1998 | Thompson et al. . |
| 5,824,514 | 10/1998 | Kauffman et al. . |
| 5,830,696 | 11/1998 | Short . |
| 5,830,721 | 11/1998 | Stemmer et al. . |
| 5,834,252 | 11/1998 | Stemmer et al. . |
| 5,837,458 | 11/1998 | Minshull et al. . |
| 5,851,813 | 12/1998 | Desrosiers . |
| 5,858,725 | 1/1999 | Crowe et al. . |
| 5,871,974 | 2/1999 | Huse . |
| 5,928,905 | 7/1999 | Stemmer et al. . |
| 5,939,250 | 8/1999 | Short . |
| 5,955,358 | 9/1999 | Huse . |
| 5,958,672 | 9/1999 | Short . |
| 5,965,408 | 10/1999 | Short . |
| 5,965,415 | 10/1999 | Radman et al. . |
| 5,976,862 | 11/1999 | Kauffman et al. . |
| 6,030,779 | 2/2000 | Short . |
| 6,054,267 | 4/2000 | Short . |
| 6,057,103 | 5/2000 | Short . |

FOREIGN PATENT DOCUMENTS

| | | |
|---|---|---|
| WO 96/33207 | 10/1996 | (WO) . |
| WO 97/07205 | 2/1997 | (WO) . |
| WO 97/20078 | 6/1997 | (WO) . |
| WO 97/25410 | 7/1997 | (WO) . |
| WO 97/35966 | 10/1997 | (WO) . |
| WO 98/01581 | 1/1998 | (WO) . |
| WO 98/28416 | 7/1998 | (WO) . |
| WO 98/41622 | 9/1998 | (WO) . |
| WO 98/41623 | 9/1998 | (WO) . |
| WO 98/41653 | 9/1998 | (WO) . |
| WO 98/42832 | 10/1998 | (WO) . |

OTHER PUBLICATIONS

Balint et al., "Antibody Engineering By Parsimonious Mutagenesis", *Gene*, 137(1):109–118 (1993).

Bartel et al., "Isolation of New Ribozymes From a Large Pool of Random Sequences", *Science*, 261:1411–1418 (1993).

Beaudry et al., "Directed Evolution of an RNA Enzyme," *Science*, 257:635–641 (1992).

Berger et al., "Phoenix Mutagenesis: One–Step Reassembly of Multiply Cleaved Plasmids With Mixtures of Mutant and Wild–Type Fragments," *Anal. Biochem.*, 214:571–579 (1993).

Berkhout et al., "In Vivo Selection of Randomly Mutated Retroviral Genomes," *Nucleic Acids Research*, 21(22):5020–5024 (1993).

Cadwell et al., "Randomization of Genes by PCR Mutagenesis," *PCR Methods and Applications*, 2:28–33 (1992).

Calogero et al., "In Vivo Recombination and the Production of Hybrid Genes," *Microbiology Letter*, 76:41–44 (1992).

Caren et al., "Efficient Sampling of Protein Sequence Space for Multiple Mutants," *Biotechnology*, 12(5):517–520 (1994).

Crameri et al., "Commbinatorial Multiple Cassette Mutagenesis Creates All The Permutations Of Mutants And Wild–Type Sequences", *Biotechniques*, 18(2):194–196 (1995).

Crameri et al., "Improved Green Fluorescent Protein By Molecular Evolution Using DNA Shuffling", *Nat. Biotechnol.*, 14(3):315–319 (1996).

Crameri et al., "Construction And Evolution Of Antibody–Phage Libraries By DNA Shuffling", *Nat. Med.*, 2(1):100–102 (1996).

Crameri et al., "Molecular Evolution Of An Arsenate Detoxification Pathway By DNA Shuffling", *Nat. Biotechnol.*, 15(5):436–438 (1997).

Crameri et al., "DNA Shuffling Of A Family Of Genes From Diverse Species Accelerates Directed Evolution", *Nature*, 391(3664):288–291 (1998).

Delagrave et al., "Recursive Ensemble Mutagenesis," *Protein Engineering*, 6(3):327–331 (1993).

Feinberg et al., "A Technique for Radiolabeling DNA Restriction Endonuclease Fragments to High Specific Activity," *Anal. Biochem.*, 132:6–13 (1983).

Fisch et al., "A Strategy Of Exon Shuffling For Making Large Peptide Repertoires Displayed On Filamentous Bacteriophage", *Proc Natl Acad Sci USA*, 93(15):7761–7766 (1996).

Gates et al., "Affinity Selective Isolation Of Ligands From Peptide Libraries Through Display On A Lac Repressor 'Headpiece Dimer'", *J. Mol. Biol.*, 255(3):373–386 (1996).

Gram et al., "In Vivo Selection and Affinity Maturation of Antibodies From a Naïve Combinatorial Immunoglobulin Library", *Proc. Natl. Acad. Sci. USA*, 89:3576–3580 (1992).

Greener et al., "An Efficient Random Mutagenesis Technique Using An E. coli Mutator Strain", *Methods in Molecular Biology*, 57:375–385 (1995).

Heim et al., "Wavelength Mutations And Posttranslational Autoxidation Of Green Fluorescent Protein", *Proc. Natl. Acad. Sci. USA*, 91(26):12501–12504 (1994).

Hermes et al., "Searching Sequence Space by Definably Random Mutagenesis: Improving the Catalytic Potency of an Enzyme," *Proc. Natl. Acad. Sci. USA*, 87(2):696–700 (1990).

Ho et al., "Site–Directed Mutagenesis by Overlap Extension Using the Polymerase Chain Reaction," *Gene*, 77:51–59 (1989).

Horton et al., "Engineering Hybrid Genes Without the Use of Restriction Enzymes: Gene Splicing by Overlap Extension," *Gene*, 77:61–68 (1989).

Jones et al., "Recombinant Circle PCR and Recombination PCR for Site–Specific Mutagenesis Without PCR Product Purification," *Biotechniques* 12(4):528–534 (1992).

Kim et al., "Human Immunodeficiency Virus Reverse Transcriptase," *The Journal of Biological Chemistry*, 271(9):4872–4878 (1996).

Leung et al., "A Method for Random Mutagenesis of a Defined DNA Segment Using a Modified Polymerase Chain Reaction," *Techniques*, 1:11–15 (1989).

Marks et al., "By–Passing Immunization: Building High Affinity Human Antibodies by Chain Shuffling," *Bio/Technology*, 10:779–783 (1992).

Marton et al., "DNA Nicking Favors PCR Recombination", *Nucleic Acids Res.*, 19(9):2423–2426 (1991).

Meyerhans et al., "DNA Recombination During PCR," *Nucleic Acids Research*, 18(7):1687–1691 (1990).

Near, "Gene Conversion Of Immunoglobulin Variable Regions In Mutagenesis Cassettes By Replacement PCR Mutagenesis", *Biotechniques*, 12(1):88–97 (1992).

Oliphant et al., "Cloning of Random–Sequence Oligodeoxynucleotides," *Gene*, 44(2–3):177–183 (1986).

Perlak, "Single Step Large Scale Site–Directed In Vitro Mutagenesis Using Multiple Oligonucleotides", *Nucleic Acids Res.*, 18(24):7457–7458 (1990).

*Pharmacia Catalog*, pp. 70–71 (1993 Edition).

Pompon et al., "Protein Engineering by cDNA Recombination in Yeasts: Shuffling of Mammalian Cytochrome P–450 Functions," *Gene*, 83(1):15–24 (1989).

Rao et al., "Recombination and Polymerase Error Facilitate Restoration of Infectivity in Brome Mosaic Virus," *Journal of Virology*, 67(2):969–979 (1993).

Rapley, "Enhancing PCR Amplification And Sequencing Using DNA–Binding Proteins", *Mol. Biotechnol.*, 2(3):295–298 (1994).

Reidhaar–Olson et al., "Combinatorial Cassette Mutagenesis as a Probe of the Informational Content of Protein Sequences," *Science*, 241:53–57 (1988).

Stemmer, "Rapid Evolution of a Protein in Vitro by DNA Shuffling," *Nature*, 370:389–391 (1994).

Stemmer, "DNA Shuffling by Random Fragmentation and Reassembly: In Vitro Recombination for Molecular Evolution" *Proc. Natl. Acad. Sci. USA*, 91(22):10747–10751 (1994).

Stemmer et al., "Selection of an Active Single Chain FV Antibody from a Protein Linker Library Prepared by Enzymatic Inverse PCR," *Biotechniques*, 14(2):256–265 (1992).

Stemmer, "Searching Sequence Space", *Biotechnology*, 13:549–553 (1995).

Stemmer et al., "Single–Step Assembly Of A Gene And Entire Plasmid From Large Numbers Of Oligodeoxyribonucleotides", *Gene*, 164(1):49–53 (1995).

Stemmer, "The Evolution of Molecular Computation", *Science*, 270(241):1510 (1995).

Stemmer, "Sexual PCR and Assembly PCR", *Encylopedia Mol. Biol.*, VCH Publishers, New York, pp. 447–457 (1996).

Wang et al., "Identification Of Glial Filament Protein And Vimentin In The Same Intermediate Filament System In Human Glioma Cells", *Proc. Natl. Acad. Sci. USA*, 81(7):2102–2106 (1984).

Weber et al., "Formation of Genes Coding for Hybrid Proteins by Recombination Between Related, Cloned Genes in E. Coli," *Nucleic Acids Research*, 11(16):5661–5669 (1983).

Weisberg et al., "Simultaneous Mutagenesis Of Multiple Sites: Application Of The Ligase Chain Reaction Using PCR Products Instead Of Oligonucleotides", *BioTechniques*, 15(1):68–76 (1993).

Winter et al., "Making Antibodies By Phage Display Technology", *Ann. Rev. Immunol.*, 12:433–455 (1994).

Zhang et al., "Directed Evolution Of A Fucosidase From A Galactosidase By DNA Shuffling And Screening", *Proc. Natl. Acad. Sci. USA*, 94(9):4504–4509 (1997).

Zhao et al., "Molecular Evolution by Staggered Extension Process (StEP) In Vitro Recombination", *Nature Biotech.*, 16:258–261 (1998).

Andersson et al., "Muller's ratchet decreases fitness of a DNA–based microbe", *PNAS*, 93: 906–907 (Jan. 1996).

Bailey, "Toward a Science of Metabolic Engineering", *Science*, 252: 1668–1680 (1991).

Barrett et al., "Genotypic analysis of multiple loci in somatic cells by whole genome amplification", *Nuc. Acids Res.*, 23(17):3488–3492 (1995).

Cameron et al., "Cellular and Metabolic Engineering An Overview", *Applied Biochem. Biotech.*, 38: 105–140 (1993).

Chakrabarty, "Microbial Degradation of Toxic Chemicals: Evolutionary Insights and Practical Considerations", *ASM News*, 62(3); 130–137 (1996).

Chater, "The Improving Prospects for Yield Increase by Genetic Engineering in Antibiotic–Producing Streptomycetes", *Biotechnology*, 8: 115–121 (Feb. 1990).

Chen et al., "Tuning the activity of an enzyme for unusual environments: Sequential random mutagenesis of subtilisin E for catalysis in dimethylformamide", *PNAS*, 90: 5618–5622 (Jun. 1993).

Dieffenbach et al., *PCR Primer, A Laboratory Manual*, Cold Spring Harbor Laboratory Press, pp. 583–589, 591–601, 603–612, and 613–621 (1995).

Evnin et al., "Substrate specificity of trypsin investigated by using a genetic selection", *PNAS*, 87: 6659–6663 (Sep. 1990).

Fang et al., "Human Strand–specific Mismatch Repiar Occurs by a Bidirectional Mechanism Similar to That of the Bacterial Reaction", *J. Biol. Chem.*, 268(16): 11838–11844 (Jun. 5, 1993).

Ippolito et al., "Structure assisted redesign of a protein–zinc–binding site with femtomolar affinity", *PNAS*, 92: 5017–5021 (May 1995).

Kellogg et al., "Plasmid–Assisted Molecular Breeding: New Technique for Enhanced Biodegradation of Persistent Toxic Chemicals", *Science*, 214: 1133–1135 (Dec. 4, 1981).

Kunkel, "Rapid and efficient site–specific mutagenesis without phenotypic selection", *PNAS*, 82: 488–493 (Jan. 1985).

Levichkin et al., "A New Approach to Construction of Hybrid Genes: Homolog Recombination Method", *Mol. Biology*, 29(5) part 1: 572–577 (1995).

Lewis et al., "Efficient site directed in vitro mutagenesis using ampicilin selection", *Nuc. Acids Res.*, 18(12): 3439–3443 (1990).

Moore et al., "Directed evolution of a para–nitrobenzyl esterase for aqueous–organic solvents", *Nature Biotech.*, 14: 458–467 (Apr. 1996).

Omura, "Philosophy of New Drug Discovery", *Microbiol. Rev.*, 50(3): 259–279 (Sep. 1986).

Piepersberg, "Pathway Engineering in Secondary Metabolite–Producing Actinomycetes", *Crit. Rev. Biotech.*, 14(3):251–285 (1994).

Prasher, "Using GFP to see the light", *TIG*, 11(8) (Aug. 1995).

Rice et al., "Random PCR mutagenesis screening of secreted proteins by direct expression in mammalian cells", *PNAS*, 89: 5467–5471 (Jun. 1992).

Simpson et al., "Two paradigms of metabolic engineering applied to amino acid biosynthesis", *Biochem. Soc. Transactions*, vol. 23 (1995).

Steele et al., "Techniques for Selection of Industrially Important Microorganisms", *Ann. Rev. Microbiol.*, 45: 89–106 (1991).

Stephanopoulos et al., "Metabolic engineering—methodologies and future prospects", *Trends Biotech.* 11: 392–396 (1993).

Stephanopoulos, "Metabolic engineering", *Curr. Opin. Biotech.*, 5: 196–200 (1994).

Wehmeier, "New multifunctional *Escherichia coli*—Streptomyces shuttle vectors allowing blue–white screening on XGal plates", *Gene*, 165: 149–150 (1995).

Atreya et al., "Construction of in–frame chimeric plant genes by simplified PCR strategies," *Plant Mol. Biol.*, 19:517–522 (1992).*

Bock et al., "Selection of single–stranded DNA molecules that bind and inhibit human thrombin," *Nature*, 355:564–566 (Feb. 2, 1992).*

Clackson et al., "Making antibody fragments using phage display libraries," *Nature*, 352:624–628 (Aug. 15, 1991).*

Crameri et al., "10(20)–Fold aptamer library amplification without gel purification," *Nuc. Acids Res.*, 21(18):4410 (1993).*

Cull et al., "Screening for receptor ligands using large libraries of peptides linked to the C terminus of the lac repressor," *PNAS*, 89:1865–1869 (Mar. 1992).*

Cwirla et al., "Peptides on phage: A vast library of peptides for identifying ligands," *PNAS*, 87:6378–6382 (Aug. 1990).*

Daugherty et al., "Polymerase chain reaction facilitates the cloning, CDR–grafting, and rapid expression of a murine monoclonal antibody directed against the CD18 component of leukocyte integrins," *Nuc. Acids Res.*, 19(9):2471–2476 (1991).*

Delagrave et al., "Searching Sequence Space to Engineer Proteins: Exponential Ensemble Mutagenesis," *Biotechnology*, 11:1548–1552 (Dec. 1993).*

Dube et al., "Artificial mutants Generated by the Insertion of Random Oligonucleotides into the Putative Nucleoside Binding Site of the HSV–1 Thymidine Kinase Gene," *Biochemistry*, 30(51):11760–11767 (1991).

Fullen et al., "Genetic Algorithms and Recursive Ensemble Mutagenesis in Protein Engineering," *Complexity Int.'l 1994 I*, printed from website http://www.csu.edu.au/ci/vol1/fuellen/REM.html on Dec. 7, 1999.

Ghosh et al., "Arginine–395 Is Required for Efficient in Vivo and in Vitro Aminoacylation of tRNAs by *Escherichia coli* Methionyl–tRNA Stnthetase," *Biochemistry*, 30:11767–11774 (1991).

Goldman et al., "An Algorithmically Optimized Combinatorial Library Screened by digital Imaging Spectroscopy," *Biotechnology*, 10:1557–1561 (Dec. 1992).

Harlow et al., "Construction of Linker–Scanning Mutations using the Polymerase Chain Reaction," *Methods in Mol. Biol.*, 31:87–96 (1994).

Heda et al., "A simple in vitro site directed mutagenesis of concatamerized cDNA by inverse polymerase chain reaction," *Nuc. Acids Res.*, 20(19):5241–5242 (1992).

Ho et al., "DNA and Protein Engineering Using the Polymerase Chain Reaction: Splicing by Overlap Extension," *DNA and Protein Eng. Techniques*, 2(2):50–55 (1990).

Hodgson, "The Whys and Wherefores of DNA Amplification," *Biotechnology*, 11:940–942 (Aug. 1993).

Horton et al., "Gene Splicing by Overlap Extension," *Mehtods in Enzymology*, 217:270–279 (1993).

Horton et al., "Gene Splicing by Overlap Extension: Tailor–Made Genes Using the Polymerase chain Reaction," *BioTechniques*, 8(5):528–535 (May 1990).

Jayaraman et al., "Polymerase chain reaction–mediated gene synthesis: Synthesis of a gene coding for isozyme c of horseradish peroxidase," *PNAS*, 88:4084–4088 (May 1991).

Jones et al., "A Rapid Method for Recombination and Site–Specific Mutagenesis by Placing Homologous ends on DNA Using Polymerase Chain Reaction," *BioTechniques*, 10(1):62–66 (1991).

Joyce, G. F., "Directed Molecular Evolution," *Scientific American*, (Dec. 1992).

Klug et al., "Creating chimeric molecules by PCR directed homologous DNA recombination," *Nuc. Acids Res.*, 19(10):2793 (1991).

Krishman et al., "Direct and crossover PCR amplification to facilitate Tn5supF–based sequencing of λ phage clones," *Nuc. Acids Res.*, 19(22):6177–6182 (1991).

Lowman, H.B. et al., "Affinity Maturation of Human Growth Hormone by Monovalent Phage Display," *J. Mol. Biol.*, 234:564–578 (1993).

Majumder, K., "Ligation–free gene synthesis by PCR: synthesis and mutagenesis at multiple loci of a chimeric gene encoding OmpA signal peptide and hirudin," *Gene*, 110:89–94 (1992).

Marks et al., "By–passing Immunization, Human Antibodies from V–gene Libraries Displayed on Phage," *J. Mol. Biol.*, 222:581–597 (1991).

McCafferty et al., "Phage antibodies: filamentous phage displaying antibody variable domains," *Nature*, 348:552–554 (Dec. 6, 1990).

Morl et al., "Group II intron RNA–catalyzed recombination of RNA in vitro," *Nuc. Acids Res.*, 18(22):6545–6551 (1990).

Mullis et al., "Specific Synthesis of DNA in Vitro via a Polymerase–Catalyzed Chain Reaction," *Methods in Enzymology*, 155:335–351 (1987).

Mullis et al., "Specific Enzymatic Amplification of DNA In Vitro; The Polymerase Chain Reaction," Cold Spring Harbor Symposia on Quantitative Biology, 51:263–273 (1986).

Nissim et al., "Antibody fragments from a 'single pot' display library as immunochemical reagents," *EMBO Journal*, 13(3):692–698 (1994).

Osuna et al., "Combinatorial mutagenesis of three major groove–contacting residues of Eco RI: single and double amino acid replacements retaining methyltransferase–sensitive activities," *Gene*, 106:7–12 (1991).

Paabo et al., "DNA Damage Promotes Jumping between Templates during Enzymatic Amplification," *J. Biol. Chem.*, 265(8):4718–4721 (Mar. 15, 1990).

Robles et al., "Hydropathy and Molar Volume Constraints on Combinatorial mutants of the Photosynthetic Reaction Center," *J. Mol. Biol.*, 232:242–252 (1993).

Saiki et al., "Diagnosis of sickle Cell Anemia and β–Thalassemia with Enzymatically Amplified DNA and Nonradioactive Allele–Specific Oligonucleotide Probes," *New England J. of Medicine*, 319(9):537–541 (Sep. 1, 1988).

Saike et al., "Analysis of enzymatically amplified β–globin and HLA–DQα DNA with allele–specific oligonucleotide probes," *Nature*, 324:163–166 (Nov. 13, 1986).

Saiki et al., "Enzymatic Amplification of β–Globin Genomic Sequences and Restriction Site analysis for Diagnosis of Sickle Cell Anemia," *Science*, 230:1350–1354 (Dec. 20, 1985).

Saiki et al., "Primer–Directed Enzymatic Amplificaiton of DNA with a Thermostabl;e DNA Polymerase," *Science*, 239:487–491 (Jan. 20, 1988).

Sambrook et al., *Molecular Cloning, A Laboratory Manual*, Cold Spring Laboratory Press, Cold Spring Harbor, New York (1989).

Scharf et al., "Direct Cloning and Sequence Analysis of Enzymatically Amplified Genomic Sequences," *Science*, 233:1076–1078 (Sep. 1986).

Scott et al., "Searching for Peptide Ligands with an Epitope Library," *Science*, 249:386–390 (Jul. 20, 1990).

Sikorski et al., "In Vitro Mutagenesis and Planned Shuffling: From Cloned Gene to Mutant Yeast," *Methods in Enzymology*, 194:302–318 (1991).

Smith et al., "Unwanted Mutations in PCR Mutagenesis: Avoiding the Predictable," *PCR Methods and Applications*, 2(3):253–257 (Feb. 1993).

Villarreal et al., "A General Method of Polymerase–Chain––Reaction–Enabled Protein Domain Mutagenesis: Construction of a Human Protein S–Osteonectin Gene," *Analytical Biochem.*, 197:362–367 (1991).

Weissenhorn et al., "Chimerization of antibodies by isolation of rearranged genomic variable regions by the polymerase chain reaction," *Gene*, 106:273–277 (1991).

Yao et al., "Site–directed Mutagenesis of Herpesvirus Glycoprotein Phosphorylation Sites by Recombination Polymerase Chain Reaction," *PCR Methods and Applications*, 1(3):205–207 (Feb. 1992).

Yolov et al., "Constructing DNA by polymerase recombination," *Nuc. Acids Res.*, 18(13):3983–3986 (1990).

Yon et al., "Precise gene fusion by PCR," *Nuc. Acids Res.*, 17(12):4895 (1989).

Youvan et al., "Recursive Ensemble Mutagenesis: A Combinatorial Optimization Technique for Protein Engineering," from Parallel Problem Solving from Nature, 2, Manner eds., pp. 401–410 (1992).

Zoller, M.J., "New recombinant DNA methodology for protein engineering," *Curr. Opin. Biotech.*, 3:348–354 (1992).

Opposition Statement in matter of Australian Patent Application 703264 (Affymax Technologies NV), filed by Diversa Corporation on Sep. 23, 1999.

\* cited by examiner

M     CTGCACCTGAATGGCCAGAACATCAACCAAC

II     CTGCATCTGCAAGGCCAGCACATGGAACAAC

M     ACCTGTCCTGTGTAATGAAAGACGGCACTCC

II     ACCTCAGCTGCGTACTGAAAGACGATAAGCC

M     GAGCAAAGTGGAGTTCGAGTCTGCTGAGTTC

II     TAACAAGCTGGAATTCGAGTCTGCTCAGTTC

M     ACTATGGAATCTGTGCTTCCTAA

II     ACCATGCAGTTTGTCTCGAGCTAA

*FIG. 5B.*

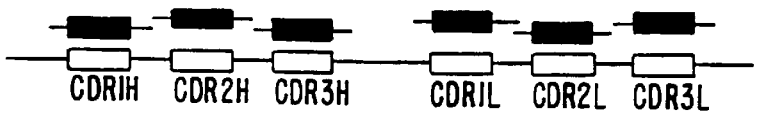
FIG. 7A.
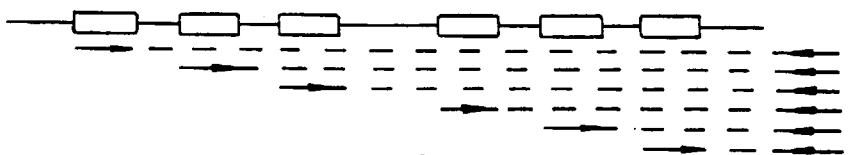
FIG. 7B.
FIG. 7C.
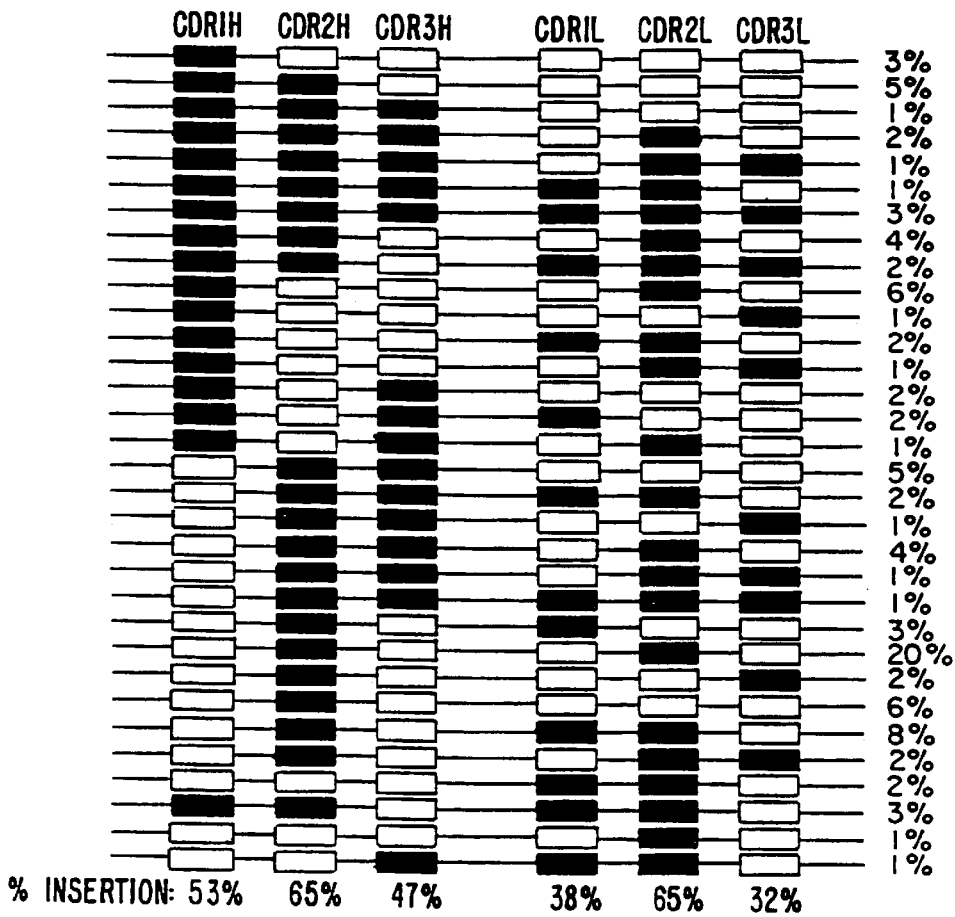
FIG. 7D.

| CELL | Tet COLONIES | Amp COLONIES | COLONY PCR |
|---|---|---|---|
| TG-1 | 131 | 21 | 3/3 AT 1 KB |
| JC8679 | 123 | 31 | 4/4 AT 1 KB |
| VECTOR CONTROL | 51 | 0 | |

| CELL | Tet COLONIES | Amp COLONIES | COLONY PCR |
|---|---|---|---|
| TG-1 | 28 | 54 | 7/7 AT 1 KB |
| JC8679 | 149 | 117 | 3/3 AT 1 KB |
| VECTOR CONTROL | 51 | 0 | |

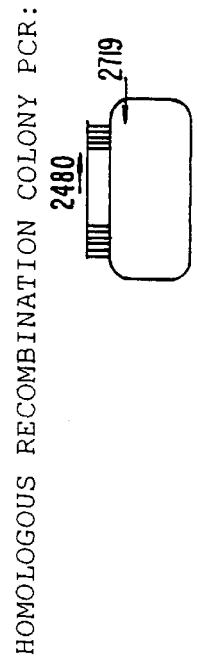

| APPROACH | AMP COLONIES | AMP TET COLONIES | % HOMOLOGOUS RECOMBINATION | COMMENT |
|---|---|---|---|---|
| 1-CUT VECTOR 1 INSERT JC8679 | 4,000 | 1,500 | 100% (N=14) | EFFICIENT INSERTION BY HOMOLOGOUS RECOMBINATION WITH CO-ELECTROPORATED VECTOR |
| 2-CUT VECTOR 2 INSERTS JC8679 | 2,000 | 16 | 100% (N=2) | 100x LESS EFFICIENT THAN 1 FRAGMENT |
| 3-UNCUT VECTOR 1 INSERT JC8679 | 16 | 0 | | HOMOLOGOUS INSERTION DEPENDS ON FREE ENDS |
| 4-NO VECTOR 1 INSERT JC8679::pUCSfi-Sfi | 5,000 | 10,000 | 70% (N=7) | IF VECTOR IS IN CELLS ALREADY, HIGH EFFICIENCY OCCURS EVEN THROUGH VECTOR IS UNCUT |
| 5-NO VECTOR 1 INSERT JC8679 | 2,000 | 0 | | -CONTROL: NON-HOMOLOGOUS INSERTION INTO CHROMOSOME |
| 6-CUT VECTOR NO INSERT JC8679 | N.D. | 0 | | -CONTROL: NO AMP BACKGROUND |

FIG. 11A.

HOMOLOGOUS RECOMBINATION COLONY PCR:

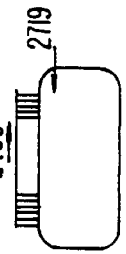

FIG. 11B.

| ORIS | DRUG$^R$ | PROMOTERS |
|---|---|---|
| A ── ORI-PUC ──→── B | B ── AMPICILLIN$^R$ ──←── ← C | D ── LACO LACP ── E |
| A ── ORI-PUC ──←── B | B →── AMPICILLIN$^R$ ──→── C | D ── LACI LACO LACP ──← E |
| A ── ORI-PBR ──→── B | B →── TETRACYCLINE$^R$ ──→── C | D ── LACI$^Q$ LACO LACP ──← E |
| A ── ORI-PBR ──→── B | B ── TETRACYCLINE$^R$ ──←── ← C | D ── LACP ──← E |
| A ── ORI-PAT ──→── B | B →── CHLORAMPHENICOL$^R$ ──→── ← C | D ── LACUV5 ── E |
| A ── ORI-PAT ──←── B | B ── CHLORAMPHENICOL$^R$ ──←── ← C | D ── PHOA P ──→── E |
|  | B ── KANAMYCIN$^R$ ──→── C | D ── TACP ──→── E |
|  | B ── KANAMYCIN$^R$ ──←── ←C | D ── ARABAD ARAP ──← E |
|  | B →── STREPTOMYCIN$^R$ ──→── C | D ── TRPP ──→── E |
|  | B ── STREPTOMYCIN$^R$ ──←── ←C | D ── λPR ──→── E |
|  |  | D CI$^{857}$ λPL ── E |
|  |  | D CI λPL ── E |
|  |  | D ── λPL ── E |

| TERMINATORS | SINGLE PEPTIDES |
|---|---|
| F ── M13 ── G | E ── OMPF ── F |
| F ── ØX174 ── G | E ── PHOA ── F |
| F ── P2200P ── G | E ── OMPA ── F |
| F ── TRP ── G | E ── SSTII ── F |
| F ── S10 ── G | E ── PELB ── F |
|  | E ── BLA ── F |

SS DNA ORI
M13

*FIG. 13.*

| A.A. RESIDUE | | WILDTYPE | CYCLE 1 | CYCLE 2 | CYCLE 3 |
|---|---|---|---|---|---|
| | 38 | GCA A | GCT A | GCT A | GCT A |
| | 68 | GGT G | GGC G | | |
| | 72 | TTT F | TTC F | | |
| | 73 | TCC S | CCC P | | |
| | 100 | TTT F | TCT S | TCT S | TCT S |
| | 127 | AAA K | GAA E | | |
| | 138 | CTT L | CTC L | CTC L | CTC L |
| | 147 | AAC N | TAC Y | | |
| | 154 | ATG M | ACG T | ACG T | ACG T |
| | 161 | GGA G | GGC G | | |
| | 164 | GTT V | GCT A | GCT A | GCT A |
| | 185 | CAA Q | | CGA R | |
| | 226 | ACA T | ACT T | ACT T | ACT T |
| | 235 | GAG E | GAC D | | |

SPLICING FRAMES
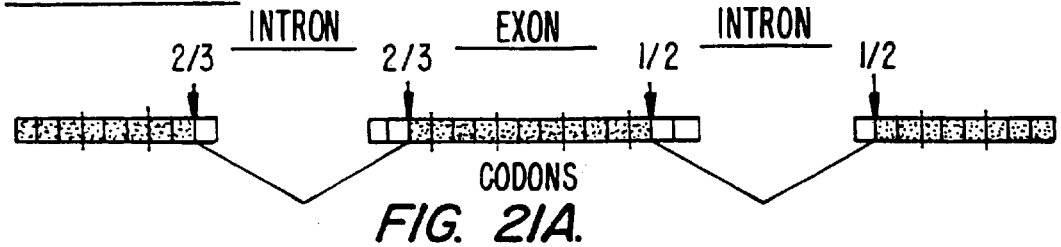
FIG. 21A.
INTRON CLASSES
1/2 ——————— 1/2
2/3 ——————— 2/3
3/1 ——————— 3/1
EXON CLASSES
1/2 ▭ 1/2   1/2 ▭ 2/3   1/2 ▭ 3/1
2/3 ▭ 1/2   2/3 ▭ 2/3   2/3 ▭ 3/1
3/1 ▭ 1/2   3/1 ▭ 2/3   3/1 ▭ 3/1
FIG. 21B.
EXAMPLES OF EXON FAMILIES
IMMUNOGLOBULIN
1/2 ▭ 1/2
FIG. 21C.
EXON LIBRARIES
ONE EXON CLASS
1/2 ▭ 1/2   1/2 ▭ 1/2   1/2 ▭ 1/2   1/2 ▭ 1/2   1/2 ▭ 1/2
FIG. 21D.
MIXED EXON CLASSES - RANDOM          $(1/9)^n$ OUT OF FRAME
2/3 ▭ 1/2   3/1 ▭ 2/3   1/2 ▭ 3/1   1/2 ▭ 2/3   3/1 ▭ 3/1
FIG. 21E.
MIXED EXON CLASSES - INTRON CLASS DIRECTED   ALWAYS IN FRAME
1/2 ▭ 2/3   2/3 ▭ 3/1   3/1 ▭ 1/2   1/2 ▭ 3/1   3/1 ▭ 2/3
       2/3         3/1         1/2         3/1
FIG. 21F.
HOMOLOGY DIRECTED SHUFFLING
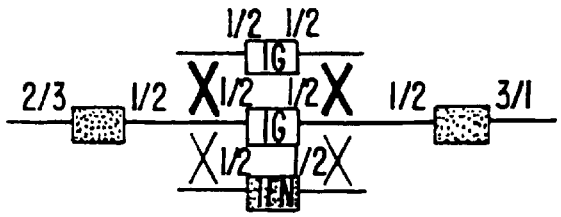
FIG. 21G.

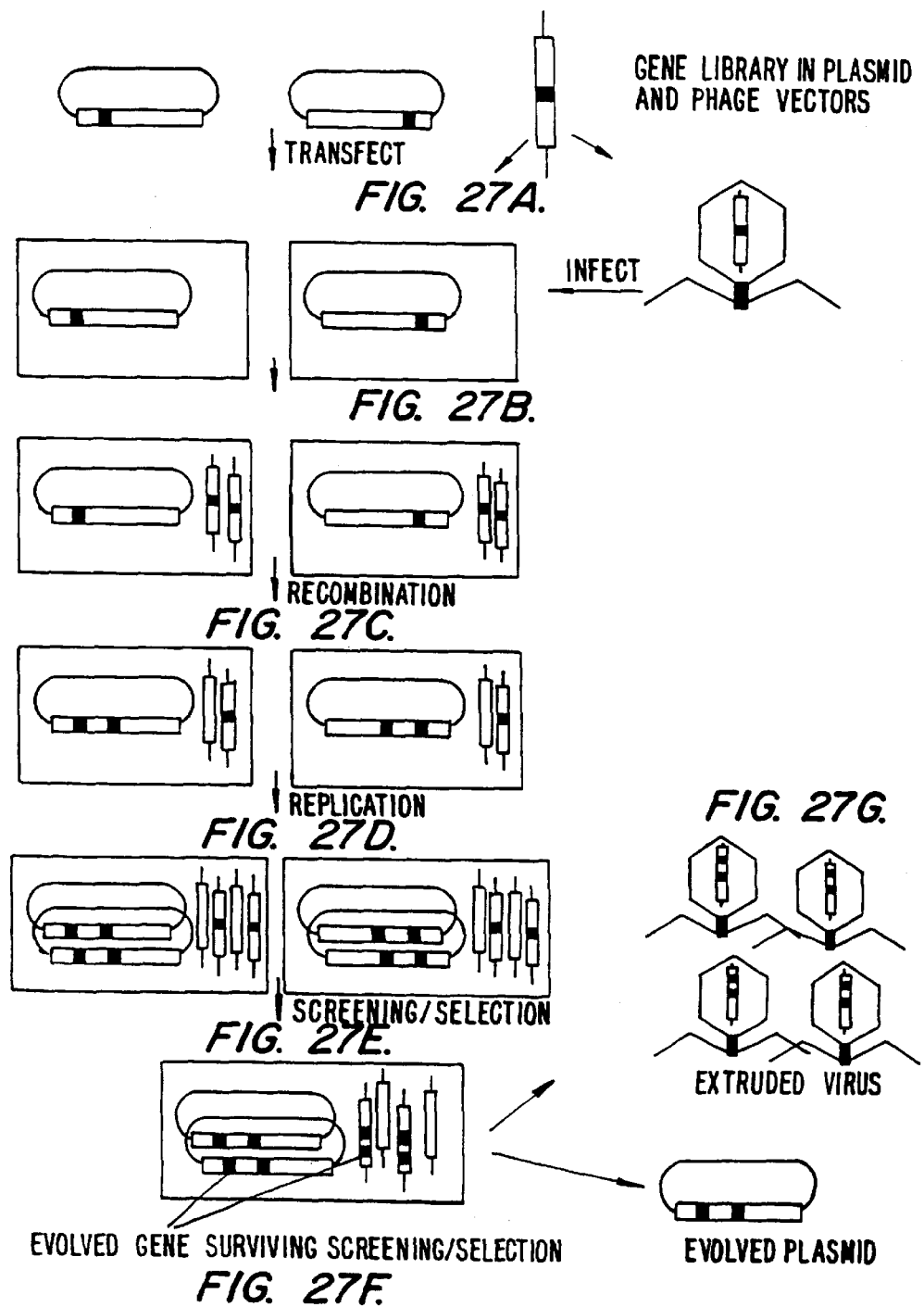

METHODS FOR GENERATING POLYNUCLEOTIDES HAVING DESIRED CHARACTERISTICS BY ITERATIVE SELECTION AND RECOMBINATION

This application is a divisional of 08/621,859 filed Mar. 25, 1996, the disclosure of which is incorporated by reference, which is a continuation-in-part of U.S. Ser. No. 08/564,955, filed Nov. 30, 1995, now U.S. Pat. No. 5,811,238, and a continuation-in-part of U.S. Ser. No. 08/537,874, filed Mar. 4, 1996, now U.S. Pat. No. 5,830,721 which is the national phase of PCT/U.S. Ser. No. 95/02126, filed Feb. 17, 1995, which is a continuation-in-part of U.S. Ser. No. 08/198,431, filed Feb. 17, 1994 now U.S. Pat. No. 5,605,793.

FIELD OF THE INVENTION

The present invention relates to a method for the production of polynucleotides conferring a desired phenotype and/or encoding a protein having an advantageous predetermined property which is selectable or can be screened for. In an aspect, the method is used for generating and selecting or screening for desired nucleic acid fragments encoding mutant proteins.

BACKGROUND AND DESCRIPTION OF RELATED ART

The complexity of an active sequence of a biological macromolecule, e.g. proteins, DNA etc., has been called its information content ("IC"; 5–9). The information content of a protein has been defined as the resistance of the active protein to amino acid sequence variation, calculated from the minimum number of invariable amino acids (bits) required to describe a family of related sequences with the same function (9, 10). Proteins that are sensitive to random mutagenesis have a high information content. In 1974, when this definition was coined, protein diversity existed only as taxonomic diversity.

Molecular biology developments such as molecular libraries have allowed the identification of a much larger number of variable bases, and even to select functional sequences from random libraries. Most residues can be varied, although typically not all at the same time, depending on compensating changes in the context. Thus a 100 amino acid protein can contain only 2,000 different mutations, but $20^{100}$ possible combinations of mutations.

Information density is the Information Content/unit length of a sequence. Active sites of enzymes tend to have a high information density. By contrast, flexible linkers in enzymes have a low information density (8).

Current methods in widespread use for creating mutant proteins in a library format are error-prone polymerase chain reaction (11, 12, 19) and cassette mutagenesis (8, 20, 21, 22, 40, 41, 42), in which the specific region to be optimized is replaced with a synthetically mutagenized oligonucleotide. Alternatively, mutator strains of host cells have been employed to add mutational frequency (Greener and Callahan (1995) *Strategies in Mol. Biol.* 7: 32). In each case, a 'mutant cloud' (4) is generated around certain sites in the original sequence.

Error-prone PCR uses low-fidelity polymerization conditions to introduce a low level of point mutations randomly over a long sequence. Error prone PCR can be used to mutagenize a mixture of fragments of unknown sequence. However, computer simulations have suggested that point mutagenesis alone may often be too gradual to allow the block changes that are required for continued sequence evolution. The published error-prone PCR protocols are generally unsuited for reliable amplification of DNA fragments greater than 0.5 to 1.0 kb, limiting their practical application. Further, repeated cycles of error-prone PCR lead to an accumulation of neutral mutations, which, for example, may make a protein immunogenic.

In oligonucleotide-directed mutagenesis, a short sequence is replaced with a synthetically mutagenized oligonucleotide. This approach does not generate combinations of distant mutations and is thus not significantly combinatorial. The limited library size relative to the vast sequence length means that many rounds of selection are unavoidable for protein optimization. Mutagenesis with synthetic oligonucleotides requires sequencing of individual clones after each selection round followed by grouping into families, arbitrarily choosing a single family, and reducing it to a consensus motif, which is resynthesized and reinserted into a single gene followed by additional selection. This process constitutes a statistical bottleneck, it is labor intensive and not practical for many rounds of mutagenesis.

Error-prone PCR and oligonucleotide-directed mutagenesis are thus useful for single cycles of sequence fine tuning but rapidly become limiting when applied for multiple cycles.

Error-prone PCR can be used to mutagenize a mixture of fragments of unknown sequence (11, 12). However, the published error-prone PCR protocols (11, 12) suffer from a low processivity of the polymerase. Therefore, the protocol is very difficult to employ for the random mutagenesis of an average-sized gene. This inability limits the practical application of error-prone PCR.

Another serious limitation of error-prone PCR is that the rate of down-mutations grows with the information content of the sequence. At a certain information content, library size, and mutagenesis rate, the balance of down-mutations to up-mutations will statistically prevent the selection of further improvements (statistical ceiling).

Finally, repeated cycles of error-prone PCR will also lead to the accumulation of neutral mutations, which can affect, for example, immunogenicity but not binding affinity.

Thus error-prone PCR was found to be too gradual to allow the block changes that are required for continued sequence evolution (1, 2).

In cassette mutagenesis, a sequence block of a single template is typically replaced by a (partially) randomized sequence. Therefore, the maximum information content that can be obtained is statistically limited by the number of random sequences (i.e., library size). This constitutes a statistical bottleneck, eliminating other sequence families which are not currently best, but which may have greater long term potential.

Further, mutagenesis with synthetic oligonucleotides requires sequencing of individual clones after each selection round (20). Therefore, this approach is tedious and is not practical for many rounds of mutagenesis.

Error-prone PCR and cassette mutagenesis are thus best suited and have been widely used for fine-tuning areas of comparatively low information content. An example is the selection of an RNA ligase ribozyme from a random library using many rounds of amplification by error-prone PCR and selection (13).

It is becoming increasingly clear our scientific tools for the design of recombinant linear biological sequences such as protein, RNA and DNA are not suitable for generating the necessary sequence diversity needed to optimize many desired properties of a macromolecule or organism. Finding better and better mutants depends on searching more and more sequences within larger and larger libraries, and increasing numbers of cycles of mutagenic amplification and selection are necessary. However as discussed above, the existing mutagenesis methods that are in widespread use have distinct limitations when used for repeated cycles.

Evolution of most organisms occurs by natural selection and sexual reproduction. Sexual reproduction ensures mixing and combining of the genes of the offspring of the selected individuals. During meiosis, homologous chromosomes from the parents line up with one another and cross-over part way along their length, thus swapping genetic material. Such swapping or shuffling of the DNA allows organisms to evolve more rapidly (1, 2). In sexual recombination, because the inserted sequences were of proven utility in a homologous environment, the inserted sequences are likely to still have substantial information content once they are inserted into the new sequence.

Marton et al., (27) describes the use of PCR in vitro to monitor recombination in a plasmid having directly repeated sequences. Marton et al. discloses that recombination will occur during PCR as a result of breaking or nicking of the DNA. This will give rise to recombinant molecules. Meyerhans et al. (23) also disclose the existence of DNA recombination during in vitro PCR.

The term Applied Molecular Evolution ("AME") means the application of an evolutionary design algorithm to a specific, useful goal. While many different library formats for AME have been reported for polynucleotides (3, 11–14), peptides and proteins (phage (15–17), lacI (18) and polysomes, in none of these formats has recombination by random cross-overs been used to deliberately create a combinatorial library.

Theoretically there are 2,000 different single mutants of a 100 amino acid protein. A protein of 100 amino acids has $20^{100}$ possible combinations of mutations, a number which is too large to exhaustively explore by conventional methods. It would be advantageous to develop a system which would allow the generation and screening of all of these possible combination mutations.

Winter and coworkers (43,44) have utilized an in vivo site specific recombination system to combine light chain antibody genes with heavy chain antibody genes for expression in a phage system. However, their system relies on specific sites of recombination and thus is limited. Hayashi et al. (48) report simultaneous mutagenesis of antibody CDR regions in single chain antibodies (scFv) by overlap extension and PCR.

Caren et al. (45) describe a method for generating a large population of multiple mutants using random in vivo recombination. However, their method requires the recombination of two different libraries of plasmids, each library having a different selectable marker. Thus the method is limited to a finite number of recombinations equal to the number of selectable markers existing, and produces a concomitant linear increase in the number of marker genes linked to the selected sequence(s). Caren et al. does not describe the use of multiple selection cycles; recombination is used solely to construct larger libraries.

Calogero et al. (46) and Galizzi et al. (47) report that in vivo recombination between two homologous but truncated insect-toxin genes on a plasmid can produce a hybrid gene. Radman et al. (49) report in vivo recombination of substantially mismatched DNA sequences in a host cell having defective mismatch repair enzymes, resulting in hybrid molecule formation.

It would be advantageous to develop a method for the production of mutant proteins which method allowed for the development of large libraries of mutant nucleic acid sequences which were easily searched. The invention described herein is directed to the use of repeated cycles of point mutagenesis, nucleic acid shuffling and selection which allow for the directed molecular evolution in vitro of highly complex linear sequences, such as proteins through random recombination.

Accordingly, it would be advantageous to develop a method which allows for the production of large libraries of mutant DNA, RNA or proteins and the selection of particular mutants for a desired goal. The invention described herein is directed to the use of repeated cycles of mutagenesis, in vivo recombination and selection which allow for the directed molecular evolution in vivo and in vitro of highly complex linear sequences, such as DNA, RNA or proteins through recombination.

Further advantages of the present invention will become apparent from the following description of the invention with reference to the attached drawings.

SUMMARY OF THE INVENTION

The present invention is directed to a method for generating a selected polynucleotide sequence or population of selected polynucleotide sequences, typically in the form of amplified and/or cloned polynucleotides, whereby the selected polynucleotide sequence(s) possess a desired phenotypic characteristic (e.g., encode a polypeptide, promote transcription of linked polynucleotides, bind a protein, and the like) which can be selected for. One method of identifying polypeptides that possess a desired structure or functional property, such as binding to a predetermined biological macromolecule (e.g., a receptor), involves the screening of a large library of polypeptides for individual library members which possess the desired structure or functional property conferred by the amino acid sequence of the polypeptide.

In a general aspect, the invention provides a method, termed "sequence shuffling", for generating libraries of recombinant polynucleotides having a desired characteristic which can be selected or screened for. Libraries of recombinant polynucleotides are generated from a population of related-sequence polynucleotides which comprise sequence regions which have substantial sequence identity and can be homologously recombined in vitro or in vivo. In the method, at least two species of the related-sequence polynucleotides are combined in a recombination system suitable for generating sequence-recombined polynucleotides, wherein said sequence-recombined polynucleotides comprise a portion of at least one first species of a related-sequence polynucleotide with at least one adjacent portion of at least one second species of a related-sequence polynucleotide. Recombination systems suitable for generating sequence-recombined polynucleotides can be either: (1) in vitro systems for homologous recombination or sequence shuffling via amplification or other formats described herein, or (2) in vivo systems for homologous recombination or site-specific recombination as described herein. The population of sequence-recombined polynucleotides comprises a subpopulation of polynucleotides which possess desired or advantageous characteristics and which can be selected by a suitable selection or screening method. The selected sequence-recombined polynucleotides, which are typically related-sequence polynucleotides, can then be subjected to at least one recursive cycle wherein at least one selected sequence-recombined polynucleotide is combined with at least one distinct species of related-sequence polynucleotide (which may itself be a selected sequence-recombined polynucleotide) in a recombination system suitable for generating sequence-recombined polynucleotides, such that additional generations of sequence-recombined polynucleotide sequences are generated from the selected sequence-recombined polynucleotides obtained by the selection or screening method employed. In this manner, recursive sequence recombination generates library members which are sequence-recombined polynucleotides possessing desired characteristics. Such characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property.

The present invention provides a method for generating libraries of displayed polypeptides or displayed antibodies suitable for affinity interaction screening or phenotypic screening. The method comprises (1) obtaining a first plurality of selected library members comprising a displayed polypeptide or displayed antibody and an associated polynucleotide encoding said displayed polypeptide or displayed antibody, and obtaining said associated polynucleotides or copies thereof wherein said associated polynucleotides comprise a region of substantially identical sequence, optionally introducing mutations into said polynucleotides or copies, and (2) pooling and fragmenting, by nuclease digestion, partial extension PCR amplification, PCR stuttering, or other suitable fragmenting means, typically producing random fragments or fragment equivalents, said associated polynucleotides or copies to form fragments thereof under conditions suitable for PCR amplification, performing PCR amplification and optionally mutagenesis, and thereby homologously recombining said fragments to form a shuffled pool of recombined polynucleotides, whereby a substantial fraction (e.g., greater than 10 percent) of the recombined polynucleotides of said shuffled pool are not present in the first plurality of selected library members, said shuffled pool composing a library of displayed polypeptides or displayed antibodies suitable for affinity interaction screening. Optionally, the method comprises the additional step of screening the library members of the shuffled pool to identify individual shuffled library members having the ability to bind or otherwise interact (e.g., such as catalytic antibodies) with a predetermined macromolecule, such as for example a proteinaceous receptor, peptide, oligosaccharide, virion, or other predetermined compound or structure. The displayed polypeptides, antibodies, peptidomimetic antibodies, and variable region sequences that are identified from such libraries can be used for therapeutic, diagnostic, research, and related purposes (e.g., catalysts, solutes for increasing osmolarity of an aqueous solution, and the like), and/or can be subjected to one or more additional cycles of shuffling and/or affinity selection. The method can be modified such that the step of selecting is for a phenotypic characteristic other than binding affinity for a predetermined molecule (e.g., for catalytic activity, stability, oxidation resistance, drug resistance, or detectable phenotype conferred on a host cell).

In one embodiment, the first plurality of selected library members is fragmented and homologously recombined by PCR in vitro. Fragment generation is by nuclease digestion, partial extension PCR amplification, PCR stuttering, or other suitable fragmenting means, such as described herein. Stuttering is fragmentation by incomplete polymerase extension of templates. A recombination format based on very short PCR extension times was employed to create partial PCR products, which continue to extend off a different template in the next (and subsequent) cycle(s).

In one embodiment, the first plurality of selected library members is fragmented in vitro, the resultant fragments transferred into a host cell or organism and homologously recombined to form shuffled library members in vivo.

In one embodiment, the first plurality of selected library members is cloned or amplified on episomally replicable vectors, a multiplicity of said vectors is transferred into a cell and homologously recombined to form shuffled library members in vivo.

In one embodiment, the first plurality of selected library members is not fragmented, but is cloned or amplified on an episomally replicable vector as a direct repeat or indirect (or inverted) repeat, which each repeat comprising a distinct species of selected library member sequence, said vector is transferred into a cell and homologously recombined by intra-vector or inter-vector recombination to form shuffled library members in vivo.

In an embodiment, combinations of in vitro and in vivo shuffling are provided to enhance combinatorial diversity.

The present invention provides a method for generating libraries of displayed antibodies suitable for affinity interaction screening. The method comprises (1) obtaining a first plurality of selected library members comprising a displayed antibody and an associated polynucleotide encoding said displayed antibody, and obtaining said associated polynucleotides or copies thereof, wherein said associated polynucleotides comprise a region of substantially identical variable region framework sequence, and (2) pooling and fragmenting said associated polynucleotides or copies to form fragments thereof under conditions suitable for PCR amplification and thereby homologously recombining said fragments to form a shuffled pool of recombined polynucleotides comprising novel combinations of CDRs, whereby a substantial fraction (e.g., greater than 10 percent) of the recombined polynucleotides of said shuffled pool comprise CDR combinations which are not present in the first plurality of selected library members, said shuffled pool composing a library of displayed antibodies comprising CDR permutations and suitable for affinity interaction screening. Optionally, the shuffled pool is subjected to affinity screening to select shuffled library members which bind to a predetermined epitope (antigen) and thereby selecting a plurality of selected shuffled library members. Optionally, the plurality of selected shuffled library members can be shuffled and screened iteratively, from 1 to about 1000 cycles or as desired until library members having a desired binding affinity are obtained.

Accordingly, one aspect of the present invention provides a method for introducing one or more mutations into a template double-stranded polynucleotide, wherein the template double-stranded polynucleotide has been cleaved or PCR amplified (via partial extension or stuttering) into random fragments of a desired size, by adding to the resultant population of double-stranded fragments one or more single or double-stranded oligonucleotides, wherein said oligonucleotides comprise an area of identity and an area of heterology to the template polynucleotide; denaturing the resultant mixture of double-stranded random fragments and oligonucleotides into single-stranded fragments; incubating the resultant population of single-stranded fragments with a polymerase under conditions which result in the annealing of said single-stranded fragments at regions of identity between the single-stranded fragments and formation of a mutagenized double-stranded polynucleotide; and repeating the above steps as desired.

In another aspect the present invention is directed to a method of producing recombinant proteins having biological activity by treating a sample comprising double-stranded template polynucleotides encoding a wild-type protein under conditions which provide for the cleavage of said template polynucleotides into random double-stranded fragments having a desired size; adding to the resultant population of random fragments one or more single or double-stranded oligonucleotides, wherein said oligonucleotides comprise areas of identity and areas of heterology to the template polynucleotide; denaturing the resultant mixture of double-stranded fragments and oligonucleotides into single-stranded fragments; incubating the resultant population of single-stranded fragments with a polymerase under conditions which result in the annealing of said single-stranded fragments at the areas of identity and formation of a mutagenized double-stranded polynucleotide; repeating the above steps as desired; and then expressing the recombinant protein from the mutagenized double-stranded polynucleotide.

A third aspect of the present invention is directed to a method for obtaining a chimeric polynucleotide by treating a sample comprising different double-stranded template polynucleotides wherein said different template polynucleotides contain areas of identity and areas of heterology under conditions which provide for the cleavage of said template polynucleotides into random double-stranded fragments of a desired size; denaturing the resultant random double-stranded fragments contained in the treated sample into single-stranded fragments; incubating the resultant single-stranded fragments with polymerase under conditions which provide for the annealing of the single-stranded fragments at the areas of identity and the formation of a chimeric double-stranded polynucleotide sequence comprising template polynucleotide sequences; and repeating the above steps as desired.

A fourth aspect of the present invention is directed to a method of replicating a template polynucleotide by combining in vitro single-stranded template polynucleotides with small random single-stranded fragments resulting from the cleavage and denaturation of the template polynucleotide, and incubating said mixture of nucleic acid fragments in the presence of a nucleic acid polymerase under conditions wherein a population of double-stranded template polynucleotides is formed.

The invention also provides the use of polynucleotide shuffling, in vitro and/or in vivo to shuffle polynucleotides encoding polypeptides and/or polynucleotides comprising transcriptional regulatory sequences.

The invention also provides the use of polynucleotide shuffling to shuffle a population of viral genes (e.g., capsid proteins, spike glycoproteins, polymerases, proteases, etc.) or viral genomes (e.g., paramyxoviridae, orthomyxoviridae, herpesviruses, retroviruses, reoviruses, rhinoviruses, etc.). In an embodiment, the invention provides a method for shuffling sequences encoding all or portions of immunogenic viral proteins to generate novel combinations of epitopes as well as novel epitopes created by recombination; such shuffled viral proteins may comprise epitopes or combinations of epitopes which are likely to arise in the natural environment as a consequence of viral evolution (e.g., such as recombination of influenza virus strains).

The invention also provides the use of polynucleotide shuffling to shuffle a population of protein variants, such as taxonomically-related, structurally-related, and/or functionally-related enzymes and/or mutated variants thereof to create and identify advantageous novel polypeptides, such as enzymes having altered properties of catalysis, temperature profile, stability, oxidation resistance, or other desired feature which can be selected for. Methods suitable for molecular evolution and directed molecular evolution are provided. Methods to focus selection pressure(s) upon specific portions of polynucleotides (such as a segment of a coding region) are provided.

The invention also provides a method suitable for shuffling polynucleotide sequences for generating gene therapy vectors and replication-defective gene therapy constructs, such as may be used for human gene therapy, including but not limited to vaccination vectors for DNA-based vaccination, as well as anti-neoplastic gene therapy and other gene therapy formats.

The invention provides a method for generating an enhanced green fluorescent protein (GFP) and polynucleotides encoding same, comprising performing DNA shuffling on a GFP encoding expression vector and selecting or screening for variants having an enhanced desired property, such as enhanced fluorescence. In a variation, an embodiment comprises a step of error-prone or mutagenic amplification, propagation in a mutator strain (e.g., a host cell having a hypermutational phenotype; $mut^L$, etc.; yeast strains such as those described in Klein (1995) *Progr. Nucl. Acid Res. Mol. Biol.* 51: 217, incorporated herein by reference), chemical mutagenesis, or site-directed mutagenesis. In an embodiment, the enhanced GFP protein comprises a point mutation outside the chromophore region (amino acids 64–69), preferably in the region from amino acid 100 to amino acid 173, with specific preferred embodiments at residue 100, 154, and 164; typically, the mutation is a substitution mutation, such as F100S, M154T or V164A. In an embodiment, the mutation substitutes a hydrophilic residue for a hydrophobic residue. In an embodiment, multiple mutations are present in the enhanced GFP protein and its encoding polynucleotide. The invention also provides the use of such an enhanced GFP protein, such as for a diagnostic reporter for assays and high throughput screening assays and the like.

The invention also provides for improved embodiments for performing in vitro sequence shuffling. In one aspect, the improved shuffling method includes the addition of at least one additive which enhances the rate or extent of reannealing or recombination of related-sequence polynucleotides. In an embodiment, the additive is polyethylene glycol (PEG), typically added to a shuffling reaction to a final concentration of 0.1 to 25 percent, often to a final concentration of 2.5 to 15 percent, to a final concentration of about 10 percent. In an embodiment, the additive is dextran sulfate, typically added to a shuffling reaction to a final concentration of 0.1 to 25 percent, often at about 10 percent. In an embodiment, the additive is an agent which reduces sequence specificity of reannealing and promotes promiscuous hybridization and/or recombination in vitro. In an alternative embodiment, the additive is an agent which increases sequence specificity of reannealing and promotes high fidelity hybridization and/or recombination in vitro. Other long-chain polymers which do not interfere with the reaction may also be used (e.g., polyvinylpyrrolidone, etc.).

In one aspect, the improved shuffling method includes the addition of at least one additive which is a cationic detergent. Examples of suitable cationic detergents include but are not limited to: cetyltrimethylammonium bromide (CTAB), dodecyltrimethylammonium bromide (DTAB), and tetramethylammonium chloride (TMAC), and the like.

In one aspect, the improved shuffling method includes the addition of at least one additive which is a recombinogenic protein that catalyzes or non-catalytically enhances homologous pairing and/or strand exchange in vitro. Examples of suitable recombinogenic proteins include but are not limited to: *E. coli* recA protein, the T4 uvsX protein, the rec1 protein from *Ustilago maydis*, other recA family recombinases from other species, single strand binding protein (SSB), ribonucleoprotein A1, and the like. Shuffling can be used to improve one or more properties of a recombinogenic protein; for example, mutant sequences encoding recA can be shuffled and improved heat-stable variants selected by recursive sequence recombination.

Non-specific (general recombination) recombinases such as Topoisomerase I, Topoisomerase II (Tse et al. (1980) *J. Biol. Chem.* 255: 5560; Trask et al. (1984) *EMBO J*. 3: 671, incorporated herein by reference) and the like can be used to catalyze in vitro recombination reactions to shuffle a plurality of related sequence polynucelotide species by the recursive methods of the invention.

In one aspect, the improved shuffling method includes the addition of at least one additive which is an enzyme having an exonuclease activity which is active at removing non-templated nucleotides introduced at 3' ends of product polynucleotides in shuffling amplification reactions catalyzed by a non-proofreading polymerase. An example of a suitable enzyme having an exonuclease activity includes but is not limited to Pfu polymerase. Other suitable polymerases include, but are not limited to: *Thermus flavus* DNA polymerase (Tfl) *Thermus thermophilus* DNA polymerase (Tth) *Thermococcus litoralis* DNA polymerase (Tli, Vent) *Pyrococcus Woesei* DNA polymerase (Pwo) *Thermotoga maritima* DNA polymerase (UltMa) *Thermus brockianus* DNA polymerase (Thermozyme) *Pyrococcus furiosus* DNA polymerase (Pfu) Thermococcus sp. DNA polymerase (9°Nm) Pyrococcus sp. DNA polymerase ('Deep Vent') Bacteriophage T4 DNA polymerase Bacteriophage T7 DNA polymerase *E. coli* DNA polymerase I (native and Klenow) *E. coli* DNA polymerase III.

In an aspect, the improved shuffling method comprises the modification wherein at least one cycle of amplification (i.e., extension with a polymerase) of reannealed fragmented library member polynucleotides is conducted under conditions which produce a substantial fraction, typically at least 20 percent or more, of incompletely extended amplification products. The amplification products, including the incompletely extended amplification products are denatured and subjected to at least one additional cycle of reannealing and amplification. This variation, wherein at least one cycle of reannealing and amplification provides a substantial fraction of incompletely extended products, is termed "stuttering" and in the subsequent amplification round the incompletely extended products reanneal to and prime extension on different sequence-related template species.

In an aspect, the improved shuffling method comprises the modification wherein at least one cycle of amplification is conducted using a collection of overlapping single-stranded DNA fragments of varying lengths corresponding to a first polynucleotide species or set of related-sequence polynucleotide species, wherein each overlapping fragment can each hybridize to and prime polynucleotide chain extension from a second polynucleotide species serving as a template, thus forming sequence-recombined polynucleotides, wherein said sequence-recombined polynucleotides comprise a portion of at least one first polynucleotide species with an adjacent portion of the second polynucleotide species which serves as a template. In a variation, the second polynucleotide species serving as a template contains uracil (i.e., a Kunkel-type template) and is substantially non-replicable in cells. This aspect of the invention can also comprise at least two recursive cycles of this variation.

In an embodiment, PCR can be conducted wherein the nucleotide mix comprises a nucleotide species having uracil as the base. The PCR product(s) can then be fragmented by digestion with UDG-glycosylase which produces strand breaks. The fragment size can be controlled by the fraction of uracil-containing NTP in the PCR mix.

In an aspect, the improved shuffling method comprises the modification wherein at least one cycle of amplification is conducted with an additive or polymerase in suitable conditions which promote template switching. In an embodiment where Taq polymerase is employed for amplification, addition of recA or other polymerases (e.g., viral polymerases, reverse transcriptase) enhances template switching. Template-switching can also be increased by increasing the DNA template concentration, among other means known by those skilled in the art.

In an embodiment of the general method, libraries of sequence-recombined polynucleotides are generated from sequence-related polynucleotides which are naturally-occurring genes or alleles of a gene. In this aspect, at least two naturally-occurring genes and/or alleles which comprise regions of at least 50 consecutive nucleotides which have at least 70 percent sequence identity, preferably at least 90 percent sequence identity, are selected from a pool of gene sequences, such as by hybrid selection or via computerized sequence analysis using sequence data from a database. In an aspect, at least three naturally-occurring genes and/or alleles which comprise regions of at least 50 consecutive nucleotides which have at least 70 percent sequence identity, prefereably at least 90 percent sequence identity, are selected from a pool of gene sequences, such as by hybrid selection or via computerized sequence analysis using sequence data from a database. The selected sequences are obtained as polynucleotides, either by cloning or via DNA synthesis, and shuffled by any of the various embodiments of the invention.

In an embodiment of the invention, multi-pool shuffling is performed. Shuffling of multiple pools of polynucleotide sequences allows each separate pool to generate a different combinatorial solution to produce the desired property. In this variation, the pool of parental polynucleotides sequences (or any subsequent shuffled library or selected pool of library members) is subdivided (or segregated) into two or more discrete pools of sequences and are separately subjected to one or more rounds of recursive sequence recombination and selection (or screening). If desired, optionally, selected library members from each separate pool may be recombined (integrated) in latter rounds of shuffling. Alternatively, multiple separate parental pools may be used. Inbreeding, wherein selected (or screened) library members within a pool are crossed with each other by the recursive sequence recombination methods of the invention, can be performed, alone or in combination with outbreeding, wherein library members of different pools are crossed with each other by the recursive sequence recombination methods of the invention.

In an embodiment of the invention, the method comprises the further step of removing non-shuffled products (e.g., parental sequences) from sequence-recombined polynucleotides produced by any of the disclosed shuffling methods. Non-shuffled products can be removed or avoided by performing amplification with: (1) a first PCR primer which hybridizes to a first parental polynucleotide species but does not substantially hybridize to a second parental polynucleotide species, and (2) a second PCR primer which hybridizes to a second parental polynucleotide species but does not substantially hybridize to the first parental polynucleotide species, such that amplification occurs from templates comprising the portion of the first parental sequence which hybridizes to the first PCR primer and also comprising the portion of the second parental sequence which hybridizes to the second PCR primer, thus only sequence-recombined polynucleotides are amplified.

The invention also provides for alternative embodiments for performing in vivo sequence shuffling. In one aspect, the alternative shuffling method includes the use of inter-plasmidic recombination, wherein libraries of sequence-recombined polynucleotide sequences are obtained by genetic recombination in vivo of compatible or non-compatible multicopy plasmids inside suitable host cells. When non-compatible plasmids are used, typically each plasmid type has a distinct selectable marker and selction for retention of each desired plasmid type is applied. The related-sequence polynucleotide sequences to be recombined are separately incorporated into separately replicable multicopy vectors, typically bacterial plasmids each having a distinct and separately selectable marker gene (e.g., a drug resistance gene). Suitable host cells are transformed with both species of plasmid and cells expressing both selectable marker genes are selected and sequence-recombined sequences are recovered and can be subjected to additional rounds of shuffling by any of the means described herein.

In one aspect, the alternative shuffling method includes the use of intra-plasmidic recombination, wherein libraries of sequence-recombined polynucleotide sequences are obtained by genetic recombination in vivo of direct or inverted sequence repeats located on the same plasmid. In a variation, the sequences to be recombined are flanked by site-specific recombination sequences and the polynucleotides are present in a site-specific recombination system, such as an integron (Hall and Collins (1995) *Mol. Microbiol.* 15: 593, incorporated herein by reference) and can include insertion sequences, transposons (e.g., IS1), and the like. Introns have a low rate of natural mobility and can be used as mobile genetic elements both in prokaryotes and eukaryotes. Shuffling can be used to improve the performance of mobile genetic elements. These high frequency recombination vehicles can be used for the rapid optimization of large sequences via transfer of large sequence blocks. Recombination between repeated, interspersed, and diverged DNA sequences, also called "homeologous" sequences, is typically suppressed in normal cells. However, in MutL and MutS cells, this suppression is relieved and the rate of intrachromosomal recombination is increased (Petit et al. (1996) *Genetics* 129: 327, incorporated herein by reference).

In an aspect of the invention, mutator strains of host cells are used to enhance recombination of more highly mismatched sequence-related polynucleotides. Bacterials strains such as MutL, MutS, MutT, or MutH or other cells expressing the Mut proteins (XL-1red; Stratagene, San Diego, Calif.) can be used as host cells for shuffling of sequence-related polynucleotides by in vivo recombination. Other mutation-prone host cell types can also be used, such as those having a proofreading-defective polymerase (Foster et al. (1995) *Proc. Natl. Acad. Sci. (U.S.A.)* 92: 7951, incorporated herein by reference). Mutator strains of yeast can be used, as can hypermutational mammalian cells, including ataxia telangiectasia cells, such as described in Luo et al. (1996) *J. Biol. Chem.* 271: 4497, incorporated herein by reference.

Other in vivo and in vitro mutagenic formats can be employed, including administering chemical or radiological mutagens to host cells. Examples of such mutagens include but are not limited to: MNU, ENU, MNNG, nitrosourea, BuDR, and the like. Ultraviolet light can also be used to generate mutations and/or to enhance the rate of recombination, such as by irradiation of cells used to enhance in vivo recombination. Ionizing radiation and clastogenic agents can also be used to enhance mutational frequency and/or to enhance recombination and/or to effect polynucleotide fragmentation.

BRIEF DESCRIPTION OF THE DRAWINGS

FIGS. 5a and 5b illustrates the regions of homology between a murine IL1-B gene (M); (SEQ. ID NO: 62) and a human IL1-B; (SEQ. ID NO: 63) gene (H) with *E. coli* codon usage. Regions of heterology are boxed. The "⌐⌐" indicate crossovers obtained upon the shuffling of the two genes.

FIG. 7 (panels A–D) illustrates the observed frequency of occurrence of certain combinations of CDRs in the shuffled DNA of the scFv. Panel (A) shows the length and mutagenesis rate of all six synthetic CDRs. Panel (B) shows library construction by shuffling scFv with all six CDRs. Panel (C) shows CDR insertion determined by PCR with primers for native CDRs. Panel (D) shows insertion rates and distributions of synthetic CDR insertions.

FIG. 11 illustrates the method for testing the efficiency of multiple rounds of homologous recombination after the introduction of polynucleotide fragments into cells for the generation of recombinant proteins.

FIG. 13 schematically shows some examples of cassettes suitable at various loci for constructing prokaryotic vector libraries by shuffling.

FIG. 15A shows fluorescence spectra indicating that the whole cell fluorescence signal from the 'wt' construct is 2.8-fold greater than from the 'Clontech' construct. The signal of the 'cycle 3' mutant is 16-fold increased over the Affymax 'wt', and 45-fold over the 'Clontech' wt construct. FIG. 15B is a comparison of excitation spectra of GFP constructs in *E. coli*. The peak excitation wavelengths are unaltered by the mutations that were selected.

FIG. 18A is a FACS analysis of clones of CHO cells expressing different GFP mutants. FIG. 18B B shows fluorescence spectroscopy of clones of CHO cells expressing different GFP mutants.

FIG. 21 schematically shows variations of the method for shuffling exons. The numbers refer to reading frames, as demonstrated in panel (A). Panel (B) shows the various classes of intron and exon relative to their individual splice frames. Panel (C) provides an example of a naturally-occurring gene (immunoglobulin V genes) suitable for shuffling. Panels D through F shows how multiple exons can be concatemerized via PCR using primers which span intron segments, so that proper splicing frames are retained, if desired. Panel (G) exemplifies the exon shuffling process (IG: immunoglobulin exon; IFN: interferon exon).

FIG. 27 shows plasmid-virus recombination.

DESCRIPTION OF THE PREFERRED EMBODIMENTS

Figure 1:
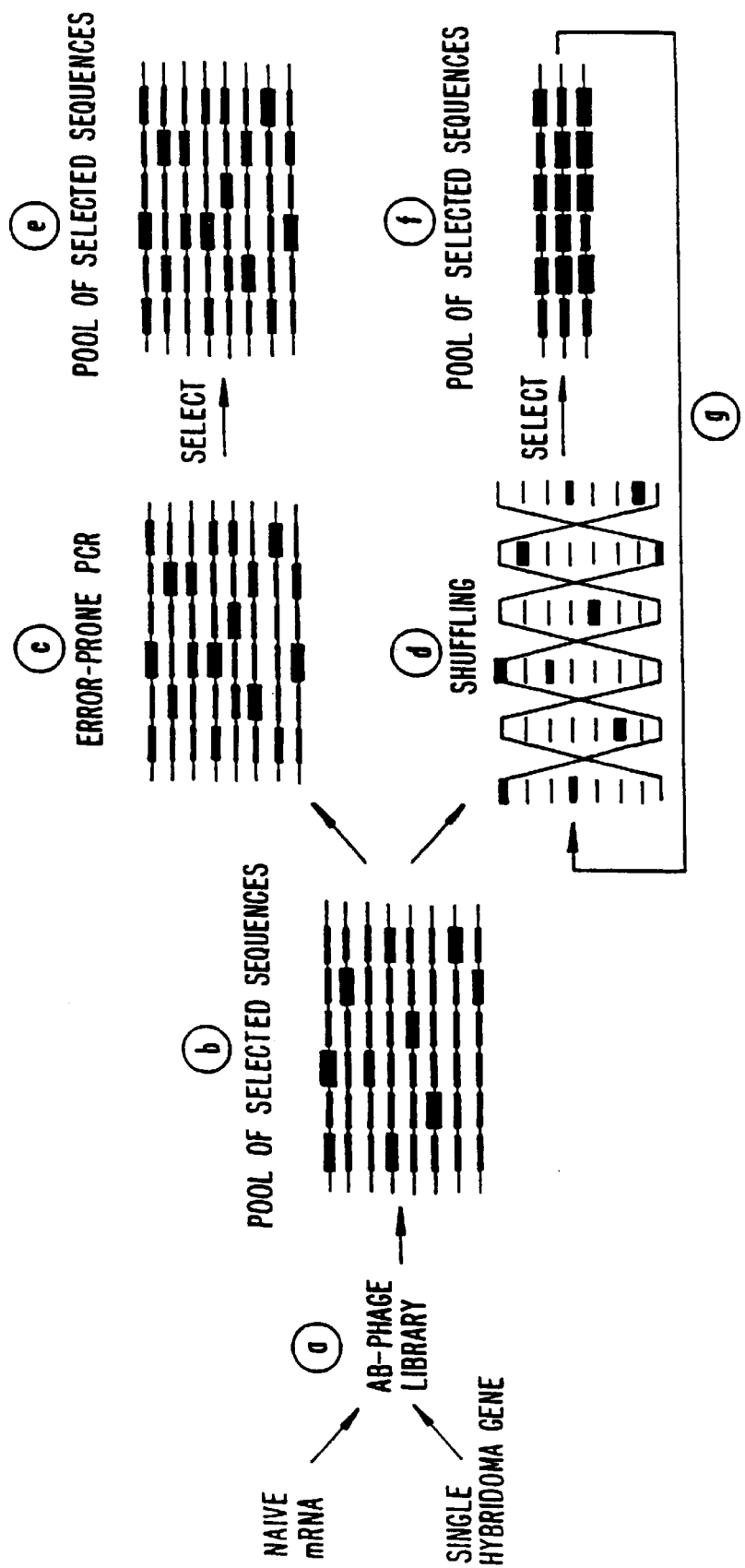
FIG. 1 is a schematic diagram comparing mutagenic shuffling over error-prone PCR; (a) the initial library; (b) pool of selected sequences in first round of affinity selection; (d) in vitro recombination of the selected sequences ('shuffling'); (f) pool of selected sequences in second round of affinity selection after shuffling; (c) error-prone PCR; (e) pool of selected sequences in second round of affinity selection after error-prone PCR.

The present invention relates to a method for nucleic acid molecule reassembly after random fragmentation and its application to mutagenesis of DNA sequences. Also described is a method for the production of nucleic acid fragments encoding mutant proteins having enhanced biological activity. In particular, the present invention also relates to a method of repeated cycles of mutagenesis, nucleic acid shuffling and selection which allow for the creation of mutant proteins having enhanced biological activity.

The present invention is directed to a method for generating a very large library of DNA, RNA or protein mutants; in embodiments where a metabolic enzyme or multicomponent pathway is subjected to shuffling, a library can compose the resultant metabolites in addition to a library of the shuffled enzyme(s). This method has particular advantages in the generation of related DNA fragments from which the desired nucleic acid fragment(s) may be selected. In particular the present invention also relates to a method of repeated cycles of mutagenesis, homologous recombination and selection which allow for the creation of mutant proteins having enhanced biological activity.

However, prior to discussing this invention in further detail, the following terms will first be defined.

DEFINITIONS

As used herein, the following terms have the following meanings:

The term "DNA reassembly" is used when recombination occurs between identical sequences.

By contrast, the term "DNA shuffling" is used herein to indicate recombination between substantially homologous but non-identical sequences, in some embodiments DNA shuffling may involve crossover via nonhomologous recombination, such as via cre/lox and/or flp/frt systems and the like, such that recombination need not require substantially homologous polynucleotide sequences. Homologous and non-homologous recombination formats can be used, and, in some embodiments, can generate molecular chimeras and/or molecular hybrids of substantially dissimilar sequences.

The term "amplification" means that the number of copies of a nucleic acid fragment is increased.

The term "identical" or "identity" means that two nucleic acid sequences have the same sequence or a complementary sequence. Thus, "areas of identity" means that regions or areas of a nucleic acid fragment or polynucleotide are identical or complementary to another polynucleotide or nucleic acid fragment.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of FIG. 1 or FIG. 2(b), or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci.* (*U.S.A.*) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

The term "homologous" or "homeologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as discussed later. Preferably the region of identity is greater than about 5 bp, more preferably the region of identity is greater than 10 bp.

The term "heterologous" means that one single-stranded nucleic acid sequence is unable to hybridize to another single-stranded nucleic acid sequence or its complement. Thus areas of heterology means that nucleic acid fragments or polynucleotides have areas or regions in the sequence which are unable to hybridize to another nucleic acid or polynucleotide. Such regions or areas are, for example, areas of mutations.

The term "cognate" as used herein refers to a gene sequence that is evolutionarily and functionally related between species. For example but not limitation, in the human genome, the human CD4 gene is the cognate gene to the mouse CD4 gene, since the sequences and structures of these two genes indicate that they are highly homologous and both genes encode a protein which functions in signaling T cell activation through MHC class II-restricted antigen recognition.

The term "wild-type" means that the nucleic acid fragment does not comprise any mutations. A "wild-type" protein means that the protein will be active at a level of activity found in nature and typically will comprise the amino acid sequence found in nature. In an aspect, the term "wild type" or "parental sequence" can indicate a starting or reference sequence prior to a manipulation of the invention.

The term "related polynucleotides" means that regions or areas of the polynucleotides are identical and regions or areas of the polynucleotides are heterologous.

The term "chimeric polynucleotide" means that the polynucleotide comprises regions which are wild-type and regions which are mutated. It may also mean that the polynucleotide comprises wild-type regions from one polynucleotide and wild-type regions from another related polynucleotide.

The term "cleaving" means digesting the polynucleotide with enzymes or breaking the polynucleotide, or generating partial length copies of a parent sequence(s) via partial PCR extension, PCR stuttering, differential fragment amplification, or other means of producing partial length copies of one or more parental sequences.

The term "population" as used herein means a collection of components such as polynucleotides, nucleic acid fragments or proteins. A "mixed population" means a collection of components which belong to the same family of nucleic acids or proteins (i.e. are related) but which differ in their sequence (i.e. are not identical) and hence in their biological activity.

The term "specific nucleic acid fragment" means a nucleic acid fragment having certain end points and having a certain nucleic acid sequence. Two nucleic acid fragments wherein one nucleic acid fragment has the identical sequence as a portion of the second nucleic acid fragment but different ends comprise two different specific nucleic acid fragments.

The term "mutations" means changes in the sequence of a wild-type nucleic acid sequence or changes in the sequence of a peptide. Such mutations may be point mutations such as transitions or transversions. The mutations may be deletions, insertions or duplications.

In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the coding RNA transcript are referred to as "downstream sequences".

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a non-pathological (undiseased) individual, such as would be typical for the species.

The term "agent" is used herein to denote a chemical compound, a mixture of chemical compounds, an array of spatially localized compounds (e.g., a VLSIPS peptide array, polynucleotide array, and/or combinatorial small molecule array), a biological macromolecule, a bacteriophage peptide display library, a bacteriophage antibody (e.g., scFv) display library, a polysome peptide display library, or an extract made from biological materials such as bacteria, plants, fungi, or animal (particularly mammalian) cells or tissues. Agents are evaluated for potential activity as antineoplastics, anti-inflammatories, or apoptosis modulators by inclusion in screening assays described hereinbelow. Agents are evaluated for potential activity as specific protein interaction inhibitors (i.e., an agent which selectively inhibits a binding interaction between two predetermined polypeptides but which does not substantially interfere with cell viability) by inclusion in screening assays described hereinbelow.

As used herein, "substantially pure" means an object species is the predominant species present (i.e., on a molar basis it is more abundant than any other individual macromolecular species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for in vitro transcription cocktails are generally physiological conditions. In general, in vitro physiological conditions comprise 50–200 mM NaCl or KCl, pH 6.5–8.5, 20–45° C. and 0.001–10 mM divalent cation (e.g., $Mg^{++}$, $Ca^{++}$); preferably about 150 mM NaCl or KCl, pH 7.2–7.6, 5 mM divalent cation, and often include 0.01–1.0 percent nonspecific protein (e.g., BSA). A non-ionic detergent (Tween, NP-40, Triton X-100) can often be present, usually at about 0.001 to 2%, typically 0.05–0.2% (v/v). Particular aqueous conditions may be selected by the practitioner according to conventional methods. For general guidance, the following buffered aqueous conditions may be applicable: 10–250 mM NaCl, 5–50 mM Tris HCl, pH 5–8, with optional addition of divalent cation(s) and/or metal chelators and/or nonionic detergents and/or membrane fractions and/or antifoam agents and/or scintillants.

Specific hybridization is defined herein as the formation of hybrids between a first polynucleotide and a second polynucleotide (e.g., a polynucleotide having a distinct but substantially identical sequence to the first polynucleotide), wherein the first polynucleotide preferentially hybridizes to the second polynucleotide under stringent hybridization conditions wherein substantially unrelated polynucleotide sequences do not form hybrids in the mixture.

As used herein, the term "single-chain antibody" refers to a polypeptide comprising a $V_H$ domain and a $V_L$ domain in polypeptide linkage, generally linked via a spacer peptide (e.g., [Gly-Gly-Gly-Gly-Ser]$_x$ (SEQ ID NO: 64)), and which may comprise additional amino acid sequences at the amino- and/or carboxy- termini. For example, a single-chain antibody may comprise a tether segment for linking to the encoding polynucleotide. As an example, a scFv is a single-chain antibody. Single-chain antibodies are generally proteins consisting of one or more polypeptide segments of at least 10 contiguous amino acids substantially encoded by genes of the immunoglobulin superfamily (e.g., see *The Immunoglobulin Gene Superfamily*, A. F. Williams and A. N. Barclay, in *Immunoqlobulin Genes*, T. Honjo, F. W. Alt, and T. H. Rabbitts, eds., (1989) Academic Press: San Diego, Calif., pp.361–387, which is incorporated herein by reference), most frequently encoded by a rodent, non-human primate, avian, porcine, bovine, ovine, goat, or human heavy chain or light chain gene sequence. A functional single-chain antibody generally contains a sufficient portion of an immunoglobulin superfamily gene product so as to retain the property of binding to a specific target molecule, typically a receptor or antigen (epitope).

As used herein, the term "complementarity-determining region" and "CDR" refer to the art-recognized term as exemplified by the Kabat and Chothia CDR definitions also generally known as hypervariable regions or hypervariable loops (Chothia and Lesk (1987) *J. Mol. Biol.* 196: 901; Chothia et al. (1989) *Nature* 342: 877; E. A. Kabat et al., Sequences of Proteins of Immunological Interest (National Institutes of Health, Bethesda, Md.) (1987); and Tramontano et al. (1990) *J. Mol. Biol.* 215: 175). Variable region domains typically comprise the amino-terminal approximately 105–115 amino acids of a naturally-occurring immunoglobulin chain (e.g., amino acids 1–110), although variable domains somewhat shorter or longer are also suitable for forming single-chain antibodies.

An immunoglobulin light or heavy chain variable region consists of a "framework" region interrupted by three hypervariable regions, also called CDR's. The extent of the framework region and CDR's have been precisely defined (see, "Sequences of Proteins of Immunological Interest," E. Kabat et al., 4th Ed., U.S. Department of Health and Human Services, Bethesda, Md. (1987)). The sequences of the framework regions of different light or heavy chains are relatively conserved within a species. As used herein, a "human framework region" is a framework region that is substantially identical (about 85% or more, usually 90–95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

As used herein, the term "variable segment" refers to a portion of a nascent peptide which comprises a random, pseudorandom, or defined kernal sequence. A variable segment can comprise both variant and invariant residue positions, and the degree of residue variation at a variant residue position may be limited; both options are selected at the discretion of the practitioner. Typically, variable segments are about 5 to 20 amino acid residues in length (e.g., 8 to 10), although variable segments may be longer and may comprise antibody portions or receptor proteins, such as an antibody fragment, a nucleic acid binding protein, a receptor protein, and the like.

As used herein, "random peptide sequence" refers to an amino acid sequence composed of two or more amino acid monomers and constructed by a stochastic or random process. A random peptide can include framework or scaffolding motifs, which may comprise invariant sequences.

As used herein "random peptide library" refers to a set of polynucleotide sequences that encodes a set of random peptides, and to the set of random peptides encoded by those polynucleotide sequences, as well as the fusion proteins containing those random peptides.

As used herein, the term "pseudorandom" refers to a set of sequences that have limited variability, so that for example the degree of residue variability at one position is different than the degree of residue variability at another position, but any pseudorandom position is allowed some degree of residue variation, however circumscribed.

As used herein, the term "defined sequence framework" refers to a set of defined sequences that are selected on a nonrandom basis, generally on the basis of experimental data or structural data; for example, a defined sequence framework may comprise a set of amino acid sequences that are predicted to form a β-sheet structure or may comprise a leucine zipper heptad repeat motif, a zinc-finger domain, among other variations. A "defined sequence kernal" is a set of sequences which encompass a limited scope of variability. Whereas (1) a completely random 10-mer sequence of the 20 conventional amino acids can be any of $(20)^{10}$ sequences, and (2) a pseudorandom 10-mer sequence of the 20 conventional amino acids can be any of $(20)^{10}$ sequences but will exhibit a bias for certain residues at certain positions and/or overall, (3) a defined sequence kernal is a subset of sequences which is less that the maximum number of potential sequences if each residue position was allowed to be any of the allowable 20 conventional amino acids (and/or allowable unconventional amino/imino acids). A defined sequence kernal generally comprises variant and invariant residue positions and/or comprises variant residue positions which can comprise a residue selected from a defined subset of amino acid residues), and the like, either segmentally or over the entire length of the individual selected library member sequence. Defined sequence kernals can refer to either amino acid sequences or polynucleotide sequences. For illustration and not limitation, the sequences $(NNK)_{10}$ (SEQ. ID NO: 65) and $(NNM)_{10}$ (SEQ. ID NO: 65), where N represents A, T, G, or C; K represents G or T; and M represents A or C, are defined sequence kernals.

As used herein "epitope" refers to that portion of an antigen or other macromolecule capable of forming a binding interaction that interacts with the variable region binding pocket of an antibody. Typically, such binding interaction is manifested as an intermolecular contact with one or more amino acid residues of a CDR.

As used herein, "receptor" refers to a molecule that has an affinity for a given ligand. Receptors can be naturally occurring or synthetic molecules. Receptors can be employed in an unaltered state or as aggregates with other species. Receptors can be attached, covalently or noncovalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, complex carbohydrates and glycoproteins, enzymes, and hormone receptors.

As used herein "ligand" refers to a molecule, such as a random peptide or variable segment sequence, that is recognized by a particular receptor. As one of skill in the art will recognize, a molecule (or macromolecular complex) can be both a receptor and a ligand. In general, the binding partner having a smaller molecular weight is referred to as the ligand and the binding partner having a greater molecular weight is referred to as a receptor.

As used herein, "linker" or "spacer" refers to a molecule or group of molecules that connects two molecules, such as a DNA binding protein and a random peptide, and serves to place the two molecules in a preferred configuration, e.g., so that the random peptide can bind to a receptor with minimal steric hindrance from the DNA binding protein.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

The term "recursive sequence recombination" as used herein refers to a method whereby a population of polynucleotide sequences are recombined with each other by any suitable recombination means (e.g., sexual PCR, homologous recombination, site-specific recombination, etc.) to generate a library of sequence-recombined species which is then screened or subjected to selection to obtain those sequence-recombined species having a desired property; the selected species are then subjected to at least one additional cycle of recombination with themselves and/or with other polynucleotide species and at subsequent selection or screening for the desired property.

Methodology

Nucleic acid shuffling is a method for recursive in vitro or in vivo homologous recombination of pools of nucleic acid fragments or polynucleotides. Mixtures of related nucleic acid sequences or polynucleotides are randomly fragmented, and reassembled to yield a library or mixed population of recombinant nucleic acid molecules or polynucleotides.

In contrast to cassette mutagenesis, only shuffling and error-prone PCR (or use of other mutation-enhancement methods; chemical mutagenesis, mutator strains, etc.) allow one to mutate a pool of sequences blindly (without sequence information other than primers).

The advantage of the mutagenic shuffling of this invention over error-prone PCR alone for repeated selection can best be explained with an example from antibody engineering. In FIG. 1 is shown a schematic diagram of DNA shuffling as described herein. The initial library can consist of related sequences of diverse origin (i.e. antibodies from naive mRNA) or can be derived by any type of mutagenesis (including shuffling) of a single antibody gene. A collection of selected complementarity determining regions ("CDRs") is obtained after the first round of affinity selection (FIG. 1). In the diagram the thick CDRs confer onto the antibody molecule increased affinity for the antigen. Shuffling allows the free combinatorial association of all of the CDR1s with all of the CDR2s with all of the CDR3s, etc. (FIG. 1).

This method differs from PCR, in that it is an inverse chain reaction. In PCR, the number of molecules grows exponentially. In shuffling, however, the number of the polymerase start sites and the number of molecules remains essentially the same. When dilution is used to allow further lengthening of the molecules, the shuffling process becomes an inverse chain reaction generating fewer molecules.

Since cross-overs occur at regions of homology, recombination will primarily occur between members of the same sequence family. This discourages combinations of CDRs that are grossly incompatible (eg. directed against different epitopes of the same antigen). It is contemplated that multiple families of sequences can be shuffled in the same reaction. Further, shuffling conserves the relative order, such that, for example, CDR1 will not be found in the position of CDR2.

Rare shufflants will contain a large number of the best (eg. highest affinity) CDRs and these rare shufflants may be selected based on their superior affinity (FIG. 1).

CDRs from a pool of 100 different selected antibody sequences can be permutated in up to $100^6$ different ways. This large number of permutations cannot be represented in a single library of DNA sequences. Accordingly, it is contemplated that multiple cycles of DNA shuffling and selection may be required depending on the length of the sequence and the sequence diversity desired.

Error-prone PCR, in contrast, keeps all the selected CDRs in the same relative sequence (FIG. 1), generating a much smaller mutant cloud.

The template polynucleotide which may be used in the methods of this invention may be DNA or RNA. It may be of various lengths depending on the size of the gene or DNA fragment to be recombined or reassembled. Preferably the template polynucleotide is from 50 bp to 50 kb. It is contemplated that entire vectors containing the nucleic acid encoding the protein of interest can be used in the methods of this invention, and in fact have been successfully used.

The template polynucleotide may be obtained by amplification using the PCR reaction (U.S. Pat. Nos. 4,683,202 and 4,683,195) or other amplification or cloning methods. However, the removal of free primers from the PCR product before fragmentation provides a more efficient result. Failure to adequately remove the primers can lead to a low frequency of crossover clones.

The template polynucleotide often should be double-stranded. A double-stranded nucleic acid molecule is required to ensure that regions of the resulting single-stranded nucleic acid fragments are complementary to each other and thus can hybridize to form a double-stranded molecule.

It is contemplated that single-stranded or double-stranded nucleic acid fragments having regions of identity to the template polynucleotide and regions of heterology to the template polynucleotide may be added to the template polynucleotide at this step. It is also contemplated that two different but related polynucleotide templates can be mixed at this step.

The double-stranded polynucleotide template and any added double-or single-stranded fragments are randomly digested into fragments of from about 5 bp to 5 kb or more. Preferably the size of the random fragments is from about 10 bp to 1000 bp, more preferably the size of the DNA fragments is from about 20 bp to 500 bp.

Alternatively, it is also contemplated that double-stranded nucleic acid having multiple nicks may be used in the methods of this invention. A nick is a break in one strand of the double-stranded nucleic acid. The distance between such nicks is preferably 5 bp to 5 kb, more preferably between 10 bp to 1000 bp.

The nucleic acid fragment may be digested by a number of different methods. The nucleic acid fragment may be digested with a nuclease, such as DNAseI or RNAse. The nucleic acid may be randomly sheared by the method of sonication or by passage through a tube having a small orifice.

It is also contemplated that the nucleic acid may also be partially digested with one or more restriction enzymes, such that certain points of cross-over may be retained statistically.

The concentration of any one specific nucleic acid fragment will not be greater than 1% by weight of the total nucleic acid, more preferably the concentration of any one specific nucleic acid sequence will not be greater than 0.1% by weight of the total nucleic acid.

The number of different specific nucleic acid fragments in the mixture will be at least about 100, preferably at least about 500, and more preferably at least about 1000.

At this step single-stranded or double-stranded nucleic acid fragments, either synthetic or natural, may be added to the random double-stranded nucleic acid fragments in order to increase the heterogeneity of the mixture of nucleic acid fragments.

It is also contemplated that populations of double-stranded randomly broken or nicked nucleic acid fragments may be mixed or combined at this step. Damaged DNA can be exploited to enhance recombination via the nicked portions which can participate in strand invasion, formation of recombination junctions, serve as free 3' ends for hybrid formation and the like.

Where insertion of mutations into the template polynucleotide is desired, single-stranded or double-stranded nucleic acid fragments having a region of identity to the template polynucleotide and a region of heterology to the template polynucleotide may be added in a 20 fold excess by weight as compared to the total nucleic acid, more preferably the single-stranded nucleic acid fragments may be added in a 10 fold excess by weight as compared to the total nucleic acid.

Where a mixture of different but related template polynucleotides is desired, populations of nucleic acid fragments from each of the templates may be combined at a ratio of less than about 1:100, more preferably the ratio is less than about 1:40. For example, a backcross of the wild-type polynucleotide with a population of mutated polynucleotide may be desired to eliminate neutral mutations (e.g., mutations yielding an insubstantial alteration in the phenotypic property being selected for). In such an example, the ratio of randomly digested wild-type polynucleotide fragments which may be added to the randomly digested mutant polynucleotide fragments is approximately 1:1 to about 100:1, and more preferably from 1:1 to 40:1.

The mixed population of random length nucleic acid fragments are denatured to form single-stranded nucleic acid fragments and then reannealed. Only those single-stranded nucleic acid fragments having regions of homology with other single-stranded nucleic acid fragments will reanneal.

The random length nucleic acid fragments may be denatured by heating. One skilled in the art could determine the conditions necessary to completely denature the double stranded nucleic acid. Preferably the temperature is from 80° C. to 100° C., more preferably the temperature is from 90° C. to 96° C. Other methods which may be used to denature the nucleic acid fragments include pressure (36) and pH.

The nucleic acid fragments may be reannealed by cooling. Preferably the temperature is from 20° C. to 75° C., more preferably the temperature is from 40° C. to 65° C. If a high frequency of crossovers is needed based on an average of only 4 consecutive bases of homology, recombination can be forced by using a low annealing temperature, although the process becomes more difficult. The degree of renaturation which occurs will depend on the degree of homology between the population of single-stranded nucleic acid fragments.

Renaturation can be accelerated by the addition of polyethylene glycol ("PEG") or salt. The salt concentration is preferably from 0 mM to about 400 mM, more preferably the salt concentration is from 10 mM to 100 mM. The salt may be KCl or NaCl. The concentration of PEG is preferably from 0% to 20%, more preferably from 5% to 10%. Higher concentrations of salt and/or PEG can be used, if desired.

The annealed nucleic acid fragments are next incubated in the presence of a nucleic acid polymerase and dNTP's (i.e. DATP, dCTP, dGTP and dTTP). The nucleic acid polymerase may be the Klenow fragment, the Taq polymerase or any other DNA polymerase known in the art.

The approach to be used for the assembly depends on the minimum degree of homology that should still yield crossovers. If the areas of identity are large, Taq polymerase can be used with an annealing temperature of between 45–65° C. If the areas of identity are small, Klenow polymerase can be used with an annealing temperature of between 20–30° C. One skilled in the art could vary the temperature of annealing to increase the number of cross-overs achieved.

The polymerase may be added to the random nucleic acid fragments prior to annealing, simultaneously with annealing or after annealing.

The cycle of denaturation, renaturation and incubation in the presence of polymerase can be referred to as shuffling or reassembly of the nucleic acid. This cycle is repeated for a desired number of times. Preferably the cycle is repeated from 2 to 50 times, more preferably the sequence is repeated from 10 to 40 times. The term "shuffling" encompasses a broader range of recursive recombination processes which can include, but are not obligated to, PCR amplification or similar amplification methods; thus, shuffling can involve homologous recombination, site-specific recombination, chimera formation (e.g., Levichkin et al. op.cit), and the like, so long as used recursively (i.e., for more than one cycle of sequence recombination) with selection and/or screening. Non-deterministic recombination, such as general homologous recombination can be used in combination with or in place of deterministic recombination, such as site-specific recombination where the sites of recombination are known and/or defined.

The resulting nucleic acid is a larger double-stranded polynucleotide of from about 50 bp to about 100 kb, preferably the larger polynucleotide is from 500 bp to 50 kb.

This larger polynucleotide fragment may contain a number of copies of a nucleic acid fragment having the same size as the template polynucleotide in tandem. This concatemeric fragment is then digested into single copies of the template polynucleotide. The result will be a population of nucleic acid fragments of approximately the same size as the template polynucleotide. The population will be a mixed population where single or double-stranded nucleic acid fragments having an area of identity and an area of heterology have been added to the template polynucleotide prior to shuffling. Alternatively, the concatemer can be introduced (e.g., via electroporation. lipofection, or the like) directly without monomerization. For large sequences, it can be desirable to subdivide the large sequence into several subportions which are separately shuffled with other substantially similar portions, and the pool of resultant shuffled subportions are then ligated, typically in original order, to generate a pool of shuffled large sequences which can then be used for transformation of a host cell, or the like.

These fragment are then cloned into the appropriate vector and the ligation mixture used to transform bacteria.

It is contemplated that the single nucleic acid fragments may be obtained from the larger concatemeric nucleic acid fragment by amplification of the single nucleic acid fragments prior to cloning by a variety of methods including PCR (U.S. Pat. Nos. 4,683,195 and 4,683,202) rather than by digestion of the concatemer. Alternatively, the concatemer can be introduced (e.g., via electroporation. lipofection, or the like) directly without monomerization.

The vector used for cloning is not critical provided that it will accept a DNA fragment of the desired size. If expression of the DNA fragment is desired, the cloning vehicle should further comprise transcription and translation signals next to the site of insertion of the DNA fragment to allow expression of the DNA fragment in the host cell. Preferred vectors include the pUC series and the pBR series of plasmids.

The resulting bacterial population will include a number of recombinant DNA fragments having random mutations. This mixed population may be tested to identify the desired recombinant nucleic acid fragment. The method of selection will depend on the DNA fragment desired.

For example, if a DNA fragment which encodes for a protein with increased binding efficiency to a ligand is desired, the proteins expressed by each of the DNA fragments in the population or library may be tested for their ability to bind to the ligand by methods known in the art (i.e. panning, affinity chromatography). If a DNA fragment which encodes for a protein with increased drug resistance is desired, the proteins expressed by each of the DNA fragments in the population or library may be tested for their ability to confer drug resistance to the host organism. One skilled in the art, given knowledge of the desired protein, could readily test the population to identify DNA fragments which confer the desired properties onto the protein.

It is contemplated that one skilled in the art could use a phage display system in which fragments of the protein are expressed as fusion proteins on the phage surface (Pharmacia, Milwaukee Wis.). The recombinant DNA molecules are cloned into the phage DNA at a site which results in the transcription of a fusion protein, a portion of which is encoded by the recombinant DNA molecule. The phage containing the recombinant nucleic acid molecule undergoes replication and transcription in the cell. The leader sequence of the fusion protein directs the transport of the fusion protein to the tip of the phage particle. Thus the fusion protein which is partially encoded by the recombinant DNA molecule is displayed on the phage particle for detection and selection by the methods described above.

It is further contemplated that a number of cycles of nucleic acid shuffling may be conducted with nucleic acid fragments from a subpopulation of the first population, which subpopulation contains DNA encoding the desired recombinant protein. In this manner, proteins with even higher binding affinities or enzymatic activity could be achieved.

It is also contemplated that a number of cycles of nucleic acid shuffling may be conducted with a mixture of wild-type nucleic acid fragments and a subpopulation of nucleic acid from the first or subsequent rounds of nucleic acid shuffling in order to remove any silent mutations from the subpopulation.

Any source of nucleic acid, in purified form can be utilized as the starting nucleic acid. Thus the process may employ DNA or RNA including messenger RNA, which DNA or RNA may be single or double stranded. In addition, a DNA-RNA hybrid which contains one strand of each may be utilized. The nucleic acid sequence may be of various lengths depending on the size of the nucleic acid sequence to be mutated. Preferably the specific nucleic acid sequence is from 50 to 50000 base pairs. It is contemplated that entire vectors containing the nucleic acid encoding the protein of interest may be used in the methods of this invention.

The nucleic acid may be obtained from any source, for example, from plasmids such a pBR322, from cloned DNA or RNA or from natural DNA or RNA from any source including bacteria, yeast, viruses and higher organisms such as plants or animals. DNA or RNA may be extracted from blood or tissue material. The template polynucleotide may be obtained by amplification using the polynucleotide chain reaction (PCR) (U.S. Pat. Nos. 4,683,202 and 4,683,195). Alternatively, the polynucleotide may be present in a vector present in a cell and sufficient nucleic acid may be obtained by culturing the cell and extracting the nucleic acid from the cell by methods known in the art.

Any specific nucleic acid sequence can be used to produce the population of mutants by the present process. It is only necessary that a small population of mutant sequences of the specific nucleic acid sequence exist or be created prior to the present process.

The initial small population of the specific nucleic acid sequences having mutations may be created by a number of different methods. Mutations may be created by error-prone PCR. Error-prone PCR uses low-fidelity polymerization conditions to introduce a low level of point mutations randomly over a long sequence. Alternatively, mutations can be introduced into the template polynucleotide by oligonucleotide-directed mutagenesis. In oligonucleotide-directed mutagenesis, a short sequence of the polynucleotide is removed from the polynucleotide using restriction enzyme digestion and is replaced with a synthetic polynucleotide in which various bases have been altered from the original sequence. The polynucleotide sequence can also be altered by chemical mutagenesis. Chemical mutagens include, for example, sodium bisulfite, nitrous acid, hydroxylamine, hydrazine or formic acid. Other agents which are analogues of nucleotide precursors include nitrosoguanidine, 5-bromouracil, 2-aminopurine, or acridine. Generally, these agents are added to the PCR reaction in place of the nucleotide precursor thereby mutating the sequence. Intercalating agents such as proflavine, acriflavine, quinacrine and the like can also be used. Random mutagenesis of the polynucleotide sequence can also be achieved by irradiation with X-rays or ultraviolet light. Generally, plasmid DNA or DNA fragments so mutagenized are introduced into *E. coli* and propagated as a pool or library of mutant plasmids.

Alternatively the small mixed population of specific nucleic acids may be found in nature in that they may consist of different alleles of the same gene or the same gene from different related species (i.e., cognate genes). Alternatively, they may be related DNA sequences found within one species, for example, the immunoglobulin genes.

Once the mixed population of the specific nucleic acid sequences is generated, the polynucleotides can be used directly or inserted into an appropriate cloning vector, using techniques well-known in the art.

The choice of vector depends on the size of the polynucleotide sequence and the host cell to be employed in the methods of this invention. The templates of this invention may be plasmids, phages, cosmids, phagemids, viruses (e.g., retroviruses, parainfluenzavirus, herpesviruses, reoviruses, paramyxoviruses, and the like), or selected portions thereof (e.g., coat protein, spike glycoprotein, capsid protein). For example, cosmids, phagemids, YACs, and BACs are preferred where the specific nucleic acid sequence to be mutated is larger because these vectors are able to stably propagate large nucleic acid fragments.

If the mixed population of the specific nucleic acid sequence is cloned into a vector it can be clonally amplified by inserting each vector into a host cell and allowing the host cell to amplify the vector. This is referred to as clonal amplification because while the absolute number of nucleic acid sequences increases, the number of mutants does not increase.

Parallel PCR

In parallel PCR a large number of different PCR reactions occur in parallel in the same vessel, with the products of one reaction priming the products of another reaction. As the PCR products prime each other, the average product size increases with the number of PCR cycles.

By using multiple primers in parallel, sequences in excess of 50 kb can be amplified. Whole genes and whole plasmids can be assembled in a single tube from synthetic oligonucleotides by parallel PCR. Sequences can be randomly mutagenized at various levels by random fragmentation and reassembly of the fragments by mutual priming. Site-specific mutations can be introduced into long sequences by random fragmentation of the template followed by reassembly of the fragments in the presence of mutagenic oligonucleotides. A particularly useful application of parallel PCR is called sexual PCR.

In sexual PCR, also called DNA shuffling, parallel PCR is used to perform in vitro recombination on a pool of DNA sequences. A mixture of related but not identical DNA sequences (typically PCR products, restriction fragments or whole plasmids) is randomly fragmented, for example by DNAseI treatment. These random fragments are then reassembled by parallel PCR. As the random fragments and their PCR products prime each other, the average size of the fragments increases with the number of PCR cycles. Recombination, or crossover, occurs by template switching, such as when a DNA fragment derived from one template primes on the homologous position of a related but different template. For example, sexual PCR can be used to construct libraries of chimaeras of genes from different species ('zoo libraries'). Sexual PCR is useful for in vitro evolution of DNA sequences. The libraries of new mutant combinations that are obtained by sexual PCR are selected for the best recombinant sequences at the DNA, RNA, protein or small molecule level. This process of recombination, selection and amplification is repeated for as many cycles as necessary to obtain a desired property or function.

Most versions of parallel PCR do not use primers. The DNA fragments, whether synthetic, obtained by random digestion, or by PCR with primers, serve as the template as well as the primers. Because the concentration of each different end sequence in the reassembly reaction is very low, the formation of primer dimer is not observed, and if erroneous priming occurs, it can only grow at the same rate as the correctly annealed product. Parallel PCR requires many cycles of PCR because only half of the annealed pairs have extendable overhangs and the concentration of 3' ends is low.

Utility

The DNA shuffling method of this invention can be performed blindly on a pool of unknown sequences. By adding to the reassembly mixture oligonucleotides (with ends that are homologous to the sequences being reassembled) any sequence mixture can be incorporated at any specific position into another sequence mixture. Thus, it is contemplated that mixtures of synthetic oligonucleotides, PCR fragments or even whole genes can be mixed into another sequence library at defined positions. The insertion of one sequence (mixture) is independent from the insertion of a sequence in another part of the template. Thus, the degree of recombination, the homology required, and the diversity of the library can be independently and simultaneously varied along the length of the reassembled DNA.

This approach of mixing two genes may be useful for the humanization of antibodies from murine hybridomas. The approach of mixing two genes or inserting mutant sequences into genes may be useful for any therapeutically used protein, for example, interleukin I, antibodies, tPA, growth hormone, etc. The approach may also be useful in any nucleic acid for example, promoters or introns or 3' untranslated region or 5' untranslated regions of genes to increase expression or alter specificity of expression of proteins. The approach may also be used to mutate ribozymes or aptamers.

Shuffling requires the presence of homologous regions separating regions of diversity. If the sequences to be shuffled are not substantially identical, it is typically preferable to employ intron-based shuffling and/or site-specific recombination. Scaffold-like protein structures may be particularly suitable for shuffling. The conserved scaffold determines the overall folding by self-association, while displaying relatively unrestricted loops that mediate the specific binding. Examples of such scaffolds are the immunoglobulin beta-barrel, and the four-helix bundle (24). This shuffling can be used to create scaffold-like proteins with various combinations of mutated sequences for binding.

In Vitro Shuffling

The equivalents of some standard genetic matings may also be performed by shuffling in vitro. For example, a 'molecular backcross' can be performed by repeated mixing of the mutant's nucleic acid with the wild-type nucleic acid while selecting for the mutations of interest. As in traditional breeding, this approach can be used to combine phenotypes from different sources into a background of choice. It is useful, for example, for the removal of neutral mutations that affect unselected characteristics (i.e. immunogenicity). Thus it can be useful to determine which mutations in a protein are involved in the enhanced biological activity and which are not, an advantage which cannot be achieved by error-prone mutagenesis or cassette mutagenesis methods.

Large, functional genes can be assembled correctly from a mixture of small random fragments. This reaction may be of use for the reassembly of genes from the highly fragmented DNA of fossils (25). In addition random nucleic acid fragments from fossils may be combined with nucleic acid fragments from similar genes from related species.

It is also contemplated that the method of this invention can be used for the in vitro amplification of a whole genome from a single cell as is needed for a variety of research and diagnostic applications. DNA amplification by PCR is in practice limited to a length of about 40 kb. Amplification of a whole genome such as that of E. coli (5,000 kb) by PCR would require about 250 primers yielding 125 forty kb fragments. This approach is not practical due to the unavailability of sufficient sequence data. On the other hand, random digestion of the genome with DNAseI, followed by gel purification of small fragments will provide a multitude of possible primers. Use of this mix of random small fragments as primers in a PCR reaction alone or with the whole genome as the template should result in an inverse chain reaction with the theoretical endpoint (assuming dilution and additional PCR) of a single concatemer containing many copies of the genome.

100 fold amplification in the copy number and an average fragment size of greater than 50 kb may be obtained when only random fragments are used (see Example 2). It is thought that the larger concatemer is generated by overlap of many smaller fragments. The quality of specific PCR products obtained using synthetic primers will be indistinguishable from the product obtained from unamplified DNA. It is expected that this approach will be useful for the mapping of genomes.

The polynucleotide to be shuffled can be fragmented randomly or non-randomly, at the discretion of the practitioner.

In Vivo Shuffling

In an embodiment of in vivo shuffling, the mixed population of the specific nucleic acid sequence is introduced into bacterial (e.g., Archeaebacteria) or eukaryotic cells under conditions such that at least two different nucleic acid sequences are present in each host cell. The fragments can be introduced into the host cells by a variety of different methods. The host cells can be transformed with the fragments using methods known in the art, for example treatment with calcium chloride. If the fragments are inserted into a phage genome, the host cell can be transfected with the recombinant phage genome having the specific nucleic acid sequences. Alternatively, the nucleic acid sequences can be introduced into the host cell using electroporation, natural competence, transduction, transfection, lipofection, biolistics, conjugation, and the like or other suitable method of introducing a polynucleotide sequence into a cell.

In general, in this embodiment, the specific nucleic acids sequences will be present in vectors which are capable of stably replicating the sequence in the host cell. In addition, it is contemplated that the vectors will encode a marker gene such that host cells having the vector can be selected or screened. This ensures that the mutated specific nucleic acid sequence can be recovered after introduction into the host cell. However, it is contemplated that the entire mixed population of the specific nucleic acid sequences need not be present on a vector sequence. Rather only a sufficient number of sequences need be cloned into vectors to ensure that after introduction of the fragments into the host cells each host cell contains two vector species having at least one related-sequence nucleic acid sequence present therein. It is also contemplated that rather than having a subset of the population of the specific nucleic acids sequences cloned into vectors, this subset may be already stably integrated into the host cell.

It has been found that when two fragments which have regions of identity are inserted into the host cells, homologous recombination occurs between the two fragments. Such recombination between the two mutated specific nucleic acid sequences will result in the production of substantially all combinations of all or most of the mutations (as limited by library size and propagation efficiency, etc.).

It has also been found that the frequency of recombination is increased if some of the mutated specific nucleic acid sequences are present on linear nucleic acid molecules. Therefore, in a preferred embodiment, some of the specific nucleic acid sequences are present on linear nucleic acid fragments. In an embodiment, the nucleic acid molecules are single-stranded or substantially single-stranded, such as single-stranded phage genomes which may or may not comprise heterologous sequences. M13 phage is an example of a suitable ssDNA template, and M13 has the advantage that the M13 virus can be shuffled in prokaryotic cells (e.g., E. coli), and then used to transfer DNA into mammalian cells.

After transformation, the host cell transformants are placed under selection to identify those host cell transformants which contain mutated specific nucleic acid sequences having the qualities desired. For example, if increased resistance to a particular drug is desired then the transformed host cells may be subjected to increased concentrations of the particular drug and those transformants producing mutated proteins able to confer increased drug resistance will be selected. If the enhanced ability of a particular protein to bind to a receptor is desired, then expression of the protein can be induced from the transformants and the resulting protein assayed in a ligand binding assay by methods known in the art to identify that subset of the mutated population which shows enhanced binding to the ligand. Alternatively, the protein can be expressed in another system to ensure proper processing.

Once a subset of the first recombed specific nucleic acid sequences (daughter sequences) having the desired characteristics are identified, they are then subject to a second round of recombination.

In the second cycle of recombination, the recombined specific nucleic acid sequences may be mixed with the original mutated specific nucleic acid sequences (parent sequences) and the cycle repeated as described above. In this way a set of second recombined specific nucleic acids sequences can be identified which have enhanced characteristics or encode for proteins having enhanced properties. This cycle can be repeated a number of times as desired.

It is also contemplated that in the second or subsequent recombination cycle, a backcross can be performed. A molecular backcross can be performed by mixing the desired specific nucleic acid sequences with a large number of the wild-type sequence, such that at least one wild-type nucleic acid sequence and a mutated nucleic acid sequence are present in the same host cell after transformation. Recombination with the wild-type specific nucleic acid sequence will eliminate those neutral or weakly contributory mutations that may affect unselected characteristics such as immunogenicity but not the selected characteristics.

In another embodiment of this invention, it is contemplated that during the first round a subset of the specific nucleic acid sequences can be fragmented prior to introduction into the host cell. The size of the fragments must be large enough to contain some regions of identity with the other sequences so as to homologously recombine with the other sequences. These fragments, ssDNA or dsDNA, can be coated with RecA in vitro to promote hybridization and/or integration into the host DNA. The size of the fragments will range from 0.03 kb to 100 kb more preferably from 0.2 kb to 10 kb. It is also contemplated that in subsequent rounds, all of the specific nucleic acid sequences other than the sequences selected from the previous round may be cleaved into fragments prior to introduction into the host cells. "Cleavage" may be by nuclease digestion, PCR amplification (via partial extension or stuttering), or other suitable means for generating partial length polynucleotides of parent sequence(s).

Fragmentation of the sequences can be accomplished by a variety of methods known in the art. The sequences can be randomly fragmented or fragmented at specific sites in the nucleic acid sequence. Random fragments can be obtained by breaking the nucleic acid or exposing it to harsh physical treatment (e.g., shearing or irradiation) or harsh chemical agents (e.g., by free radicals; metal ions; acid treatment to depurinate and cleave). Random fragments can also be obtained, in the case of DNA by the use of DNase or like nuclease, or by other means as discussed herein. The sequences can be cleaved at specific sites by the use of restriction enzymes. The fragmented sequences can be single-stranded or double-stranded. If the sequences were originally single-stranded they can be denatured with heat, chemicals or enzymes prior to insertion into the host cell. The reaction conditions suitable for separating the strands of nucleic acid are well known in the art. Furthermore, partial PCR extension, PCR stuttering, and other related methods for producing partial length copies of a parental sequence can be used to effect "fragmentation", e.g., to obtain a hybrid product which contains segments derived from different parental sequences.

The steps of this process can be repeated indefinitely, being limited only by the number of possible mutants which can be achieved. After a certain number of cycles, all possible mutants will have been achieved and further cycles are redundant.

In an embodiment the same mutated template nucleic acid is repeatedly recombined and the resulting recombinants selected for the desired characteristic.

Therefore, the initial pool or population of mutated template nucleic acid is cloned into a vector capable of replicating in bacteria such as E. coli. The particular vector is not essential, so long as it is capable of autonomous replication in E. coli or integration into a host chromosome. In a preferred embodiment, the vector is designed to allow the expression and production of any protein encoded by the mutated specific nucleic acid linked to the vector. It is also preferred that the vector contain a gene encoding for a selectable marker.

The population of vectors containing the pool of mutated nucleic acid sequences is introduced into the E. coli host cells. The vector nucleic acid sequences may be introduced by transformation, transfection or infection in the case of phage. The concentration of vectors used to transform the bacteria is such that a number of vectors is introduced into each cell. Once present in the cell, the efficiency of homologous recombination is such that homologous recombination occurs between the various vectors. This results in the generation of mutants (daughters) having a combination of mutations which differ from the original parent mutated sequences.

The host cells are then replicated, typically clonally, and selected for the marker gene present on the vector. Only those cells having a plasmid will grow under the selection.

The host cells which contain a vector are then tested for the presence of favorable mutations. Such testing may consist of placing the cells under selective pressure, for example, if the gene to be selected is an improved drug resistance gene. If the vector allows expression of the protein encoded by the mutated nucleic acid sequence, then such selection may include allowing expression of the protein so encoded, isolation of the protein and testing of the protein to determine whether, for example, it binds with increased efficiency to the ligand of interest.

Once a particular pool of daughter mutated nucleic acid sequence has been identified which confers the desired characteristics, the nucleic acid is isolated either already linked to the vector or separated from the vector. This nucleic acid is then recombined with itself or with similarly selected pools) and the cycle is repeated; optionally parental sequences can be used for subsequent rounds of recombination, in place of or in addition to other selected daughter species.

It has been shown that by this method nucleic acid sequences having enhanced desired properties can be selected.

In an alternate embodiment, the first generation of mutants are retained in the cells and the first generation of mutant sequences are added again to the cells. Accordingly, the first cycle of Embodiment I is conducted as described above. However, after the daughter nucleic acid sequences are identified, the host cells containing these sequences are retained.

The daughter mutated specific nucleic acid population, either as fragments or cloned into the same vector is introduced into the host cells already containing the daughter nucleic acids. Recombination is allowed to occur in the cells and the next generation of recombinants, or granddaughters are selected by the methods described above.

This cycle can be repeated a number of times until the nucleic acid or peptide having the desired characteristics is obtained. It is contemplated that in subsequent cycles, the population of mutated sequences which are added to the preferred mutants may come from the parental mutants or any subsequent generation.

In an alternative embodiment, the invention provides a method of conducting a "molecular" backcross of the obtained recombinant specific nucleic acids (one species or a pool of several species) in order to eliminate any neutral mutations. Neutral mutations are those mutations which do not confer onto the nucleic acid or peptide the desired properties. Such mutations may however confer on the nucleic acid or peptide undesirable characteristics. Accordingly, it is desirable to eliminate such neutral mutations. The methods of this invention provide a means of doing so.

In this embodiment, after the mutant nucleic acid, having the desired characteristics, is obtained by the methods of the embodiments, the nucleic acid, the vector having the nucleic acid or the host cell, tissue, or individual organism containing the vector and nucleic acid is isolated.

The nucleic acid or vector is then introduced into the host cell with a large excess of the wild-type nucleic acid. The nucleic acid of the mutant and the nucleic acid of the wild-type sequence are allowed to recombine. The resulting recombinants are placed under the same selection as the mutant nucleic acid. Only those recombinants which retained the desired characteristics will be selected. Any silent mutations which do not provide the desired characteristics will be lost through recombination with the wild-type DNA. This cycle can be repeated a number of times until all of the silent mutations are eliminated.

Thus the methods of this invention can be used in a molecular backcross to eliminate unnecessary, weakly contributing, and/or silent mutations.

Utility

The in vivo recombination method of this invention can be performed blindly on a pool of unknown mutants or alleles of a specific nucleic acid fragment or sequence, or family of diverse but related sequences or sequences which share one or more recombinogenic sequences (e.g., a site-specific recombination site, a localized segment of sequence homology having substantial identity for homoloogus recombination, a homologous recombination "hotspot" sequence, a restriction site, etc.) suitable for recursive recombination. However, it is not necessary to know the actual DNA or RNA sequence of the specific nucleic acid fragment.

The approach of using recombination within a mixed population of genes can be useful for the generation of any useful proteins, for example, interleukin I, antibodies, tPA, growth hormone, etc. This approach may be used to generate proteins having altered specificity or activity. The approach may also be useful for the generation of mutant nucleic acid sequences, for example, promoter regions, introns, exons, enhancer sequences, 3' untranslated regions or 5' untranslated regions of genes. Thus this approach may be used to generate genes having increased rates of expression. This approach may also be useful in the study of repetitive DNA sequences. Finally, this approach may be useful to mutate ribozymes or aptamers.

Scaffold-like regions separating regions of diversity in proteins may be particularly suitable for the methods of this invention. The conserved scaffold determines the overall folding by self-association, while displaying relatively unrestricted loops that mediate the specific binding. Examples of such scaffolds are the immunoglobulin beta barrel, and the four-helix bundle. The methods of this invention can be used to create scaffold-like proteins with various combinations of mutated sequences for binding.

The equivalents of some standard genetic matings may also be performed by the methods of this invention. For example, a "molecular" backcross can be performed by repeated mixing of the mutant's nucleic acid with the wild-type nucleic acid while selecting for the mutations of interest. As in traditional breeding, this approach can be used to combine phenotypes from different sources into a background of choice. It is useful, for example, for the removal of neutral mutations that affect unselected characteristics (i.e. immunogenicity). Thus it can be useful to determine which mutations in a protein are involved in the enhanced biological activity and which are not.

Peptide Display Methods

The present method can be used to shuffle, by in vitro and/or in vivo recombination by any of the disclosed methods, and in any combination, polynucleotide sequences selected by peptide display methods, wherein an associated polynucleotide encodes a displayed peptide which is screened for a phenotype (e.g., for affinity for a predetermined receptor (ligand).

An increasingly important aspect of biopharmaceutical drug development and molecular biology is the identification of peptide structures, including the primary amino acid sequences, of peptides or peptidomimetics that interact with biological macromolecules. One method of identifying peptides that possess a desired structure or functional property, such as binding to a predetermined biological macromolecule (e.g., a receptor), involves the screening of a large library or peptides for individual library members which possess the desired structure or functional property conferred by the amino acid sequence of the peptide.

In addition to direct chemical synthesis methods for generating peptide libraries, several recombinant DNA methods also have been reported. One type involves the display of a peptide sequence, antibody, or other protein on the surface of a bacteriophage particle or cell. Generally, in these methods each bacteriophage particle or cell serves as an individual library member displaying a single species of displayed peptide in addition to the natural bacteriophage or cell protein sequences. Each bacteriophage or cell contains the nucleotide sequence information encoding the particular displayed peptide sequence; thus, the displayed peptide sequence can be ascertained by nucleotide sequence determination of an isolated library member.

A well-known peptide display method involves the presentation of a peptide sequence on the surface of a filamentous bacteriophage, typically as a fusion with a bacteriophage coat protein. The bacteriophage library can be incubated with an immobilized, predetermined macromolecule or small molecule (e.g., a receptor) so that bacteriophage particles which present a peptide sequence that binds to the immobilized macromolecule can be differentially partitioned from those that do not present peptide sequences that bind to the predetermined macromolecule. The bacteriophage particles (i.e., library members) which are bound to the immobilized macromolecule are then recovered and replicated to amplify the selected bacteriophage subpopulation for a subsequent round of affinity enrichment and phage replication. After several rounds of affinity enrichment and phage replication, the bacteriophage library members that are thus selected are isolated and the nucleotide sequence encoding the displayed peptide sequence is determined, thereby identifying the sequence(s) of peptides that bind to the predetermined macromolecule (e.g., receptor). Such methods are further described in PCT patent publication Nos. 91/17271, 91/18980, and 91/19818 and 93/08278.

The latter PCT publication describes a recombinant DNA method for the display of peptide ligands that involves the production of a library of fusion proteins with each fusion protein composed of a first polypeptide portion, typically comprising a variable sequence, that is available for potential binding to a predetermined macromolecule, and a second polypeptide portion that binds to DNA, such as the DNA vector encoding the individual fusion protein. When transformed host cells are cultured under conditions that allow for expression of the fusion protein, the fusion protein binds to the DNA vector encoding it. Upon lysis of the host cell, the fusion protein/vector DNA complexes can be screened against a predetermined macromolecule in much the same way as bacteriophage particles are screened in the phage-based display system, with the replication and sequencing of the DNA vectors in the selected fusion protein/vector DNA complexes serving as the basis for identification of the selected library peptide sequence(s).

Other systems for generating libraries of peptides and like polymers have aspects of both the recombinant and in vitro chemical synthesis methods. In these hybrid methods, cell-free enzymatic machinery is employed to accomplish the in vitro synthesis of the library members (i.e., peptides or polynucleotides). In one type of method, RNA molecules with the ability to bind a predetermined protein or a predetermined dye molecule were selected by alternate rounds of selection and PCR amplification (Tuerk and Gold (1990) *Science* 249: 505; Ellington and Szostak (1990) *Nature* 346: 818). A similar technique was used to identify DNA sequences which bind a predetermined human transcription factor (Thiesen and Bach (1990) *Nucleic Acids Res.* 18: 3203; Beaudry and Joyce (1992) *Science* 257; 635; PCT patent publication Nos. 92/05258 and 92/14843). In a similar fashion, the technique of in vitro translation has been used to synthesize proteins of interest and has been proposed as a method for generating large libraries of peptides. These methods which rely upon in vitro translation, generally comprising stabilized polysome complexes, are described further in PCT patent publication Nos. 88/08453, 90/05785, 90/07003, 91/02076, 91/05058, and 92/02536. Applicants have described methods in which library members comprise a fusion protein having a first polypeptide portion with DNA binding activity and a second polypeptide portion having the library member unique peptide sequence; such methods are suitable for use in cell-free in vitro selection formats, among others.

A variation of the method is recursive sequence recombination performed by intron-based recombination, wherein the sequences to be recombined are present as exons (e.g., in the form of exons, whether naturally occurring or artificial) which may share substantial, little, or no sequence identity and which are separated by one or more introns (which may be naturally occurring intronic sequences or not) which share sufficient sequence identity to support homologous recombination between introns. For example but not limitation, a population of polynucleotides comprises library members wherein each library member has one or more copies of a first set of exons linked via a first set of introns to one or more copies of a second set of exons linked via a second set of introns to one or more copies of a third set of exons. Each of the members of the first set of exons may share substantial, little, or no sequence identity with each other or with members of the second or third sets of exons. Similarly, each of the members of the second set of exons may share substantial, little, or no sequence identity with each other or with members of the first or third sets of exons. Similarly, each of the members of the third set of exons may share substantial, little, or no sequence identity with each other or with members of the first or second sets of exons. Each of the members of the each set (first, second, third, etc.) of introns shares sufficient sequence identity with the other members of the set to support recombination (homologous or site-specific recombination, including restriction site-mediated recombination) between members of the same intron set, but typically not with members of other intron sets (e.g., the second or third sets), such that intra-set recombination between introns of the library members occurs and generates a pool of recombined library members wherein the first set of exons, second set of exons, and third set of exons are effectively shuffled with each other.

The displayed peptide sequences can be of varying lengths, typically from 3–5000 amino acids long or longer, frequently from 5–100 amino acids long, and often from about 8–15 amino acids long. A library can comprise library members having varying lengths of displayed peptide sequence, or may comprise library members having a fixed length of displayed peptide sequence. Portions or all of the displayed peptide sequence(s) can be random, pseudorandom, defined set kernal, fixed, or the like. The present display methods include methods for in vitro and in vivo display of single-chain antibodies, such as nascent scFv on polysomes or scFv displayed on phage, which enable large-scale screening of scFv libraries having broad diversity of variable region sequences and binding specificities.

The present invention also provides random, pseudorandom, and defined sequence framework peptide libraries and methods for generating and screening those libraries to identify useful compounds (e.g., peptides, including single-chain antibodies) that bind to receptor molecules or epitopes of interest or gene products that modify peptides or RNA in a desired fashion. The random, pseudorandom, and defined sequence framework peptides are produced from libraries of peptide library members that comprise displayed peptides or displayed single-chain antibodies attached to a polynucleotide template from which the displayed peptide was synthesized. The mode of attachment may vary according to the specific embodiment of the invention selected, and can include encapsidation in a phage particle or incorporation in a cell.

A method of affinity enrichment allows a very large library of peptides and single-chain antibodies to be screened and the polynucleotide sequence encoding the desired peptide(s) or single-chain antibodies to be selected. The pool of polynucleotides can then be isolated and shuffled to recombine combinatorially the amino acid sequence of the selected peptide(s) (or predetermined portions thereof) or single-chain antibodies (or just $V_H$, $V_L$, or CDR portions thereof). Using these methods, one can identify a peptide or single-chain antibody as having a desired binding affinity for a molecule and can exploit the process of shuffling to converge rapidly to a desired high-affinity peptide or scFv. The peptide or antibody can then be synthesized in bulk by conventional means for any suitable use (e.g., as a therapeutic or diagnostic agent).

A significant advantage of the present invention is that no prior information regarding an expected ligand structure is required to isolate peptide ligands or antibodies of interest. The peptide identified can have biological activity, which is meant to include at least specific binding affinity for a selected receptor molecule and, in some instances, will further include the ability to block the binding of other compounds, to stimulate or inhibit metabolic pathways, to act as a signal or messenger, to stimulate or inhibit cellular activity, and the like.

The present invention also provides a method for shuffling a pool of polynucleotide sequences selected by affinity screening a library of polysomes displaying nascent peptides (including single-chain antibodies) for library members which bind to a predetermined receptor (e.g., a mammalian proteinaceous receptor such as, for example, a peptidergic hormone receptor, a cell surface receptor, an intracellular protein which binds to other protein(s) to form intracellular protein complexes such as heterodimers and the like) or epitope (e.g., an immobilized protein, glycoprotein, oligosaccharide, and the like).

Polynucleotide sequences selected in a first selection round (typically by affinity selection for binding to a receptor (e.g., a ligand) by any of these methods are pooled and the pool(s) is/are shuffled by in vitro and/or in vivo recombination to produce a shuffled pool comprising a population of recombined selected polynucleotide sequences. The recombined selected polynucleotide sequences are subjected to at least one subsequent selection round. The polynucleotide sequences selected in the subsequent selection round (s) can be used directly (as a pool or in individual clones), sequenced, and/or subjected to one or more additional rounds of shuffling and subsequent selection. Selected sequences can also be backcrossed with polynucleotide sequences encoding neutral sequences (i.e., having insubstantial functional effect on binding), such as for example by backcrossing with a wild-type or naturally-occurring sequence substantially identical to a selected sequence to produce native-like functional peptides, which may be less immunogenic. Generally, during backcrossing subsequent selection is applied to retain the property of binding (or other desired selectable or screenable property or phenotype) to the predetermined receptor (ligand). Other properties are exemplified by the capacity to block a predetermined binding interaction (e.g., act as a partial or complete antagonist or competitive binding species) or to exhibit a catalytic function, or the like, among others.

Prior to or concomitant with the shuffling of selected sequences, the sequences can be mutagenized. In one embodiment, selected library members are cloned in a prokaryotic vector (e.g., plasmid, phagemid, or bacteriophage) wherein a collection of individual colonies (or plaques) representing discrete library members are produced. Individual selected library members can then be manipulated (e.g., by site-directed mutagenesis, cassette mutagenesis, chemical mutagenesis, PCR mutagenesis, and the like) to generate a collection of library members representing a kernal of sequence diversity based on the sequence of the selected library member. The sequence of an individual selected library member or pool can be manipulated to incorporate random mutation, pseudorandom mutation, defined kernal mutation (i.e., comprising variant and invariant residue positions and/or comprising variant residue positions which can comprise a residue selected from a defined subset of amino acid residues), codon-based mutation, and the like, either segmentally or over the entire length of the individual selected library member sequence. The mutagenized selected library members are then shuffled by in vitro and/or in vivo recombinatorial shuffling as disclosed herein.

The invention also provides peptide libraries comprising a plurality of individual library members of the invention, wherein (1) each individual library member of said plurality comprises a sequence produced by shuffling of a pool of selected sequences, and (2) each individual library member comprises a variable peptide segment sequence or single-chain antibody segment sequence which is distinct from the variable peptide segment sequences or single-chain antibody sequences of other individual library members in said plurality (although some library members may be present in more than one copy per library due to uneven amplification, stochastic probability, or the like).

The invention also provides a product-by-process, wherein selected polynucleotide sequences having (or encoding a peptide having) a predetermined binding specificity are formed by the process of: (1) screening a displayed peptide or displayed single-chain antibody library against a predetermined receptor (e.g., ligand) or epitope (e.g., antigen macromolecule) and identifying and/or enriching library members which bind to the predetermined receptor or epitope to produce a pool of selected library members, (2) shuffling by recombination of the selected library members (or amplified or cloned copies thereof) which binds the predetermined epitope and has been thereby isolated and/or enriched from the library to generate a shuffled library, and (3) screening the shuffled library against the predetermined receptor (e.g., ligand) or epitope (e.g., antigen macromolecule) and identifying and/or enriching shuffled library members which bind to the predetermined receptor or epitope to produce a pool of selected shuffled library members.

Antibody Display and Screening Methods

The present method can be used to shuffle, by in vitro and/or in vivo recombination by any of the disclosed methods, and in any combination, polynucleotide sequences selected by antibody display methods, wherein an associated polynucleotide encodes a displayed antibody which is screened for a phenotype (e.g., for affinity for binding a predetermined antigen (ligand).

Various molecular genetic approaches have been devised to capture the vast immunological repertoire represented by the extremely large number of distinct variable regions which can be present in immunoglobulin chains. The naturally-occurring germline immunoglobulin heavy chain locus is composed of separate tandem arrays of variable (V) segment genes located upstream of a tandem array of diversity (D) segment genes, which are themselves located upstream of a tandem array of joining (J) region genes, which are located upstream of the constant ($C_H$) region genes. During B lymphocyte development, V-D-J rearrangement occurs wherein a heavy chain variable region gene ($V_H$) is formed by rearrangement to form a fused D-J segment followed by rearrangement with a V segment to form a V-D-J joined product gene which, if productively rearranged, encodes a functional variable region ($V_H$) of a heavy chain. similarly, light chain loci rearrange one of several V segments with one of several J segments to form a gene encoding the variable region ($V_L$) of a light chain.

The vast repertoire of variable regions possible in immunoglobulins derives in part from the numerous combinatorial possibilities of joining V and J segments (and, in the case of heavy chain loci, D segments) during rearrangement in B cell development. Additional sequence diversity in the heavy chain variable regions arises from non-uniform rearrangements of the D segments during V-D-J joining and from N region addition. Further, antigen-selection of specific B cell clones selects for higher affinity variants having nongermline mutations in one or both of the heavy and light chain variable regions; a phenomenon referred to as "affinity maturation" or "affinity sharpening". Typically, these "affinity sharpening" mutations cluster in specific areas of the variable region, most commonly in the complementarity-determining regions (CDRs).

In order to overcome many of the limitations in producing and identifying high-affinity immunoglobulins through antigen-stimulated B cell development (i.e., immunization), various prokaryotic expression systems have been developed that can be manipulated to produce combinatorial antibody libraries which may be screened for high-affinity antibodies to specific antigens. Recent advances in the expression of antibodies in *Escherichia coli* and bacteriophage systems (see, "Alternative Peptide Display Methods", infra) have raised the possibility that virtually any specificity can be obtained by either cloning antibody genes from characterized hybridomas or by de novo selection using antibody gene libraries (e.g., from Ig CDNA).

Combinatorial libraries of antibodies have been generated in bacteriophage lambda expression systems which may be screened as bacteriophage plaques or as colonies of lysogens (Huse et al. (1989) *Science* 246: 1275; Caton and Koprowski (1990) *Proc. Natl. Acad. Sci. (U.S.A.)* 87: 6450; Mullinax et al (1990) *Proc. Natl. Acad. Sci. (U.S.A.)* 87: 8095; Persson et al. (1991) *Proc. Natl. Acad. Sci. (U.S.A.)* 88: 2432). Various embodiments of bacteriophage antibody display libraries and lambda phage expression libraries have been described (Kang et al. (1991) *Proc. Natl. Acad. Sci. (U.S.A.)* 88: 4363; Clackson et al. (1991) *Nature* 352: 624; McCafferty et al. (1990) *Nature* 348: 552; Burton et al. (1991) *Proc. Natl. Acad. Sci. (U.S.A.)* 88: 10134; Hoogenboom et al. (1991) *Nucleic Acids Res.* 19: 4133; Chang et al. (1991) *J. Immunol.* 147: 3610; Breitling et al. (1991) *Gene* 104: 147; Marks et al. (1991) *J. Mol. Biol.* 222: 581; Barbas et al. (1992) *Proc. Natl. Acad. Sci. (U.S.A.)* 89: 4457; Hawkins and Winter (1992) *J. Immunol.* 22: 867; Marks et al. (1992) *Biotechnology* 10: 779; Marks et al. (1992) *J. Biol. Chem.* 267: 16007; Lowman et al (1991) *Biochemistry* 30: 10832; Lerner et al. (1992) *Science* 258: 1313, incorporated herein by reference). Typically, a bacteriophage antibody display library is screened with a receptor (e.g., polypeptide, carbohydrate, glycoprotein, nucleic acid) that is immobilized (e.g., by covalent linkage to a chromatography resin to enrich for reactive phage by affinity chromatography) and/or labeled (e.g., to screen plaque or colony lifts).

One particularly advantageous approach has been the use of so-called single-chain fragment variable (scFv) libraries (Marks et al. (1992) *Biotechnology* 10: 779; Winter G and Milstein C (1991) *Nature* 349: 293; Clackson et al. (1991) op.cit.; Marks et al. (1991) *J. Mol. Biol.* 222: 581; Chaudhary et al. (1990) *Proc. Natl. Acad. Sci. (USA)* 87: 1066; Chiswell et al. (1992) *TIBTECH* 10: 80; McCafferty et al. (1990) op.cit.; and Huston et al. (1988) *Proc. Natl. Acad. Sci. (USA)* 85: 5879). Various embodiments of scFv libraries displayed on bacteriophage coat proteins have been described.

Beginning in 1988, single-chain analogues of Fv fragments and their fusion proteins have been reliably generated by antibody engineering methods. The first step generally involves obtaining the genes encoding $V_H$ and $V_L$ domains with desired binding properties; these V genes may be isolated from a specific hybridoma cell line, selected from a combinatorial V-gene library, or made by V gene synthesis. The single-chain Fv is formed by connecting the component V genes with an oligonucleotide that encodes an appropriately designed linker peptide, such as (Gly-Gly-Gly-Gly-Ser)$_3$ (SEQ. ID NO: 67) or equivalent linker peptide(s). The linker bridges the C-terminus of the first V region and N-terminus of the second, ordered as either $V_H$-linker-$V_L$ or $V_L$-linker-$V_H$. In principle, the scFv binding site can faithfully replicate both the affinity and specificity of its parent antibody combining site.

Thus, scFv fragments are comprised of $V_H$ and $V_L$ domains linked into a single polypeptide chain by a flexible linker peptide. After the scFv genes are assembled, they are cloned into a phagemid and expressed at the tip of the M13 phage (or similar filamentous bacteriophage) as fusion proteins with the bacteriophage pIII (gene 3) coat protein. Enriching for phage expressing an antibody of interest is accomplished by panning the recombinant phage displaying a population scFv for binding to a predetermined epitope (e.g., target antigen, receptor).

The linked polynucleotide of a library member provides the basis for replication of the library member after a screening or selection procedure, and also provides the basis for the determination, by nucleotide sequencing, of the identity of the displayed peptide sequence or $V_H$ and $V_L$ amino acid sequence. The displayed peptide(s) or single-chain antibody (e.g., scFv) and/or its $V_H$ and $V_L$ domains or their CDRs can be cloned and expressed in a suitable expression system. Often polynucleotides encoding the isolated $V_H$ and $V_L$ domains will be ligated to polynucleotides encoding constant regions ($C_H$ and $C_L$) to form polynucleotides encoding complete antibodies (e.g., chimeric or fully-human), antibody fragments, and the like. Often polynucleotides encoding the isolated CDRs will be grafted into polynucleotides encoding a suitable variable region framework (and optionally constant regions) to form polynucleotides encoding complete antibodies (e.g., humanized or fully-human), antibody fragments, and the like. Antibodies can be used to isolate preparative quantities of the antigen by immunoaffinity chromatography. Various other uses of such antibodies are to diagnose and/or stage disease (e.g., neoplasia), and for therapeutic application to treat disease, such as for example: neoplasia, autoimmune disease, AIDS, cardiovascular disease, infections, and the like.

Various methods have been reported for increasing the combinatorial diversity of a scFv library to broaden the repertoire of binding species (idiotype spectrum). The use of PCR has permitted the variable regions to be rapidly cloned either from a specific hybridoma source or as a gene library from non-immunized cells, affording combinatorial diversity in the assortment of $V_H$ and $V_L$ cassettes which can be combined. Furthermore, the $V_H$ and $V_L$ cassettes can themselves be diversified, such as by random, pseudorandom, or directed mutagenesis. Typically, $V_H$ and $V_L$ cassettes are diversified in or near the complementarity-determining regions (CDRs), often the third CDR, CDR3. Enzymatic inverse PCR mutagenesis has been shown to be a simple and reliable method for constructing relatively large libraries of scFv site-directed mutants (Stemmer et al. (1993) *Biotechniques* 14: 256), as has error-prone PCR and chemical mutagenesis (Deng et al. (1994) *J. Biol. Chem.* 269: 9533). Riechmann et al. (1993) *Biochemistry* 32: 8848 showed semirational design of an antibody scFv fragment using site-directed randomization by degenerate oligonucleotide PCR and subsequent phage display of the resultant scFv mutants. Barbas et al. (1992) op.cit. attempted to circumvent the problem of limited repertoire sizes resulting from using biased variable region sequences by randomizing the sequence in a synthetic CDR region of a human tetanus toxoid-binding Fab.

CDR randomization has the potential to create approximately $1 \times 10^{20}$ CDRs for the heavy chain CDR3 alone, and a roughly similar number of variants of the heavy chain CDR1 and CDR2, and light chain CDR1–3 variants. Taken individually or together, the combinatorics of CDR randomization of heavy and/or light chains requires generating a prohibitive number of bacteriophage clones to produce a clone library representing all possible combinations, the vast majority of which will be non-binding. Generation of such large numbers of primary transformants is not feasible with current transformation technology and bacteriophage display systems. For example, Barbas et al. (1992) op.cit. only generated $5 \times 10^7$ transformants, which represents only a tiny fraction of the potential diversity of a library of thoroughly randomized CDRS.

Despite these substantial limitations, bacteriophage display of scFv has already yielded a variety of useful antibodies and antibody fusion proteins. A bispecific single chain antibody has been shown to mediate efficient tumor cell lysis (Gruber et al. (1994) *J. Immunol.* 152: 5368). Intracellular expression of an anti-Rev scFv has been shown to inhibit HIV-1 virus replication in vitro (Duan et al. (1994) *Proc. Natl. Acad. Sci.* (*USA*) 91: 5075), and intracellular expression of an anti-p21$^{ras}$ scFv has been shown to inhibit meiotic maturation of Xenopus oocytes (Biocca et al. (1993) *Biochem. Biophys. Res. Commun.* 197: 422. Recombinant scFv which can be used to diagnose HIV infection have also been reported, demonstrating the diagnostic utility of scFv (Lilley et al. (1994) *J. Immunol. Meth.* 171: 211). Fusion proteins wherein an scFv is linked to a second polypeptide, such as a toxin or fibrinolytic activator protein, have also been reported (Holvost et al. (1992) *Eur. J. Biochem.* 210: 945; Nicholls et al. (1993) *J. Biol. Chem.* 268: 5302).

If it were possible to generate scFv libraries having broader antibody diversity and overcoming many of the limitations of conventional CDR mutagenesis and randomization methods which can cover only a very tiny fraction of the potential sequence combinations, the number and quality of scFv antibodies suitable for therapeutic and diagnostic use could be vastly improved. To address this, the in vitro and in vivo shuffling methods of the invention are used to recombine CDRs which have been obtained (typically via PCR amplification or cloning) from nucleic acids obtained from selected displayed antibodies. Such displayed antibodies can be displayed on cells, on bacteriophage particles, on polysomes, or any suitable antibody display system wherein the antibody is associated with its encoding nucleic acid(s). In a variation, the CDRs are initially obtained from mRNA (or cDNA) from antibody-producing cells (e.g., plasma cells/splenocytes from an immunized wild-type mouse, a human, or a transgenic mouse capable of making a human antibody as in WO92/03918, WO93/12227, and WO94/25585), including hybridomas derived therefrom.

Polynucleotide sequences selected in a first selection round (typically by affinity selection for displayed antibody binding to an antigen (e.g., a ligand) by any of these methods are pooled and the pool(s) is/are shuffled by in vitro and/or in vivo recombination, especially shuffling of CDRs (typically shuffling heavy chain CDRs with other heavy chain CDRs and light chain CDRs with other light chain CDRs) to produce a shuffled pool comprising a population of recombined selected polynucleotide sequences. The recombined selected polynucleotide sequences are expressed in a selection format as a displayed antibody and subjected to at least one subsequent selection round. The polynucleotide sequences selected in the subsequent selection round(s) can be used directly, sequenced, and/or subjected to one or more additional rounds of shuffling and subsequent selection until an antibody of the desired binding affinity is obtained. Selected sequences can also be backcrossed with polynucleotide sequences encoding neutral antibody framework sequences (i.e., having insubstantial functional effect on antigen binding), such as for example by backcrossing with a human variable region framework to produce human-like sequence antibodies. Generally, during backcrossing subsequent selection is applied to retain the property of binding to the predetermined antigen.

Alternatively, or in combination with the noted variations, the valency of the target epitope may be varied to control the average binding affinity of selected scFv library members. The target epitope can be bound to a surface or substrate at varying densities, such as by including a competitor epitope, by dilution, or by other method known to those in the art. A high density (valency) of predetermined epitope can be used to enrich for scFv library members which have relatively low affinity, whereas a low density (valency) can preferentially enrich for higher affinity scFv library members.

For generating diverse variable segments, a collection of synthetic oligonucleotides encoding random, pseudorandom, or a defined sequence kernal set of peptide sequences can be inserted by ligation into a predetermined site (e.g., a CDR). Similarly, the sequence diversity of one or more CDRs of the single-chain antibody cassette(s) can be expanded by mutating the CDR(s) with site-directed mutagenesis, CDR-replacement, and the like. The resultant DNA molecules can be propagated in a host for cloning and amplification prior to shuffling, or can be used directly (i.e., may avoid loss of diversity which may occur upon propagation in a host cell) and the selected library members subsequently shuffled.

Displayed peptide/polynucleotide complexes (library members) which encode a variable segment peptide sequence of interest or a single-chain antibody of interest are selected from the library by an affinity enrichment technique. This is accomplished by means of a immobilized macromolecule or epitope specific for the peptide sequence of interest, such as a receptor, other macromolecule, or other epitope species. Repeating the affinity selection procedure provides an enrichment of library members encoding the desired sequences, which may then be isolated for pooling and shuffling, for sequencing, and/or for further propagation and affinity enrichment.

The library members without the desired specificity are removed by washing. The degree and stringency of washing required will be determined for each peptide sequence or single-chain antibody of interest and the immobilized predetermined macromolecule or epitope. A certain degree of control can be exerted over the binding characteristics of the nascent peptide/DNA complexes recovered by adjusting the conditions of the binding incubation and the subsequent washing. The temperature, pH, ionic strength, divalent cations concentration, and the volume and duration of the washing will select for nascent peptide/DNA complexes within particular ranges of affinity for the immobilized macromolecule. Selection based on slow dissociation rate, which is usually predictive of high affinity, is often the most practical route. This may be done either by continued incubation in the presence of a saturating amount of free predetermined macromolecule, or by increasing the volume, number, and length of the washes. In each case, the rebinding of dissociated nascent peptide/DNA or peptide/RNA complex is prevented, and with increasing time, nascent peptide/DNA or peptide/RNA complexes of higher and higher affinity are recovered.

Additional modifications of the binding and washing procedures may be applied to find peptides with special characteristics. The affinities of some peptides are dependent on ionic strength or cation concentration. This is a useful characteristic for peptides that will be used in affinity purification of various proteins when gentle conditions for removing the protein from the peptides are required.

One variation involves the use of multiple binding targets (multiple epitope species, multiple receptor species), such that a scFv library can be simultaneously screened for a multiplicity of scFv which have different binding specificities. Given that the size of a scFv library often limits the diversity of potential scFv sequences, it is typically desirable to use scFv libraries of as large a size as possible. The time and economic considerations of generating a number of very large polysome scFv-display libraries can become prohibitive. To avoid this substantial problem, multiple predetermined epitope species (receptor species) can be concomitantly screened in a single library, or sequential screening against a number of epitope species can be used. In one variation, multiple target epitope species, each encoded on a separate bead (or subset of beads), can be mixed and incubated with a polysome-display scFv library under suitable binding conditions. The collection of beads, comprising multiple epitope species, can then be used to isolate, by affinity selection, scFv library members. Generally, subsequent affinity screening rounds can include the same mixture of beads, subsets thereof, or beads containing only one or two individual epitope species. This approach affords efficient screening, and is compatible with laboratory automation, batch processing, and high throughput screening methods.

A variety of techniques can be used in the present invention to diversify a peptide library or single-chain antibody library, or to diversify, prior to or concomitant with shuffling, around variable segment peptides or $V_H$, $V_L$, or CDRs found in early rounds of panning to have sufficient binding activity to the predetermined macromolecule or epitope. In one approach, the positive selected peptide/polynucleotide complexes (those identified in an early round of affinity enrichment) are sequenced to determine the identity of the active peptides. Oligonucleotides are then synthesized based on these active peptide sequences, employing a low level of all bases incorporated at each step to produce slight variations of the primary oligonucleotide sequences. This mixture of (slightly) degenerate oligonucleotides is then cloned into the variable segment sequences at the appropriate locations. This method produces systematic, controlled variations of the starting peptide sequences, which can then be shuffled. It requires, however, that individual positive nascent peptide/polynucleotide complexes be sequenced before mutagenesis, and thus is useful for expanding the diversity of small numbers of recovered complexes and selecting variants having higher binding affinity and/or higher binding specificity. In a variation, mutagenic PCR amplification of positive selected peptide/polynucleotide complexes (especially of the variable region sequences, the amplification products of which are shuffled in vitro and/or in vivo and one or more additional rounds of screening is done prior to sequencing. The same general approach can be employed with single-chain antibodies in order to expand the diversity and enhance the binding affinity/specificity, typically by diversifying CDRs or adjacent framework regions prior to or concomitant with shuffling. If desired, shuffling reactions can be spiked with mutagenic oligonucleotides capable of in vitro recombination with the selected library members. Thus, mixtures of synthetic oligonucleotides and PCR fragments (synthesized by error-prone or high-fidelity methods) can be added to the in vitro shuffling mix and be incorporated into resulting shuffled library members (shufflants).

The present invention of shuffling enables the generation of a vast library of CDR-variant single-chain antibodies. One way to generate such antibodies is to insert synthetic CDRs into the single-chain antibody and/or CDR randomization prior to or concomitant with shuffling. The sequences of the synthetic CDR cassettes are selected by referring to known sequence data of human CDR and are selected in the discretion of the practitioner according to the following guidelines: synthetic CDRs will have at least 40 percent positional sequence identity to known CDR sequences, and preferably will have at least 50 to 70 percent positional sequence identity to known CDR sequences. For example, a collection of synthetic CDR sequences can be generated by synthesizing a collection of oligonucleotide sequences on the basis of naturally-occurring human CDR sequences listed in Kabat et al. (1991) op.cit.; the pool(s) of synthetic CDR sequences are calculated to encode CDR peptide sequences having at least 40 percent sequence identity to at least one known naturally-occurring human CDR sequence. Alternatively, a collection of naturally-occurring CDR sequences may be compared to generate consensus sequences so that amino acids used at a residue position frequently (i.e., in at least 5 percent of known CDR sequences) are incorporated into the synthetic CDRs at the corresponding position(s). Typically, several (e.g., 3 to about 50) known CDR sequences are compared and observed natural sequence variations between the known CDRs are tabulated, and a collection of oligonucleotides encoding CDR peptide sequences encompassing all or most permutations of the observed natural sequence variations is synthesized. For example but not for limitation, if a collection of human $V_H$ CDR sequences have carboxy-terminal amino acids which are either Tyr, Val, Phe, or Asp, then the pool(s) of synthetic CDR oligonucleotide sequences are designed to allow the carboxy-terminal CDR residue to be any of these amino acids. In some embodiments, residues other than those which naturally-occur at a residue position in the collection of CDR sequences are incorporated: conservative amino acid substitutions are frequently incorporated and up to 5 residue positions may be varied to incorporate nonconservative amino acid substitutions as compared to known naturally-occurring CDR sequences. Such CDR sequences can be used in primary library members (prior to first round screening) and/or can be used to spike in vitro shuffling reactions of selected library member sequences. Construction of such pools of defined and/or degenerate sequences will be readily accomplished by those of ordinary skill in the art.

The collection of synthetic CDR sequences comprises at least one member that is not known to be a naturally-occurring CDR sequence. It is within the discretion of the practitioner to include or not include a portion of random or pseudorandom sequence corresponding to N region addition in the heavy chain CDR; the N region sequence ranges from 1 nucleotide to about 4 nucleotides occurring at V-D and D-J junctions. A collection of synthetic heavy chain CDR sequences comprises at least about 100 unique CDR sequences, typically at least about 1,000 unique CDR sequences, preferably at least about 10,000 unique CDR sequences, frequently more than 50,000 unique CDR sequences; however, usually not more than about $1 \times 10^6$ unique CDR sequences are included in the collection, although occasionally $1 \times 10^7$ to $1 \times 10^8$ unique CDR sequences are present, especially if conservative amino acid substitutions are permitted at positions where the conservative amino acid substituent is not present or is rare (i.e., less than 0.1 percent) in that position in naturally-occurring human CDRS. In general, the number of unique CDR sequences included in a library generally should not exceed the expected number of primary transformants in the library by more than a factor of 10. Such single-chain antibodies generally bind to a predetermined antigen (e.g., the immunogen) with an affinity of about at least $1\times10^7$ $M^{-1}$, preferably with an affinity of about at least $5\times10^7$ $M^{-1}$, more preferably with an affinity of at least $1\times10^8$ $M^{-1}$ to $1\times10^9$ $M^{-1}$ or more, sometimes up to $1\times10^{10}M^{-1}$ or more. Frequently, the predetermined antigen is a human protein, such as for example a human cell surface antigen (e.g., CD4, CD8, IL-2 receptor, EGF receptor, PDGF receptor), other human biological macromolecule (e.g., thrombomodulin, protein C, carbohydrate antigen, sialyl Lewis antigen, L-selectin), or nonhuman disease associated macromolecule (e.g., bacterial LPS, virion capsid protein or envelope glycoprotein) and the like.

High affinity single-chain antibodies of the desired specificity can be engineered and expressed in a variety of systems. For example, scFv have been produced in plants (Firek et al. (1993) *Plant Mol. Biol.* 23: 861) and can be readily made in prokaryotic systems (Owens R J and Young R J (1994) *J. Immunol. Meth.* 168: 149; Johnson S and Bird R E (1991) *Methods Enzymol.* 203: 88). Furthermore, the single-chain antibodies can be used as a basis for constructing whole antibodies or various fragments thereof (Kettleborough et al. (1994) *Eur. J. Immunol.* 24: 952). The variable region encoding sequence may be isolated (e.g., by PCR amplification or subcloning) and spliced to a sequence encoding a desired human constant region to encode a human sequence antibody more suitable for human therapeutic uses where immunogenicity is preferably minimized. The polynucleotide(s) having the resultant fully human encoding sequence(s) can be expressed in a host cell (e.g., from an expression vector in a mammalian cell) and purified for pharmaceutical formulation.

The DNA expression constructs will typically include an expression control DNA sequence operably linked to the coding sequences, including naturally-associated or heterologous promoter regions. Preferably, the expression control sequences will be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the mutant "engineered" antibodies.

As stated previously, the DNA sequences will be expressed in hosts after the sequences have been operably linked to an expression control sequence (i.e., positioned to ensure the transcription and translation of the structural gene). These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

In addition to eukaryotic microorganisms such as yeast, mammalian tissue cell culture may also be used to produce the polypeptides of the present invention (see, Winnacker, "From Genes to Clones," VCH Publishers, N.Y., N.Y. (1987), which is incorporated herein by reference). Eukaryotic cells are actually preferred, because a number of suitable host cell lines capable of secreting intact immunoglobulins have been developed in the art, and include the CHO cell lines, various COS cell lines, HeLa cells, myeloma cell lines, etc, but preferably transformed B-cells or hybridomas. Expression vectors for these cells can include expression control sequences, such as an origin of replication, a promoter, an enhancer (Queen et al. (1986) *Immunol. Rev.* 89: 49), and necessary processing information sites, such as ribosome binding sites, RNA splice sites, polyadenylation sites, and transcriptional terminator sequences. Preferred expression control sequences are promoters derived from immunoglobulin genes, cytomegalovirus, SV40, Adenovirus, Bovine Papilloma Virus, and the like.

Eukaryotic DNA transcription can be increased by inserting an enhancer sequence into the vector. Enhancers are cis-acting sequences of between 10 to 300 bp that increase transcription by a promoter. Enhancers can effectively increase transcription when either 5' or 3' to the transcription unit. They are also effective if located within an intron or within the coding sequence itself. Typically, viral enhancers are used, including SV40 enhancers, cytomegalovirus enhancers, polyoma enhancers, and adenovirus enhancers. Enhancer sequences from mammalian systems are also commonly used, such as the mouse immunoglobulin heavy chain enhancer.

Mammalian expression vector systems will also typically include a selectable marker gene. Examples of suitable markers include, the dihydrofolate reductase gene (DHFR), the thymidine kinase gene (TK), or prokaryotic genes conferring drug resistance. The first two marker genes prefer the use of mutant cell lines that lack the ability to grow without the addition of thymidine to the growth medium. Transformed cells can then be identified by their ability to grow on non-supplemented media. Examples of prokaryotic drug resistance genes useful as markers include genes conferring resistance to G418, mycophenolic acid and hygromycin.

The vectors containing the DNA segments of interest can be transferred into the host cell by well-known methods, depending on the type of cellular host. For example, calcium chloride transfection is commonly utilized for prokaryotic cells, whereas calcium phosphate treatment. lipofection, or electroporation may be used for other cellular hosts. Other methods used to transform mammalian cells include the use of Polybrene, protoplast fusion, liposomes, electroporation, and microinjection (see, generally, Sambrook et al., supra).

Once expressed, the antibodies, individual mutated immunoglobulin chains, mutated antibody fragments, and other immunoglobulin polypeptides of the invention can be purified according to standard procedures of the art, including ammonium sulfate precipitation, fraction column chromatography, gel electrophoresis and the like (see, generally, Scopes, R., *Protein Purification*, Springer-Verlag, N.Y. (1982)). Once purified, partially or to homogeneity as desired, the polypeptides may then be used therapeutically or in developing and performing assay procedures, immunofluorescent stainings, and the like (see, generally, *Immunological Methods*, Vols. I and II, Eds. Lefkovits and Pernis, Academic Press, New York, N.Y. (1979 and 1981)).

The antibodies generated by the method of the present invention can be used for diagnosis and therapy. By way of illustration and not limitation, they can be used to treat cancer, autoimmune diseases, or viral infections. For treatment of cancer, the antibodies will typically bind to an antigen expressed preferentially on cancer cells, such as erbB-2, CEA, CD33, and many other antigens and binding members well known to those skilled in the art.

Yeast Two-Hybrid Screening Assays

Shuffling can also be used to recombinatorially diversify a pool of selected library members obtained by screening a two-hybrid screening system to identify library members which bind a predetermined polypeptide sequence. The selected library members are pooled and shuffled by in vitro and/or in vivo recombination. The shuffled pool can then be screened in a yeast two hybrid system to select library members which bind said predetermined polypeptide sequence (e.g., and SH2 domain) or which bind an alternate predetermined polypeptide sequence (e.g., an SH2 domain from another protein species).

An approach to identifying polypeptide sequences which bind to a predetermined polypeptide sequence has been to use a so-called "two-hybrid" system wherein the predetermined polypeptide sequence is present in a fusion protein (Chien et al. (1991) *Proc. Natl. Acad. Sci.* (*USA*) 88: 9578). This approach identifies protein-protein interactions in vivo through reconstitution of a transcriptional activator (Fields S and Song O (1989) *Nature* 340: 245), the yeast Gal4 transcription protein. Typically, the method is based on the properties of the yeast Gal4 protein, which consists of separable domains responsible for DNA-binding and transcriptional activation. Polynucleotides encoding two hybrid proteins, one consisting of the yeast Gal4 DNA-binding domain fused to a polypeptide sequence of a known protein and the other consisting of the Gal4 activation domain fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacZ, HIS3) which is operably linked to a Gal4 binding site. Typically, the two-hybrid method is used to identify novel polypeptide sequences which interact with a known protein (Silver S C and Hunt S W (1993) *Mol. Biol. Rep.* 17: 155; Durfee et al. (1993) *Genes Devel.* 7; 555; Yang et al. (1992) *Science* 257: 680; Luban et al. (1993) *Cell* 73: 1067; Hardy et al. (1992) *Genes Devel.* 6; 801; Bartel et al. (1993) *Biotechnigues* 14: 920; and Vojtek et al. (1993) *Cell* 74: 205). However, variations of the two-hybrid method have been used to identify mutations of a known protein that affect its binding to a second known protein (Li B and Fields S (1993) *FASEB J.* 7: 957; Lalo et al. (1993) *Proc. Natl. Acad. Sci.* (*USA*) 90: 5524; Jackson et al. (1993) *Mol. Cell. Biol.* 13; 2899; and Madura et al. (1993) *J. Biol. Chem.* 268: 12046). Two-hybrid systems have also been used to identify interacting structural domains of two known proteins (Bardwell et al. (1993) *med. Microbiol.* 8: 1177; Chakraborty et al. (1992) *J. Biol. Chem.* 267: 17498; Staudinger et al. (1993) *J. Biol. Chem.* 268: 4608; and Milne G T and Weaver D T (1993) *Genes Devel.* 7; 1755) or domains responsible for oligomerization of a single protein (Iwabuchi et al. (1993) *Oncogene* 8; 1693; Bogerd et al. (1993) *J. Virol.* 67: 5030). Variations of two-hybrid systems have been used to study the in vivo activity of a proteolytic enzyme (Dasmahapatra et al. (1992) *Proc. Natl. Acad. Sci.* (*USA*) 89: 4159). Alternatively, an *E. coli*/BCCP interactive screening system (Germino et al. (1993) *Proc. Natl. Acad. Sci.* (*U.S.A.*) 90: 933; Guarente L (1993) *Proc. Natl. Acad. Sci.* (*U.S.A.*) 90: 1639) can be used to identify interacting protein sequences (i.e., protein sequences which heterodimerize or form higher order heteromultimers). Sequences selected by a two-hybrid system can be pooled and shuffled and introduced into a two-hybrid system for one or more subsequent rounds of screening to identify polypeptide sequences which bind to the hybrid containing the predetermined binding sequence. The sequences thus identified can be compared to identify consensus sequence(s) and consensus sequence kernals.

Improvements/Alternative Formats

Additives

In one aspect, the improved shuffling method includes the addition of at least one additive which enhances the rate or extent of reannealing or recombination of related-sequence polynucleotides. In general, additives which increase hybrid stability of mismatched sequences can be used to enhance the frequency of generating substantially mutated library members (i.e., having a greater mutational density). In addition to additives, modulation of the ionic strength (e.g., $Na^+$ and/or $K^+$ ion concentration) can modulate the relative stability of mismatched hybrids, such that increased salt concentration can increase the frequency of mismatched hybrids and contribute to formation of library members having multiple mutations.

In an embodiment, the additive is polyethylene glycol (PEG), typically added to a shuffling reaction to a final concentration of 0.1 to 25 percent, often to a final concentration of 2.5 to 15 percent, to a final concentration of about 10 percent. In an embodiment, the additive is dextran sulfate, typically added to a shuffling reaction to a final concentration of 0.1 to 25 percent, often at about 10 percent. In an embodiment, the additive is an agent which reduces sequence specificity of reannealing and promotes promiscuous hybridization and/or recombination in vitro. In an alternative embodiment, the additive is an agent which increases sequence specificity of reannealing and promotes high fidelity hybridization and/or recombination in vitro. Other long-chain polymers which do not interfere with the reaction may also be used (e.g., polyvinylpyrrolidone, etc.).

In one aspect, the improved shuffling method includes the addition of at least one additive which is a cationic detergent. Examples of suitable cationic detergents include but are not limited to: cetyltrimethylammonium bromide (CTAB), dodecyltrimethylammonium bromide (DTAB), and tetramethylammonium chloride (TMAC), and the like.

In one aspect, the improved shuffling method includes the addition of at least one additive which is a recombinogenic protein that catalzyes or non-catalytically enhances homologous pairing and/or strand exchange in vitro. Examples of suitable recombinogenic proteins include but are not limited to: *E. coli* recA protein, the T4 uvsX protein, the rec1 protein from *Ustilago maydis*, other recA family recombinases from other species, single strand binding protein (SSB), ribonucleoprotein A1, and the like. Nucleases and proofreading polymerases are often included to improve the maintenance of 3' end integrity. Each of these protein additives can themselves be improved by multiple rounds of recursive sequence recombination and selection and/or screening. The invention embraces such improved additives and their use to further enhance shuffling.

Recombinase Proteins

Recombinases are proteins that, when included with an exogenous targeting polynucleotide, provide a measurable increase in the recombination frequency and/or localization frequency between the targeting polynucleotide and an endogenous predetermined DNA sequence. In the present invention, recombinase refers to a family of RecA-like recombination proteins all having essentially all or most of the same functions, particularly: (i) the recombinase protein's ability to properly bind to and position targeting polynucleotides on their homologous targets and (ii) the ability of recombinase protein/targeting polynucleotide complexes to efficiently find and bind to complementary endogenous sequences. The best characterized recA protein is from *E. coli*, in addition to the wild-type protein a number of mutant recA-like proteins have been identified (e.g., recA803). Further, many organisms have recA-like recombinases with strand-transfer activities (e.g., Fugisawa et al., (1985) *Nucl. Acids Res.* 13: 7473; Hsieh et al., (1986) *Cell* 44: 885; Hsieh et al., (1989) *J. Biol. Chem.* 264: 5089; Fishel et al., (1988) *Proc. Natl. Acad. Sci. USA* 85: 3683; Cassuto et al., (1987) *Mol. Gen. Genet.* 208: 10; Ganea et al., (1987) *Mol. Cell Biol.* 7: 3124; Moore et al., (1990) *J. Biol. Chem.* 19: 11108; Keene et al., (1984) *Nucl. Acids Res.* 12: 3057; Kimiec, (1984) *Cold Spring Harbor Symp.* 48:675; Kimeic, (1986) *Cell* 44: 545; Kolodner et al., (1987) *Proc. Natl. Acad. Sci. USA* 84 :5560; Sugino et al., (1985) *Proc. Natl. Acad. Sci. USA* 85: 3683; Halbrook et al., (1989) *J. Biol. Chem.* 264: 21403; Eisen et al., (1988) *Proc. Natl. Acad. Sci. USA* 85: 7481; McCarthy et al., (1988) *Proc. Natl. Acad. Sci. USA* 85: 5854; Lowenhaupt et al., (1989) *J. Biol. Chem.* 264: 20568, which are incorporated herein by reference. Examples of such recombinase proteins include, for example but not limitation: recA, recA803, uvsX, and other recA mutants and recA-like recombinases (Roca, A. I. (1990) *Crit. Rev. Biochem. Molec. Biol.* 25: 415), sep1 (Kolodner et al. (1987) *Proc. Natl. Acad. Sci. (U.S.A.)* 84: 5560; Tishkoff et al. *Molec. Cell. Biol.* 11: 2593), RuvC (Dunderdale et al. (1991) *Nature* 354: 506), DST2, KEM1, XRN1 (Dykstra et al. (1991) *Molec. Cell. Biol.* 11: 2583), STPα/DST1 (Clark et al. (1991) *Molec. Cell. Biol.* 11: 2576), HPP-1 (Moore et al. (1991) *Proc. Natl. Acad. Sci. (U.S.A.)* 88: 9067), other eukaryotic recombinases (Bishop et al. (1992) *Cell* 69: 439; Shinohara et al. (1992) *Cell* 69: 457); incorporated herein by reference. RecA may be purified from *E. coli* strains, such as *E. coli* strains JC12772 and JC15369 (available from A. J. Clark and M. Madiraju, University of California-Berkeley). These strains contain the recA coding sequences on a "runaway" replicating plasmid vector present at a high copy number per cell. The recA803 protein is a high-activity mutant of wild-type recA. The art teaches several examples of recombinase proteins, for example, from Drosophila, yeast, plant, human, and non-human mammalian cells, including proteins with biological properties similar to recA (i.e., recA-like recombinases).

RecA protein is typically obtained from bacterial strains that overproduce the protein: wild-type *E. coli* recA protein and mutant recA803 protein may be purified from such strains. Alternatively, recA protein can also be purchased from, for example, Pharmacia (Piscataway, N.J.).

RecA protein forms a nucleoprotein filament when it coats a single-stranded DNA. In this nucleoprotein filament, one monomer of recA protein is bound to about 3 nucleotides. This property of recA to coat single-stranded DNA is essentially sequence independent, although particular sequences favor initial loading of recA onto a polynucleotide (e.g., nucleation sequences). The nucleoprotein filament(s) can be formed on essentially any sequence-related polypeptide to be suffled and can be formed in cells (e.g., bacterial, yeast, or mammalian cells), forming complexes with both single-stranded and double-stranded DNA.

Site-specific recombination can be used to accomplish recursive sequence recombination. Typically, sequences to be shuffled are flanked by one or more site-specific recombination sequences, such as for example a FLP recombination target site (FRT) often consisting of the two inverted 13 base repeats and an 8 bp spacer (O'Gorman et al. (1991) *Science* 251: 1351; Parsons et al. (1990) *J. Biol. Chem.* 265: 4527; Amin et al. (1991) *Mol. Cell. Biol.* 11: 4497, incorporated herein by reference). When FRT sequences are employed, the FLP recombinase is typically also employed, either in vitro or expressed in a host cell wherein the sequences to be recombined are introduced or are already present. Alternatives to the FLP/FRT system include, but are not limited to, the cre/lox system of phage P1 (Hoess and Abremski (1985) *J. Mol. Biol.* 181: 351), the γ/δ resolvase (Steitz et al. (1990) *Quarterly Rev. Biophys.* 23: 205), the attB/attP system of λ (Nunes-Duby et al. (1987) *Cell* 50: 779), and like site-specific recombination systems from bacteriophages λ, φ80, P22, P2, P4, P1, and other like site-specific recombination systems selected by the practioner. Guidance regarding the integrase family of recombinases is found in Argos et al. (1986) *EMBO J.* 5: 433, incorporated herein by reference.

Exonuclease

In one aspect, the improved shuffling method includes the addition of at least one additive which is an enzyme having an exonuclease activity which is active at removing non-templated nucleotides introduced at 3' ends of product polynucleotides in shuffling amplification reactions catalyzed by a non-proofreading polymerase. An examples of a suitable enzyme having an exonuclease activity includes but is not limited to Pfu polymerase. Examples of exonucleases are:

Bal31

Bacteriophage Lambda exonuclease

*E. coli* Exonuclease I

*E. coli* Exonuclease III

*E. coli* Exonuclease VII

Bacteriophage T7 gene 6.

Stuttering

In an aspect, the improved shuffling method comprises the modification wherein at least one cycle of amplification (i.e., extension with a polymerase) of reannealed fragmented library member polynucleotides is conducted under conditions which produce a substantial fraction, typically at least 20 percent or more, of incompletely extended amplification products. The amplification products, including the incompletely extended amplification products are denatured and subjected to at least one additional cycle of reannealing and amplification. This variation, wherein at least one cycle of reannealing and amplification provides a substantial fraction of incompletely extended products, is termed "stuttering" and in the subsequent amplification round the incompletely extended products reanneal to and prime extension on different sequence-related template species.

In an aspect, the improved shuffling method comprises the modification wherein at least one cycle of amplification is conducted using a collection of overlapping single-stranded DNA fragments of varying lengths corresponding to a first polynucleotide species or set of related-sequence polynucleotide species, wherein each overlapping fragment can each hybridize to and prime polynucleotide chain extension from a second polynucleotide species serving as a template, thus forming sequence-recombined polynucleotides, wherein said sequence-recombined polynucleotides comprise a portion of at least one first polynucleotide species with an adjacent portion of the second polynucleotide species which serves as a template. In a variation, the second polynucleotide species serving as a template contains uracil (i.e., a Kunkel-type template) and is substantially non-replicable in cells. This aspect of the invention can also comprise at least two recursive cycles of this variation. In one embodiment, recursive cycles of shuffling using the method of Levitchkin et al. (1995) *Mol. Biol.* 29: 572, which produces partial extension PCR fragments is used to generate chimeras from a pool of parental sequences which are recursively shuffled.

In an aspect, the improved shuffling method comprises the modification wherein at least one cycle of amplification is conducted with an additive or polymerase in suitable conditions which promote template switching. In an embodiment where Taq polymerase is employed for amplification, addition of recA or other polymerases enhances template switching. Template-switching can also be increased by increasing the DNA template concentration, among other means known by those skilled in the art.

In an embodiment of the general method, libraries of sequence-recombined polynucleotides are generated from sequence-related polynucleotides which are naturally-occurring genes or alleles of a gene. In this aspect, at least three naturally-occurring genes and/or alleles which comprise regions of at least 50 consecutive nucleotides which have at least 70 percent sequence identity, prefereably at least 90 percent sequence identity, are selected from a pool of gene sequences, such as by hybrid selection or via computerized sequence analysis using sequence data from a database. The selected sequences are obtained as polynucleotides, either by cloning or via DNA synthesis, and shuffled by any of the various embodiments of the invention.

In an embodiment of the invention, the method comprises the further step of removing non-shuffled products (e.g., parental sequences) from sequence-recombined polynucleotides produced by any of the disclosed shuffling methods. Non-shuffled products can be removed or avoided by performing amplification with: (1) a first PCR primer which hybridizes to a first parental polynucleotide species but does not substantially hybridize to a second parental polynucleotide species, and (2) a second PCR primer which hybridizes to a second parental polynucleotide species but does not substantially hybridize to the first parental polynucleotide species, such that amplification occurs on from templates comprising the portion of the first parental sequence which hybridizes to the first PCR primer and also comprising the portion of the second parental sequence which hybridizes to the second PCR primer, thus only sequence-recombined polynucleotides are amplified.

In an embodiment of the invention,. "bridging" genes can be synthesized. If two or more parental polynucelotides (e.g., genes) lack satisfactory sequence similarity for efficient homologous recombination or for efficient cross-priming for PCR amplification, intermediate (or "bridging") genes can be synthesized which share sufficient sequence identity with the parental sequences. The bridging gene need not be active or confer a phenotype or selectable property, it need only provide a template having sufficient sequence identity to accomplish shuffling of the parental sequences. The intermediate homology of the bridging gene, and the necessary sequence(s) can be determined by computer or manually.

The invention also provides additional formats for performing recursive recombination in vivo, either in procaryotic or eucaryotic cells. These formats include recombination between plasmids, recombination between viruses, recombination between plasmid and virus, recombination between a chromosome and plasmid or virus and intramolecular recombination (e.g., between two sequences on a plasmid). Recursive recombination can be performed entirely in vivo whereby successive rounds of in vivo recombination are interspersed by rounds of selection or screening. In vivo formats can also be used in combination with in vitro formats. For example, one can perform one round of in vitro shuffling, a round of selection, a round of in vivo shuffling, a further round of selection, a further round of in vitro shuffling and a further round of selection and so forth. The various in vivo formats are now considered in turn.

(a) Plasmid-Plasmid Recombination

The initial substrates for recombination are a collection of polynucleotides comprising variant forms of a gene. The variant forms usually show substantial sequence identity to each other sufficient to allow homologous recombination between substrates. The diversity between the polynucleotides can be natural (e.g., allelic or species variants), induced (e.g., error-prone PCR, synthetic genes, codon-usage altered sequence variants), or the result of in vitro recombination. There should be at least sufficient diversity between substrates that recombination can generate more diverse products than there are starting materials. There must be at least two substrates differing in at least two positions. However, commonly a library of substrates of $10^3$–$10^8$ members is employed. The degree of diversity depends on the length of the substrate being recombined and the extent of the functional change to be evolved. Diversity at between 0.1–25% of positions is typical.

The diverse substrates are incorporated into plasmids. The plasmids are often standard cloning vectors, e.g., bacterial multicopy plasmids. However, in some methods to be described below, the plasmids include MOB functions. The substrates can be incorporated into the same or different plasmids. Often at least two different types of plasmid having different types of selection marker are used to allow selection for cells containing at least two types of vector. Also, where different types of plasmid are employed, the different plasmids can come from two distinct incompatibility groups to allow stable co-existence of two different plasmids within the cell. Nevertheless, plasmids from the same incompatibility group can still co-exist within the same cell for sufficient time to allow homologous recombination to occur.

Plasmids containing diverse substrates are initially introduced into cells by any transfection methods (e.g., chemical transformation, natural competence, transduction, electroporation or biolistics). Often, the plasmids are present at or near saturating concentration (with respect to maximum transfection capacity) to increase the probability of more than one plasmid entering the same cell. The plasmids containing the various substrates can be transfected simultaneously or in multiple rounds. For example, in the latter approach cells can be transfected with a first aliquot of plasmid, transfectants selected and propagated, and then infected with a second aliquot of plasmid.

Having introduced the plasmids into cells, recombination between substrates to generate recombinant genes occurs within cells containing multiple different plasmids merely by propagating the cells. However, cells that receive only one plasmid are less able to participate in recombination and the potential contribution of substrates on such plasmids to evolution is wasted. The rate of evolution can be increased by allowing all substrates to participate in recombination. Such can be achieved by subjecting transfected cells to electroporation. The conditions for electroporation are the same as those conventionally used for introducing exogenous DNA into cells (e.g., 1,000–2,500 volts, 400 $\mu$F and a 1–2 mM gap). Under these conditions, plasmids are exchanged between cells allowing all substrates to participate in recombination. In addition the products of recombination can undergo further rounds of recombination with each other or with the original substrate. The rate of evolution can also be increased by use of conjugative transfer. To exploit conjugative transfer, substrates can be cloned into plasmids having MOB genes and tra genes are also provided in cis or in trans to the MOB genes. The effect of conjugative transfer is very similar to electroporation in that it allows plasmids to move between cells and allows recombination between any substrate, and the products of previous recombination to occur merely by propagating the culture. The details of how conjugative transfer is exploited in these vectors are discussed in more detail below. The rate of evolution can also be increased by use of mutator host cells (e.g., Mut L, S, D, T, H; human ataxia telengiectasia cells).

The time for which cells are propagated and recombination is allowed to occur, of course, varies with the cell type but is generally not critical, because even a small degree of recombination can substantially increase diversity relative to the starting materials. Cells bearing plasmids containing recombined genes are subject to screening or selection for a desired function. For example, if the substrate being evolved contains a drug resistance gene, one would select for drug resistance. Cells surviving screening or selection can be subjected to one or more rounds of screening/selection followed by recombination or can be subjected directly to an additional round of recombination.

The next round of recombination can be achieved by several different formats independently of the previous round. For example, a further round of recombination can be effected simply by resuming the electroporation or conjugation-mediated intercellular transfer of plasmids described above. Alternatively, a fresh substrate or substrates, the same or different from previous substrates, can be transfected into cells surviving selection/screening. Optionally, the new substrates are included in plasmid vectors bearing a different selective marker and/or from a different incompatibility group than the original plasmids. As a further alternative, cells surviving selection/screening can be subdivided into two subpopulations, plasmid DNA extracted from one subpopulation and transfected into the other, where the substrates from the plasmids from the two subpopulations undergo a further round of recombination. In either of the latter two options, the rate of evolution can be increased by employing electroporation, conjugation or mutator cells, as described above. In a still further variation, DNA from cells surviving screening/selection can be extracted and subjected to in vitro DNA shuffling.

After the second round of recombination, a second round of screening/selection is performed, preferably under conditions of increased stringency. If desired, further rounds of recombination and selection/screening can be performed using the same strategy as for the second round. With successive rounds of recombination and selection/screening, the surviving recombined substrates evolve toward acquisition of a desired phenotype. Typically, in this and other methods of in vivo recursive recombination, the final product of recombination that has acquired the desired phenotype differs from starting substrates at 0.1%–25% of positions and has evolved at a rate orders of magnitude in excess (e.g., by at least 10-fold, 100-fold, 1000-fold, or 10,000 fold) of the rate of naturally acquired mutation of about 1 mutation per $10^{-9}$ positions per generation (see Anderson & Hughes, *Proc. Natl. Acad. Sci. USA* 93, 906–907 (1996)).

FIG. 26 shows an exemplary scheme of plasmid-plasmid recombination. Panel A of the figure shows a library of variant genes cloned into a plasmid. The library is then introduced into cells. Some cells take up a single plasmid and other cells take up two plasmids as shown in panel B. For cells having taken up two plasmids, the plasmids recombine to give the products shown in panel C. Plasmids can then be transferred between cells by electroporation or conjugation as shown in panel D, and further recombination can occur to give the products shown in panel E. Screening/ selection then isolates plasmids bearing genes that have evolved toward acquisition of the property that selection/ screening is designed to identify. In the course of selection, a cell bearing two plasmids of which only one contributes to the selected phenotype, may lose the other plasmid, as shown in panel F.

(b) Virus-Plasmid Recombination

The strategy used for plasmid-plasmid recombination can also be used for virus-plasmid recombination; usually, phage-plasmid recombination. However, some additional comments particular to the use of viruses are appropriate. The initial substrates for recombination are cloned into both plasmid and viral vectors. It is usually not critical which substrate(s) are inserted into the viral vector and which into the plasmid, although usually the viral vector should contain different substrate(s) from the plasmid. As before, the plasmid typically contains a selective marker. The plasmid and viral vectors can both be introduced into cells by transfection as described above. However, a more efficient procedure is to transfect the cells with plasmid, select transfectants and infect the transfectants with virus. Because the efficiency of infection of many viruses approaches 100% of cells, most cells transfected and infected by this route contain both a plasmid and virus bearing different substrates.

Homologous recombination occurs between plasmid and virus generating both recombined plasmids and recombined virus. For some viruses, such as filamentous phage, in which intracellular DNA exists in both double-stranded and single-stranded forms, both can participate in recombination. Provided that the virus is not one that rapidly kills cells, recombination can be augmented by use of electroporation or conjugation to transfer plasmids between cells. Recombination can also be augmented for some types of virus by allowing the progeny virus from one cell to reinfect other cells. For some types of virus, virus infected-cells show resistance to superinfection. However, such resistance can be overcome by infecting at high multiplicity and/or using mutant strains of the virus in which resistance to superinfection is reduced.

The result of infecting plasmid-containing cells with virus depends on the nature of the virus. Some viruses, such as filamentous phage, stably exist with a plasmid in the cell and also extrude progeny phage from the cell. Other viruses, such as lambda having a cosmid genome, stably exist in a cell like plasmids without producing progeny virions. Other viruses, such as the T-phage and lytic lambda, undergo recombination with the plasmid but ultimately kill the host cell and destroy plasmid DNA. For viruses that infect cells without killing the host, cells containing recombinant plasmids and virus can be screened/selected using the same approach as for plasmid-plasmid recombination. Progeny virus extruded by cells surviving selection/screening can also be collected and used as substrates in subsequent rounds of recombination. For viruses that kill their host cells, recombinant genes resulting from recombination reside only in the progeny virus. If the screening or selective assay requires expression of recombinant genes in a cell, the recombinant genes should be transferred from the progeny virus to another vector, e.g., a plasmid vector, and retransfected into cells before selection/screening is performed.

For filamentous phage, the products of recombination are present in both cells surviving recombination and in phage extruded from these cells. The dual source of recombinant products provides some additional options relative to the plasmid-plasmid recombination. For example, DNA can be isolated from phage particles for use in a round of in vitro recombination. Alternatively, the progeny phage can be used to transfect or infect cells surviving a previous round of screening/selection, or fresh cells transfected with fresh substrates for recombination. In an aspect, the invention employs recombination between multiple single-stranded species, such as single-stranded bacteriophages and/or phagemids.

FIG. 27 illustrates a scheme for virus-plasmid recombination. Panel A shows a library of variant forms of gene cloned into plasmid and viral vectors. The plasmids are then introduced into cells as shown in panel B. The viral genomes are packaged in vitro and used to infect the cells in panel B. The viral genomes can undergo replication within the cell, as shown in panel C. The viral genomes undergo recombination with plasmid genomes generating the plasmid and viral forms shown in panel D. Both plasmids and viral genomes can undergo further rounds of replication and recombination generating the structures shown in panels E and F. Screening/selection identifies cells containing plasmid and/or viral genomes having genes that have evolved best to allow survival of the cell in the screening/selection process, as shown in panel G. These viral genomes are also present in viruses extruded by such cells.

(c) Virus-Virus Recombination

The principles described for plasmid-plasmid and plasmid-viral recombination can be applied to virus-virus recombination with a few modifications. The initial substrates for recombination are cloned into a viral vector. Usually, the same vector is used for all substrates. Preferably, the virus is one that, naturally or as a result of mutation, does not kill cells. After insertion, viral genomes are usually packaged in vitro. The packaged viruses are used to infect cells at high multiplicity such that there is a high probability that a cell will receive multiple viruses bearing different substrates.

After the initial round of infection, subsequent steps depend on the nature of infection as discussed in the previous section. For example, if the viruses have phagemid genomes such as lambda cosmids or M13, F1 or Fd phagemids, the phagemids behave as plasmids within the cell and undergo recombination simply by propagating the cells. Recombination is particularly efficient between single-stranded forms of intracellular DNA. Recombination can be augmented by electroporation of cells. Following selection/screening, cosmids containing recombinant genes can be recovered from surviving cells (e.g., by heat induction of a cos$^-$ lysogenic host cell), repackaged in vitro, and used to infect fresh cells at high multiplicity for a further round of recombination.

If the viruses are filamentous phage, recombination of replicating form DNA occurs by propagating the culture of infected cells. Selection/screening identifies colonies of cells containing viral vectors having recombinant genes with improved properties, together with phage extruded from such cells. Subsequent options are essentially the same as for plasmid-viral recombination.

Figure 28:
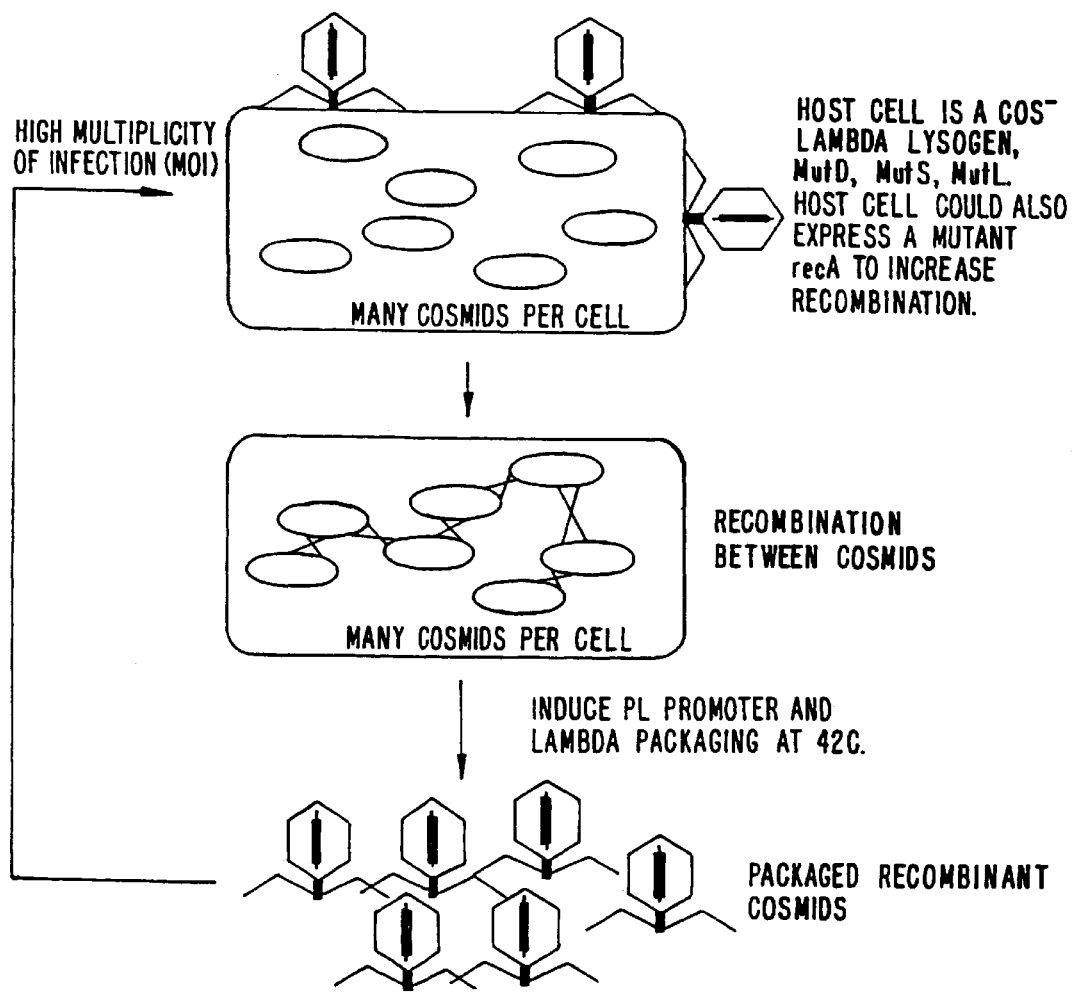
FIG. 28 shows virus-virus recombination.
Figure 29A:
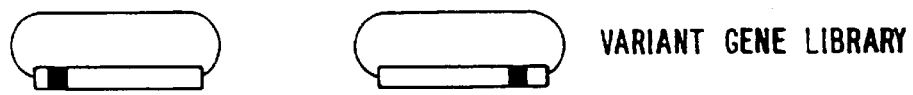
FIG. 29 shows plasmid-chromosome recombination.
Figure 29B:
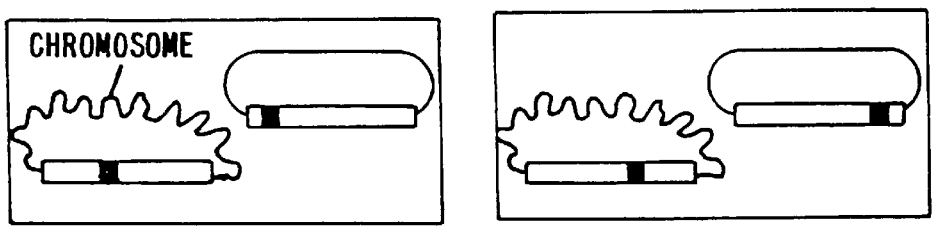
Figure 29C:
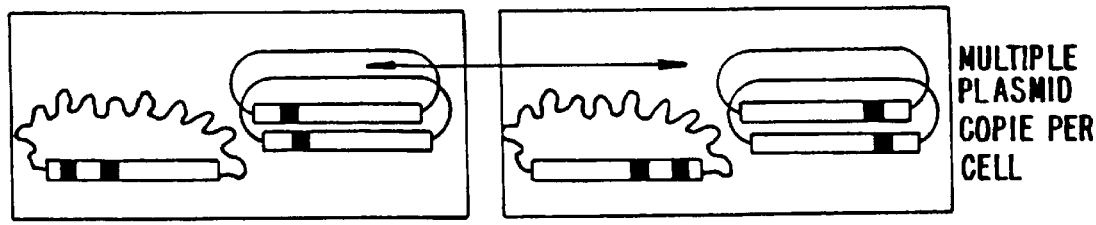
Figure 29D:
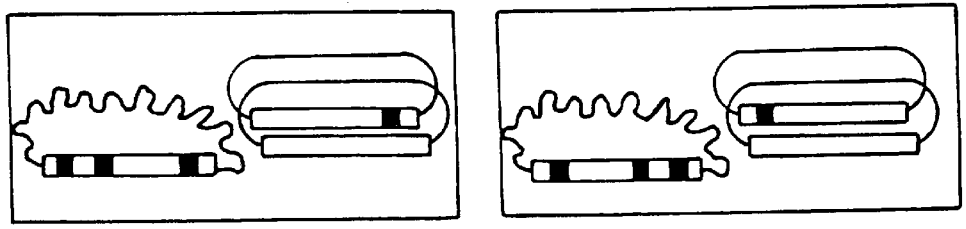
Figure 29E:
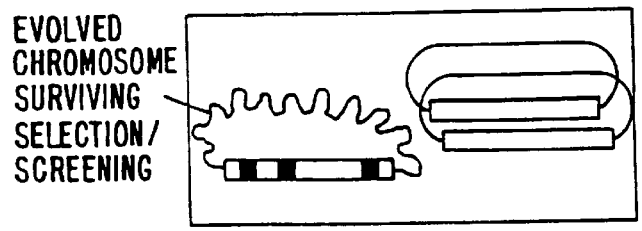
Figure 30A:
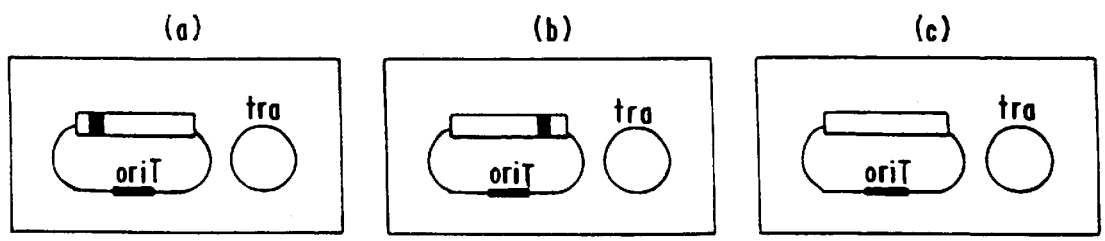
FIG. 30 shows conjugation-mediated recombination.
Figure 30B:
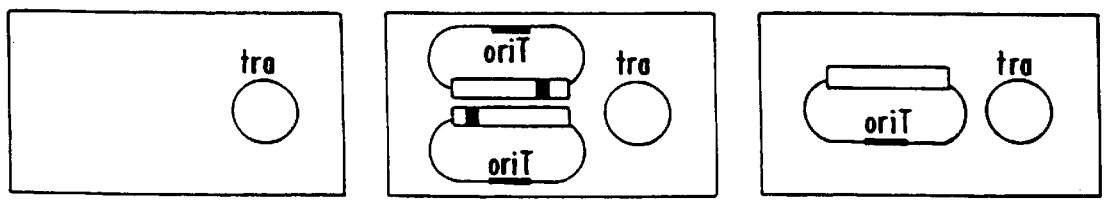
Figure 30C:
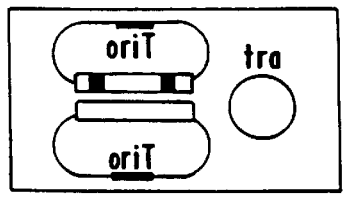
Figure 30D:
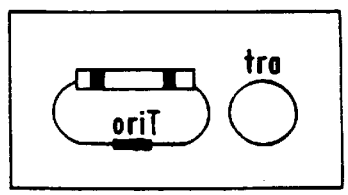

FIG. 28 shows an example of virus-virus recombination. A library of diverse genes is cloned into a lambda cosmid. The recombinant cosmid DNA is packaged in vitro and used to infect host cells at high multiplicitity such that many cosmids bearing different inserts enter the same cell. The cell chosen is a cos$^-$ lambda lysogen, which on induction, packages cosmid DNA without packaging lysogenic DNA. Cosmids recombine within the cell. Recombination can be accelerated by the use of host cells that are MutD, MutS, MutL and/or express a modified recA. Induction of the lysogen results in release of packaged recombinant cosmids, having greater diversity than the starting materials.

(d) Chromosome-Plasmid Recombination

This format can be used to evolve both the chromosomal and plasmid-borne substrates. The format is particularly useful in situations in which many chromosomal genes contribute to a phenotype or one does not know the exact location of the chromosomal gene(s) to be evolved. The initial substrates for recombination are cloned into a plasmid vector. If the chromosomal gene(s) to be evolved are known, the substrates constitute a family of sequences showing a high degree of sequence identity but some divergence from the chromosomal gene. If the chromosomal genes to be evolved have not been located, the initial substrates usually constitute a library of DNA segments of which only a small number show sequence identity to the gene or gene(s) to be evolved. Divergence between plasmid-borne substrate and the chromosomal gene(s) can be induced by mutagenesis or by obtaining the plasmid-borne substrates from a different species than that of the cells bearing the chromosome.

The plasmids bearing substrates for recombination are transfected into cells having chromosomal gene(s) to be evolved. Evolution can occur simply by propagating the culture, and can be accelerated by transferring plasmids between cells by conjugation or electroporation. Evolution can be further accelerated by use of mutator host cells or by seeding a culture of nonmutator host cells being evolved with mutator host cells and inducing intercellular transfer of plasmids by electroporation or conjugation. Preferably, mutator host cells used for seeding contain a negative selection marker to facilitate isolation of a pure culture of the nonmutator cells being evolved. Selection/screening identifies cells bearing chromosomes and/or plasmids that have evolved toward acquisition of a desired function.

Subsequent rounds of recombination and selection/screening proceed in similar fashion to those described for plasmid-plasmid recombination. For example, further recombination can be effected by propagating cells surviving recombination in combination with electroporation or conjugative transfer of plasmids. Alternatively, plasmids bearing additional substrates for recombination can be introduced into the surviving cells. Preferably, such plasmids are from a different incompatibility group and bear a different selective marker than the original plasmids to allow selection for cells containing at least two different plasmids. As a further alternative, plasmid and/or chromosomal DNA can be isolated from a subpopulation of surviving cells and transfected into a second subpopulation. Chromosomal DNA can be cloned into a plasmid vector before transfection.

FIG. 29 illustrates a scheme for plasmid-chromosome shuffling. Panel A shows variant forms of a gene cloned into a plasmid vector. The plasmids are introduced into cells as shown in panel B. In the cells, the plasmids replicate and undergo recombination with a chromosomal copy of the gene, as shown in panel C. Exchange of plasmids between cells can be effected by electroporation or conjugation as shown in panel D. The chromosomal genes in the two cells shown in panel D have evolved to different variant forms. Screening/selection identifies the cell bearing the chromosomal gene that has evolved that has acquired a desired property that allows the cell to survive screening/selection, as shown in panel E.

(e) Virus-Chromosome Recombination

As in the other methods described above, the virus is usually one that does not kill the cells, and is often a phage or phagemid. The procedure is substantially the same as for plasmid-chromosome recombination. Substrates for recombination are cloned into the vector. Vectors including the substrates can then be transfected into cells or in vitro packaged and introduced into cells by infection. Viral genomes recombine with host chromosomes merely by propagating a culture. Evolution can be accelerated by allowing intercellular transfer of viral genomes by electroporation, or reinfection of cells by progeny virions. Screening/selection identifies cells having chromosomes and/or viral genomes that have evolved toward acquisition of a desired function.

There are several options for subsequent rounds of recombination. For example, viral genomes can be transferred between cells surviving selection/recombination by electroporation. Alternatively, viruses extruded from cells surviving selection/screening can be pooled and used to superinfect the cells at high multiplicity. Alternatively, fresh substrates for recombination can be introduced into the cells, either on plasmid or viral vectors.

e. Evolution of Genes by Conjugative Transfer

As noted above, the rate of in vivo evolution of plasmids DNA can be accelerated by allowing transfer of plasmids between cells by conjugation. Conjugation is the transfer of DNA occurring during contact between cells. See Guiney (1993) in: *Bacterial Conjugation* (Clewell, ed., Plenum Press, New York), pp. 75–104; Reimmann & Haas in *Bacterial Conjugation* (Clewell, ed., Plenum Press, New York 1993), at pp.137–188 (incorporated by reference in their entirety for all purposes). Conjugation occurs between many types of gram negative bacteria, and some types of gram positive bacteria. Conjugative transfer is also known between bacteria and plant cells (Agrobacterium tumefaciens) or yeast. As discussed in copending application attorney docket no. 16528J-014612, the genes responsible for conjugative transfer can themselves be evolved to expand the range of cell types (e.g., from bacteria to mammals) between which such transfer can occur.

Conjugative transfer is effected by an origin of transfer (oriT) and flanking genes (MOB A, B and C), and 15–25 genes, termed tra, encoding the structures and enzymes necessary for conjugation to occur. The transfer origin is defined as the site required in cis for DNA transfer. Tra genes include tra A, B, C, D, E, F, G, H, I, J, K, L, M, N, P, Q, R, S, T, U, V, W, X, Y, Z, virAB (alleles 1–11), C, D, E, G, IHF, and FinOP. OriT is sometimes also designated as a tra gene. Other cellular enzymes, including those of the RecBCD pathway, RecA, SSB protein, DNA gyrase, DNA polI, and DNA ligase, are also involved in conjugative transfer. RecE or recF pathways can substitute for RecBCD.

The tra genes and MOB genes can be expressed in cis or trans to oriT. Vectors undergoing conjugation also have an origin of replication which is classified as belonging to an incompatibility group such as Inc A, B, C, D, E, F (I–VI), H (I, Y), i (1, 2, 5, ALPHA), J, K, L, M, N, P (ALPHA, BETA, 1 ALPHA, 3, 7, 10, 13) Q, R (H1, H2, H3) S, T, U, W, X, Z. Only vectors from different incompatibility groups can stably co-exist in the same cell. However, when two vectors from the same incompatibility group are transfected into the same cell, the vectors transiently coexist for sufficient time that recombination can occur between the vectors.

One structural protein encoded by a tra gene is the sex pilus, a filament constructed of an aggregate of a single polypeptide protruding from the cell surface. The sex pilus binds to a polysaccharide on recipient cells and forms a conjugative bridge through which DNA can transfer. This process activates a site-specific nuclease encoded by a MOB gene, which specifically cleaves DNA to be transferred at oriT. The cleaved DNA is then threaded through the conjugation bridge by the action of other tra enzymes.

DNA is transferred more efficiently between cells when present as a component of the mobilizable vector. However, some mobilizable vectors integrate into the host chromosome and thereby mobilize adjacent genes from the chromosome. The F plasmid of *E. coli*, for example, integrates into the chromosome at high frequency and mobilizes genes unidirectional from the site of integration. Other mobilizable vectors do not spontaneously integrate into a host chromosome at high efficiency but can be induced to do by growth under particular conditions (e.g., treatment with a mutagenic agent, growth at a nonpermissive temperature for plasmid replication). See Reimann & Haas in *Bacterial Conjugation* (ed. Clewell, Plenum Press, NY 1993), Ch. 6.

Conjugation provides a means of recombining gene(s) in vivo to generate diverse recombinant forms of the gene(s). As in other methods of recursive recombination, iterative cycles of recombination and selection/screening can be used to evolve the gene(s) toward acquisition of a new or improved property. As in any method of recursive recombination, the first step is to generate a library of diverse forms of the gene or genes to be evolved. The diverse forms can be the result of natural diversity, the application of traditional mutagenesis methods (e.g., error-prone PCR or cassette mutagenesis) or the result of any of the other recombination formats discussed in this application, or any combination of these. The number of diverse forms can vary widely from about 10 to 100, $10^4$, $10^6$, $10^8$ or $10^{10}$. Often, the gene(s) of interest are mutagenized as discrete units. However, if the location of gene(s) is not known or a large number of genes are to be evolved simultaneously, initial diversity can be generated by in situ mutagenesis of a chromosome containing the gene(s).

The library of diverse forms of a gene or gene(s) is introduced into cells containing the apparatus necessary for conjugative transfer (assuming that the library is not already contained in such cells), usually in an arrangement such that the genes can be expressed. For example, if the gene(s) are mutagenized in the absence of essential regulatory sequences such as promoter, these sequences are reattached before introduction into cells. Similarly, if a fragment of a gene is mutagenized in isolation, the mutagenesis products are usually reassociated with unchanged flanking sequences before being introduced into cells. The apparatus necessary for conjugative transfer comprises a vector having an origin of transfer together with the mob and tra genes whose expression is necessary for conjugative transfer to occur. These genes can be included in the vector, in one or more different vectors, or in the chromosome. The library of diverse forms of the gene to be evolved is usually inserted into the vector containing the origin of transfer (see FIG. 30). However, in some situations the library of diverse forms of the gene can be present in the chromosome or a second vector, as well as, or instead of in the vector containing the origin of transfer. The library of diverse forms can be inserted in different places in different cells.

A vector bearing a library of variant forms contains at least one origin of replication. If transfer between different cell types is contemplated, the vector can contain two origins of replication, one functional in each cell type (i.e., shuttle vector). Alternatively, if it is intended that transferred genes should integrate into the chromosome of recipient cells, it is preferable that the vector not contain an origin of replication functional in the recipient cells (i.e., a suicide vector). The oriT site and/or MOB genes can be introduced into a vector by cloning or transposing the RK2/RP4 MOB function (Guiney, *J. Mol. Biol.* 162, 699–703 (1982)), or by cointegrate formation with a MOB-containing plasmid. A convenient method for large plasmids is to use 'Tn5-Mob', which is the Tn5 transposon containing the oriT of RP4. For example, pUC-like mobilizable vectors pK18 and pK19 (Schafer et al. (1995) Gene 145:69–73) are suitable starting vectors for cloning the tra gene library to be evolved.

Although not necessary, recombination is sometimes facilitated by inserting the diverse gene library into two different kinds of vectors having different incompatibility origins. Each vector should have an oriT and the cell should express MOB and tra functions suitable for mobilization of both vectors. Use of two such kinds of vectors allows stable coexistence of multiple vectors within the same cell and increases the efficiency of recombination between the vectors.

The collection of cells is propagated in any suitable media to allow gene expression to occur. Tra and mob genes are expressed and mediate transfer of the mobilizable vector between cells. If the diverse library is cloned into a mobilizable vector, its members are transferred as components of the vector. If the diverse library, or certain elements of the library, are in trans to the mobilizable vector, they are transferred only if the mobilizable vector integrates into or proximate to the elements. As discussed above, integration frequently occurs spontaneously for the *E. coli* F plasmid and can be induced for other mobilizable vectors.

As a result of transfer of members of the diverse library between cells, some of the cells come to contain more than one member of the diverse library. The multiple members undergo recombination within such cells generating still further diversity in a library of recombinant forms. In general, the longer cells are propagated the more recombinant forms are generated. Generally, recombination results in more than one recombination product within the same cell. If both recombination products are on vectors and the vectors are from the same incompatibility group, one of the vectors is lost as the cells are propagated. This process occurs faster if the cells are propagated on selective media in which one or other of the recombinant products confers a selective advantage. After a suitable period of recombination, which depends on the cell type and its growth cycle time, the recombinant forms are subject to screening or selection. Because the recombinant forms are already present in cells, this format for recombination is particularly amenable to alternation with cycles of in vivo screening or selection. The conditions for screening or selection, of course, depend on the property which it is desired that the gene(s) being evolved acquire or improve in. For example, if the property is drug resistance, recombinant forms having the best drug resistance can be selected by exposure to the drug. Alternatively, if a cluster of genes is being evolved to produce a drug as a secondary metabolite, cells bearing recombinant clusters of the genes can be screened by overlaying colonies of cell bearing recombinant cluster with a lawn of cells that are sensitive to the drug. colonies having recombinant clusters resulting in production of the best drug are identified from holes in the lawn. If the gene being evolved confers enhanced growth characteristics, cells bearing the best genes can be selected by growth competition. Antibiotic production can be growth rate advantage if cells are competing with other cell types for growth.

Screening/selection produces a subpopulation of cells expressing recombinant forms of gene(s) that have evolved toward acquisition of a desired property. These recombinant forms can then be subjected to further rounds of recombination and screening/selection in any order. For example, a second round of screening/selection can be performed analogous to the first resulting in greater enrichment for genes having evolved toward acquisition of the desired property. Optionally, the stringency of selection can be increased between rounds (e.g., if selecting for drug resistance, the concentration of drug in the media can be increased). Further rounds of recombination can also be performed by an analogous strategy to the first round generating further recombinant forms of the gene(s). Alternatively, further rounds of recombination can be performed by any of the other molecular breeding formats discussed. Eventually, a recombinant form of the gene(s) is generated that has fully acquired the desired property.

FIG. 30 provides an example of how a drug resistance gene can be evolved by conjugative transfer. Panel A shows a library of diverse genes cloned into a mobilizable vector bearing as oriT. The vectors are present in cells containing a second vector which provides tra functions. Conjugative transfer results in movement of the mobilizable vectors between cells, such that different vectors bearing different variant forms of a gene occupy the same cell, as shown in panel B. The different forms of the gene recombine to give the products shown in panel C. After conjugation and recombination has proceeded for a desired time, cells are selected to identify those containing the recombined genes, as shown in panel D.

In one aspect, the alternative shuffling method includes the use of intra-plasmidic recombination, wherein libraries of sequence-recombined polynucleotide sequences are obtained by genetic recombination in vivo of direct sequence repeats located on the same plasmid. In a variation, the sequences to be recombined are flanked by site-specific recombination sequences and the polynucleotides are present in a site-specific recombination system, such as an integron (Hall and Collins (1995) *Mol. Microbiol.* 15: 593, incorporated herein by reference).

In an aspect of the invention, mutator strains of host cells are used to enhance recombination of more highly mismatched sequence-related polynucleotides. Bacterials strains such as MutL, MutS, or MutH or other cells expressing the Mut proteins (XL-1red; Stratagene, San Diego, Calif.) can be used as host cells for shuffling of sequence-related polynucleotides by in vivo recombination. Other mutation-prone host cel types can also be used, such as those having a proofreading-defective polymerase (Foster et al. (1995) *Proc. Natl. Acad. Sci.* (*U.S.A.*) 92: 7951, incorporated herein by reference). Other in vivo mutagenic formats can be employed, including adminstering chemical or radiological mutagens to host cells. Examples of such mutagens include but are not limited to: ENU, MMNG, nitrosourea, BuDR, and the like.

Shuffling can be used to evolve polymerases capable of incorporation of base analogs in PCR or PCR-like amplification reactions. A DNA polymerase which is evolved to use base analogs can be used to copy DNA by PCR into a chemical form which gives more resolvable fragmentation patterns in mass spectrometry, such as for mass spectrometry DNA sequencing. The base analogs can have fewer and/or more favorable fragmentation sites to enhance or facilitate the interpretation of the mass spectrum patterns.

Variant polymerases can also be evolved by recursive sequence recombination to incorporate non-natural nucleotides or nucleotide analogs, such as phosphorothioate nucleotides. Phosphorothioate nucleotides made with such variant polymerases can provide many uses, including naked DNA gene therapy vectors which are resistant to nuclease degradation. Other examples of properties of polymerases which can be modified via recursive sequence recombination include, but are not limited to, processivity, error rate, proofreading, thermal stability, oxidation resistance, nucleotide preferences, template specificity, and the like, among others.

In an embodiment, fluorescence-activated cell sorting or analogous methodology is used to screen for host cells, typically mammalian cells, insect cells, or bacterial cells, comprising a library member of a recursively recombined sequence library, wherein the host cell having a library member conferring a desired phenotype can be selected on the basis of fluorescence or optical density at one or more detection wavelengths. In one embodiment, for example, each library member typically encodes an enzyme, which may be secreted from the cell or may be intracellular, and the enzyme catalyzes conversion of a chromogenic or fluorogenic substrate, which may be capable of diffusing into the host cell (e.g., if said enzyme is not secreted). Host cells containing library members are contained in fluid drops or gel drops and passed by a detection apparatus where the drops are illuminated with an excitation wavelength and a detector measures either fluorescent emission wavelength radiation and/or measures optical density (absoption) at one or more excitatory wavelength(s). The cells suspended in drops are passed across a sample detector under conditions wherein only about one individual cell is present in a sample detection zone at a time. A source, illuminates each cell and a detector, typically a photomultiplier or photodiode, detects emitted radiation. The detector controls gating of the cell in the detection zone into one of a plurality of sample collection regions on the basis of the signal(s) detected. A general description of FACS apparatus and methods in provided in U.S. Pat. Nos. 4,172,227; 4,347,935; 4,661,913; 4,667,830; 5,093,234; 5,094,940; and 5,144,224, incorporated herein by reference. A suitable alternative to convnetional FACS is available from One Cell Systems, Inc. Cambridge, Mass.

As can be appreciated from the disclosure above, the present invention has a wide variety of applications. Accordingly, the following examples are offered by way of illustration, not by way of limitation.

EXPERIMENTAL EXAMPLES

In the examples below, the following abbreviations have the following meanings. If not defined below, then the abbreviations have their art recognized meanings.

| ml | = milliliter |
|---|---|
| μl | = microliters |
| μM | = micromolar |
| nM | = nanomolar |
| PBS | = phosphate buffered saline |
| ng | = nanograms |
| μg | = micrograms |
| IPTG | = isopropylthio-β-D-galactoside |
| bp | = basepairs |
| kb | = kilobasepairs |
| dNTP | = deoxynucleoside triphosphates |
| PCR | = polymerase chain reaction |
| X-gal | = 5-bromo-4-chloro-3-indolyl-β-D-galactoside |
| DNAseI | = deoxyribonuclease |
| PBS | = phosphate buffered saline |

-continued

| CDR | = complementarity determining regions |
|---|---|
| MIC | = minimum inhibitory concentration |
| scFv | = single-chain Fv fragment of an antibody |

In general, standard techniques of recombination DNA technology are described in various publications, e.g. Sambrook et al., 1989, Molecular Cloning: A Laboratory Manual, Cold Spring Harbor Laboratory; Ausubel et al., 1987, Current Protocols in Molecular Biology, vols. 1 and 2 and supplements, and Berger and Kimmel, *Methods in Enzymology. Volume* 152. *Guide to Molecular Cloning Techniques* (1987), Academic Press, Inc., San Diego, Calif., each of which is incorporated herein in their entirety by reference. Restriction enzymes and polynucleotide modifying enzymes were used according to the manufacturers recommendations. Oligonucleotides were synthesized on an Applied Biosystems Inc. Model 394 DNA synthesizer using ABI chemicals. If desired, PCR amplimers for amplifying a predetermined DNA sequence may be selected at the discretion of the practitioner.

EXAMPLES

Example 1

LacZ Alpha Gene Reassembly

1) Substrate preparation

The substrate for the reassembly reaction was the dsDNA polymerase chain reaction ("PCR") product of the wild-type LacZ alpha gene from pUC18. (FIG. 2) (28; Gene Bank No. XO2514) The primer sequences were 5'AAAGCGTC-GATTTTTGTGAT3' (SEQ ID NO:1) and 5'ATGGGGTTC-CGCGCACATTT3' (SEQ ID NO:2). The free primers were removed from the PCR product by Wizard PCR prep (Promega, Madison Wis.) according to the manufacturer's directions. The removal of the free primers was found to be important.

2) DNAseI digestion

About 5 μg of the DNA substrate was digested with 0.15 units of DNAseI (Sigma, St. Louis Mo.) in 100 μl of [50 mM Tris-HCl pH 7.4, 1 mM $MgCl_2$], for 10–20 minutes at room temperature. The digested DNA was run on a 2% low melting point agarose gel.

Fragments of 10–70 basepairs (bp) were purified from the 2% low melting point agarose gels by electrophoresis onto DE81 ion exchange paper (Whatman, Hillsborough Oreg.). The DNA fragments were eluted from the paper with 1 M NaCl and ethanol precipitated.

3) DNA Reassembly

The purified fragments were resuspended at a concentration of 10–30 ng/μl in PCR Mix (0.2 mM each dNTP, 2.2 mM $MgCl_2$, 50 mM KCl, 10 mM Tris-HCl pH 9.0, 0.1% Triton X-100, 0.3 μl Taq DNA polymerase, 50 μl total volume). No primers were added at this point. A reassembly program of 94° C. for 60 seconds, 30–45 cycles of [94° C. for 30 seconds, 50–55° C. for 30 seconds, 72° C. for 30 seconds] and 5 minutes at 72° C. was used in an MJ Research (Watertown Mass.) PTC-150 thermocycler. The PCR reassembly of small fragments into larger sequences was followed by taking samples of the reaction after 25, 30, 35, 40 and 45 cycles of reassembly (FIG. 2).

Whereas the reassembly of 100–200 bp fragments can yield a single PCR product of the correct size, 10–50 base fragments typically yield some product of the correct size, as well as products of heterogeneous molecular weights. Most of this size heterogeneity appears to be due to single-stranded sequences at the ends of the products, since after restriction enzyme digestion a single band of the correct size is obtained.

4) PCR with primers

Figure 2:
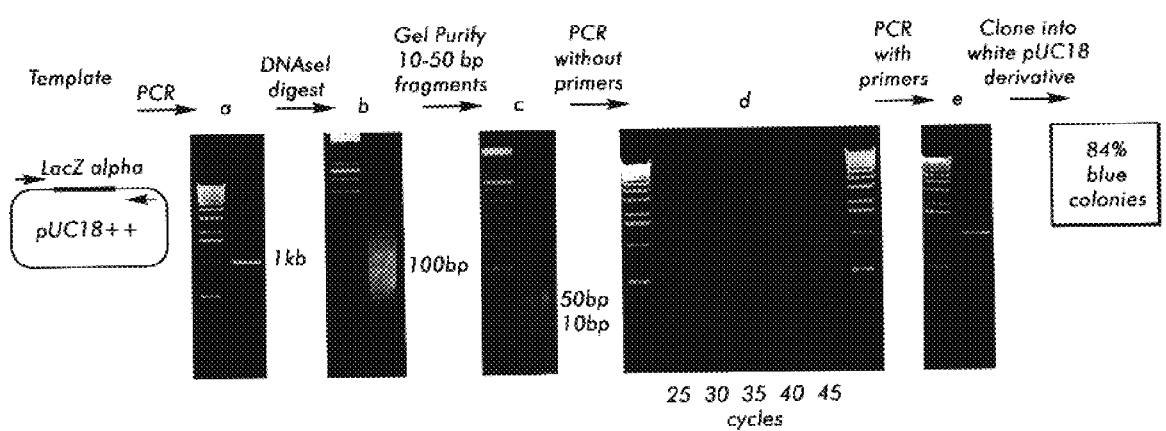
FIG. 2 illustrates the reassembly of a 1.0 kb LacZ alpha gene fragment from 10–50 bp random fragments. (a) Photograph of a gel of PCR amplified DNA fragment having the LacZ alpha gene. (b) Photograph of a gel of DNA fragments after digestion with DNAseI. (c) Photograph of a gel of DNA fragments of 10–50 bp purified from the digested LacZ alpha gene DNA fragment; (d) Photograph of a gel of the 10–50 bp DNA fragments after the indicated number of cycles of DNA reassembly; (e) Photograph of a gel of the recombination mixture after amplification by PCR with primers.

After dilution of the reassembly product into the PCR Mix with 0.8 µM of each of the above primers (SEQ ID Nos: 1 and 2) and about 15 cycles of PCR, each cycle consisting of [94° C. for 30 seconds, 50° C. for 30 seconds and 72° C. for 30 seconds], a single product of the correct size was obtained (FIG. 2).

5) Cloning and analysis

The PCR product from step 4 above was digested with the terminal restriction enzymes BamHI and EcoO109 and gel purified as described above in step 2. The reassembled fragments were ligated into pUC18 digested with BamHI and EcoO109. *E. coli* were transformed with the ligation mixture under standard conditions as recommended by the manufacturer (Stratagene, San Diego Calif.) and plated on agar plates having 100 µg/ml ampicillin, 0.004% X-gal and 2 mM IPTG. The resulting colonies having the HinDIII-NheI fragment which is diagnostic for the ++ recombinant were identified because they appeared blue.

This Example illustrates that a 1.0 kb sequence carrying the LacZ alpha gene can be digested into 10–70 bp fragments, and that these gel purified 10–70 bp fragments can be reassembled to a single product of the correct size, such that 84% (N=377) of the resulting colonies are LacZ$^+$ (versus 94% without shuffling; FIG. 2).

The DNA encoding the LacZ gene from the resulting LacZ$^-$ colonies was sequenced with a sequencing kit (United States Biochemical Co., Cleveland Ohio) according to the manufacturer's instructions and the genes were found to have point mutations due to the reassembly process (Table 1). 11/12 types of substitutions were found, and no frameshifts.

TABLE 1

Mutations introduced by mutagenic shuffling

| Transitions | Frequency | Transversions | Frequency |
|---|---|---|---|
| G - A | 6 | A - T | 1 |
| A - G | 4 | A - C | 2 |
| C - T | 7 | C - A | 1 |
| T - C | 3 | C - G | 0 |
|  |  | G - C | 3 |
|  |  | G - T | 2 |
|  |  | T - A | 1 |
|  |  | T - G | 2 |

A total of 4,437 bases of shuffled lacZ DNA were sequenced.

The rate of point mutagenesis during DNA reassembly from 10–70 bp pieces was determined from DNA sequencing to be 0.7% (N=4,473), which is similar to error-prone PCR. Without being limited to any theory it is believed that the rate of point mutagenesis may be lower if larger fragments are used for the reassembly, or if a proofreading polymerase is added.

When plasmid DNA from 14 of these point-mutated LacZ$^-$ colonies were combined and again reassembled/shuffled by the method described above, 34% (N=291) of the resulting colonies were LacZ$^+$, and these colonies presumably arose by recombination of the DNA from different colonies.

The expected rate of reversal of a single point mutation by error-prone PCR, assuming a mutagenesis rate of 0.7% (10), would be expected to be <1%.

Thus large DNA sequences can be reassembled from a random mixture of small fragments by a reaction that is surprisingly efficient and simple. One application of this technique is the recombination or shuffling of related sequences based on homology.

Example 2

LacZ Gene and Whole Plasmid DNA Shuffling

1) LacZ gene shuffling

Figure 3A:
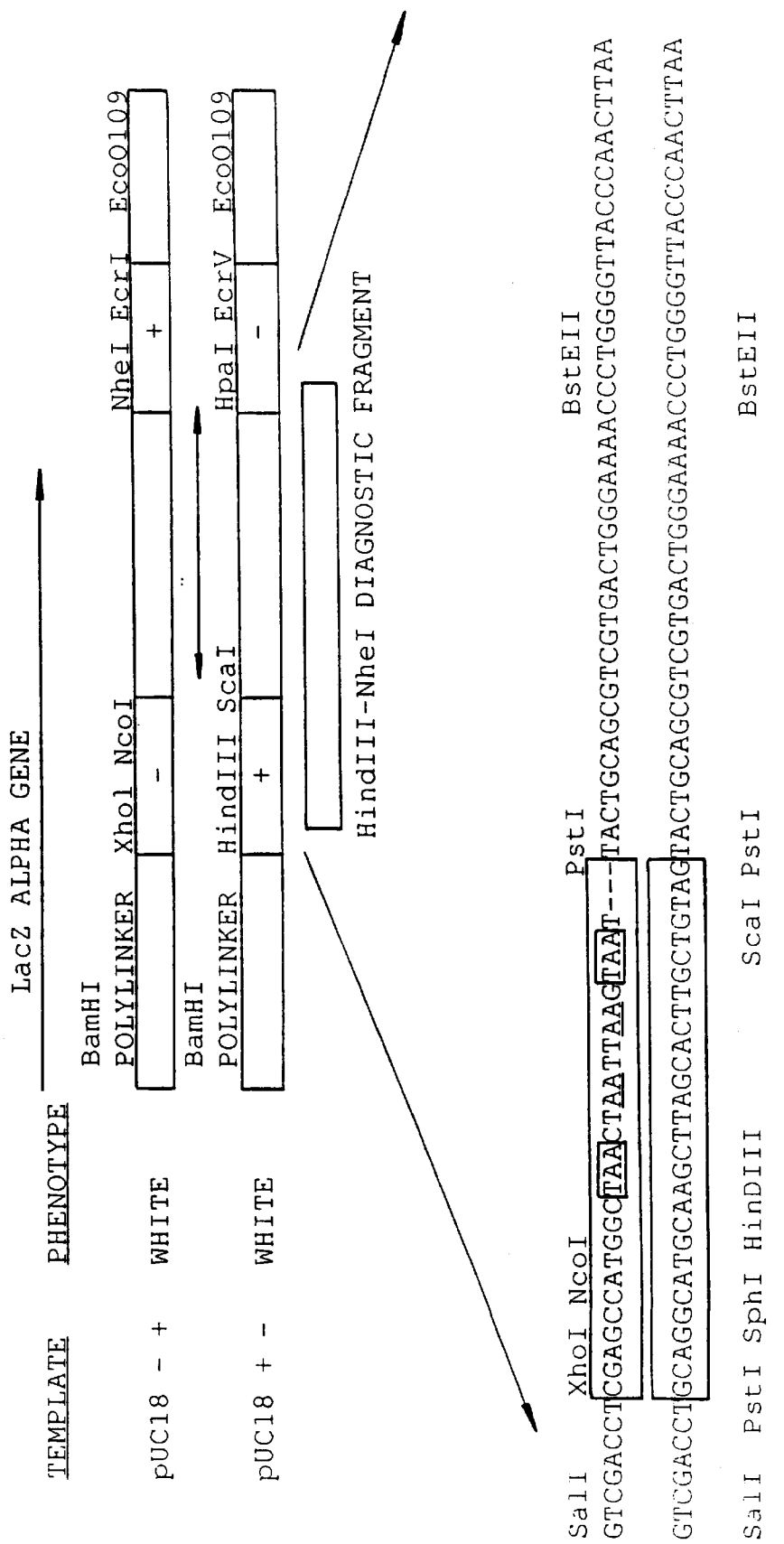
FIG. 3 (SEQ. ID NOS: 58–61) is a schematic illustration of the LacZ alpha gene stop codon mutants and their DNA sequences. The boxed regions are heterologous areas, serving as markers. The stop codons are located in smaller boxes or underlined. "+" indicates a wild-type gene and "−" indicates a mutated area in the gene.
Figure 3B:
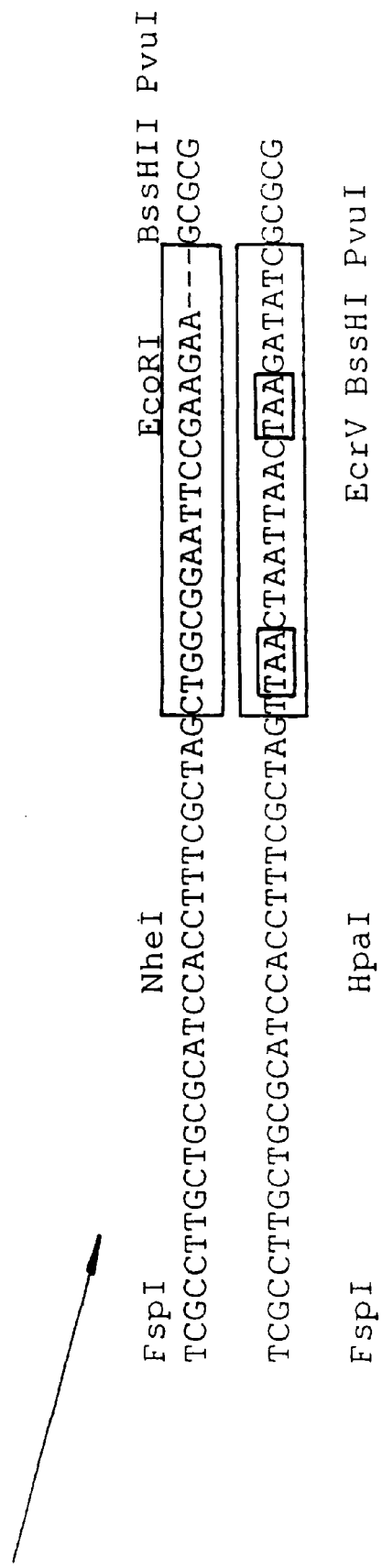

Crossover between two markers separated by 75 bases was measured using two LacZ gene constructs. Stop codons were inserted in two separate areas of the LacZ alpha gene to serve as negative markers. Each marker is a 25 bp non-homologous sequence with four stop codons, of which two are in the LacZ gene reading frame. The 25 bp non-homologous sequence is indicated in FIG. 3 by a large box. The stop codons are either boxed or underlined. A 1:1 mixture of the two 1.0 kb LacZ templates containing the +– and –+ versions of the LacZ alpha gene (FIG. 3) was digested with DNAseI and 100–200 bp fragments were purified as described in Example 1. The shuffling program was conducted under conditions similar to those described for reassembly in Example 1 except 0.5 µl of polymerase was added and the total volume was 100 µl.

After cloning, the number of blue colonies obtained was 24%; (N=386) which is close to the theoretical maximum number of blue colonies (i.e. 25%), indicating that recombination between the two markers was complete. All of the 10 blue colonies contained the expected HindIII-NheI restriction fragment.

2) Whole plasmid DNA shuffling

Whole 2.7 kb plasmids (pUC18–+ and pUC18+–) were also tested. A 1:1 mixture of the two 2.9 kb plasmids containing the +– and –+ versions of the LacZ alpha gene (FIG. 3) was digested with DNAseI and 100–200 bp fragments were purified as described in Example 1. The shuffling program was conducted under conditions similar to those described for reassembly in step (1) above except the program was for 60 cycles [94° C. for 30 seconds, 55° C. for 30 seconds, 72° C. for 30 seconds]. Gel analysis showed that after the shuffling program most of the product was greater than 20 kb. Thus, whole 2.7 kb plasmids (pUC18 –+ and pUC18 +–) were efficiently reassembled from random 100–200 bp fragments without added primers.

After digestion with a restriction enzyme having a unique site on the plasmid (EcoO109), most of the product consisted of a single band of the expected size. This band was gel purified, religated and the DNA used to transform *E. coli*. The transformants were plated on 0.004% X-gal plates as described in Example 1. 11% (N=328) of the resulting plasmids were blue and thus ++ recombinants.

3) Spiked DNA Shuffling

Figure 4:
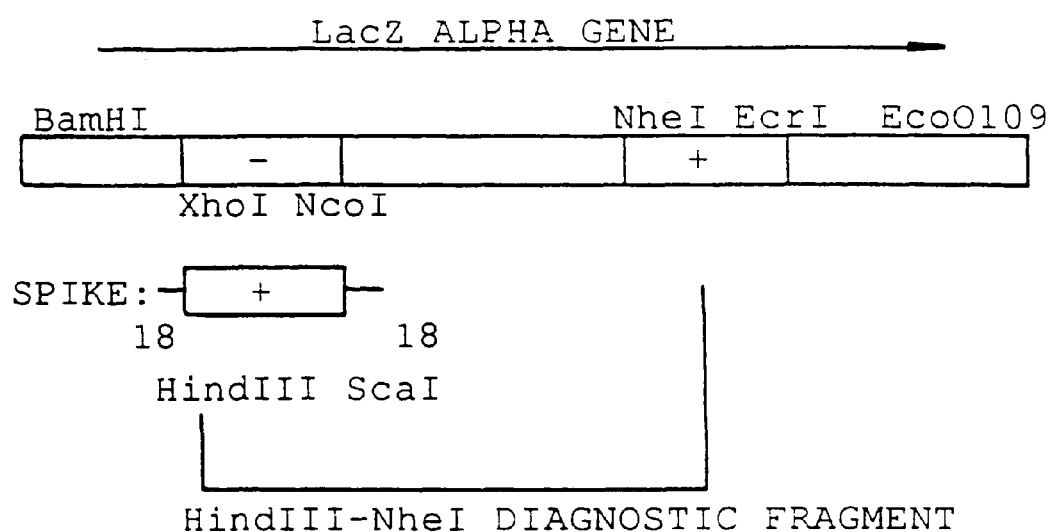
FIG. 4 is a schematic illustration of the introduction or spiking of a synthetic oligonucleotide into the reassembly process of the LacZ alpha gene.

Oligonucleotides that are mixed into the shuffling mixture can be incorporated into the final product based on the homology of the flanking sequences of the oligonucleotide to the template DNA (FIG. 4). The LacZ$^-$stop codon mutant (pUC18 –+) described above was used as the DNAseI digested template. A 66 mer oligonucleotide, including 18 bases of homology to the wild-type LacZ gene at both ends was added into the reaction at a 4-fold molar excess to correct stop codon mutations present in the original gene. The shuffling reaction was conducted under conditions similar to those in step 2 above. The resulting product was digested, ligated and inserted into *E. coli* as described above.

TABLE 2

| | % blue colonies |
|---|---|
| Control | 0.0 (N > 1000) |
| Top strand spike | 8.0 (N = 855) |
| Bottom strand spike | 9.3 (N = 620) |
| Top and bottom strand spike | 2.1 (N = 537) | ssDNA appeared to be more efficient than dsDNA, presumably due to competitive hybridization. The degree of incorporation can be varied over a wide range by adjusting the molar excess, annealing temperature, or the length of homology.

Example 3

DNA Reassembly in the Complete Absence of Primers

Plasmid pUC18 was digested with restriction enzymes EcoRI, EcoO109, XmnI and AlwNI, yielding fragments of approximately 370, 460, 770 and 1080 bp. These fragments were electrophoresed and separately purified from a 2% low melting point agarose gel (the 370 and 460 basepair bands could not be separated), yielding a large fragment, a medium fragment and a mixture of two small fragments in 3 separate tubes.

Each fragment was digested with DNAseI as described in Example 1, and fragments of 50–130 bp were purified from a 2% low melting point agarose gel for each of the original fragments.

PCR mix (as described in Example 1 above) was added to the purified digested fragments to a final concentration of 10 ng/µl of fragments. No primers were added. A reassembly reaction was performed for 75 cycles [94° C. for 30 seconds, 60° C. for 30 seconds] separately on each of the three digested DNA fragment mixtures, and the products were analyzed by agarose gel electrophoresis.

The results clearly showed that the 1080, 770 and the 370 and 460 bp bands reformed efficiently from the purified fragments, demonstrating that shuffling does not require the use of any primers at all.

Example 4

IL-1β Gene Shuffling

This example illustrates that crossovers based on homologies of less than 15 bases may be obtained. As an example, a human and a murine IL-1β gene were shuffled.

Figure 5A:
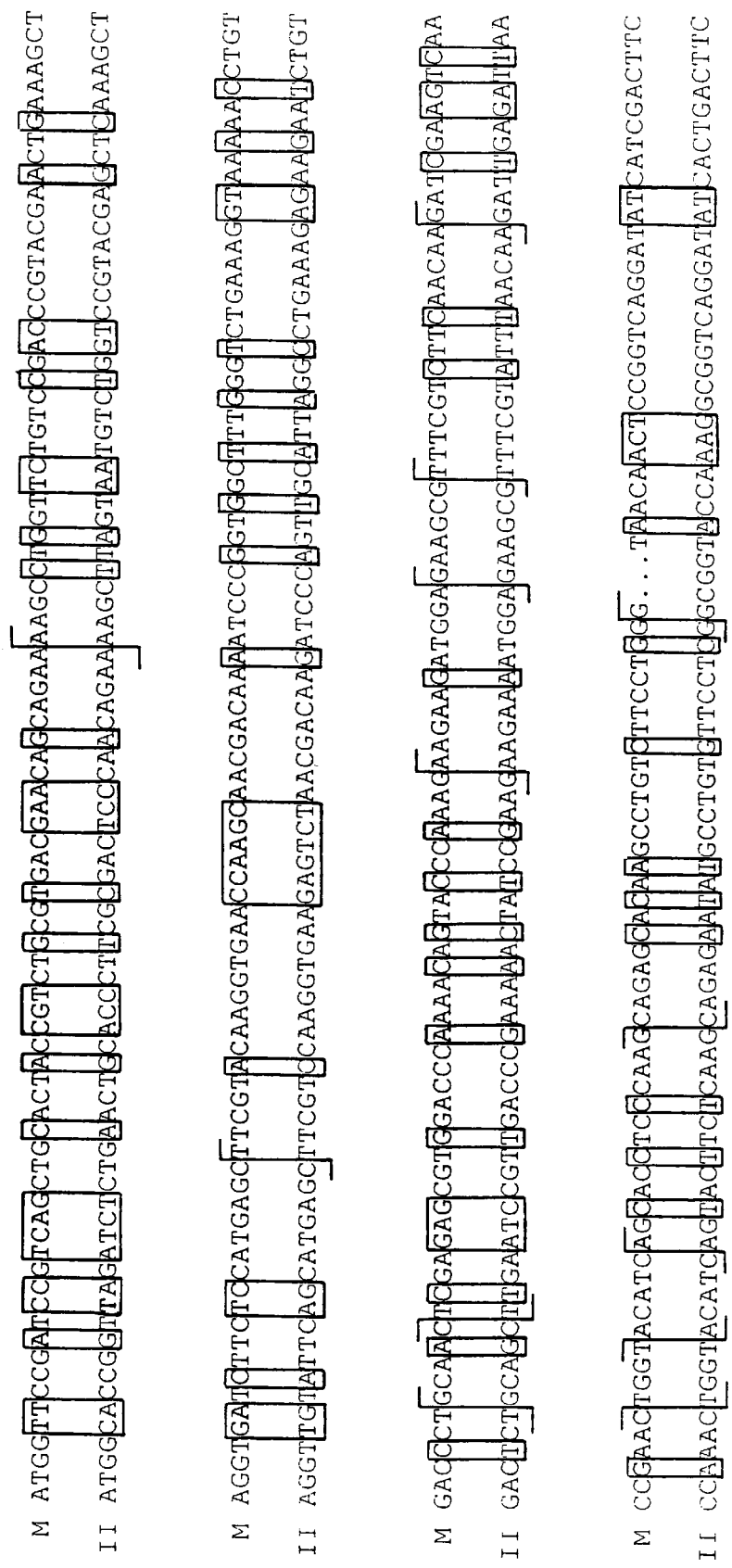
Figure 6:
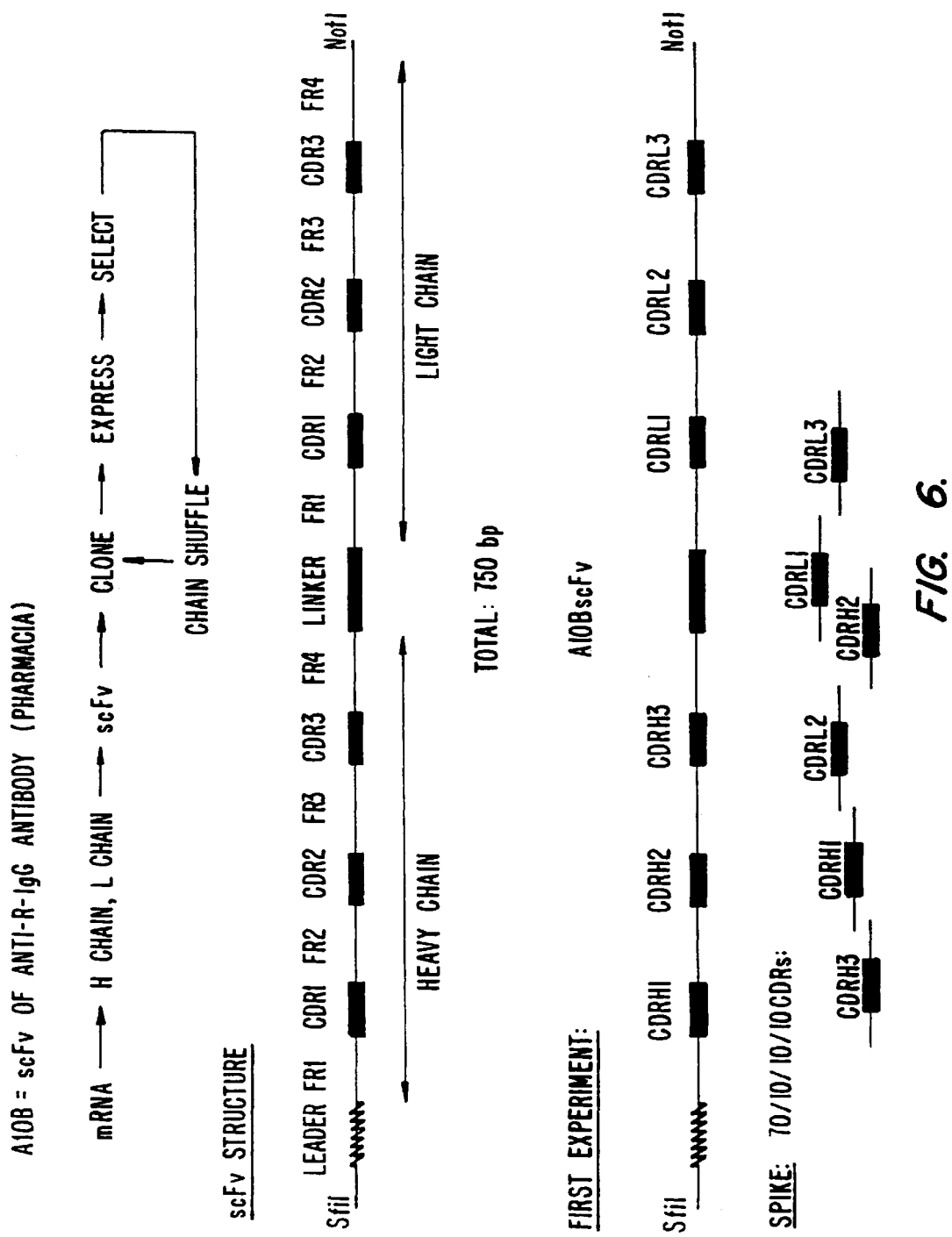
FIG. 6 is a schematic diagram of the antibody CDR shuffling model system using the scFv of anti-rabbit IgG antibody (A10B).
Figure 8:
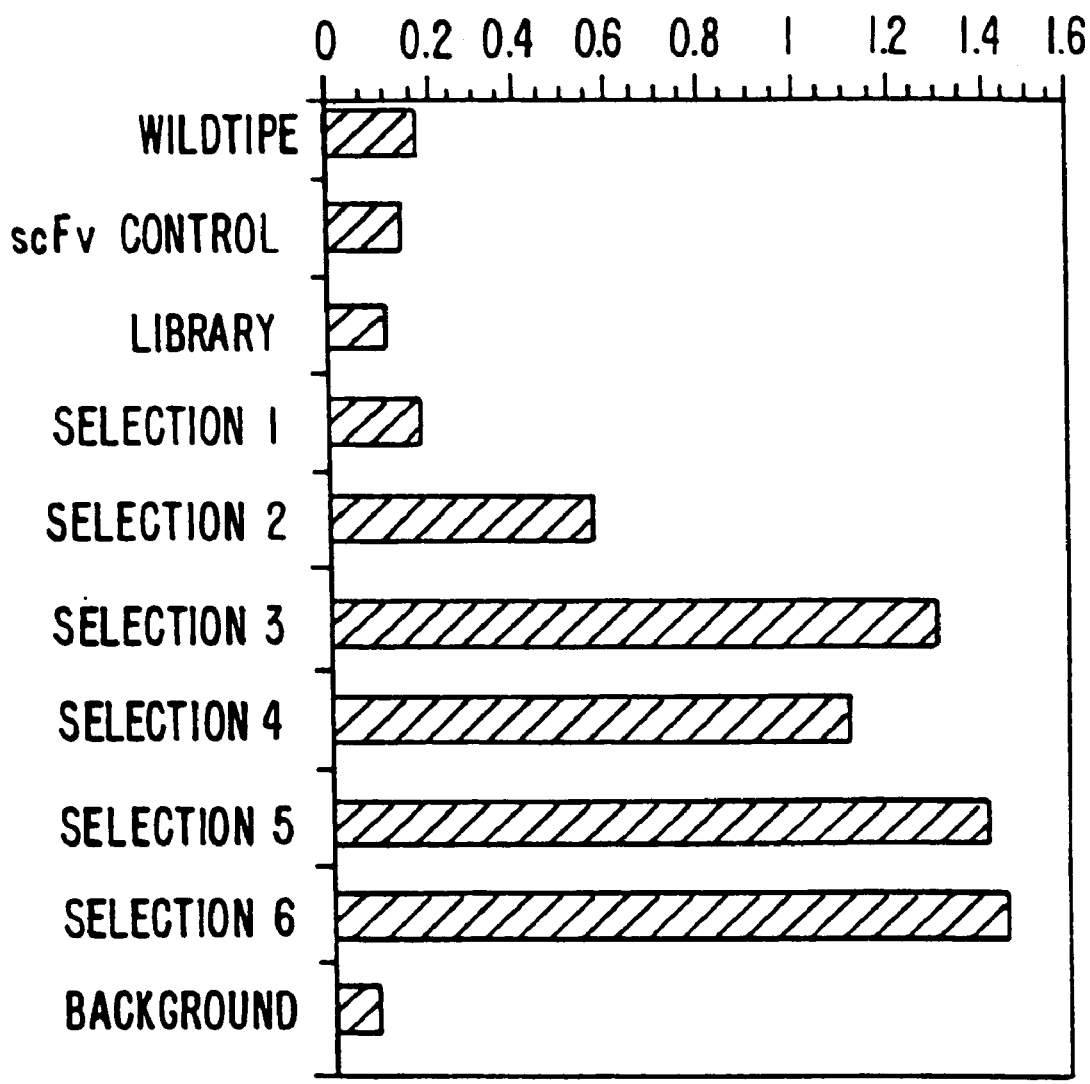
FIG. 8 illustrates the improved avidity of the scFv anti-rabbit antibody after DNA shuffling and each cycle of selection.

A murine IL1-β gene (BBG49) and a human IL1-β gene with *E. coli* codon usage (BBG2; R&D Systems, Inc., Minneapolis Minn.) were used as templates in the shuffling reaction. The areas of complete homology between the human and the murine IL-1β sequences are on average only 4.1 bases long (FIG. 5, regions of heterology are boxed).

Preparation of dsDNA PCR products for each of the genes, removal of primers, DNAseI digestion and purification of 10–50 bp fragments was similar to that described above in Example 1. The sequences of the primers used in the PCR reaction were 5'TTAGGCACCCCAGGCTTT3' (SEQ ID NO:3) and 5'ATGTGCTGCAAGGCGATT3' (SEQ ID NO:4).

The first 15 cycles of the shuffling reaction were performed with the Klenow fragment of DNA polymerase I, adding 1 unit of fresh enzyme at each cycle. The DNA was added to the PCR mix of Example 1 which mix lacked the polymerase. The manual program was 94° C. for 1 minute, and then 15 cycles of: [95° C. for 1 minute, 10 seconds on dry ice/ethanol (until frozen), incubate about 20 seconds at 25° C., add 1U of Klenow fragment and incubate at 25° C. for 2 minutes]. In each cycle after the denaturation step, the tube was rapidly cooled in dry ice/ethanol and reheated to the annealing temperature. Then the heat-labile polymerase was added. The enzyme needs to be added at every cycle. Using this approach, a high level of crossovers was obtained, based on only a few bases of uninterrupted homology (FIG. 5, positions of cross-overs indicated by "⌋⌐")

After these 15 manual cycles, Taq polymerase was added and an additional 22 cycles of the shuffling reaction [94° C. for 30 seconds, 35° C. for 30 seconds] without primers were performed.

The reaction was then diluted 20-fold. The following primers were added to a final concentration of 0.8 µM: 5'AACGCCGCATGCAAGCTTGGATCCTTATT3' (SEQ ID NO:5) and 5'AAAGCCCTCTAGATGATTACGAAT-TCATAT3' (SEQ ID NO:6) and a PCR reaction was performed as described above in Example 1. The second primer pair differed from the first pair only because a change in restriction sites was deemed necessary.

After digestion of the PCR product with XbaI and SphI, the fragments were ligated into XbaI-SphI-digested pUC18. The sequences of the inserts from several colonies were determined by a dideoxy DNA sequencing kit (United States Biochemical Co., Cleveland Ohio) according to the manufacturer's instructions.

A total of 17 crossovers were found by DNA sequencing of nine colonies. Some of the crossovers were based on only 1–2 bases of uninterrupted homology.

It was found that to force efficient crossovers based on short homologies, a very low effective annealing temperature is required. With any heat-stable polymerase, the cooling time of the PCR machine (94° C. to 25° C. at 1–2 degrees/second) causes the effective annealing temperature to be higher than the set annealing temperature. Thus, none of the protocols based on Taq polymerase yielded crossovers, even when a ten-fold excess of one of the ILL-β genes was used. In contrast, a heat-labile polymerase, such as the Klenow fragment of DNA polymerase I, can be used to accurately obtain a low annealing temperature.

Example 5

DNA Shuffling of the TEM-1 Betalactamase Gene

The utility of mutagenic DNA shuffling for directed molecular evolution was tested in a betalactamase model system. TEM-1 betalactamase is a very efficient enzyme, limited in its reaction rate primarily by diffusion. This example determines whether it is possible to change its reaction specificity and obtain resistance to the drug cefotaxime that it normally does not hydrolyze.

The minimum inhibitory concentration (MIC) of cefotaxime on bacterial cells lacking a plasmid was determined by plating 10 µl of a $10^{-2}$ dilution of an overnight bacterial culture (about 1000 cfu) of *E. coli* XL1-blue cells (Stratagene, San Diego Calif.) on plates with varying levels of cefotaxime (Sigma, St. Louis Mo.), followed by incubation for 24 hours at 37° C.

Growth on cefotaxime is sensitive to the density of cells, and therefore similar numbers of cells needed to be plated on each plate (obtained by plating on plain LB plates). Platings of 1000 cells were consistently performed.

1) Initial Plasmid Construction

A pUC18 derivative carrying the bacterial TEM-1 beta-lactamase gene was used (28). The TEM-1 betalactamase gene confers resistance to bacteria against approximately 0.02 μg/ml of cefotaxime. SfiI restriction sites were added 5' of the promoter and 3' of the end of the gene by PCR of the vector sequence with two primers: Primer A (SEQ ID NO:7): 5'TTCTATTGACGGCCTGTCA GGCCTCATATATACTTTAGATTGATTT3' and Primer B (SEQ ID NO:8): 5'TTGACGCACTGGCCATGGT GGCCAAAAATAAACAAATAGGGGTTCCGCGCACA TTT3' and by PCR of the betalactamase gene sequence with two other primers: Primer C (SEQ ID NO:9): 5'AACTGAC-CACGGCCTGACA GGCCGGTCTGACAGTTACCAATGCTT, and Primer D (SEQ ID NO:10): 5'AACCTGTCCTGGCCACCAT GGCCTAAATACATTCAAATATGTAT.

The two reaction products were digested with SfiI, mixed, ligated and used to transform bacteria.

The resulting plasmid was pUC182Sfi. This plasmid contains an Sfi1 fragment carrying the TEM-1 gene and the P-3 promoter.

The minimum inhibitory concentration of cefotaxime for *E. coli* XL1-blue (Stratagene, San Diego Calif.) carrying this plasmid was 0.02 μg/ml after 24 hours at 37° C.

The ability to improve the resistance of the betalactamase gene to cefotaxime without shuffling was determined by stepwise replating of a diluted pool of cells (approximately $10^7$ cfu) on 2-fold increasing drug levels. Resistance up to 1.28 μg/ml could be obtained without shuffling. This represented a 64 fold increase in resistance.

2) DNAseI digestion

The substrate for the first shuffling reaction was dsDNA of 0.9 kb obtained by PCR of pUC182Sfi with primers C and D, both of which contain a SfiI site.

The free primers from the PCR product were removed by Wizard PCR prep (Promega, Madison Wis.) at every cycle.

About 5 μg of the DNA substrate(s) was digested with 0.15 units of DNAseI (Sigma, St. Louis Mo.) in 100 μl of 50 mM Tris-HCl pH 7.4, 1 mM $MgCl_2$, for 10 min at room temperature. Fragments of 100–300 bp were purified from 2% low melting point agarose gels by electrophoresis onto DE81 ion exchange paper (Whatman, Hillsborough Oreg.), elution with 1 M NaCl and ethanol precipitation by the method described in Example 1.

3) Gene shuffling

The purified fragments were resuspended in PCR mix (0.2 mM each dNTP, 2.2 mM $MgCl_2$, 50 mM KCl, 10 mM Tris-HCl pH 9.0, 0.1% Triton X-100), at a concentration of 10–30 ng/μl. No primers were added at this point. A reassembly program of 94° C. for 60 seconds, then 40 cycles of [94° C. for 30 seconds, 50–55° C. for 30 seconds, 72° C. for 30 seconds] and then 72° C. for 5 minutes was used in an MJ Research (Watertown Mass.) PTC-150 thermocycler.

4) Amplification of Reassembly Product with primers

After dilution of the reassembly product into the PCR mix with 0.8 μM of each primer (C and D) and 20 PCR cycles [94° C. for 30 seconds, 50° C. for 30 seconds, 72° C. for 30 seconds] a single product 900 bp in size was obtained.

5) Cloning and analysis

After digestion of the 900 bp product with the terminal restriction enzyme SfiI and agarose gel purification, the 900 bp product was ligated into the vector pUC182Sfi at the unique SfiI site with T4 DNA ligase (BRL, Gaithersburg Md.). The mixture was electroporated into *E. coli* XL1-blue cells and plated on LB plates with 0.32–0.64 μg/ml of cefotaxime (Sigma, St. Louis Mo.). The cells were grown for up to 24 hours at 37° C. and the resulting colonies were scraped off the plate as a pool and used as the PCR template for the next round of shuffling.

6) Subsequent Reassembly Rounds

The transformants obtained after each of three rounds of shuffling were plated on increasing levels of cefotaxime. The colonies (>100, to maintain diversity) from the plate with the highest level of cefotaxime were pooled and used as the template for the PCR reaction for the next round.

A mixture of the cefotaxime$^r$ colonies obtained at 0.32–0.64 μg/ml in Step (5) above were used as the template for the next round of shuffling. 10 ul of cells in LB broth were used as the template in a reassembly program of 10 minutes at 99° C., then 35 cycles of [94° C. for 30 seconds, 52° C. for 30 seconds, 72° C. for 30 seconds] and then 5 minutes at 72° C. as described above.

The reassembly products were digested and ligated into pUC182Sfi as described in step (5) above. The mixture was electroporated into *E. coli* XL1-blue cells and plated on LB plates having 5–10 μg/ml of cefotaxime.

Colonies obtained at 5–10 μg/ml were used for a third round similar to the first and second rounds except the cells were plated on LB plates having 80–160 μg/ml of cefotaxime. After the third round, colonies were obtained at 80–160 μg/ml, and after replating on increasing concentrations of cefotaxime, colonies could be obtained at up to 320 μg/ml after 24 hours at 37° C. (MIC=320 μg/ml).

Growth on cefotaxime is dependent on the cell density, requiring that all the MICs be standardized (in our case to about 1,000 cells per plate). At higher cell densities, growth at up to 1280 μg/ml was obtained. The 5 largest colonies grown at 1,280 μg/ml were plated for single colonies twice, and the Sfi1 inserts were analyzed by restriction mapping of the colony PCR products.

One mutant was obtained with a 16,000 fold increased resistance to cefotaxime (MIC=0.02 μg/ml to MIC=320 μg/ml).

After selection, the plasmid of selected clones was transferred back into wild-type *E. coli* XL1-blue cells (Stratagene, San Diego Calif.) to ensure that none of the measured drug resistance was due to chromosomal mutations.

Three cycles of shuffling and selection yielded a $1.6 \times 10^4$-fold increase in the minimum inhibitory concentration of the extended broad spectrum antibiotic cefotaxime for the TEM-1 betalactamase. In contrast, repeated plating without shuffling resulted in only a 16-fold increase in resistance (error-prone PCR or cassette mutagenesis).

7) Sequence analysis

All 5 of the largest colonies grown at 1,280 μg/ml had a restriction map identical to the wild-type TEM-1 enzyme. The SfiI insert of the plasmid obtained from one of these colonies was sequenced by dideoxy DNA sequencing (United States Biochemical Co., Cleveland Ohio) according to the manufacturer's instructions. All the base numbers correspond to the revised pBR322 sequence (29), and the amino acid numbers correspond to the ABL standard numbering scheme (30). The amino acids are designated by their three letter codes and the nucleotides by their one letter codes. The term G4205A means that nucleotide 4205 was changed from guanidine to adenine.

Nine single base substitutions were found. G4205A is located between the −35 and −10 sites of the betalactamase P3 promoter (31). The promoter up-mutant observed by Chen and Clowes (31) is located outside of the Sfi1 fragment used here, and thus could not have been detected. Four mutations were silent (A3689G, G3713A, G3934A and T3959A), and four resulted in an amino acid change (C3448T resulting in Gly238Ser, A3615G resulting in Met182Thr, C3850T resulting in Glu104Lys, and G4107A resulting in Ala18Val).

8) Molecular Backcross

Molecular backcrossing with an excess of the wild-type DNA was then used in order to eliminate non-essential mutations.

Molecular backcrossing was conducted on a selected plasmid from the third round of DNA shuffling by the method identical to normal shuffling as described above, except that the DNAseI digestion and shuffling reaction were performed in the presence of a 40-fold excess of wild-type TEM-1 gene fragment. To make the backcross more efficient, very small DNA fragments (30 to 100 bp) were used in the shuffling reaction. The backcrossed mutants were again selected on LB plates with 80–160 µg/ml of cefotaxime (Sigma, St. Louis Mo.).

This backcross shuffling was repeated with DNA from colonies from the first backcross round in the presence of a 40-fold excess of wild-type TEM-1 DNA. Small DNA fragments (30–100 bp) were used to increase the efficiency of the backcross. The second round of backcrossed mutants were again selected on LB plates with 80–160 µg/ml of cefotaxime.

The resulting transformants were plated on 160 µg/ml of cefotaxime, and a pool of colonies was replated on increasing levels of cefotaxime up to 1,280 µg/ml. The largest colony obtained at 1,280 µg/ml was replated for single colonies.

This backcrossed mutant was 32,000 fold more resistant than wild-type. (MIC=640 µg/ml) The mutant strain is 64-fold more resistant to cefotaxime than previously reported clinical or engineered TEM-1-derived strains. Thus, it appears that DNA shuffling is a fast and powerful tool for at least several cycles of directed molecular evolution.

The DNA sequence of the SfiI insert of the backcrossed mutant was determined using a dideoxy DNA sequencing kit (United States Biochemical Co., Cleveland Ohio) according to the manufacturer's instructions (Table 3). The mutant had 9 single base pair mutations. As expected, all four of the previously identified silent mutations were lost, reverting to the sequence of the wild-type gene. The promoter mutation (G4205A) as well as three of the four amino acid mutations (Glu104Lys, Met182Thr, and Gly238Ser) remained in the backcrossed clone, suggesting that they are essential for high level cefotaxime resistance. However, two new silent mutations (T3842C and A3767G), as well as three new mutations resulting in amino acid changes were found (C3441T resulting in Arg241His, C3886T resulting in Gly92Ser, and G4035C resulting in Ala42Gly). While these two silent mutations do not affect the protein primary sequence, they may influence protein expression level (for example by mRNA structure) and possibly even protein folding (by changing the codon usage and therefore the pause site, which has been implicated in protein folding).

TABLE 3

Mutations in Betalactamase

| Mutation Type | Non-Backcrossed | Backcrossed |
| --- | --- | --- |
| amino acid change | Ala18Lys | — |
|  | Glu104Lys | Glu104Lys |
|  | Met182Thr | Met182Thr |

TABLE 3-continued

Mutations in Betalactamase

| Mutation Type | Non-Backcrossed | Backcrossed |
| --- | --- | --- |
|  | Gly238Ser | Gly238Ser |
|  | — | Ala42Gly |
|  | — | Gly92Ser |
| silent | T3959A | — |
|  | G3934A | — |
|  | G3713A | — |
|  | A3689G | — |
|  | — | T3842C |
|  | — | A3767G |
| promoter | G4205A | G4205A |

Both the backcrossed and the non-backcrossed mutants have a promoter mutation (which by itself or in combination results in a 2–3 fold increase in expression level) as well as three common amino acid changes (Glu104Lys, Met182Thr and Gly238Ser). Glu104Lys and Gly238Ser are mutations that are present in several cefotaxime resistant or other TEM-1 derivatives (Table 4).

9) Expression Level Comparison

The expression level of the betalactamase gene in the wild-type plasmid, the non-backcrossed mutant and in the backcrossed mutant was compared by SDS-polyacrylamide gel electrophoresis (4–20%; Novex, San Diego Calif.) of periplasmic extracts prepared by osmotic shock according to the method of Witholt, B. (32).

Purified TEM-1 betalactamase (Sigma, St. Louis Mo.) was used as a molecular weight standard, and *E. coli* XL1-blue cells lacking a plasmid were used as a negative control.

The mutant and the backcrossed mutant appeared to produce a 2–3 fold higher level of the betalactamase protein compared to the wild-type gene. The promoter mutation appeared to result in a 2–3 times increase in betalactamase.

Example 6

Construction of Mutant Combinations of the TEM-1 Betalactamase Gene

To determine the resistance of different combinations of mutations and to compare the new mutants to published mutants, several mutants were constructed into an identical plasmid background. Two of the mutations, Glu104Lys and Gly238Ser, are known as cefotaxime mutants. All mutant combinations constructed had the promoter mutation, to allow comparison to selected mutants. The results are shown in Table 4.

Specific combinations of mutations were introduced into the wild-type pUC182Sfi by PCR, using two oligonucleotides per mutation.

The oligonucleotides to obtain the following mutations were:

Ala42Gly
 (SEQ ID NO:11) AGTTGGGTG
 GACGAGTGGGTTACATCGAACT and (SEQ ID
 NO:12) AACCCACTCGT
 CCACCCAACTGATCTTCAGCAT;
Gln39Lys:
 (SEQ ID NO:13) AGTAAAAGATGCTGAAGAT
 AAGTTGGGTGCAC GAGTGGGTT and (SEQ ID
 NO:14) ACTTATCTTCAGCATCTTTTACTT;
Gly92Ser:
 (SEQ ID NO:15) AAGAGCAACTC
 AGTCGCCGCATACACTATTCT and (SEQ ID NO:16) ATGGCGGCGAC TGAGTTGCTCTTGCCCGGCGTCAAT;
Glu104Lys:
(SEQ ID NO:17) TATTCTCAGAATGACTTGGTT AAGTACTCACCAGT CACAGAA and (SEQ ID NO:18) TTAACCAAGTCATTCTGAGAAT;
Met182Thr:
(SEQ ID NO:19) AACGACGAGCGTGACACCACGA CGCCTGTAGCAATG and (SEQ ID NO:20) TCGTG-GTGTCACGCTCGTCGTT;
Gly238Ser alone:
(SEQ ID NO:21) TTGCTGATAAATCTGGAGCC AGTGAGCGTGGGTCTC GCGGTA and (SEQ ID NO:22) TGGCTCCAGATTTATCAGCAA;
Gly238Ser and Arg241His (combined):
(SEQ ID NO:23) ATGCTCAC TGGCTCCAGATTTATCAGCAAT and
(SEQ ID NO:24) TCTGGAGCCAGTGAGC ATGGGTCTCGCGGTATCATT; G4205A:
(SEQ ID NO:25) AACCTGTCCTGGCCACCAT GGCCTAAATACAATCAAA TATGTATCCGCT TATGAGACAATAACCCTGATA.

These separate PCR fragments were gel purified away from the synthetic oligonucleotides. 10 ng of each fragment were combined and a reassembly reaction was performed at 94° C. for 1 minute and then 25 cycles; [94° C. for 30 sec, 50° C. for 30 seconds and 72° C. for 45 seconds]. PCR was performed on the reassembly product for 25 cycles in the presence of the SfiI-containing outside primers (primers C and D from Example 5). The DNA was digested with Sfi1 and inserted into the wild-type pUC182Sfi vector. The following mutant combinations were obtained (Table 4).

TABLE 4

| Name | Genotype | MIC | Source of MIC |
|------|----------|-----|---------------|
| TEM-1 | Wild-type | 0.02 | |
| | Glu104Lys | 0.08 | 10 |
| | Gly238Ser | 016 | 10 |
| TEM-15 | Glu104Lys/Gly238Ser* | 10 | |
| TEM-3 | Glu104Lys/Gly238Ser/Gln39Lys | 102–32 | 37, 15 |
| ST-4 | Glu104Lys/Gly238Ser/Met182 Thr* | 10 | |
| ST-1 | Glu104Lys/Gly238Ser/Met182 Thr/Ala18Val/T3959A/G3713A/ G3934A/A3689G* | 320 | |
| ST-2 | Glu104Lys/Gly238Ser/Met182Thr/ Ala42Gly/Gly92Ser/Arg241His/ T3842C/A3767G* | 640 | |
| ST-3 | Glu104Lys/Gly238Ser/Met182Thr/ Ala42Gly/Gly92Ser/Arg241His* | 640 | |

*All of these mutants additionally contain the G4205A promoter mutation.

It was concluded that conserved mutations account for 9 of 15 doublings in the MIC.

Glu104Lys alone was shown to result only in a doubling of the MIC to 0.08 µg/ml, and Gly238Ser (in several contexts with one additional amino acid change) resulted only in a MIC of 0.16 µg/ml (26). The double mutant Glu104Lys/Gly238Ser has a MIC of 10 µg/ml. This mutant corresponds to TEM-15.

These same Glu104Lys and Gly238Ser mutations, in combination with Gln39Lys (TEM-3) or Thr263Met (TEM-4) result in a high level of resistance (2–32 µg/ml for TEM-3 and 8–32 µg/ml for TEM-4 (34, 35).

A mutant containing the three amino acid changes that were conserved after the backcross (Glu104Lys/Met182Thr/Gly238Ser) also had a MIC of 10 µg/ml. This meant that the mutations that each of the new selected mutants had in addition to the three known mutations were responsible for a further 32 to 64-fold increase in the resistance of the gene to cefotaxime.

The naturally occurring, clinical TEM-1-derived enzymes (TEM-1–19) each contain a different combination of only 5–7 identical mutations (reviews). Since these mutations are in well separated locations in the gene, a mutant with high cefotaxime resistance cannot be obtained by cassette mutagenesis of a single area. This may explain why the maximum MIC that was obtained by the standard cassette mutagenesis approach is only 0.64 µg/ml (26). For example, both the Glu104Lys as well as the Gly238Ser mutations were found separately in this study to have MICs below 0.16 µg/ml. Use of DNA shuffling allowed combinatoriality and thus the Glu104Lys/Gly238Ser combination was found, with a MIC of 10 µg/ml.

An important limitation of this example is the use of a single gene as a starting point. It is contemplated that better combinations can be found if a large number of related, naturally occurring genes are shuffled. The diversity that is present in such a mixture is more meaningful than the random mutations that are generated by mutagenic shuffling. For example, it is contemplated that one could use a repertoire of related genes from a single species, such as the pre-existing diversity of the immune system, or related genes obtained from many different species.

Example 7

Improvement of Antibody A10B by DNA Shuffling of a Library of all six mutant CDRs.

The A10B scFv antibody, a mouse anti-rabbit IgG, was a gift from Pharmacia (Milwaukee Wis.). The commercially available Pharmacia phage display system was used, which uses the pCANTAB5 phage display vector.

The original A10B antibody reproducibly had only a low avidity, since clones that only bound weakly to immobilized antigen (rabbit IgG), (as measured by phage ELISA (Pharmacia assay kit) or by phage titer) were obtained. The concentration of rabbit IgG which yielded 50% inhibition of the A10B antibody binding in a competition assay was 13 picomolar. The observed low avidity may also be due to instability of the A10B clone.

The A10B scFv DNA was sequenced (United States Biochemical Co., Cleveland Ohio) according to the manufacturer's instructions. The sequence was similar to existing antibodies, based on comparison to Kabat (33).

1) Preparation of phage DNA

Phage DNA having the A10B wild-type antibody gene (10 ul) was incubated at 99° C. for 10 min, then at 72° C. for 2 min. PCR mix (50 mM KCl, 10 mM Tris-HCl pH 9.0, 0.1% Triton X-100, 200 µM each dNTP, 1.9 mM MgCl), 0.6 µm of each primer and 0.5 µl Taq DNA Polymerase (Promega, Madison Wis.) was added to the phage DNA. A PCR program was run for 35 cycles of [30 seconds at 94° C., 30 seconds at 45° C., 45 seconds at 72° C.]. The primers used were: 5' ATGATTACGCCAAGCTTT 3' (SEQ ID NO:26) and 5"TTGTCGTCTTTCCAGACGTT 3' (SEQ ID NO:27).

The 850 bp PCR product was then electrophoresed and purified from a 2% low melting point agarose gel.

2) Fragmentation 300 ng of the gel purified 850 bp band was digested with 0.18 units of DNAse I (Sigma, St. Louis Mo.) in 50 mM Tris-HCl pH 7.5, 10 mM MgCl for 20 minutes at room temperature. The digested DNA was separated on a 2% low melting point agarose gel and bands between 50 and 200 bp were purified from the gel.

3) Construction of Test Library

The purpose of this experiment was to test whether the insertion of the CDRs would be efficient.

The following CDR sequences having internal restriction enzyme sites were synthesized. "CDR H" means a CDR in the heavy chain and "CDR L" means a CDR in the light chain of the antibody. CDR Oligos with restriction sites:

CDR H1 (SEQ ID NO:34)
    5'TTCTGGCTACATCTTCACAGAAT-TCATCTAGATTTGGGTGAGGCAGACGC-CTGAA3'

CDR H2 (SEQ ID NO:35)
    5'ACAGGGACTTGAGTGGATTGGAATCA-CAGTCAAGCTTATCCTTTATCTCAG-GTCTCGAGT TCCAAGTACTTAAAGGGCCA-CACTGAGTGTA 3'

CDR H3 (SEQ ID NO:36)
    5'TGTCTATTTCTGTGCTAGATCTTGACTG-CAGTCTTATACGAGGATCCATTGGGGCCAAGG GACCAGGTCA 3'

CDR L1 (SEQ ID NO:37)
    5'AGAGGGTCACCATGACCTGCG-GACGTCTTTAAGCGATCGGGCTGATGGC-CTGGTACCAAC AGAAGCCTGGAT 3'

CDR L2 (SEQ ID NO:38)
    5'TCCCCCAGACTCCTGATTTATTAAGG-GAGATCTAAACAGCTGTTGGTC-CCTTTTCGCTTCAGT 3'

CDR L3 (SEQ ID NO:39)
    5'ATGCTGCCACTTATTACTGCTTCT-GCGCGCTTAAAGGATATCTTCATTTCG-GAGGGGGGA CCAAGCT 3'

The CDR oligos were added to the purified A10B antibody DNA fragments of between 50 to 200 bp from step (2) above at a 10 fold molar excess. The PCR mix (50 mM KCl, 10 mM Tris-HCl pH 9.0, 0.1% Triton x-100, 1.9 mM MgCl, 200 μm each dNTP, 0.3 μl Taq DNA polymerase (Promega, Madison Wis.), 50 μl total volume) was added and the shuffling program run for 1 min at 94° C., 1 min at 72° C., and then 35 cycles: 30 seconds at 94° C., 30 seconds at 55° C., 30 seconds at 72° C.

1 μl of the shuffled mixture was added to 100 μl of a PCR mix (50 mM KCl, 10 mM Tris-HCl pH 9.0, 0.1% Triton X-100, 200 μm each dNTP, 1.9 mM MgCl, 0.6 μM each of the two outside primers (SEQ ID NO:26 and 27, see below), 0.5 μl Taq DNA polymerase) and the PCR program was run for 30 cycles of [30 seconds at 94° C., 30 seconds at 45° C., 45 seconds at 72° C.]. The resulting mixture of DNA fragments of 850 basepair size was phenol/chloroform extracted and ethanol precipitated.

The outside primers were:
Outside Primer 1: SEQ ID NO:27
    5' TTGTCGTCTTTCCAGACGTT 3'
Outside Primer 2: SEQ ID NO:26
    5' ATGATTACGCCAAGCTTT 3'

The 850 bp PCR product was digested with the restriction enzymes SfiI and NotI, purified from a low melting point agarose gel, and ligated into the pCANTAB5 expression vector obtained from Pharmacia, Milwaukee Wis. The ligated vector was electroporated according to the method set forth by Invitrogen (San Diego Calif.) into TG1 cells (Pharmacia, Milwaukee Wis.) and plated for single colonies.

The DNA from the resulting colonies was added to 100 μl of a PCR mix (50 mM KCl, 10 mM Tris-HCl pH 9.0, 0.1% Triton X-100, 200 μm each dNTP, 1.9 mM MgCl, 0.6 μM of Outside primer 1 (SEQ ID No. 27; see below) six inside primers (SEQ ID NOS:40–45; see below), and 0.5 μl Taq DNA polymerase) and a PCR program was run for 35 cycles of [30 seconds at 94° C., 30 seconds at 45° C., 45 seconds at 72° C.]. The sizes of the PCR products were determined by agarose gel electrophoresis, and were used to determine which CDRs with restriction sites were inserted.

CDR Inside Primers:
    H 1 (SEQ ID NO:40) 5' AGAATTCATCTAGATTTG 3',
    H 2 (SEQ ID NO:41) 5' GCTTATCCTTTATCTCAGGTC 3',
    H 3 (SEQ ID NO:42) 5' ACTGCAGTCTTATACGAG-GAT 3'
    L 1 (SEQ ID NO:43) 5' GACGTCTTTAAGCGATCG 3',
    L 2 (SEQ ID NO:44) 5' TAAGGGAGATCTAAACAG 3',
    L 3 (SEQ ID NO:45) 5' TCTGCGCGCTTAAAGGAT 3'

The six synthetic CDRs were inserted at the expected locations in the wild-type A10B antibody DNA (FIG. 7). These studies showed that, while each of the six CDRs in a specific clone has a small chance of being a CDR with a restriction site, most of the clones carried at least one CDR with a restriction site, and that any possible combination of CDRs with restriction sites was generated.

4) Construction of Mutant Complementarity Determining Regions ("CDRs")

Based on our sequence data six oligonucleotides corresponding to the six CDRs were made. The CDRs (Kabat definition) were synthetically mutagenized at a ratio of 70 (existing base):10:10:10, and were flanked on the 5' and 3' sides by about 20 bases of flanking sequence, which provide the homology for the incorporation of the CDRs when mixed into a mixture of unmutagenized antibody gene fragments in a molar excess. The resulting mutant sequences are given below.

oligos for CDR Library
CDR H1 (SEQ ID NO:28)
    5'TTCTGGCTACATCTTCACAA CTTATGATATAGACTGGGTGAGGCAGACGCCT GAA 3'

CDR H2 (SEQ ID NO:29)
    5'ACAGGGACTTGAGTGGATTGGA TGGATTTTTCCTGGAGAGGGTGGTACTGAATA CAATGA GAAGTTCAAGGGCAGGGCCACACTGAGTGTA 3'

CDR H3 (SEQ ID NO:30)
    5'TGTCTATTTCTGTGCTAGA GGGGACTACTATAGGCGCTACTTTGACTTGTG GGGCCAAGG GACCACGGTCA 3'

CDR L1 (SEQ ID NO:31)
    5'AGAGGGTCACCATGACCTGCA GTGCCAGCTCAGGTATACGTTACATATATTGG TACCAAC AGAAGCCTGGAT 3'

CDR L2 (SEQ ID NO:32)
    5'TCCCCCAGACTCCTGATTTAT GACACATCCAACGTGGCTCCTGGAGTCCCTTT TCGCTTCAGT 3'

CDR L3 (SEQ ID NO:33)
    5'ATGCTGCCACTTATTACTTGCC AGGAGTGGAGTGGTTATCCGTACACGTTCGG AGGGGGG ACCAAGCT 3'.

Bold and underlined sequences were the mutant sequences synthesized using a mixture of nucleosides of 70:10:10:10 where 70% was the wild-type nucleoside.

A 10 fold molar excess of the CDR mutant oligos were added to the purified A10B antibody DNA fragments between 50 to 200 bp in length from step (2) above. The PCR mix (50 mM KCl, 10 mM Tris-HCl pH 9.0, 0.1% Triton x-100, 1.9 mM MgCl, 200 μm each dNTP, 0.3 μl Taq DNA polymerase (Promega, Madison Wis.), 50 μl total volume) was added and the shuffling program run for 1 min at 94° C., 1 min at 72° C., and then 35 cycles: [30 seconds at 94° C., 30 seconds at 55° C., 30 seconds at 72° C.].

1 μl of the shuffled mixture was added to 100 μl of a PCR mix (50 mM KCl, 10 mM Tris-HCl pH 9.0, 0.1% Triton X-100, 200 μm each dNTP, 1.9 mM MgCl, 0.6 μM each of the two outside primers (SEQ ID NO:26 and 27, see below), 0.5 μl Taq DNA polymerase) and the PCR program was run for 30 cycles of [30 seconds at 94° C., 30 seconds at 45° C, 45 seconds at 72° C.]. The resulting mixture of DNA fragments of 850 basepair size was phenol/chloroform extracted and ethanol precipitated.

The outside primers were:

Outside Primer 1: (SEQ ID NO:27)5' TTGTCGTCTTTC-CAGACGTT 3'

Outside Primer 2: (SEQ ID NO:26)5' ATGATTACGC-CAAGCTTT 3'

5) Cloning of the scFv Antibody DNA into pCANTAB5

The 850 bp PCR product was digested with the restriction enzymes SfiI and NotI, purified from a low melting point agarose gel, and ligated into the pCANTAB5 expression vector obtained from Pharmacia, Milwaukee Wis. The ligated vector was electroporated according to the method set forth by Invitrogen (San Diego Calif.) into TG1 cells (Pharmacia, Milwaukee Wis.) and the phage library was grown up using helper phage following the guidelines recommended by the manufacturer.

The library that was generated in this fashion was screened for the presence of improved antibodies, using six cycles of selection.

6) Selection of high affinity clones 15 wells of a 96 well microtiter plate were coated with Rabbit IgG (Jackson Immunoresearch, Bar Harbor Me.) at 10 μg /well for 1 hour at 37° C., and then blocked with 2% non-fat dry milk in PBS for 1 hour at 37° C.

100 μl of the phage library (1×10$^{10}$ cfu) was blocked with 100 μl of 2% milk for 30 minutes at room temperature, and then added to each of the 15 wells and incubated for 1 hour at 37° C.

Then the wells were washed three times with PBS containing 0.5% Tween-20 at 37° C. for 10 minutes per wash. Bound phage was eluted with 100 μl elution buffer (Glycine-HCl, pH 2.2), followed by immediate neutralization with 2M Tris pH 7.4 and transfection for phage production. This selection cycle was repeated six times.

After the sixth cycle, individual phage clones were picked and the relative affinities were compared by phage ELISA, and the specificity for the rabbit IgG was assayed with a kit from Pharmacia (Milwaukee Wis.) according to the methods recommended by the manufacturer.

The best clone has an approximately 100-fold improved expression level compared with the wild-type A10B when tested by the Western assay. The concentration of the rabbit IgG which yielded 50% inhibition in a competition assay with the best clone was 1 picomolar. The best clone was reproducibly specific for rabbit antigen. The number of copies of the antibody displayed by the phage appears to be increased.

Example 8

In Vivo Recombination via Direct Repeats of Partial Genes

A plasmid was constructed with two partial, inactive copies of the same gene (beta-lactamase) to demonstrate that recombination between the common areas of these two direct repeats leads to full-length, active recombinant genes.

A pUC18 derivative carrying the bacterial TEM-1 beta-lactamase gene was used (Yanish-Perron et al., 1985, Gene 33:103–119). The TEM-1 betalactamase gene ("Bla") confers resistance to bacteria against approximately 0.02 μg/ml of cefotaxime. Sfi1 restriction sites were added 5' of the promoter and 3' of the end of the betalactamase gene by PCR of the vector sequence with two primers:

Primer A (SEQ ID NO: 46)
   5'   TTCTATTGACGGCCTGTCAGGCCT-CATATATACTTTAGATTGATTT 3'

PRIMER B (SEQ ID NO: 47)
   5'   TTGACGCACTGGCCATGGTGGC-CAAAAATAAACAAATAGGGGTTCCGCGCAC ATT 3' and by PCR of the beta-lactamase gene sequence with two other primers:

Primer C (SEQ ID NO: 48)
   5' AACTGACCACGGCCTGACAGGCCGGTCT-GACAGTTACCAATGCTT 3'

Primer D (SEQ ID NO: 49)
   5'   AACCTGTCCTGGCCACCATGGC-CTAAATACATTCAAATATGTAT 3'

The two reaction products were digested with Sfi1, mixed, ligated and used to transform competent *E. coli* bacteria by the procedure described below. The resulting plasmid was pUC182Sfi-Bla-Sfi. This plasmid contains an Sfi1 fragment carrying the Bla gene and the P-3 promoter.

The minimum inhibitory concentration of cefotaxime for *E. coli* XL1-blue (Stratagene, San Diego Calif.) carrying pUC182Sfi-Bla-Sfi was 0.02 μg/ml after 24 hours at 37° C.

The tetracycline gene of pBR322 was cloned into pUC18Sfi-Bla-Sfi using the homologous areas, resulting in pBR322TetSfi-Bla-Sfi. The TEM-1 gene was then deleted by restriction digestion of the pBR322TetSfi-Bla-Sfi with SspI and FspI and blunt-end ligation, resulting in pUC322TetSfi-Sfi.

Overlapping regions of the TEM-1 gene were amplified using standard PCR techniques and the following primers:

Primer 2650 (SEQ ID NO: 50) 5' TTCTTAGACGTCAG-GTGGCACTT 3'

Primer 2493 (SEQ ID NO: 51) 5' TTT TAA ATC AAT CTA AAG TAT 3'

Figure 9:
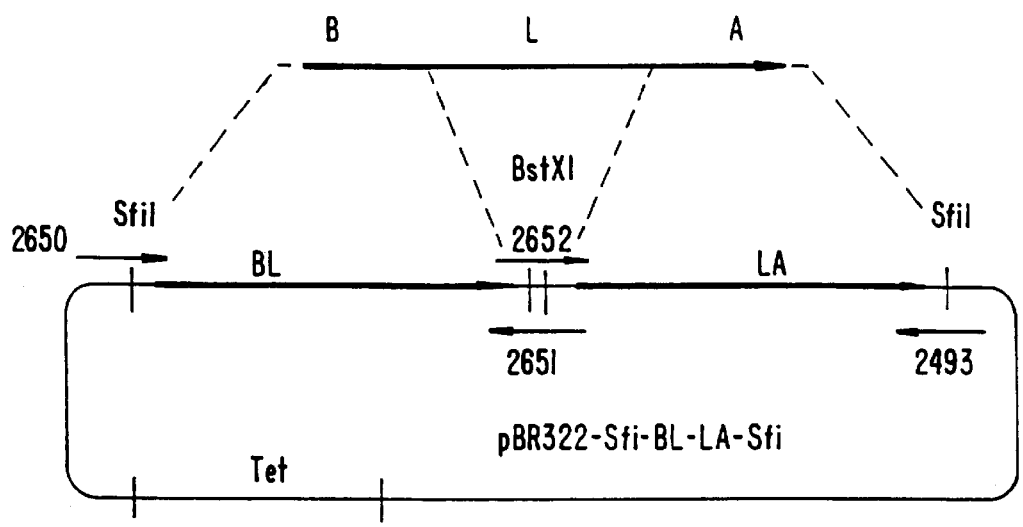
FIG. 9 schematically portrays pBR322-Sfi-BL-LA-Sfi and in vivo intraplasmidic recombination via direct repeats, as well as the rate of generation of ampicillin-resistant colonies by intraplasmidic recombination reconstituting a functional betalactamase gene.

Primer 2651 (SEQ ID NO: 52) 5 ' TGCTCATCCAC-GAGTGTGGAGAAGTGGTCCTGCAACTTTAT 3', and Primer 2652 (SEQ ID NO: 53) ACCACTTCTCCA-CACTCGTGGATGAGCACTTTTAAAGTT The two resulting DNA fragments were digested with Sfi1 and BstX1 and ligated into the Sfi site of pBR322TetSfi-Sfi. The resulting plasmid was called pBR322Sfi-BL-LA-Sfi. A map of the plasmid as well as a schematic of intraplasmidic recombination and reconstitution of functional beta-lactamase is shown in FIG. 9.

The plasmid was electroporated into either TG-1 or JC8679 *E. coli* cells. *E. coli* JC8679 is RecBC sbcA (Oliner et al., 1993, NAR 21:5192). The cells were plated on solid agar plates containing tetracycline. Those colonies which grew, were then plated on solid agar plates containing 100 μg/ml ampicillin and the number of viable colonies counted. The beta-lactamase gene inserts in those transformants which exhibited ampicillin resistance were amplified by standard PCR techniques using Primer 2650 (SEQ ID NO: 50) 5' TTCTTAGACGTCAGGTGGCACTT 3' and Primer 2493 (SEQ ID NO: 51) 5' TTTTAAATCAATCTAAAGTAT 3' and the length of the insert measured. The presence of a 1 kb insert indicates that the gene was successfully recombined, as shown in FIG. 9 and Table 5.

TABLE 5

| Cell | Tet Colonies | Amp colonies | Colony PCR |
| --- | --- | --- | --- |
| TG-1 | 131 | 21 | 3/3 at 1 kb |
| JC8679 | 123 | 31 | 4/4 at 1 kb |
| vector control | 51 | 0 | |

About 17–25% of the tetracycline-resistant colonies were also ampicillin-resistant and all of the Ampicillin resistant colonies had correctly recombined, as determined by colony PCR. Therefore, partial genes located on the same plasmid will successfully recombine to create a functional gene.

Example 9

In Vivo Recombination via Direct Repeats of Full-length Genes.

A plasmid with two full-length copies of different alleles of the beta-lactamase gene was constructed. Homologous recombination of the two genes resulted in a single recombinant full-length copy of that gene.

The construction of pBR322TetSfi-Sfi and pBR322TetSfi-Bla-Sfi was described above.

The two alleles of the beta-lactamase gene were constructed as follows. Two PCR reactions were conducted with pUC18Sfi-Bla-Sfi as the template. One reaction was conducted with the following primers.
Primer 2650 (SEQ ID NO: 50) 5' TTCTTAGACGTCAG-GTGGCACTT 3'
Primer 2649 (SEQ ID NO: 68) 5' ATGGTAGTCCAC-GAGTGTGGTAGTGACAGGCCGGTCTGACAGTTA CCAATGCTT 3'
The second PCR reaction was conducted with the following primers:
Primer 2648 (SEQ ID NO: 54) 5' TGTCACTACCA-CACTCGTGGACTACCATGGCCTAAATACATTCAAA TATGTAT 3'
Primer 2493 (SEQ ID NO: 51) 5' TTT TAA ATC AAT CTA AAG TAT 3'

This yielded two Bla genes, one with a 5' Sfi1 site and a 3' BstX1 site, the other with a 5' BstX1 site and a 3' Sfi1 site.

After digestion of these two genes with BstX1 and Sfi1, and ligation into the Sfi1-digested plasmid pBR322TetSfi-Sfi, a plasmid (pBR322-Sfi-2BLA-Sfi) with a tandem repeat of the Bla gene was obtained. (See FIG. 10).

The plasmid was electroporated into E. coli cells. The cells were plated on solid agar plates containing 15 μg/ml tetracycline. Those colonies which grew, were then plated on solid agar plates containing 100 μg/ml ampicillin and the number of viable colonies counted. The Bla inserts in those transformants which exhibited ampicillin resistance were amplified by standard PCR techniques using the method and primers described in Example 8. The presence of a 1 kb insert indicated that the duplicate genes had recombined, as indicated in Table 6.

TABLE 6

| Cell | Tet Colonies | Amp Colonies | Colony PCR |
| --- | --- | --- | --- |
| TG-1 | 28 | 54 | 7/7 at 1kb |
| JC8679 | 149 | 117 | 3/3 at 1kb |
| vector control | 51 | 0 | |

Colony PCR confirmed that the tandem repeat was efficiently recombined to form a single recombinant gene.

Example 10

Multiple Cycles of Direct Repeat Recombination-Interplasmidic

In order to determine whether multiple cycles of recombination could be used to produce resistant cells more quickly, multiple cycles of the method described in Example 9 were performed.

The minus recombination control consisted of a single copy of the betalactamase gene, whereas the plus recombination experiment consisted of inserting two copies of betalactamase as a direct repeat. The tetracycline marker was used to equalize the number of colonies that were selected for cefotaxime resistance in each round, to compensate for ligation efficiencies.

In the first round, pBR322TetSfi-Bla-Sfi was digested with EcrI and subject to PCR with a 1:1 mix (1 ml) of normal and Cadwell PCR mix (Cadwell and Joyce (1992) *PCR Methods and Applications* 2: 28–33) for error prone PCR. The PCR program was 70° C. for 2 minutes initially and then 30 cycles of 94° C. for 30 seconds, 52° C. for 30 second and 72° C. for 3 minutes and 6 seconds per cycle, followed by 72° C. for 10 minutes.

The primers used in the PCR reaction to create the one Bla gene control plasmid were Primer 2650 (SEQ ID NO: 50) and Primer 2719 (SEQ ID NO; 55) 5' TTAAGGGATTTTG-GTCATGAGATT 3'. This resulted in a mixed population of amplified DNA fragments, designated collectively as Fragment #59. These fragments had a number of different mutations.

The primers used in two different PCR reactions to create the two Bla gene plasmids were Primer 2650 (SEQ ID NO: 50) and Primer 2649 (SEQ ID NO: 68) for the first gene and Primers 2648 (SEQ ID NO: 54) and Primer 2719 (SEQ ID NO: 55) for the second gene. This resulted in a mixed population of each of the two amplified DNA fragments: Fragment #89 (amplified with primers 2648 and 2719) and Fragment #90 (amplified with primers 2650 and 2649). In each case a number of different mutations had been introduced the mixed population of each of the fragments.

After error prone PCR, the population of amplified DNA fragment #59 was digested with Sfi1, and then cloned into pBR322TetSfi-Sfi to create a mixed population of the plasmid pBR322Sfi-Bla-Sfi[1].

Figure 10:
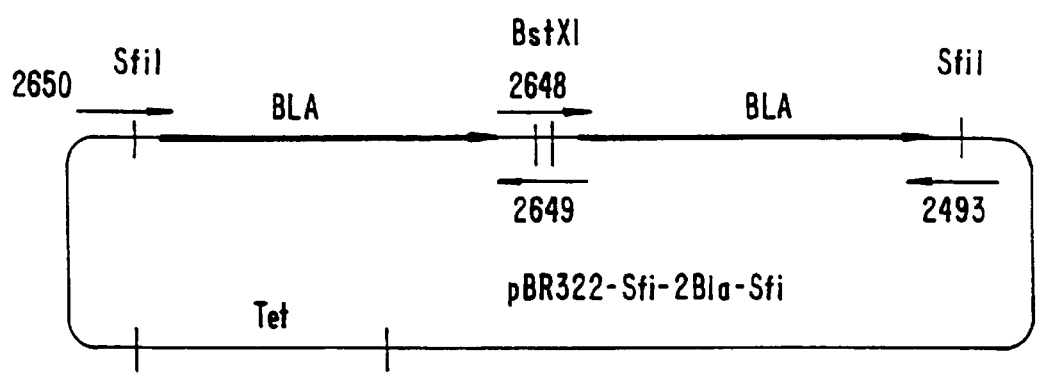
FIG. 10 schematically portrays pBR322-Sfi-2Bla-Sfi and in vivo intraplasmidic recombination via direct repeats, as well as the rate of generation of ampicillin-resistant colonies by intraplasmidic recombination reconstituting a functional betalactamase gene.

After error prone PCR, the population of amplified DNA fragments #90 and #89 was digested with SfiI and BstXI at 50° C., and ligated into pBR322TetSfi-Sfi to create a mixed population of the plasmid pBR322TetSfi-2Bla-Sfi[1] (FIG. 10).

The plasmids pBR322Sfi-Bla-Sfi[1] and pBR322Sfi-2Bla-Sfi[1] were electroporated into E. coli JC8679 and placed on agar plates having differing concentrations of cefotaxime to select for resistant strains and on tetracycline plates to titre.

An equal number of colonies (based on the number of colonies growing on tetracycline) were picked, grown in LB-tet and DNA extracted from the colonies. This was one round of the recombination. This DNA was digested with EcrI and used for a second round of error-prone PCR as described above.

After five rounds the MIC (minimum inhibitory concentration) for cefotaxime for the one fragment plasmid was 0.32 whereas the MIC for the two fragment plasmid was 1.28. The results show that after five cycles the resistance obtained with recombination was four-fold higher in the presence of in vivo recombination.

Example 11

In Vivo Recombination via Electroporation of Fragments

Competent E. coli cells containing pUC18Sfi-Bla-Sfi were prepared as described. Plasmid pUC18Sfi-Bla-Sfi contains the standard TEM-1 beta-lactamase gene as described, supra.

A TEM-1 derived cefotaxime resistance gene from pUC18Sfi-cef-Sfi, (clone ST2) (Stemmer WPC (1994) Nature 370: 389–91, incorporated herein by reference) which confers on E. coli carrying the plasmid an MIC of 640 µg/ml for cefotaxime, was obtained. In one experiment the complete plasmid pUC18Sfi-cef-Sfi DNA was electroporated into E. coli cells having the plasmid pUC18Sfi-Bla-Sfi.

In another experiment the DNA fragment containing the cefotaxime gene from pUC18Sfi-cef-Sfi was amplified by PCR using the primers 2650 (SEQ ID NO: 50) and 2719 (SEQ ID NO: 55). The resulting 1 kb PCR product was digested into DNA fragments of <100 bp by DNase and these fragments were electroporated into the competent E. coli cells which already contained pUC18Sfi-Bla-Sfi.

The transformed cells from both experiments were then assayed for their resistance to cefotaxime by plating the transformed cells onto agar plates having varying concentrations of cefotaxime. The results are indicated in Table 7.

TABLE 7

| | Colonies/ Cefotaxime Concentration | | | | |
|---|---|---|---|---|---|
| | 0.16 | 0.32 | 1.28 | 5.0 | 10.0 |
| no DNA control | 14 | | | | |
| ST-2 mutant, whole | | 4000 | 2000 | 800 | 400 |
| ST-2 mutant, fragments | | 1000 | 120 | 22 | 7 |
| Wildtype, whole | 27 | | | | |
| Wildtype, fragments | 18 | | | | |

From the results it appears that the whole ST-2 Cef gene was inserted into either the bacterial genome or the plasmid after electroporation. Because most insertions are homologous, it is expected that the gene was inserted into the plasmid, replacing the wildtype gene. The fragments of the Cef gene from St-2 also inserted efficiently into the wild-type gene in the plasmid. No sharp increase in cefotaxime resistance was observed with the introduction of the wildtype gene (whole or in fragments) and no DNA. Therefore, the ST-2 fragments were shown to yield much greater cefotaxime resistance than the wild-type fragments. It was contemplated that repeated insertions of fragments, prepared from increasing resistant gene pools would lead to increasing resistance.

Accordingly, those colonies that produced increased cefotaxime resistance with the St-2 gene fragments were isolated and the plasmid DNA extracted. This DNA was amplified using PCR by the method described above. The amplified DNA was digested with DNase into fragments (<100 bp) and 2–4 µg of the fragments were electroporated into competent E. coli cells already containing pUC322Sfi-Bla-Sfi as described above. The transformed cells were plated on agar containing varying concentrations of cefotaxime.

As a control, competent E. coli cells having the plasmid pUC18Sfi-Kan-Sfi were also used. DNA fragments from the digestion of the PCR product of pUC18Sfi-cef-Sfi were electroporated into these cells. There is no homology between the kanamycin gene and the beta-lactamase gene and thus recombination should not occur.

This experiment was repeated for 2 rounds and the results are shown in Table 8.

TABLE 8

| Round | Cef conc. | KAN control | Cef resistant colonies |
|---|---|---|---|
| 1 | 0.16–0.64 | lawn | lawn |
| replate | 0.32 | 10 small | 1000 |
| 2 | 10 | 10 | 400 |
| Replate | | 100 sm @ 2.5 | 50 @ 10 |
| 3 | 40 | 100 sm | |
| | 1280 | | 100 sm |

Example 12

Determination of Recombination Formats

This experiment was designed to determine which format of recombination generated the most recombinants per cycle.

In the first approach, the vector pUC18Sfi-Bla-Sfi was amplified with PCR primers to generate a large and small fragment. The large fragment had the plasmid and ends having portions of the Bla gene, and the small fragment coded for the middle of the Bla gene. A third fragment having the complete Bla gene was created using PCR by the method in Example 8. The larger plasmid fragment and the fragment containing the complete Bla gene were electroporated into E. coli JC8679 cells at the same time by the method described above and the transformants plated on differing concentrations of cefotaxime.

In approach 2, the vector pUC18Sfi-Bla-Sfi was amplified to produce the large plasmid fragment isolated as in approach 1 above. The two fragments each comprising a portion of the complete Bla gene, such that the two fragments together spanned the complete Bla gene werealso obtained by PCR. The large plasmid fragment and the two Bla gene fragments were all electroporated into competent E. coli JC8679 cells and the transformants plated on varying concentrations of cefotaxime.

In the third approach, both the vector and the plasmid were electroporated into E. coli JC8679 cells and the transformants were plated on varying concentrations of cefotaxime.

In the fourth approach, the complete Bla gene was electroporated into E. coli JC8679 cells already containing the vector pUCSfi-Sfi and the transformants were plated on varying concentrations of cefotaxime. As controls, the E. coli JC8679 cells were electroporated with either the complete Bla gene or the vector alone.

The results are presented in FIG. 11. The efficiency of the insertion of two fragments into the vector is 100×lower than when one fragment having the complete Bla gene is used. Approach 3 indicated that the efficiency of insertion does depend on the presence of free DNA ends since no recombinants were obtained with this approach. However, the results of approach 3 were also due to the low efficiency of electroporation of the vector. When the expression vector is already in the competent cells, the efficiency of the vector electroporation is not longer a factor and efficient homologous recombination can be achieved even with uncut vector.

Example 12

Kit for Cassette Shuffling to Optimize Vector Performance

Figure 12:
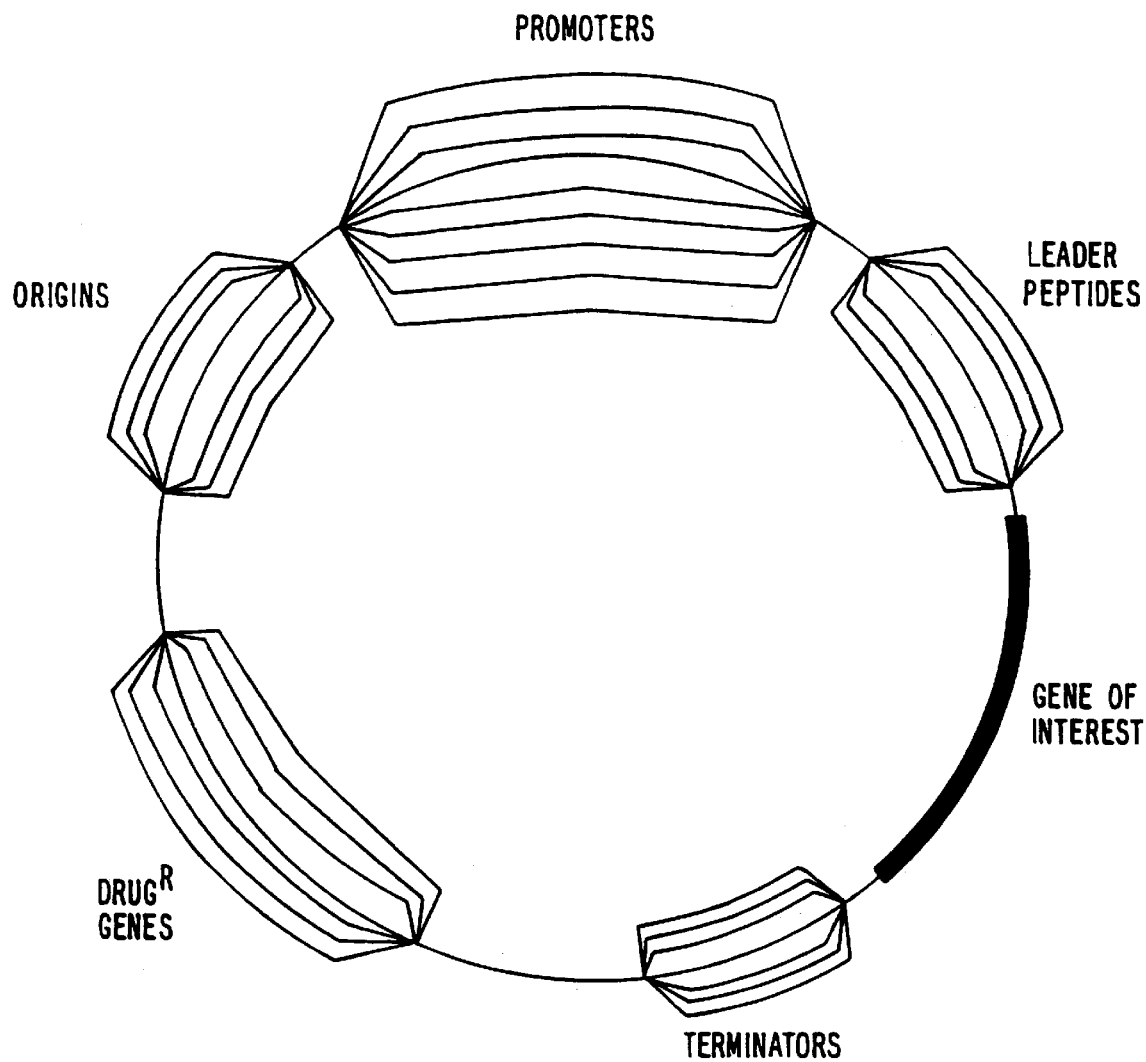
FIG. 12 schematically portrays generation of a library of vectors by shuffling cassettes at the following loci: promoter, leader peptide, terminator, selectable drug resistance gene, and origin of replication. The multiple parallel lines at each locus represent the multiplicity of cassettes for that cassette.

In order to provide a vector capable of conferring an optimized phenotype (e.g., maximal expression of a vector-encoded sequence, such as a cloned gene), a kit is provided comprising a variety of cassettes which can be shuffled, and optimized shufflants can be selected. FIG. 12 shows schematically one embodiment, with each loci having a plurality of cassettes. For example, in a bacterial expression system, FIG. 13 shows example cassettes that are used at the respective loci. Each cassette of a given locus (e.g., all promoters in this example) are flanked by substantially identical sequences capable of overlapping the flanking sequence(s) of cassettes of an adjacent locus and preferably also capable of participating in homologous recombination or non-homologous recombination (e.g., lox/cre or flp/frt systems), so as to afford shuffling of cassettes within a locus but substantially not between loci.

Cassettes are supplied in the kit as PCR fragments, which each cassette type or individual cassette species packaged in a separate tube. Vector libraries are created by combining the contents of tubes to assemble whole plasmids or substantial portions thereof by hybridization of the overlapping flanking sequences of cassettes at each locus with cassettes at the adjacent loci. The assembled vector is ligated to a predetermined gene of interest to form a vector library wherein each library member comprises the predetermined gene of interest and a combination of cassettes determined by the association of cassettes. The vectors are transferred into a suitable host cell and the cells are cultured under conditions suitable for expression, and the desired phenotype is selected.

Example 13

Shuffling to Optimize Green Fluorescent Protein (GFP) Properties

BACKGROUND

Green fluorescent protein ("GFP") is a polypeptide derived from an apopeptide having 238 amino acid residues and a molecular weight of approximately 27,000. GFP contains a chromophore formed from amino acid residues 65 through 67. As its name indicates, GFP fluoresces; it does not bioluminesce like luciferase. In vivo, the chromophore of GFP is activated by energy transfer from coelenterazine complexed with the photoprotein aequorin, with GFP exhibiting green fluorescence at 510 nm. Upon irradiation with blue or UV light, GFP exhibits green fluorescence at approximately 510 nm.

The green fluorescent protein (GFP) of the jellyfish *Aequorea victoria* is a very useful reporter for gene expression and regulation (Prasher et al. (1992) *Gene* 111: 229; Prasher et al. (1995) *Trends In Genetics* 11: 320; Chalfie et al. (1994) *Science* 263: 802, incorporated herein by reference). WO95/21191 discloses a polynucleotide sequence encoding a 238 amino acid GFP apoprotein which contains a chromophore formed from amino acids 65 through 67. WO095/21191 disclose that a modification of the cDNA for the apopeptide of A. victoria GFP results in synthesis of a peptide having altered fluorescent properties. A mutant GFP (S65T) resulting in a 4–6-fold improvement in excitation amplitude has been reported (Heim et al. (1994) *Proc. Natl. Acad. Sci.* (*U.S.A.*) 91: 12501).

OVERVIEW

Green fluorescent protein (GFP) has rapidly become a widely used reporter of gene regulation. However, in many organisms, particularly eukaryotes, the whole cell fluorescence signal was found to be too low. The goal was to improve the whole cell fluorescence of GFP for use as a reporter for gene regulation for *E. coli* and mammalian cells. The improvement of GFP by rational design appeared difficult because the quantum yield of GFP is already 0.7–0.8 (Ward et al. (1982) *Photochem. Photobiol.* 35: 803) and the expression level of GFP in a standard *E. coli* construct was already about 75% of total protein.

Improvement of GFP was performed first by synthesis of a GFP gene with improved codon usage. The GFP gene was then further improved by the disclosed method(s), consisting of recursive cycles of DNA shuffling or sexual PCR of the GFP gene, combined with visual selection of the brightest clones. The whole cell fluorescence signal in *E. coil* was optimized and selected mutants were then assayed to determine performance of the best GFP mutants in eukaryotic ceils.

A synthetic gene was synthesized having improved codon usage and having a 2.8-fold improvement of the *E. coli* whole cell fluorescence signal compared to the industry standard GFP construct (Clontech, Palo Alto, Calif.). An additional 16-fold improvement was obtained from three cycles of sexual PCR and visual screening for the brightest *E. coil* colonies, for a 45-fold improvement over the standard construct. Expressed in Chinese Hamster Ovary (CHO) cells, this shuffled mutant showed a 42-fold improvement of signal over the synthetic construct. The expression level in *E. coil* was unaltered at about 75% of total protein. The emission and excitation maxima of the GFP were also unchanged. Whereas in *E. coli* most of the wildtype GFP ends up in inclusion bodies, unable to activate its chromophore, most of the mutant protein(s) were soluble and active. The three amino acid mutations thus guide the mutant protein into the native folding pathway rather than toward aggregation. The results show that DNA sequence shuffling (sexual PCR) can solve complex practical problems and generate advantageous mutant variants rapidly and efficiently.

MATERIALS AND METHODS

GFP Gene Construction

Figure 14A:
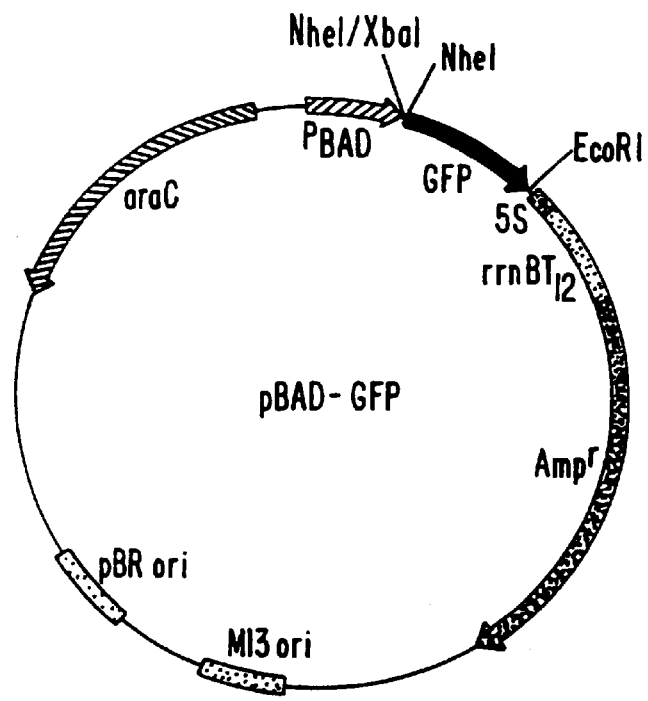
FIG. 14 shows the prokaryotic GFP expression vector PBAD-GFP (5,371 bp) was derived from pBAD18 (Guzman et al. (1995) *J. Bacteriol.* 177: 4121). The eukaryotic GFP expression vector Alpha+GFP (7,591 bp) was derived from the vector Alpha+ (Whitehorn et al. (1995) Bio/Technology 13: 1215).
Figure 14B:
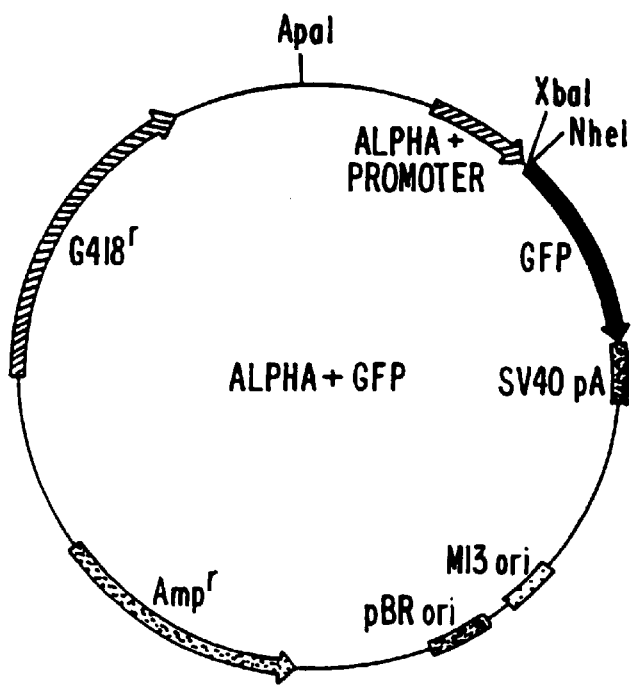

A gene encoding the GFP protein with the published sequence (Prasher et al. (1995) op.cit, incorporated herein by reference) (238 AA, 27 kD) was constructed from oligonucleotides. In contrast to the commercially available GFP construct (Clontech, Palo Alto, Calif.), the sequence included the Ala residue after the fMet, as found in the original cDNA clone. Fourteen oligonucleotides ranging from 54 to 85 bases were assembled as seven pairs by PCR extension. These segments were digested with restriction enzymes and cloned separately into the vector Alpha+GFP (Whitehorn et al. (1995) Bio/Technology 13: 1215, incorporated herein by reference) and sequenced. These segments were then ligated into the eukaryotic expression vector Alpha+ to form the full-length GFP construct, Alpha+GFP (FIG. 14). The resulting GFP gene contained altered Arginine codons at amino acid positions 73 (CGT), 80 (CGG), 96 (CGC) and 122 (CGT). To reduce codon bias and facilitate expression in E. coli, a number of other silent mutations were engineered into the sequence to create the restriction sites used in the assembly of the gene. These were S2 (AGT to AGC; to create an NheI site), K41 (AAA to AAG; HinDIII), Y74 (TAC to TAT) and P75 (CCA to CCG; BspEI), T108 (AGA to AGG; NnuI), L141 (CTC to TTG) and E142 (GAA to GAG; XhoI), S175 ( TCC to AGC; BamHI) and S202 (TCG to TCC; SalI). The 5' and 3' untranslated ends of the gene contained XbaI and EcoRI sites, respectively. The sequence of the gene was confirmed by sequencing.

Other suitable GFP vectors and sequences can be obtained from the GenBank database, such as via Internet World Wide Web, as files: CVU36202, CVU36201, XXP35SGFP, XXU19282, XXU19279, XXU19277, XXU19276, AVGFP2, AVGFP1, XXU19281, XXU19280, XXU19278, AEVGFP, and XXU17997, which are incorporated herein by reference to the same extent as if the sequence files and comments were printed and inserted herein.

The XbaI-EcoRI fragment of Alpha+GFP, containing the whole GFP gene, was subcloned into the prokaryotic expression vector pBAD18 (Guzman et al. (1995) J. Bacteriol. 177: 4121), resulting in the bacterial expression vector pBAD18-GFP (FIG. 14). In this vector GFP gene expression is under the control of the arabinose promoter/repressor (araBAD), which is inducible with arabinose (0.2%). Because this is the only construct with the original amino acid sequence, it is referred to as wildtype GFP ('wt'). A GFP-expressing bacterial vector was obtained from Clontech (Palo Alto, Calif.), which is referred to herein as 'Clontech' construct. GFP expression from the 'Clontech' construct requires IPTG induction.

Gene Shuffling and Selection

An approximately 1 kb DNA fragment containing the whole GFP gene was obtained from the PBAD-GFP vector by PCR with primers 5'-TAGCGGATCCTACCTGACGC (SEQ ID NO:56) (near NheI site) and 5'GAAAATCT-TCTCTCATCCG (SEQ ID NO:57) (near EcoRI site) and purified by Wizard PCR prep (Promega, Madison, Wis.). This PCR product was digested into random fragments with DNase I (Sigma) and 50–300 bp fragments were purified from 2% low melting point agarose gels. The purified fragments were resuspended at 10–30 ng/ul in PCR mixture (Promega, Madison, Wis.; 0.2 mM each dNTP/2.2 mM MgCl$_2$/50 MM KCl/10 mM Tris-HCL, pH 9.0/0.1% Triton-X-100) with Taq DNA polymerase (Promega) and assembled (without primers) using a PCR program of 35 cycles of 94° C. 30s, 45° C. 30s, 72° C. 30s, as described in Stemmer, WPC (1994) Nature 370: 389, incorporated herein by reference. The product of this reaction was diluted 40×into new PCR mix, and the full length product was amplified with the same two primers in a PCR of 25 cycles of 94° C. 30s, 50° C. 30s, 72° C. 30s, followed by 72° C. for 10 min. After digestion of the reassembled product with NheI and EcoRI, this library of point-mutated and in vitro recombined GFP genes was cloned back into the PBAD vector, electroporated into E. coli TG1 (Pharmacia), and plated on LB plates with 100 ug/ml ampicillin and 0.2% arabinose to induce GFP expression from the arabinose promoter.

Mutant Selection

Over a standard UV light box (365 nm) the 40 brightest colonies were selected and pooled. The pool of colonies was used as the template for a PCR reaction to obtain a pool of GFP genes. Cycles 2 and 3 were performed identical to cycle 1. The best mutant from cycle 3 was identified by growing colonies in microtiter plates and fluorescence spectrometry of the microtiter plates.

For characterization of mutants in E. coli, DNA sequencing was performed on an Applied Biosystems 391 DNA sequencer.

CHO Cell Expression of GFP

The wildtype and the cycle 2 and 3 mutant versions of the GFP gene were transferred into the eukaryotic expression vector Alpha+ (16) as an EcoRI-XbaI fragment. The plasmids were transfected into CHO cells by electroporation of $10^7$ cells in 0.8 ml with 40 μg of plasmed at 400V and 250μF. Transformants were selected using 1 mg/ml G418 for 10–12 days.

FACS analysis was carried out on a Becton Dickinson FACSTAR Plus using an Argon ion laser tuned to 488 nm. Fluorescence was observed with a 535/30 run bandpass filter.

RESULTS

Codon Usage

Figure 15A:
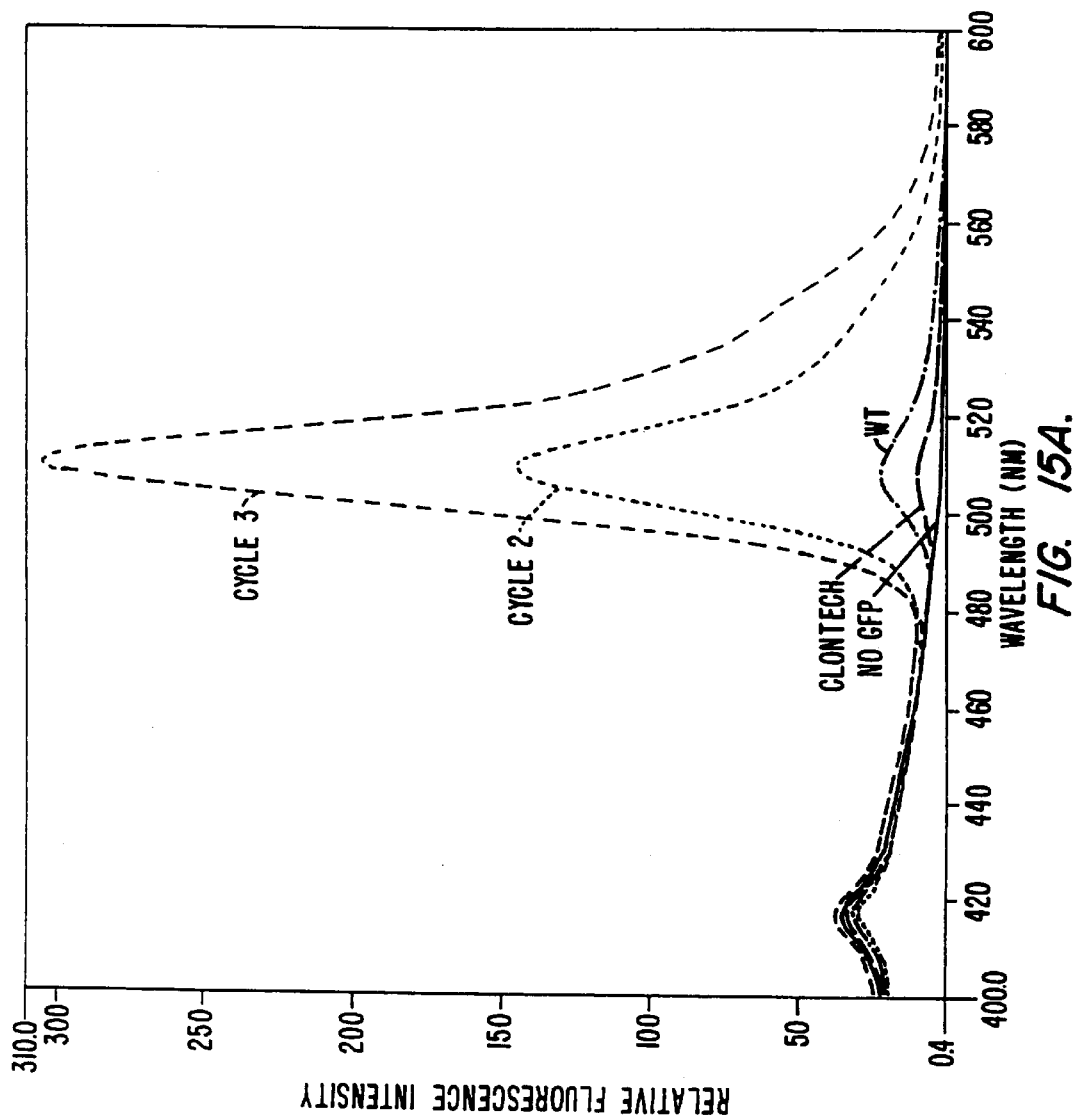
FIGS. 15A and 15B show comparison of the fluorescence of different GFP constructs in whole *E. coli* cells. Compared are the 'Clontech' construct which contains a 24 amino acid N-terminal extension, the Affymax wildtype construct ('wt', with improved codon usage), and the mutants obtained after 2 and after 3 cycles of sexual PCR and selection ('cycle 2', 'cycle 3'). The 'Clontech' construct was induced with IPTG, whereas the other constructs were induced with arabinose. All samples were assayed at equal $OD_{600}$.

E. coli expressing the synthetic GFP construct ('wt') with altered codon usage yielded a nearly 3-fold greater whole cell fluorescence signal than cells expressing the 'Clontech' construct (FIG. 15A). The comparison was performed at full induction and at equal OD$_{600}$. In addition to the substitution of poor arginine codons in the 'wt' construct and the N-terminal extension present in the 'Clontech' construct, the expression vectors and GFP promoters are quite different. The cause of the improved fluorescence signal is not enhanced expression level, it is improved protein performance.

Sexual PCR

Figure 15B:
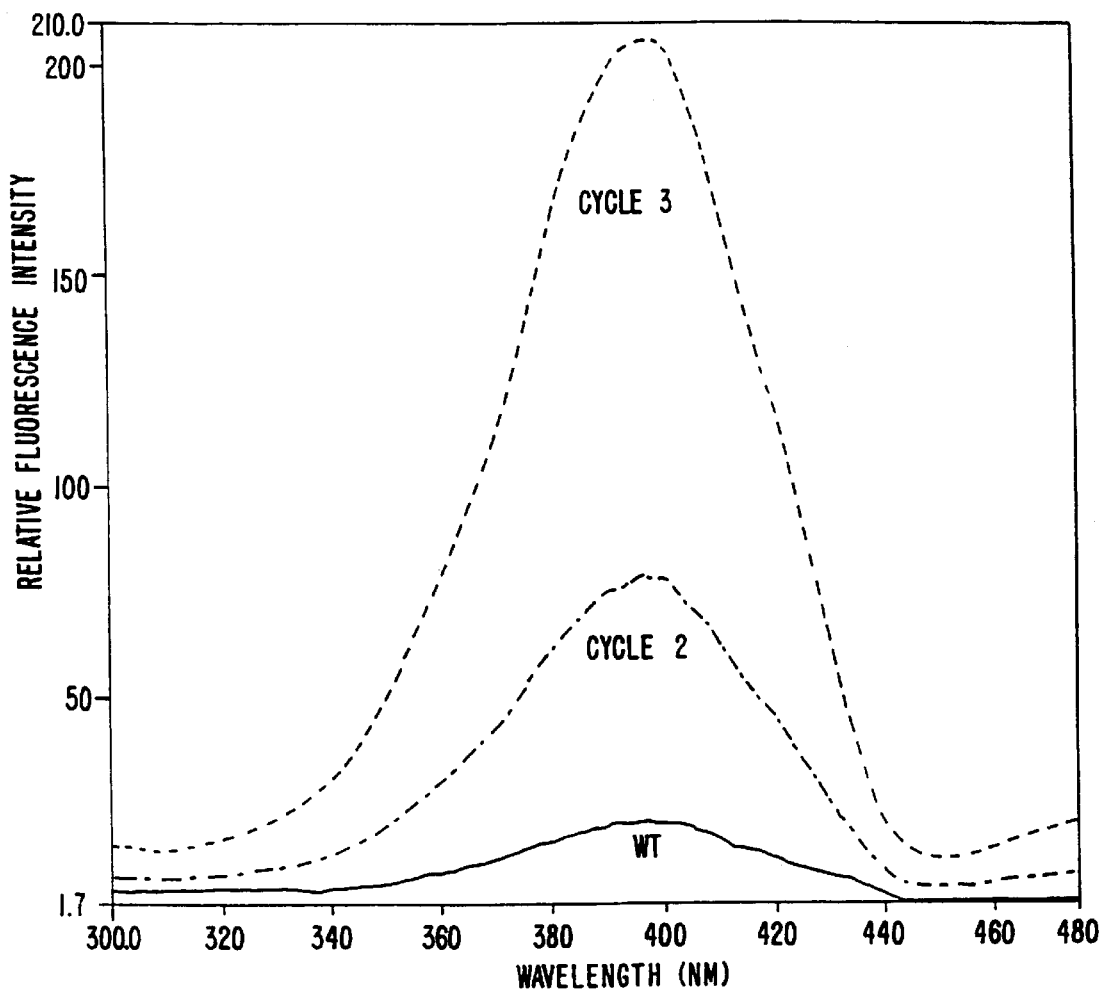
Figure 16A:
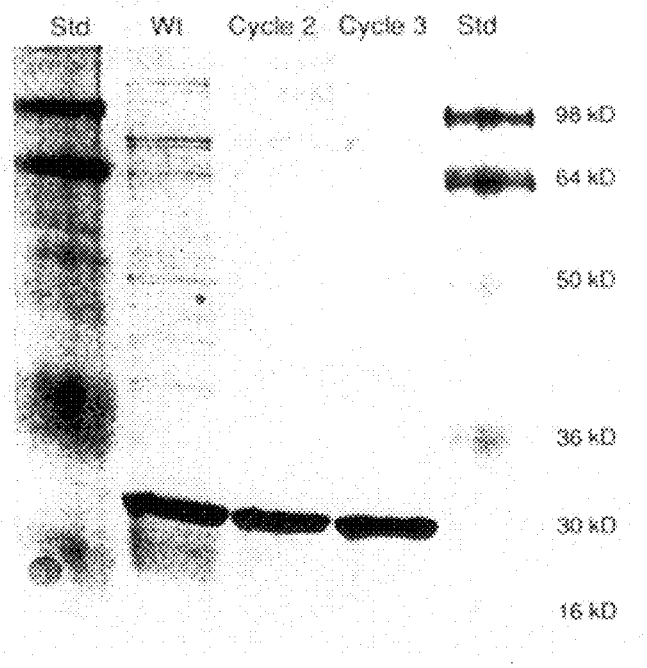
FIG. 16 shows SDS-PAGE analysis of relative GFP protein expression levels. Panel (a): 12% Tris-Glycine SDS-PAGE analysis (Novex, Encinitas, Calif.) of equal amounts (OD600) Of whole *E. coli* cells expressing the wildtype, the cycle 2 mutant or the cycle 3 mutant of GFP. Stained with Coomassie Blue. GFP (27 kD) represents about 75% of total protein, and the selection did not increase the expression level. Panel (b) 12% Tris-Glycine SDS-PAGE analysis (Novex, Encinitas, Calif.) of equal amounts (OD600) of *E. coli* fractions. Lane 1: Pellet of lysed ceils expressing wt GFP; lane 2: Supernatant of lysed ceils expressing wt GFP. Most of the wt GFP is in inclusion bodies; lane 3: Pellet of lysed cells expressing cycle 3 mutant GFP; lane 4: Supernatant of lysed cells expressing cycle 3 mutant GFP. Most of the wt GFPis soluble. The GFP that ends up in inclusion bodies does not contain the chromophore, since there is no detectable fluorescence in this fraction.
Figure 16B:
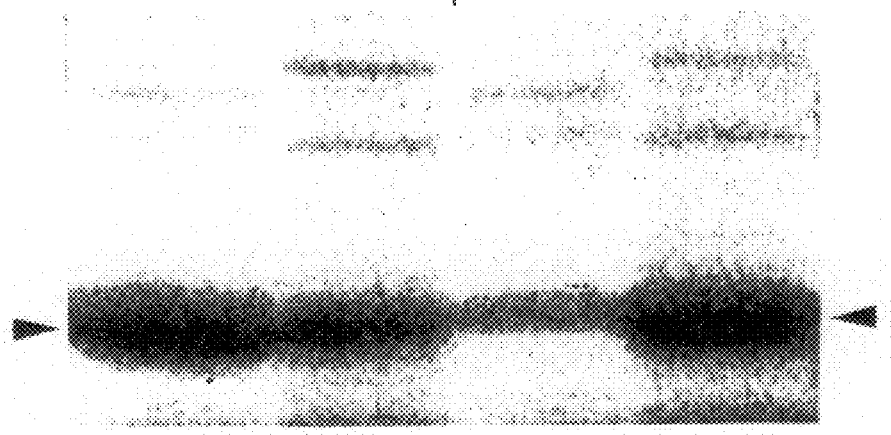
Figures 17A, 17B:
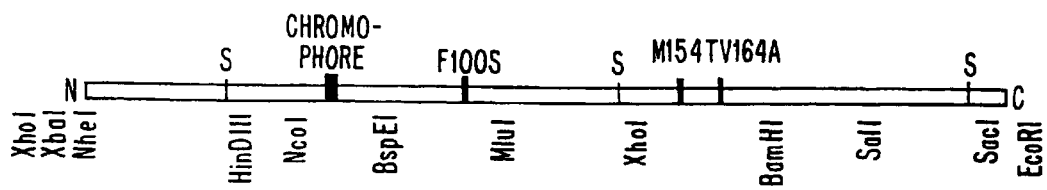
FIG. 17 shows mutation analysis of the cycle 2 and cycle 3 mutants versus wildtype GFP. Panel (A) shows that the mutations are spread out rather than clustered near the tripeptide chromophore. Mutations F100S, M154T, and V164A involve the replacement of hydrophobic residues with more hydrophilic residues. The increased hydrophilicity may help guide the protein into a native folding pathway rather than toward aggregation and inclusion body formation. Panel (B) shows a restriction map indicating the chromophore region and positions of introduced mutations.

The fluorescence signal of the synthetic 'wt' GFP construct was further improved by constructing a mutant library by sexual PCR methods as described herein and in Stemmer WPC (1994) Proc. Natl. Acad. Sci. (U.S.A.) 91: 10747 and Stemmer WPC (1994) Nature 370: 389, incorporated herein by reference, followed by plating and selection of the brightest colonies. After the second cycle of sexual PCR and selection, a mutant ('cycle 2') was obtained that was about 8-fold improved over 'wt', and 23-fold over the 'Clontech' construct. After the third cycle a mutant ('cycle 3') was obtained which was 16–18-fold improved over the 'wt' construct, and 45-fold over the 'Clontech' construct (FIG. 15B). The peak wavelengths of the excitation and emission spectra of the mutants were identical to that of the 'wt' construct (FIG. 15B). SDS-PAGE analysis of whole ceils showed that the total level of the GFP protein expressed in all three constructs was unchanged, at a surprisingly high rate of about 75% of total protein (FIG. 16, panels (a) and (b)). Fractionation of the cells by sonication and centrifugation showed that the 'wt' construct contained mostly inactive GFP in the form of inclusion bodies, whereas the 'cycle 3' mutant GFP remained mostly soluble and was able to activate its chromophore. The mutant genes were sequenced and the 'cycle 1' mutant was found to contain more mutations than the 'cycle 3' mutant (FIG. 17). The 'cycle 3' contained 3 protein mutations and 3 silent mutations relative to the 'wt' construct. Mutations F100S, M154T, and V164A involve the replacement of hydrophobic residues with more hydrophilic residues (Kyte and Doolittle, 1982). One plausible explanation is that native GFP has a hydrophobic site on its surface by which it normally binds to Aequorin, or to another protein. In the absence of this other protein, the hydrophobic site may cause aggregation and prevent autocatalytic activation of the chromophore. The three hydrophilic mutations may counteract the hydrophobic site, resulting in reduced aggregation and increased chromophore activation. Pulse chase experiments with whole bacteria at 37° C. showed that the $T_{1/2}$ for fluorophore formation was 95 minutes for both the 'wt' and the 'cycle 3' mutant GFP.

CHO Cells

Figure 18A:
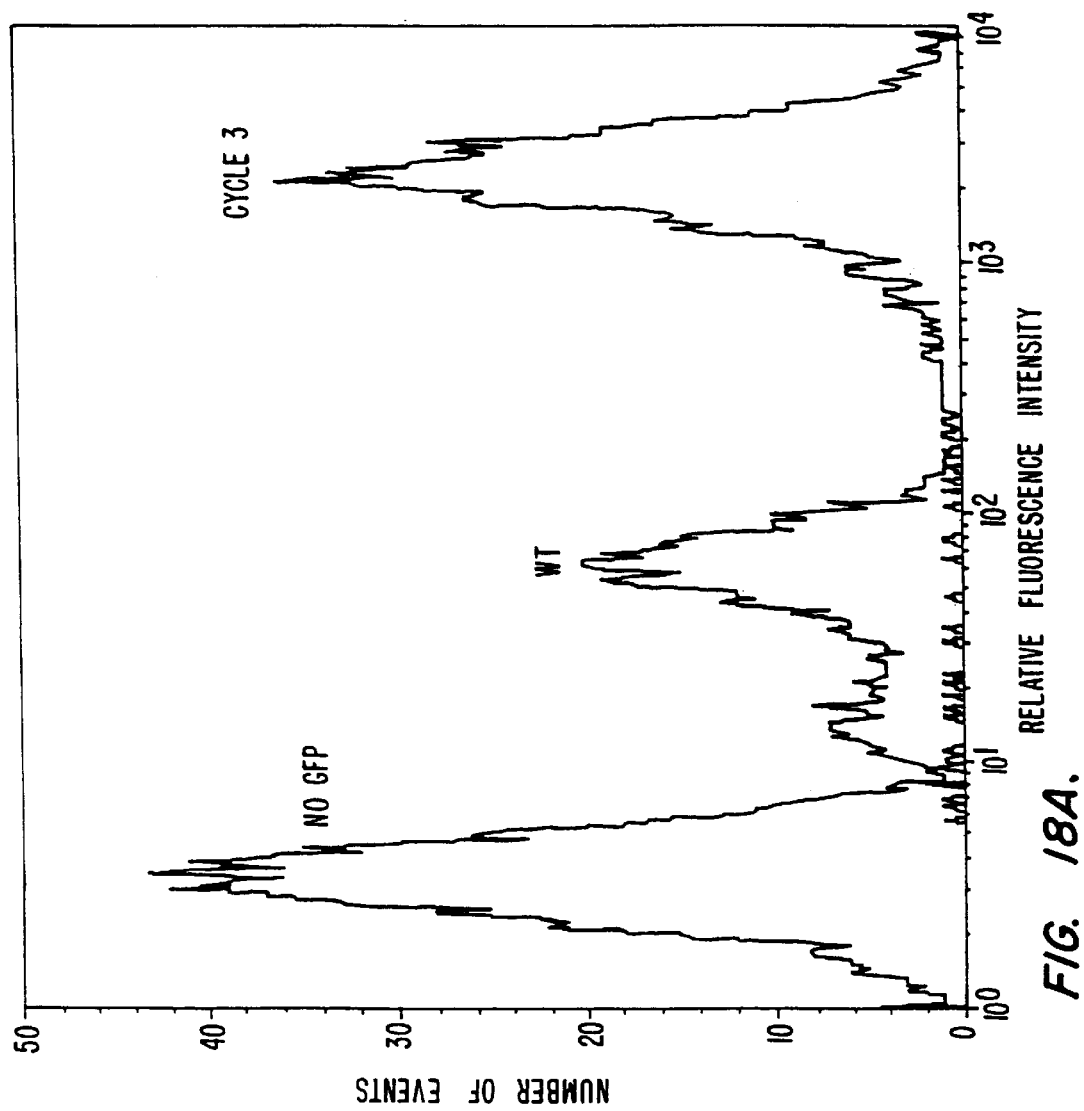
FIG. 18A and 18B show comparison of CHO cells expressing different GFP proteins.
Figure 18B:
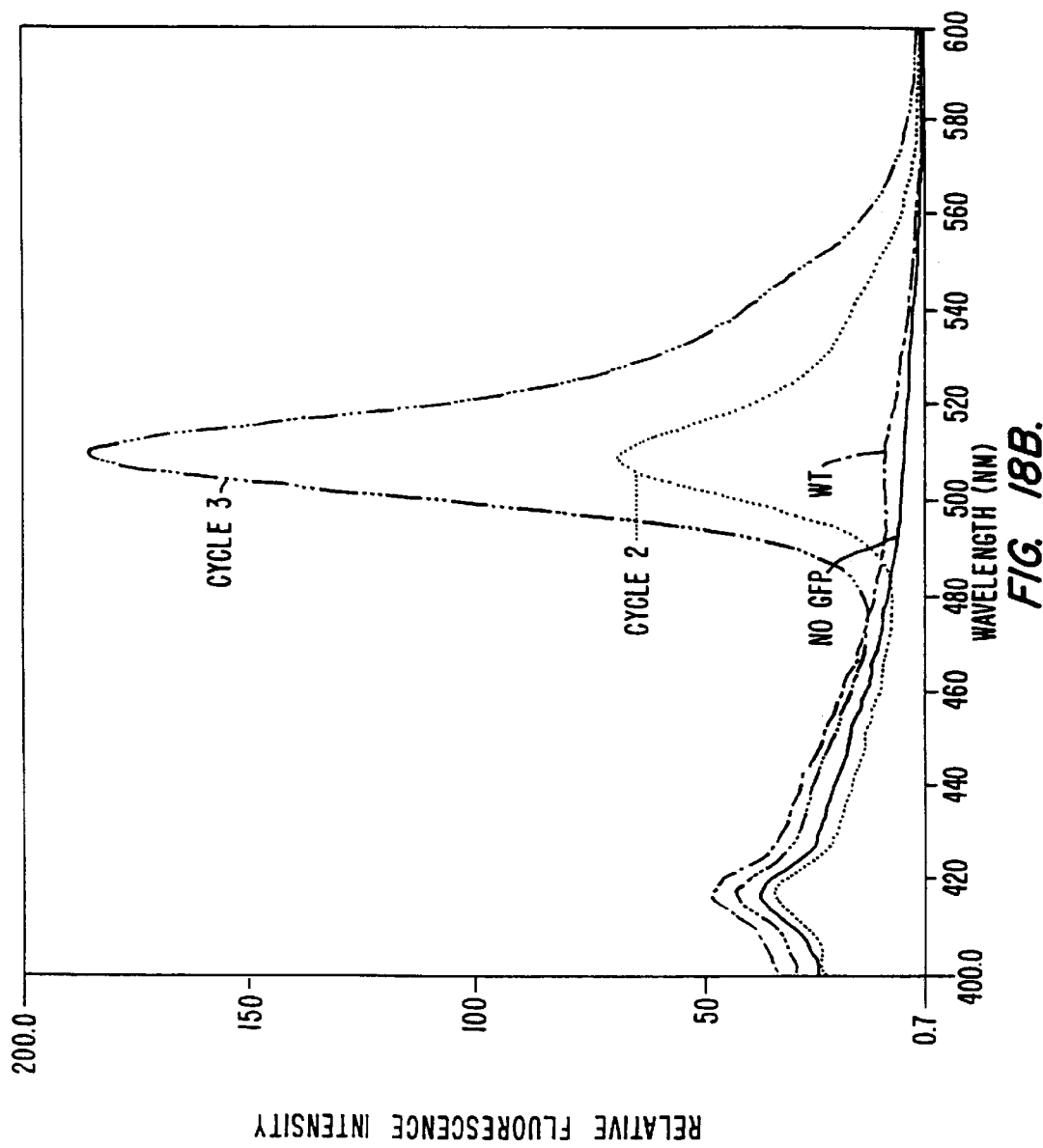

Improvements in autonomous characteristics such as self-folding can be tranferable to different cellular environments. After being selected in bacteria, the 'cycle 3' mutant GFP was transferred into the eukaryotic Alpha+ vector and expressed in chinese hamster ovary cells (CHO) . Whereas in *E. coli* the 'cycle 3' construct gave a 16–18-fold stronger signal than the 'wt' construct, fluorescence spectroscopy of CHO cells expressing the 'cycle 3' mutant showed a 42-fold greater whole cell fluorescence signal than the 'wt' construct under identical conditions (FIG. 18A). FACS sorting confirmed that the average fluorescence signal of CHO cell clones expressing 'cycle 3' was 46-fold greater than cells expressing the 'wt' construct (FIG. 18B). As for the 'wt' construct, the addition of 2 mM sodium butyrate was found to increase the fluorescence signal about 4–8 fold.

Screening Versus Selection

These results were obtained by visual screening of approximately 10,000 colonies, and the brightest 40 colonies were picked at each cycle. Significant improvements in protein function can be obtained with relatively low numbers of variants. In view of this surprising finding, sexual PCR can be combined with high throughput screening procedures as an improved process for the optimization of the large number of commercially important enzymes for which large scale mutant selections are not feasible or efficient.

Example 14

Shuffling to Generate Improved Peptide Display Libraries

BACKGROUND

Once recombinants have been characterized from a phage display library, polysome display library, or the like, it is often useful to construct and screen a second generation library that displays variants of the originally displayed sequence(s). However, because the number of combinations for polypeptides longer than seven residues is so great that all permutations will not generally be present in the primary library. Furthermore, by mutating sequences, the "sequence landscape" around the isolated sequence can be examined to find local optima.

There are several methods available to the experimenter for the purposes of mutagenesis. For example, suitable methods include site-directed mutagenesis, cassette mutagenesis, and error-prone PCR.

OVERVIEW

The disclosed method for generating mutations in vitro is known as DNA shuffling. In an embodiment of DNA shuffling, genes are broken into small, random fragments with DNase I, and then reassembled in a PCR-like reaction, but typically without any primers. The process of reassembling can be mutagenic in the absence of a proof-reading polymerase, generating up to about 0.7% error rate. These mutations consist of both transitions and transversion, often randomly distributed over the length of the reassembled segment.

Once one has isolated a phage-displayed recombinant with desirable properties, it is generally appropriate to improve or alter the binding properties through a round of molecular evolution via DNA shuffling. Second generation libraries of displayed peptides and antibodies were generated and isolated phage with improved (i.e., 3–1000 fold) apparent binding strength were produced. Thus, through repeated rounds of library generation and selection it is possible to "hill-climb" through sequence space to optimal binding.

From second generation libraries, very often stronger binding species can be isolated. Selective enrichment of such phage can be accomplished by screening with lower target concentrations immobilized on a microriter plate or in solution, combined with extensive washing or by other means known in the art. Another option is to display the mutagenized population of molecules at a lower valency on phage to select for molecules with higher affinity constants. Finally, it is possible to screen second generation libraries in the presence of a low concentration of binding inhibitor (i.e., target, ligand) that blocks the efficient binding of the parental phage.

METHODS

Exemplary Mutagenesis Protocols

A form of recombinant DNA-based mutagenesis is known as oligonucleotide-mediated site-directed mutagenesis. An oligonucleotide is designed such that can it base-pair to a target DNA, while differing in one or more bases near the center of the oligonucleotide. When this oligonucleotide is base-paired to the single-stranded template DNA, the heteroduplex is converted into double-stranded DNA in vitro; in this manner one strand of the product will carry the nucleotide sequence specific by the mutagenic oligonucleotide. These DNA molecules are then propagated in vivo and the desired recombinant is ultimately identified among the population of transformants.

A protocol for single-stranded mutagenesis is described below.

1. Prepare single-stranded DNA from M13 phage or phagemids. Isolate ~2 μg of DNA. The DNA can be isolated from a dut⁻ ung⁻ bacterial host (source) so that the recovered DNA contains uracil in place of many thymine residues.

2. Design an oligonucleotide that has at least 15 or 20 residues of complementarity to the coding regions flanking the site to be mutated. In the oligonucleotide, the region to be randomized can be represented by degenerate codons. If the non-complementary region is large (i.e., >12 nucleotides), then the flanking regions should be extended to ensure proper base pairing. The oligonucleotide should be synthesized with a 5'PO$_4$ group, as it improves the efficiency of the mutagenesis procedure; this group can also be added enzymatically with T4 polynucleotide kinase. (In an Eppendorf tube, incubate 100 ng of oligonucleotide with 2 units of T4 polynucleotide kinase in 50 mM (pH 7.5), 10 mM MgCl2,5 mM DTT, and OA mM ATP for 30 min.

3. Anneal the oligonucleotide with the single-stranded DNA in a 500 µl Eppendorf tube containing:

1 µg single-stranded DNA, 10 ng oligonucleotide, 20 mM Tr@Cl (pH 7.4), 2 mM $MgCl_2$, 50 mM NaCl.

4. Mix the solutions together and centrifuge the tube for a few seconds to recollect the liquid. Heat the tube in a flask containing water heated to 70° C. After 5 min, transfer the flask to the lab bench and let it cool to room temperature slowly.

5. Take the tube out of the water bath and put it on ice. Add the following reagents to the tube, for a total volume of 100 µl: 20 mM Tris-HCl (pH 7.4), 2 mM DTT, 0.5 mM DATP, dCTP, dGTP and dTTP, 0.4 mM ATP, 1 unit T7 DNA polymerase, 2 units T4 DNA ligase.

6. After 1 hr, add EDTA to 10 mM final concentration.

7. Take 20 µl from the sample and run on an agarose gel. Most of the single-stranded DNA should be converted to covalently-closed circular DNA. Electrophorese some controls in adjacent lanes (i.e., template, template reaction without oligonucleotide). Add T4 DNA ligase to close the double-stranded circular DNA.

8. Extract the remainder of the DNA (80 µl) by phenol extraction and recover by ethanol precipitation.

9. Electroporate into ung$^+$ bacteria.

10. Harvest the second generation phage by PEG precipitation.

Cassette Mutagenesis

A convenient means of introducing mutations at a particular site within a coding region is by cassette mutagenesis. The "cassette" can be generated several different ways: A) by annealing two oligonucleotides together and converting them into double stranded DNA; B) by first amplifying segments of DNA with oligonucleotides that carry randomized sequences and then reamplifying the DNA to create the cassette for cloning; C) by first amplifying each half of the DNA segment with oligonucleotides that carry randomized sequences, and then heating the two pieces together to create the cassette for cloning; and D) by error-prone PCR. The cassettes formed by these four procedures are fixed in length and coding frame, but have codons which are unspecified at a low frequency. Thus, cloning and expression of the cassettes will generate a plurality of peptides or proteins that have one or more mutant residues along the entire length of the cassette.

Typically, two types of mutagenesis scheme can be used. First, certain residues in a phage-displayed protein or peptide can be completely randomized. The codons at these positions can be NNN, NNK, or NNS which use 32 codons to encode all 20 residues. They can also be synthesized as preformed triplets or by mixing oligonucleotides synthesized by the split-resin method which together cover all 20 codons at each desired position. Conversely, a subset of codons can be used to favor certain amino acids and exclude others. Second, all of the codons in the cassette can have some low probability of being mutated. This is accomplished by synthesized oligonucleotides with bottles "spiked" with the other three bases or by altering the ratio of oligonucleotides mixed together by the split-resin method.

For mutagenesis of short regions, cassette mutagenesis with synthetic oligonucleotide is generally preferred. More than one cassette can be used at a time to alter several regions simultaneously. This approach is preferred when creating a library of mutant antibodies, where all six complementarity determining regions (CDR) are altered concurrently.

Random Codons

1. Design oligonucleotides with both fixed and mutated positions. The fixed positions should correspond to the cloning sites and those coding regions presumed to be essential for binding or function.

2. During synthesis of the oligonucleotide, have the oligonucleotide synthesizer deliver equimolar amounts of each base for N, guanosine and cytosine for K, guanosine and thymidine for S.

"Spiked" Codons

1. Design oligonucleotides with both fixed and mutated positions. The fixed positions should correspond to the cloning sites and those coding regions presumed to be essential for binding or function. The probability of finding n errors in an m long polynucleotide cassette synthesized with x fraction of the other three nucleotides at each position is represented by:

$P=[m!/(m-n)n!][x^n][1-x]^{m-n}$

2. During synthesis of the oligonucleotide switch out the base bottles. Use bottles with 100% of each base for the fixed positions and bottle with 100-x% of one base and x/3% of each of the other three bases. The doping ratio can also differ based on the average amino acid use in natural globular proteins or other algorithms. There is a commercially available computer program, CyberDope, which can be used to aid in determining the base mixtures for synthesizing oligonudeotides with particular doping schemes. A demonstration copy of the CyberDope program can be obtained by sending an email request to cyberdope@aol.com.

Directed Codons

1. Design oligonucleotides with both fixed and mutated positions. The fixed positions should correspond to the cloning sites and those coding regions presumed to be essential for binding or function. One method has been described for inserting a set of oligonucleotides at a specific restriction enzyme site that encodes all twenty amino acids (Kegler-Ebo et al. (1994) *Nucl. Acids Res.* 22: 1593, incorporated herein by reference).

2. During synthesis of the oligonucleotide split the resin at each codon.

Error-prone PCR

There are several protocols based on altering standard PCR conditions (Saiki et al. (1988) *Science* 239: 487, incorporated herein by reference) to elevate the level of mutation during amplification. Addition of elevated dNTP concentrations and/or $Mn^{+2}$ increase the rate of mutation significantly. Since the mutations are theoretically introduced at random, this is one mechanism for generating populations of novel proteins. On the other hand, error-prone PCR is not well suited for altering short peptide sequences because the coding regions are short, and the rate of change would be too low to generate an adequate number of mutants for selection, nor is it ideal for long proteins, because there will be many mutations within the coding region which complicates analysis.

1. Design oligonucleotide primers that flank the coding region of interest in the phage. They are often approximately 21 nucleotides in length and flank the region to be mutagenized. The fragment to be amplified can carry restriction sites within it to permit easy subcloning in the appropriate vector.

2. The following reaction is set up:
   1 pmole of each primer; 1 pmole of the DNA template; 100 mM NaCl, 1 mM MnCl$_2$, 1 mM DTT, 0.2 mM of each dNTP, 2 units of Taq DNA polymerase.
3. Cover the liquid with mineral oil.
4. Cycle 24 times between 30 sec at 94° C., 30 sec 45° C., and 30 sec at 72° C. to amplify fragments up to 1 kb. For longer fragments, the 72° C. step is lengthened by approximately 30 sec for each kb.
5. Extend the PCR reaction for 5–10 min at 72° C. to increase the fraction of molecules that are full-length. This is important if the fragment termini contain restriction sites that will be used in subcloning later.
6. The PCR reaction is optionally monitored by gel electrophoresis.
7. The PCR product is digested with the appropriate restriction enzyme(s) to generate sticky ends. The restriction fragments can be gel purified.
8. The DNA segment is cloned into a suitable vector by ligation and introduced into host cells.

DNA Shuffling

In DNA shuffling, genes are broken into small, random fragments with a phosphodiester bond lytic agent, such as DNase I, and then reassembled in a PCR-like reaction, but without requirement for any added primers. The process of reassembling can be mutagenic in the absence of a proof-reading polymerase, generating up to approximately 0.7% error when 10–50 bp fragments are used.

1. PCR amplify the fragment to be shuffled. Often it is convenient to PCR from a bacterial colony or plaque. Touch the colony or plaque with a sterile toothpick and swirl in a PCR reaction mix (buffer, deoxynucleotides, oligonucleotide primers) Remove the toothpick and beat the reaction for 10 min at 99° C. Cool the reaction to 72° C., add 1–2 units of Taq DNA polymerase, and cycle the reaction 35 times for 30 sec at 94° C., 30 sec at 45° C., 30 sec at 72° C. and finally heat the sample for 5 min at 72° C. (Given conditions are for a 1 kb gene and are modified according the the length of the sequence as described.)

2. Remove the free primers. Complete primer removal is important.
3. Approximately 2–4 μg of the DNA is fragmented with 0.15 units of DNase I (Sigma, St. Louis, Mo.) in 100 μl of 50 mM Tris-HCl (pH 7.4), 1 mM MgCl$_2$, for 5–10 min at room temperature. Freeze on dry ice, check size range of fragments on 2% low melting point agarose gel or equivalent, and thaw to continue digestion until desired size range is used. The desired size range depends on the application; for shuffling of a 1 kb gene, fragments of 100–300 bases are normally adequate.
4. The desired DNA fragment size range is gel purified from a 2% low melting point agarose gel or equivalent. A preferred method is to insert a small piece of Whatman DE-81 ion-exchange paper just in front of the DNA, run the DNA into the paper, put the paper in 0.5 ml 1.2 M NaCl in TE, vortex 30 sec, then carefully spin out all the paper, transfer the supematant and add 2 volumes of 100% ethanol to precipitate the DNA; no cooling of the sample should be necessary. The DNA pellet is then washed with 70% ethanol to remove traces of salt.
5. The DNA pellet is resuspended in PCR mix (Promega, Madison, Wis.) containing 0.2 mM each DNTP, 2.2 mM MgCl$_2$, 50 mM KCl, 10 mM Tris-HCl, pH 9.0, 0.1% Triton X100, at a concentration of about 10–30 ng of fragments per μl of PCR mix (typically 100–600 ng per 10–20 μl PCR reaction). Primers are not required to be added in this PCR reaction. Taq DNA polymerase (Promega, Madison, Wis.) alone can be used if a substantial rate of mutagenesis (up to 0.7% with 10–50 bp DNA fragments) is desired. The inclusion of a proof-reading polymerase, such as a 1:30 (vol/vol) mixture of Taq and Pfu DNA polymerase (Stratagene, San Diego, Calif.) is expected to yield a lower error rate and allows the PCR of very long sequences. A program of 30–45 cycles of 30 sec 94° C., 30 sec 45–50° C., 30 sec 72° C., hold at 4° C. is used in an MJ Research PTC-150 minicycler (Cambridge, Mass.). The progress of the assembly can be checked by gel analysis. The PCR product at this point contains the correct size product in a smear of larger and smaller sizes.

6. The correctly reassembled product of this first PCR is amplified in a second PCR reaction which contains outside primers. Aliquots of 7.5 μl of the PCR reassembly are diluted 40×with PCR mix containing 0.8 pM of each primer. A PCR program of 20 cycles of 30 sec 94° C., 30 sec 50° C., and 30–45 sec at 72° C. is run, with 5 min at 72° C. at the end.

7. The desired PCR product is then digested with terminal restriction enzymes, gel purified, and cloned back into a vector, which is often introduced into a host cell.

Site-specific recombination can also be used, for example, to shuffle heavy and light antibody chains inside infected bacterial cells as a means of increasing the binding affinity and specificity of antibody molecules. It is possible to use the Cre/lox system (Waterhouse et al. (1993) *Nucl. Acids Res.* 21: 2265; Griffiths et al. (1994) *EMBO J.* 13: 3245, incorporated by reference) and the int system.

It is possible to take recombinants and to shuffle them together to combine advantageous mutations that occur on different DNA molecules and it is also possible to take a recombinant displayed insert and to "backcross" with parental sequences by DNA shuffling to remove any mutations that do not contribute to the desired traits.

Example 15

Shuffling to Generate Improved Arsenate Detoxification Bacteria

Arsenic detoxification is important for goldmining of arsenopyrite containing gold ores and other uses, such as environmental remediation. Plasmid pGJ103, containing an operon encoding arsenate detoxification operon (Wang et al. (1989) *Bacteriol.* 171: 83, incorporated herein by reference), was obtained from Prof. Simon Silver (U. of Illinois, Chicago, Ill.). *E. coli* TG1 containing pJG103, containing the p1258 ars operon cloned into pUC19, had a MIC (minimum inhibitory concentration) of 4 μg/ml on LB amp plates. The whole 5.5 kb plasmid was fragmented with DNAse I into fragments of 100–1000 bp, and reassembled by PCR using the Perkin Elmer XL-PCR reagents. After assembling, the plasmid was digested with the unique restriction enzyme BamHI. The full length monomer was purified from the agarose gel, ligated and electroporated into *E. coli* TG1 cells. The tranformed cells were plates on a range of sodium arsenate concentrations (2, 4, 8, 16 mM in round 1), and approx. 1000 colonies from the plates with the highest arsenate levels were pooled by scraping the plates. The cells were grown in liquid in the presence of the same concentration of arsenate, and plasmid was prepared from this culture. Round 2 and 3 were identical to round 1, except that the cells were plated at higher arsenate levels. 8, 16, 32, 64 mM were used for round 2; and 32, 64, 128, 256 mM were used for selection of round 3.

The best mutants grew overnight at up to 128 mM arsenate (MIC=256), a 64-fold improvement. One of the improved strains showed that the TG1 (wildtype pGGJ103) grew in liquid at up to 10 mM, whereas the shuffled TG1(mutant pGJ103) grew at up to 150 mM arsenate concentration.

PCR program for the assembly was 94° C. 20s, 50×(94° C. 15s, 50° C. 1 min, 72° C. 30s+2s/cycle), using a circular PCR format without primers.

Four cycles of the process resulted in a 50–100-fold improvement in the resistance to arsenate conferred by the shuffled arsenate resistance operon; bacteria containing the improved operon grew on medium containing up to 500 mM arsenate.

Figure 19:
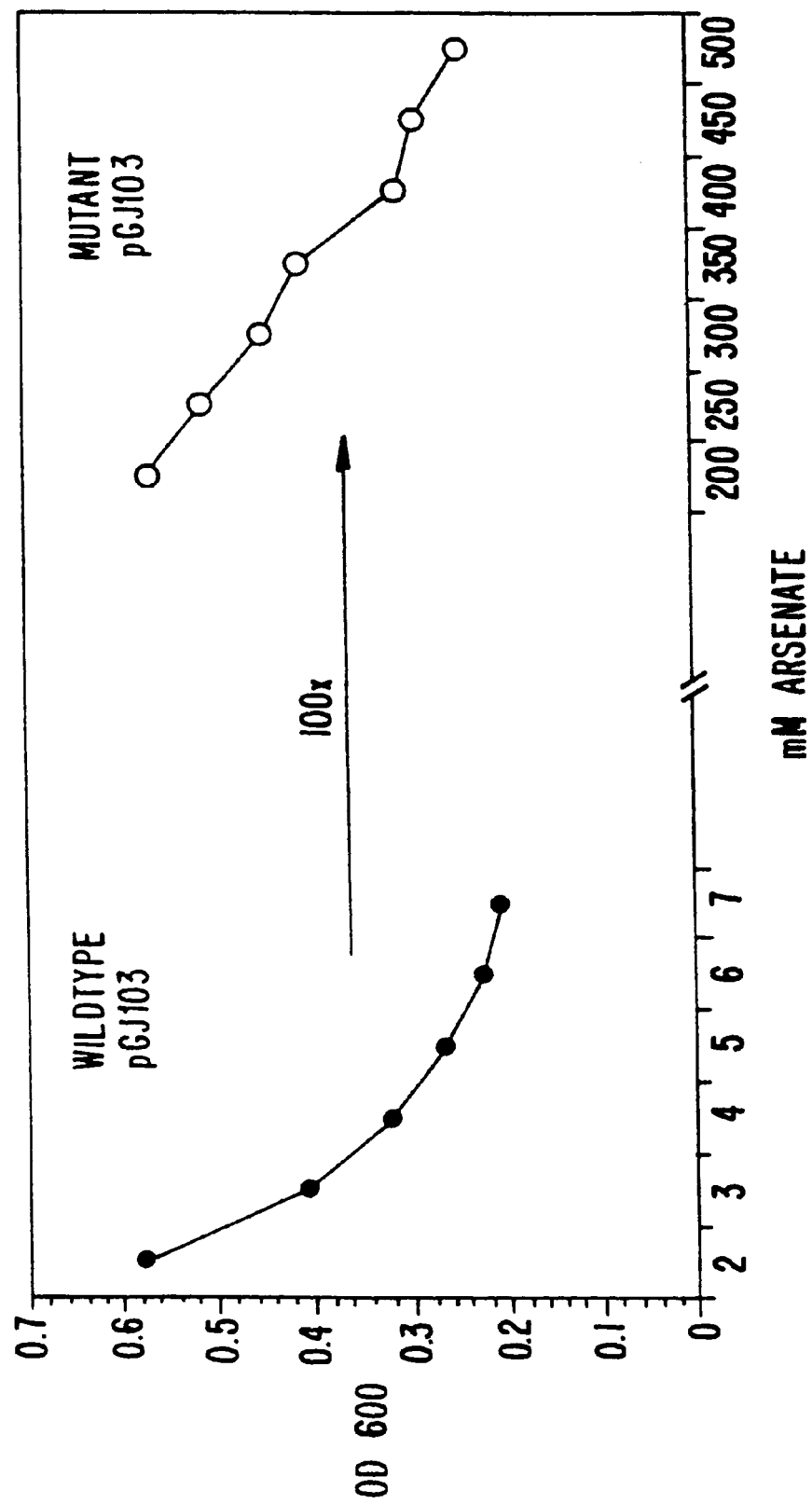
FIG. 19 shows enhancement of resistance to arsenate toxicity as a result of shuffling the pGJ103 plasmid containing the arsenate detoxification pathway operon.
Figure 20:
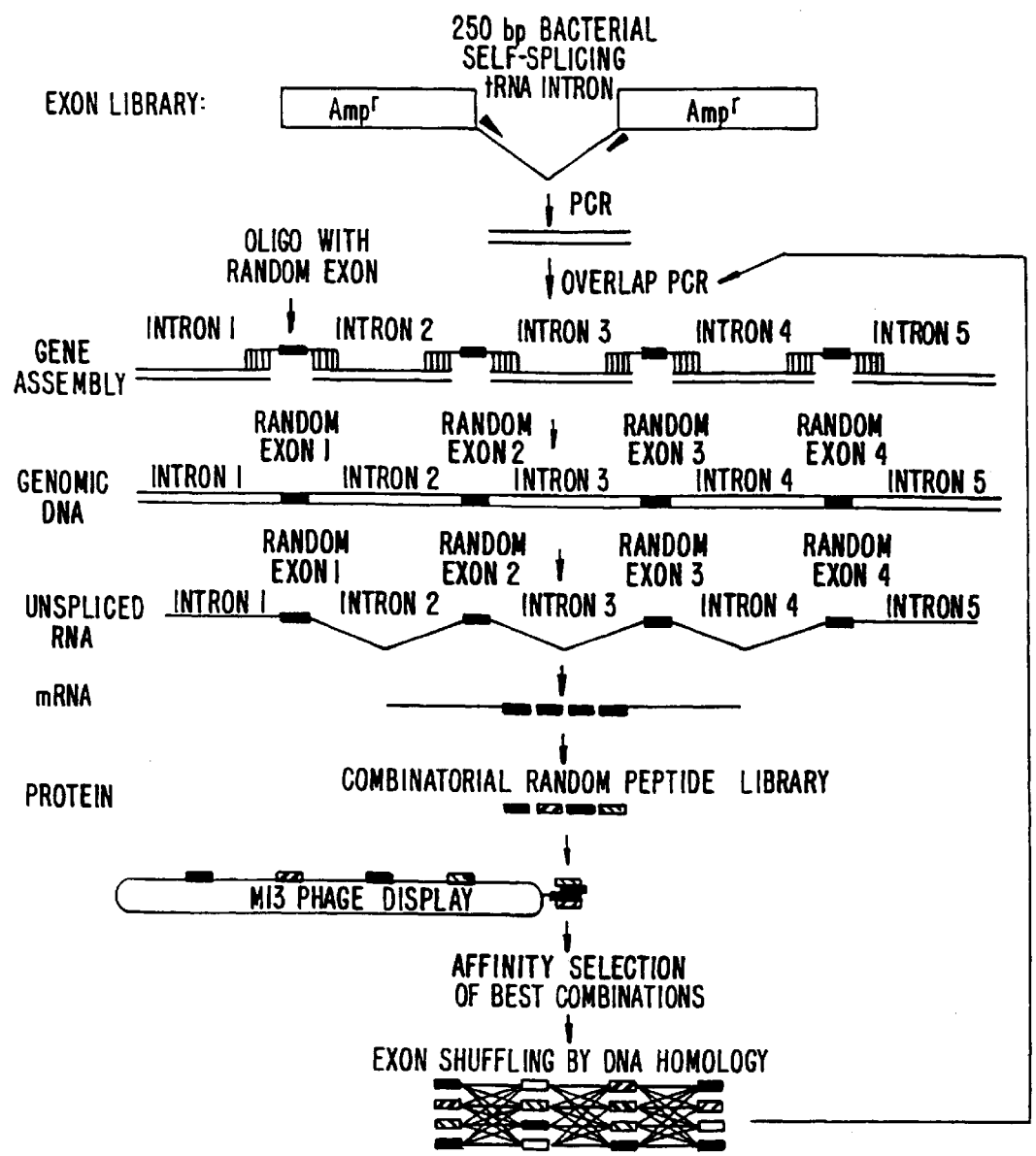
FIG. 20 schematically shows the generation of combinatorial libraires using synthetic or naturally-occurring intron sequences as the basis for recombining a plurality of exons species which can lack sequence identity (as exemplified by random sequence exons), wherein homologous and/or site-specific recombination occurs between intron sequences of distinct library members.
Figure 22A:
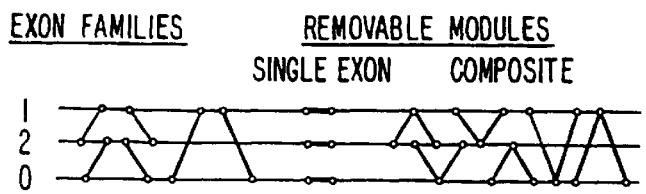
FIG. 22 schematically shows an exon splicing frame diagram for several human genes, showing that preferred units for shuffling exons begin and end in the same splicing frame, such that a splicing module (or shuffling exon) can comprise multiple naturally-occurring exons but typically has the same splicing frame at each end.
Figure 22B:
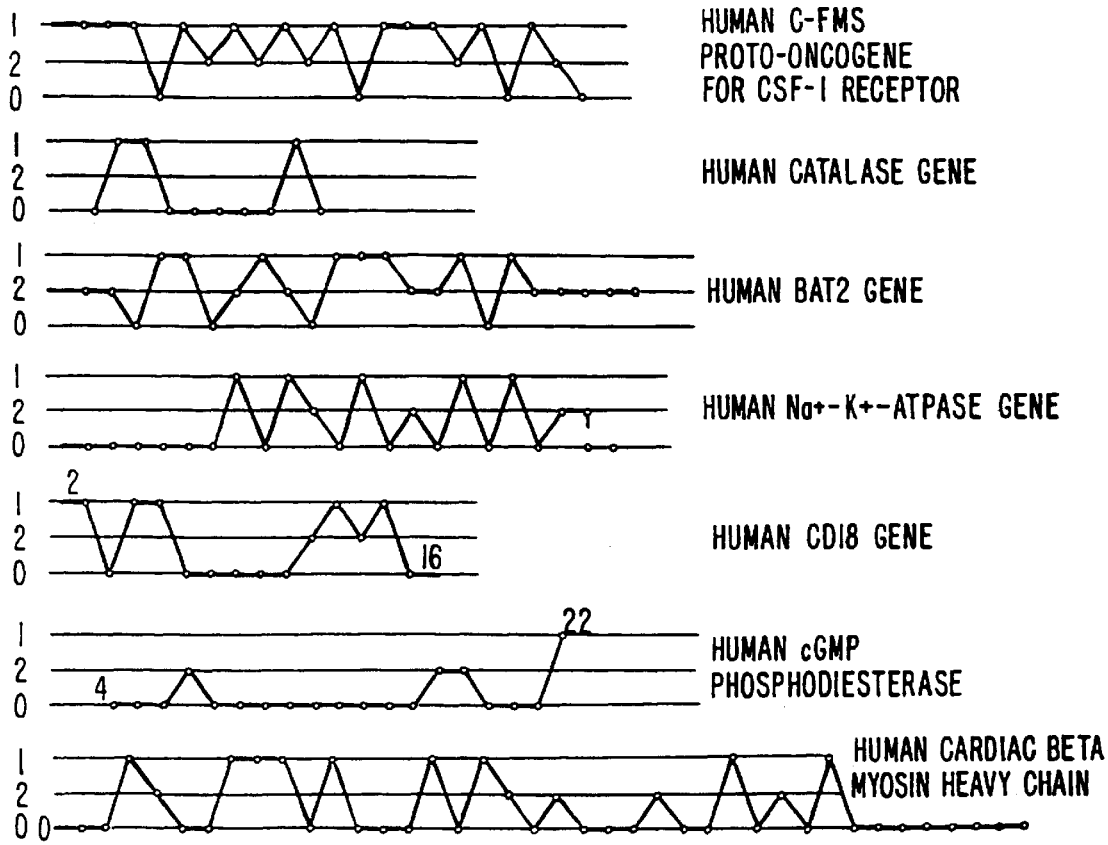
Figure 23:
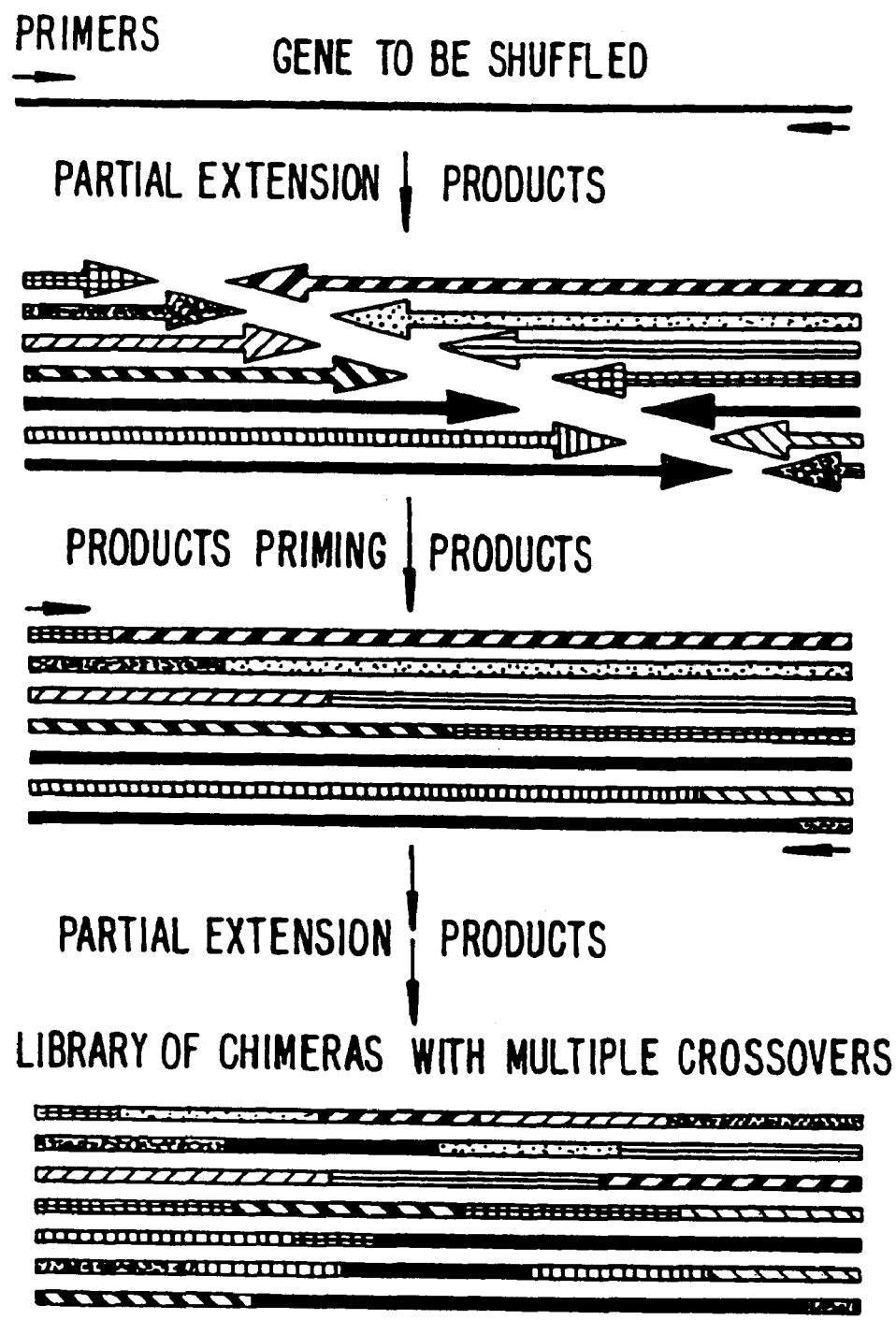
FIG. 23 schematically shows how partial PCR extension (stuttering) can be used to provide recursive sequence recombination (shuffling) resulting in a library of chimeras representing multiple crossovers.
Figures 24A, 24B, 24C:
FIG. 24 shows how stuttering can be used to shuffle a wild-type sequence with a multiply mutated sequence to generate an optimal set of mutations via shuffling.
Figure 25:
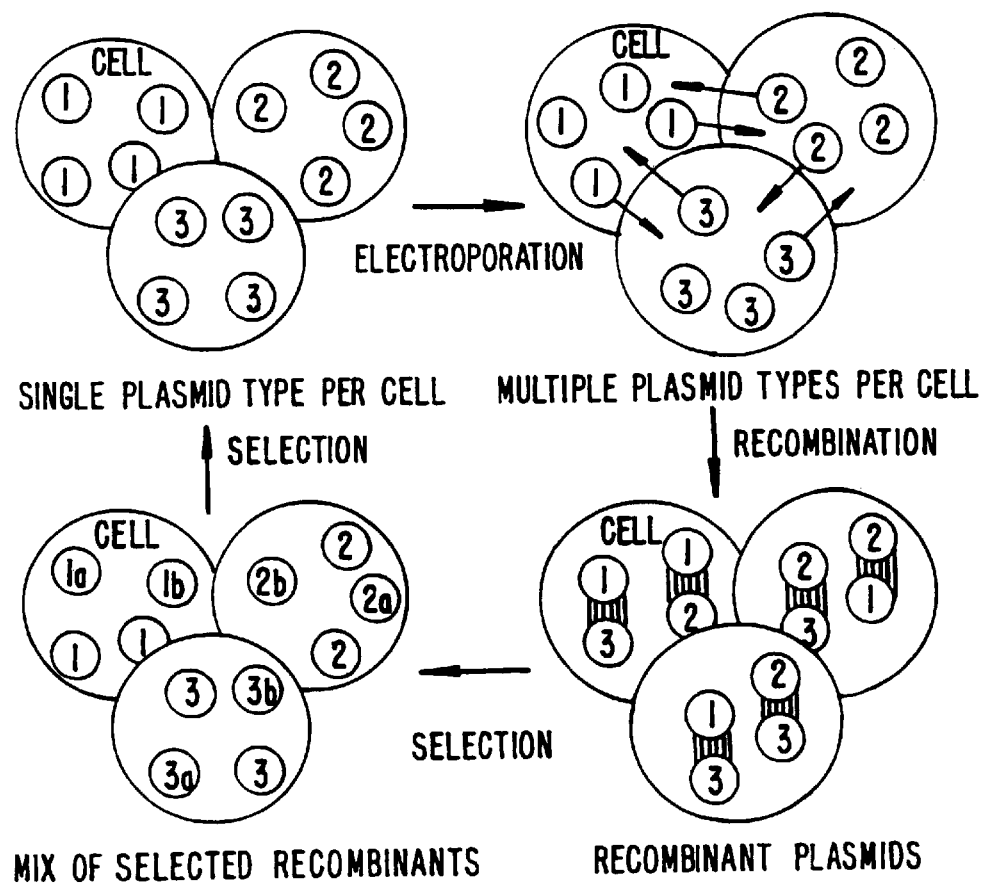
FIG. 25 schematically shows plasmid-plasmid recombination by electroporation of a cell population representing multiple plasmid species, present initially as a single plasmid species per cell prior to electroporation and multiple plasmid species per cell suitable for in vivo recombination subsequent to electroporation of the cell population.
Figure 26A:
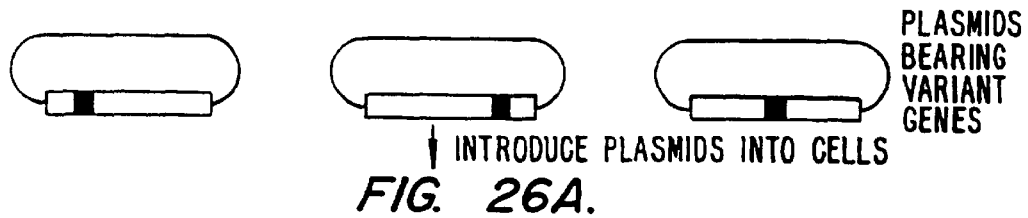
FIG. 26 shows plasmid-plasmid recombination.
Figure 26B:
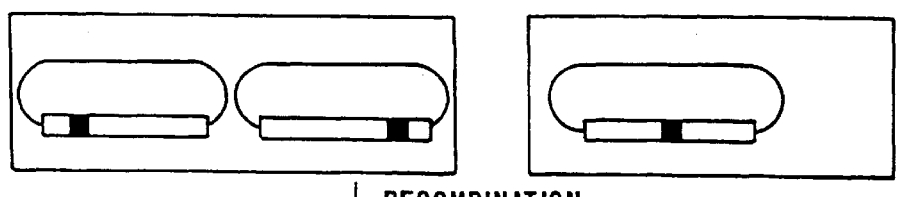
Figure 26C:
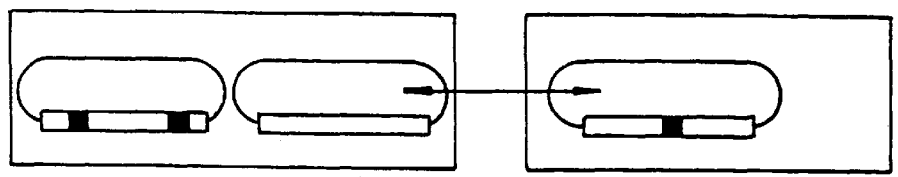
Figure 26D:
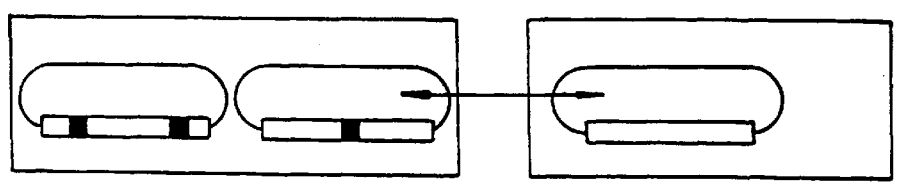
Figure 26E:
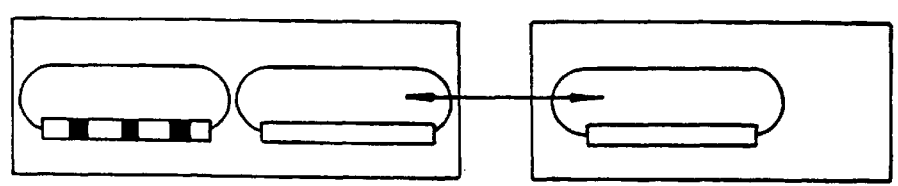
Figure 26F:
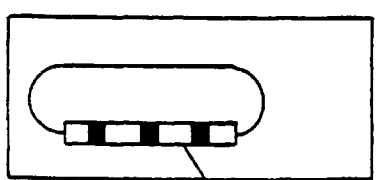

FIG. 19 shows enhancement of resistance to arsenate toxicity as a result of shuffling the pGJ103 plasmid containing the arsenate detoxification pathway operon.

Example 16

Shuffling to Generate Improved Cadmium Detoxification Bacteria

Plasmid pYW333, containing an operon for mercury detoxification is a 15.5 kb plasmid containing at least 8 genes encoding a pathway for mercury detoxification (Wang et al. (1989) *Bacteriol.* 171: 83, incorporated herein by reference), was obtained from Prof. Simon Silver (Univ. Illinois, Chicago, Ill.). 400–1500 bp fragments were obtained as described supra and assembled with the XL-PCR reagents. After direct electroporation of the assembled DNA into to *E. coli* TG1, the cells were plated on a range of levels of mercury chloride (Sigma) under a similar protocol as that described for arsenate in Example 15. The initial MIC of mercury was 50–70 μM. Four cycles of whole plasmid shuffling were performed and increased the detoxification measured as bacterial resistance to mercury from about 50–70 μM to over 1000 μM, a 15–20 fold improvement.

Example 17

Enhancement of Shuffling Reactions by Addition of Cationic Detergent

The rate of renaturation of complementary DNA strands becomes limiting for the shuffling long, complex sequences. This renaturation rate can be enhanced 10,000-fold by addition of simple cationic detergent (Pontius and Berg (1991) *PNAS* 88: 8237). The renaturation is specific and independent of up to a $10^6$-fold excess of heterologous DNA. In the presence of these agents the rate which the complementary DNA stands encounter each other in solution becomes limiting.

Addition of TMAC in an assembly reaction of a 15 kb plasmid followed by electroporation into *E. coli* resulted in the following results:

| TMAC (mM) | # Colonies |
|---|---|
| 0 | 3 |
| 15 | 88 |
| 30 | 301 |
| 60 | 15 |
| 90 | 3 |

Addition of CTAB in an assembly reaction of a 15 kb plasmid followed by electroporation into *E. coli* resulted in the following results:

| CTAB (mM) | # Colonies |
|---|---|
| 0 | 3 |
| 30 | 34 |
| 100 | 14 |
| 300 | 0 |

EXAMPLE 18

Sequence Shuffling via PCR Stuttering

Stuttering is fragmentation by incomplete polymerase extension of templates. A recombination format based on very short PCR extension times was employed to create partial PCR products, which continue to extend off a different template in the next (and subsequent) cycle(s). There was a strong growth rate bias between very similar templates, indicating that this format has significant limitations for the application to complex pools. If used with a rapid cycler such as the aircycler, this format may work better.

PCR programs used for PCR stuttering were 100 cycles of (94° C. 15 sec, 60° C. 15 sec). Two separate PCR reactions were run to obtain 1 kb PCR fragments containing the each of two GFP-negative recombination assay substrates (GFPstop1 and GFP stop2). GFP-positive recombinants can only be obtained by recombination of these two templates. The oligonucleotide primers used at the 5' end is 5'TAGCGGATCCTACCTACCTGACGC3'(SEQ ID NO:69), containing an NheI site, and the oligo at the 3' end is 5'GAAAATCTTCTCTCATCC3'(SEQ ID NO:70), containing an EcoRI site. A PCR reaction was set up with a 1ng of each GFP-negative gene as a template. Taq PCR reagents can be used, but the use of error-prone PCR conditions (Leung, 1989; Cadwell and Joyce, 1992) which reduce the processivity, can increase the percentage of GFP-positive recombinants.

A stuttering program of 50–150 cycles of 94° C. 10–20s, 60° C. 10–30s was used on a Stratagene Robocycler. The stuttered PCR product was digested with NheI and Eco RI and cloned back into pBAD18 vector digested with NheI and EcoRI and electroporated into *E. coli* and plated on amp plates. GFP-positive colonies arise by recombination between the two gFP-negative DNA sequences and were detected. The percentage of GFP-positive colonies obtained by stuttering was between 0.1–10%, depending on conditions.

A synthetic gene was designed for each protein, using the identical (optimal *E.coli*) codon usage based on the native amino acid sequence. This approach increases the DNA homology of the synthetic genes relative to the naturally occurring genes, and allows us to shuffle more distantly related sequences than would be possible without the codon usage adjustment. Each of the four genes was assembled from 30 60 mer oligos and 6 40 mers. The assembly was performed by assembly PCR as described by Stemmer et al (1995; Gene 164:49–53). After assembling, the genes were cloned into Sfi 1 sites of the vector pUC322 Sfi-BLA-Sfi (Stemmer et al (1995) Gene 164:49–53), and plated on a selective media. The minimum inhibitory activity of these four constructs for a wide variety of betalactam antibiotics was established. Cefotaxime was one of the antibiotics that was selected for optimization against. The four genes were shuffled by pooling 1 ug of the CR product of each gene, followed by DNAseI digestion of the pool and purification of 100–300 bp fragments from agarose gels. The purified fragments were reassembled by sexual PCR initially without outside primers, and then the full-length product was amplified in the presence of the outside primers. The resulting full-length genes were digested with SfiI and ligated into fresh pUC322Sfi-Sfi vector and electroporated into fresh E. coli cells, and plated on increasing concentration of several antibiotics, including cefotaxime, as described previously by Stemmer (1994) Nature 370:389–391.

A manual shuffling PCR protocol is preferred for the mixing of genes that are less than 80–90% homologous. The manual PCR uses a heat-labile DNA polymerase, such as DNA polI Klenow fragment. The initial PCR program with fragments in Klenow buffer at 10–30ng/ul and dNTPs:

1-Denature 94° C. 20s

2-Quick-cool: dry ice ethanol 5s, ice 15s

3-Add Klenow enzyme

4-Anneal/extend 2 min 25° C.

5-cycle back to denature (cycle 1)

This is repeated for 10–20 cycles to initiate the template switching, after which regular PCR with heatstable polymerases is continued for an additional 10–20 cycles to amplify the amount of product.

Example 19

Shuffling of Antibody Phage Display Libraries

A stable and well-expressed human single-chain Fv framework ($V_H$251-$V_L$A25) was obtained from an Ab-phage library constructed from naive human mRNA by selection for binding to diptheria toxin. This scFv framework was used to construct a naive Ab-phage library containing six synthetically mutated CDRs based on the germline sequences. The degree of mutagenesis of each residue was similar to its naturally occurring variability within its V-region family.

A PCR product containing the scFv gene was randomly fragmented with DNaseI digestion and fragments of 50–100 bp were purified. Synthetic oligonucleotides, each containing a mutated CDR flanked by 19 bp of homology to the scFv template, were added to the random fragments at a 10:1 molar ratio. A library of full length, mutated scFV genes was reassembled from the fragments by sexual PCR. Cloning into the pIII protein of M13 phage yielded an Ab-phage library of $4 \times 10^7$ plaque-forming units. The combinations of mutant and native CDRs were characterized by colony PCR with primers specific for the native CDRs (see, FIG. 7). All six mutated CDRs were incorporated with 32–65% efficiency and a wide variety of combinations. sequencing of the mutated CDRs showed that the observed mutation rate matched the expected rate.

This Ab-phage library was panned for two rounds in microtiter plates for binding to ten human protein targets, and seven of these targets yielded ELISA-positive clones. One target which resulted in positive clones was the human G-CSF receptor. The G-CSF receptor positive clones were subjected to a second round and one quarter of second round phage clones were ELISA-positive for binding to the G-CSF receptor.

Figure 31:
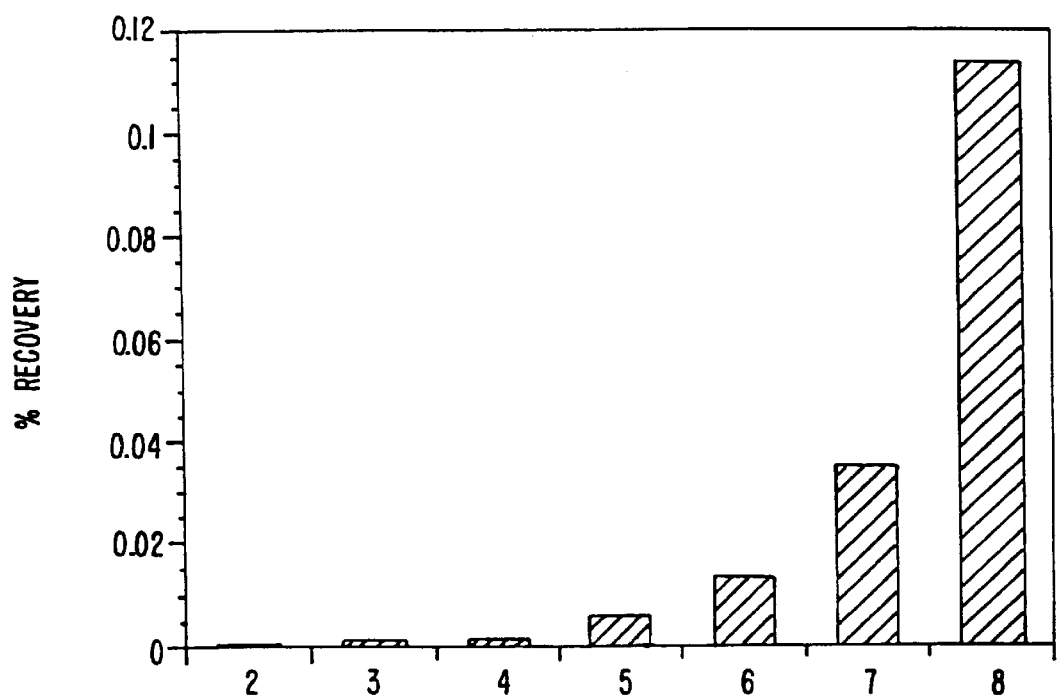
FIG. 31 shows Ab-phage recovery rate versus selection cycle. Shuffling was applied after selection rounds two to eight. Total increase is 440-fold.

This diverse pool was used to evaluate the suitability of three different sequence optimization strategies (conventional PCR, error-prone PCR, and DNA shuffling). After a single cycle of each of these alternatives, the DNA shuffling showed a seven-fold advantage, both in the percentage of Ab-phage recovered and in the G-CSF receptor-specific ELISA signal. The panning was continued for six additional cycles, shuffling the pool of scFv genes after each round. The stringency of selection was gradually increased to two one-hour washes at 50° C. in PBS-Tween in the presence of excess soluble G-CSF receptor. In rounds 3 to 8, nearly 100 percent of the clones were ELISA positive. When pools from different cycles were assayed at identical stringency, the percentage of phage bound increased 440-fold from cycle 2 to cycle 8, as shown in FIG. 31. Individual phage clones from each round showed a similar increase in specific ELISA signal.

Sequencing showed that the scFv contained an average of 34 (n=4) amino acid mutations, of which only four were present in all sequences evaluated.

Figure 32:
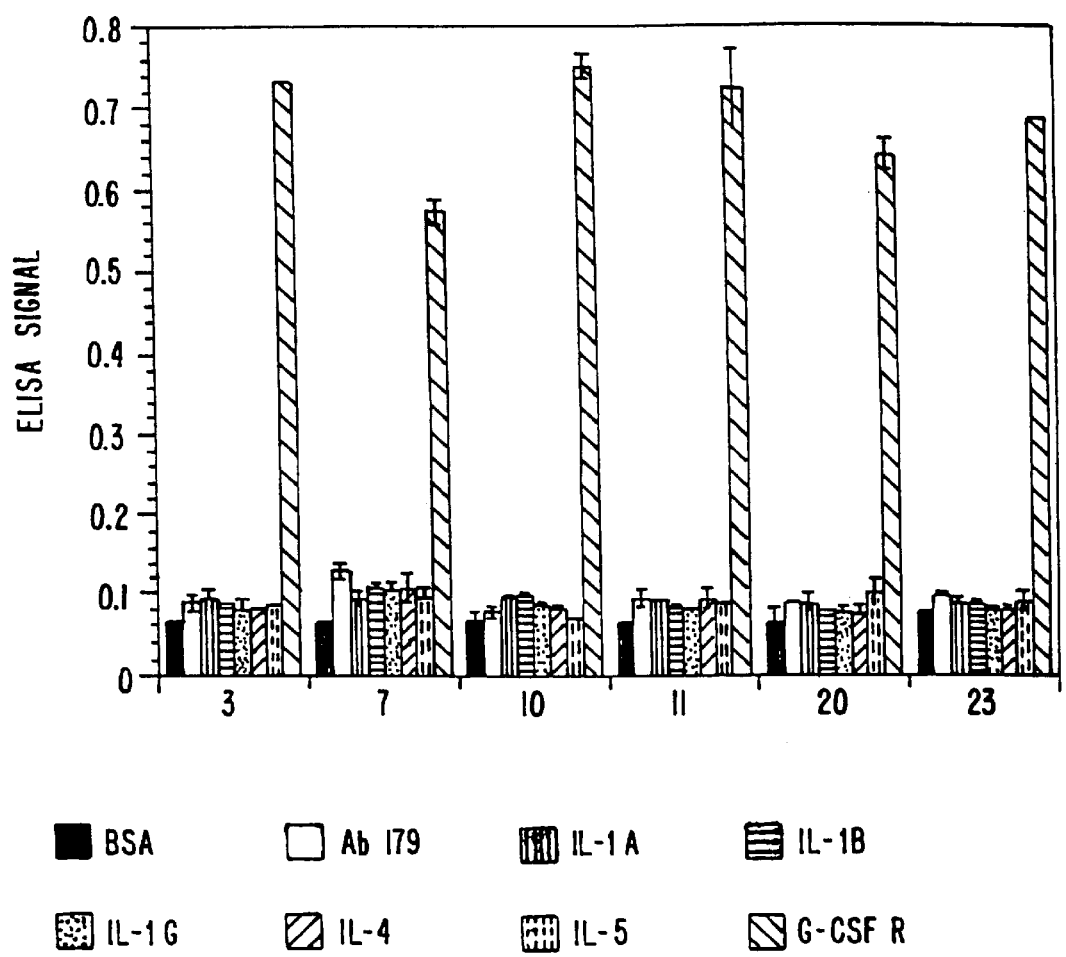
FIG. 32 shows binding specificity after ten selection rounds, including two rounds of backcrossing. ELISA signal of different Ab-phage clones for eight human protein targets.
Figure 33A:
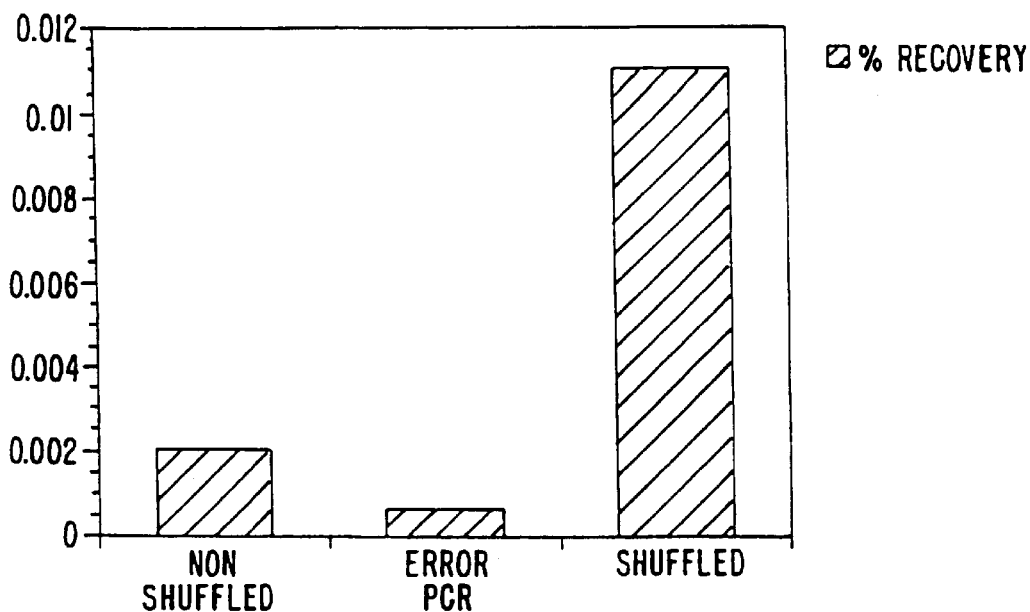
FIG. 33 shows Ab-phage recovery versus mutagenesis method.
Figure 33B:
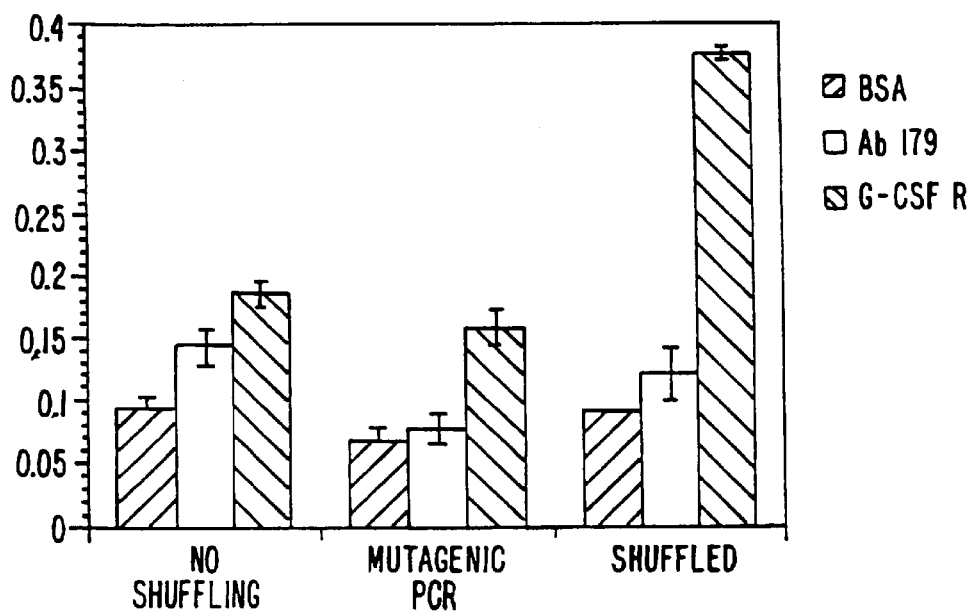

In order to reduce potential immunogenicity, neutral or weakly contributing mutations were removed by two cycles of backcrossing, with a 40-fold excess of a synthetically constructed germline scFv gene, followed by stringent panning. The average number of amino acid mutations in the backcrossed scFvs were nearly halved to 18 (n=3), of which only four were present in all sequences. The backcrossed Ab phage clones were shown to bind strongly and with excellent specificity to the human G-CSF receptor. FIG. 32 shows the effect of ten selection rounds for several human protein targets; six rounds of shuffling and two rounds of backcrossing were conducted. FIG. 33 shows the relative recovery rates of phage, by panning with BSA, Ab 179, or G-CSF receptor, after conventional PCR ("non-shuffled"), error-prone PCR, or recursive sequence recombination ("shuffled").

Example 20

Optimization of GFP in Mammalian Cells

The plasmid vector pCMV-GFP, which encodes GFP and expresses it under the control of a CMV promoter, was grown in TG1 cells and used to transfect CHO cells for transient expression assays.

Plasmid was rescued from FACS selected transiently expressing TGl cells by a proteinase K method or a PreTaq method (Gibco/BRL). Basically, the FACS collected cells were pelleted by centrifugation, freeze-thawed repetitively, incubated with either proteinase K or PreTaq, phenol/chloroform extracted, ethanol precipitated, used to transform E. coli which were then plated on Amp plates. The results were:

Proteinase K method: input-$5 \times 10^4$ rescued $3 \times 10^4$

PreTaq method: input-$5 \times 10^4$ rescued $2 \times 10^4$

The rescued plasmid was grown up and 5 jg was partially digested with DNaseI and 50 to 700 bp fragments were gel purified, ethanol precipitated, and resuspended in 330 µl of 3.3×PCR buffer, 44 µl Mg(OAc)$_2$ (Perkin-Elmer), 193 µl 40% PEG, 80 µl 10 mM dNTPs, 20 µl Tth polymerase, 2 µl Pfu polymerase, 7 µl TMAC (Sigma), and 367 µl H$_2$O. PCR was conducted on a MJ Research PTC-150 minicycler for 40 cycles (94° C., 30 sec; 50° C., 30 sec, 72° C., 60 sec) with three sets of primers, which yielded three end-overlapping PCR fragments, which together and after digestion and ligation reconstituted the entire plasmid. The PCR fragments were digested with AlwNI and the fragments were gel purified, ligated, and electroporated into TG1 cells. Plasmid DNA was prepared and electroporated into CHO cells, which were screened by FACS for the cells transiently expressing the brightest GFP signals.

While the present invention has been described with reference to what are considered to be the preferred examples, it is to be understood that the invention is not limited to the disclosed examples. To the contrary, the invention is intended to cover various modifications and equivalent arrangements included within the spirit and scope of the appended claims.

REFERENCES

The following references are cited in this application at the relevant portion of the application.

1. Holland, J. H. (1992) *Sci. Am.* July, 66–72.
2. Holland, J. H. (1992) "Adaptation in natural and artificial systems". Second edition, MIT Press, Cambridge.
3. Joyce, G. F. (1992) *Scientific American*, December, 90–97.
4. Kauffman, S. A. (1993) "The origins of order". Oxford University Press, New York.
5. Stormo, G. D. (1991) *Methods Enzymol.* 208:458–468.
6. Schneider, T. D. et al., (1986) *J. Mol. Biol.* 188:415–431.
7. Reidhaar-Olson, J. F and Sauer, R. T. (1988) *Science* 241:53–57.
8. Stemmer, W. P. C. et al., (1992) *Biotechniques* 14:256–265.
9. Yockey, H. P. (1977) *J. Theor. Biol.* 67:345–376.
10. Yockey, H. P. (1974) *J. Theor. Biol.* 46:369–380.
11. Leung, D. W. et al., (1989) *Technique* 1:11–15.
12. Caldwell, R. C. and Joyce, G. F. (1992) PCR Methods and Applications 2:28–33.
13. Bartel, D. P., and Szostak, J. W. (1993) *Science* 261:1411–1418.
14. Bock, L. C. et al., (1992) *Nature* 355:564–566.
15. Scott, J. K. and Smith, G. P. (1990) *Science* 249:386–390.
16. Cwirla, S. E. et al. (1990) *Proc. Natl. Acad. Sci. USA* 87:6378–6382.
17. McCafferty, J. et al. (1990) *Nature* 348:552–554.
18. Cull, M. G. et al., (1992) *Proc. Natl. Acad. Sci. USA* 89:1865–1869.
19. Gramm, H. et al., (1992) *Proc. Natl. Acad. Sci. USA* 89:3576–3580.
20. Arkin, A. and Youvan, D. C. (1992) *Proc. Natl. Acad. Sci. USA* 89:7811–7815.
21. Oliphant, A. R. et al., (1986) *Gene* 44:177–183.
22. Hermes, J. D. et al., (1990) *Proc. Natl. Acad. Sci. USA* 87:696–700.
23. Meyerhans, A. et al., (1990) *Nucleic Acids Res.* 18:1687–1691.
24. Osterhout, J. J. et al., (1992) *J. Am. Chem. Soc.* 114:331–337.
25. Cano, R. J. et al., (1993) *Nature* 363:536–538.
26. Palzkill and Botstein, (1992) *J. Bacteriol.* 174:5237–5243.
27. Marton et al., *Nucleic Acids Res.* 19:2423.
28. Yanish-Perron et al., [1985] *Gene* 33:103–119.
29. Watson (1988) *Gene* 70:399–403.
30. Ambler et al. (1991) *Biochem J.* 276:269–272.
31. Chen and Clowes, (1984) *Nucleic Acid Res.* 12:3219–3234.
32. Witholt, B. ([1987] *Anal. Biochem.* 164(2):320–330
33. Kabat et al., (1991) "Sequences of Proteins of Immunological Interest" U.S. Department of Health and Human Services, NIH Publication 91-3242.
34. Philippon et al., (1989) *Antimicrob Agents Chemother* 33:1131–1136.
35. Jacoby and Medeiros (1991) *Antimicrob. Agents Chemother.* 35:167–1704.
36. Coelhosampaio (1993) *Biochem.* 32:10929–10935
37. Tuerk, C. et al., (1992) *Proc. Natl. Acad. Sci. USA* 89:6988–6992.
38. U.S. Pat. No. 4,683,195
39. U.S. Pat. No. 4,683,202
40. Delagrave et al. (1993) *Protein Engineering* 6: 327–331
41. Delgrave et al. (1993) *BiolTechnology* 11: 1548–1552
42. Goldman, E R and Youvan D C (1992) *Bio/Technology* 10:1557–1561
43. Nissim et al. (1994) *EMBO J.* 13: 692–698
44. Winter et al. (1994) *Ann. Rev. Immunol.* 12: 433–55
45. Caren et al. (1994) *Bio/Technology* 12: 517–520
46. Calogero et al. (1992) *FEMS Microbiology Lett.* 97: 41–44
47. Galizzi et al. WO91/01087
48. Hayashi et al. (1994) *Biotechniques* 17: 310–315
49. Radman et al. WO90/07576

All publications, patents and patent applications are herein incorporated by reference in their entirety to the same extent as if each individual publication, patent or patent application was specifically and individually indicated to be incorporated by reference in its entirety. PCT/US95/02126 filed Feb. 17, 1995 and published on Aug. 24, 1995 as WO95/22625 is incorporated herein by reference. Copending application attorney docket No. 16528A-0196 is incorporated herein by reference.

What is claimed is:

1. A method for producing a polynucleotide having a desired functional property, said method comprising:
   (a) providing a population of homologous polynucleotides, wherein at least two of the related polynucleotides differ from each other by the presence of at least one deletion or insertion;
   (b) shuffling the homologous polynucleotides to produce a plurality of recombinant polynucleotides, and selecting or screening the population of recombinant polynucleotides to obtain at least one recombinant polynucleotide that has evolved toward the desired functional property; and, (c) shuffling the recombinant polynucleotide(s) produced in the previous step, and selecting or screening for at least one recombinant polynucleotide that has evolved toward the desired functional property.

2. The method of claim 1, further comprising the step of repeating step (c) from 1 to 50 times, until a recombinant polynucleotide has acquired the desired functional property.

3. The method of claim 1, wherein step (c) comprises selecting for at least one recombinant polynucleotide that has evolved toward the desired functional property.

4. The method of claim 1, wherein the related polynucleotides are produced by mutagenesis of a parental polynucleotide.

5. The method of claim 4, wherein at least one polynucleotide in the population of related polynucleotides differs from the parental polynucleotide by a deletion of at least one nucleotide.

6. The method of claim 4, wherein at least one polynucleotide in the population of related polynucleotides differs from the parental polynucleotide by an insertion.

7. The method of claim 6, wherein the insertion is of an oligonucleotide.

8. The method of claim 7, wherein a synthetic oligonucleotide is inserted.

9. The method of claim 7, wherein the oligonucleotide is inserted into the parental polynucleotide by ligation.

10. The method of claim 1 wherein the desired functional property is a binding activity.

11. The method of claim 1, wherein the related polynucleotides and the recombinant polynucleotides are double-stranded and at least one cycle of shuffling comprises:

a) treating the related or recombinant polynucleotides under conditions which provide for the cleavage of said polynucleotides into random double-stranded fragments of a desired size;

b) denaturing the double-stranded fragments into single-stranded fragments, whereby a mixture of overlapping single-stranded fragments is produced; and, c) incubating the resultant population of single-stranded fragments with a polymerase under conditions which result in the annealing of the single-stranded fragments at areas of similarity to form pairs of annealed fragments, said areas of similarity being sufficient for one member of a pair to prime replication of the other thereby forming recombinant polynucleotides.

12. The method of claim 11, wherein at least one cycle of shuffling comprises:

a) treating the related or recombinant polynucleotides under conditions which provide for the cleavage of said polynucleotides into random double-stranded fragments of a desired size;

b) combining the product of step (a) and one or more single or double-stranded oligonucleotides, wherein said oligonucleotides comprise an area of similarity and an area of heterology to the related or recombinant double-stranded polynucleotides;

c) denaturing the resultant mixture of double-stranded overlapping fragments and oligonucleotides into single-stranded fragments; and, c) incubating the resultant population of single-stranded fragments with a polymerase under conditions which result in the annealing of the single-stranded fragments at areas of identity similarity to form pairs of annealed fragments, said areas of similarity being sufficient for one member of a pair to prime replication of the other thereby forming recombinant polynucleotides.

13. A method for producing a polynueleotide having a desired property, said method comprising:

conducting a multi-cycle polynucleotide extension process on overlapping segments having sequences of a population of related polynucleotides under conditions whereby one segment serves as a template for extension of another segment, to generate a population of recombinant polynucleotides, wherein said related polynucleotides differ from each other by the presence of deletions or insertions; and screening or selecting recombinant polynucleotides or expression products thereof to identify at least one recombinant polynucleotide having a desired functional property.

14. A method for producing a polynucleotide having a desired property, said method comprising:

(a) choosing a plurality of polynucleotide variants to be shuffled, wherein at least one polynucleotide variant has been mutagenized;

(b) conducting a multi-cyclic polynucleotide extension process on partially annealed polynucleotide strands comprising sequences from the plurality of polynucleotide variants, the polynucleotide strands having regions of similarity and regions of heterology with each other and being partially annealed through the regions of similarity, under conditions whereby one strand serves as a template for extension of another strand with which it is partially annealed to generate a population of recombinant polynucleotides; and (c) selecting and screening recombinant polynucleotides to identify at least one polynucleotide having a desired functional property.

15. The method of claim 14 wherein said mutagenesis is the introduction of at least one deletion.

16. The method of claim 15 wherein said mutagenesis is the introduction of at least one insertion.

17. The method of claim 16 wherein said insertion is of an oligonucleotide.

18. The method of claim 17 wherein said oligonucleotide is a synthetic oliognucleotide.

19. The method of claim 16 wherein an intron sequence is introduced between exons in at least one of the polynucleotide variants.

20. The method of claim 19 wherein said intron sequence is a naturally-occurring intron sequence.

21. The method of claim 19 wherein said intron sequence is inserted between exons in at least two polynucleotide variants, and wherein the intron sequence promotes homologous recombination between the exons.

22. The method of claim 19 wherein a plurality of intron sequences are introduced in the polynucleotide variants.

23. The method of claim 22 wherein said plurality of intron sequences have sufficient sequence identity to promote homologous recombination between the exons separated by the intron sequences.

24. The method of claim 19 wherein said exon sequences are naturally occurring exons.

25. The method of claim 14 wherein said mutagenesis is oligonucleotide directed mutagenesis.

26. The method of claim 14 wherein said mutagenesis is error-prone PCR.

27. The method of claim 14 wherein said mutagenesis is chemical mutagenesis.

28. The method of claim 1 wherein said population of homologous polynucleotides comprises allelic or species variants, and wherein said deletion or insertion is naturally occurring.

29. The method of claim 1 wherein at least one cycle of shuffling comprises conducting a multi-cyclic polynucleotide extension process on partially annealed polynucleotide strands comprising sequences from the plurality of homologous polynucleotides, the polynucleotide strands having regions of similarity and regions of heterology with each other and being partially annealed through the regions of similarity, under conditions whereby one strand serves as a template for extension of another strand with which it is partially annealed to generate the recombinant polynucleotides.

30. A method of producing a polynucleotide having a desired functional property comprising:
   (a) providing a plurality of polynucleotides comprising exon sequences separated by an intron sequence, at least one of which polynucleotide is in cell-free form;
   (b) shuffling the population of polynucleotides to produce recombinant polynucleotides;
   (c) selecting or screening for recombinant polynucleotides that have evolved toward the desired property;
   (d) repeating steps 2) and 3) with the recombinant polynucleotides selected in step 3) until a recombinant polynucleotide has acquired the desired functional property.

31. The method of claim 30 wherein said intron sequence is a naturally-occurring intron sequence.

32. The method of claim 30 wherein wherein the intron sequence promotes homologous recombination between the exons.

33. The method of claim 30 wherein a plurality of intron sequences are introduced.

34. The method of claim 33 wherein at least two of said plurality of intron sequences have sufficient sequence identity to promote homologous recombination between the intron sequences.

35. The method of claim 30 wherein said exon sequences are naturally occurring exons.

36. The method of claim 30 wherein at least one shuffling step is performed in vitro.

37. The method of claim 30 wherein at least one shuffling step is performed in vivo.

38. The method of claim 30 wherein at least cycle of shuffling comprises conducting a multi-cyclic polynucleotide extension process on partially annealed polynucleotide strands comprising sequences from the plurality of polynucleotides, the polynucleotide strands having regions of similarity and regions of heterology with each other and being partially annealed through the regions of similarity, under conditions whereby one strand serves as a template for extension of another strand with which it is partially annealed to generate a population of recombinant polynucleotides.

39. The method of any one of claims 1, 13, 14, 29, 30 and 38 wherein said recombinant polynucleotides encode for recombinant polypeptides and wherein said selecting or screening step comprises:
   (a) introducing said population of recombinant polynucleotides into a population of cells
   (b) expressing said recombinant polynucleotides in said population of cells; and
   (c) selecting or screening said population of cells for the desired functional property.

40. The method of any one of claims 1, 13, 14, 29, 30 and 38 wherein said recombinant polynucleotides encode for recombinant polypeptides and wherein said selecting or screening step comprises:
   (a) expressing said recombinant polynucleotides in vitro to produce said population of recombinant polypeptides; and
   (b) selecting or screening said population of recombinant polypeptides for the desired functional property.

41. The method of any one of claims 1, 13, 14, 29, 30 and 38, wherein the recombinant polynucleotide with the desired functional property encodes an enzyme.

42. The method of any one of claims 1, 13, 14, 29, 30 and 38, wherein the recombinant polynucleotide with the desired functional property encodes a viral coat protein.

43. The method of any one of claims 1, 13, 14, 29, 30 and 38, wherein the recombinant polynucleotide with the desired functional property encodes an antibody chain.

44. The method of any one of claims 1, 13, 14, 29, 30 and 38, wherein the recombinant polynucleotide with the desired functional property encodes a polymerase.

45. The method of any one of claims 1, 13, 14, 29, 30 and 38, further comprising expressing the recombinant polynucleotide with the desired functional property to produce an expression product thereof.

46. The method of claim 1, wherein at last one shuffling step comprises generating partial length copies of the homologous polynucleotides under conditions in which at least 20% of products are partial length products, whereby the partial length products anneal in new pairings and one member of a pair primes replication of the other, thereby forming the recombinant polynucleotides.

47. The method of claim 30, wherein at least one shuffling step comprises generating partial length copies of the polynucleotides to be shuffled under conditions in which at least 20% of products are partial length products, whereby the partial length products anneal in new pairings and one member of a pair primes replication of another thereby forming the recombinant polynucleotides.

48. The method of claim 13, further comprising conducting a polynucleotide extension reaction on the related polynucleotides to be shuffled under conditions in which at least 20% of products are partial length products to generate the overlapping segments.

49. The method of claim 14, further comprising conducting a polynucleotide extension reaction on the polynucleotide variants to be shuffled under conditions in which at least 20% of products are partial length products to generate the partially annealed polynucleotide strands.

50. The method of claim 14 wherein the partially annealed polynucleotide strands are produced by providing overlapping single-stranded segments of the plurality of polynucleotide variants and incubating under annealing conditions whereby the single-stranded segments from the different polynucleotide variants anneal to form the partially annealed polynueleotide strands.

51. The method of claim 50 wherein the overlapping single-stranded segments are random segments of the polynucleotide variants.

52. The method of claim 50 wherein the overlapping single-stranded segments are non-random segments of the polynucleotide variants.

53. The method of claim 50 wherein the plurality of overlapping single-stranded segments are produced by cleaving the population of polynucleotide variants to produce a population of overlapping double-stranded fragments, and denaturing the double-stranded fragments to produce the overlapping single-stranded segments.

54. The method of claim 50 wherein the overlapping single-stranded segments are produced on a DNA synthesizer.

55. The method of claim 29 wherein the partially annealed polynucleotide strands are produced by providing overlapping single-stranded segments of the plurality of homologous polynucleotides and incubating under annealing conditions whereby the single-stranded segments from the different homologous polynucleotides anneal to form the partially annealed polynucleotide strands.

56. The method of claim 54 wherein the overlapping single-stranded segments are random segments of the homologous polynucleotides.

57. The method of claim 54 wherein the overlapping single-stranded segments are non-random segments of the homologous polynucleotides.

58. The method of claim 54 wherein the plurality of overlapping single-stranded segments are produced by cleaving the population of homologous polynucleotides to produce a population of overlapping double-stranded fragments, and denaturing the double-stranded fragments to produce the overlapping single-stranded segments.

59. The method of claim 54 wherein the overlapping single-stranded segments are produced on a DNA synthesizer.

60. The method of claim 38 wherein the partially annealed polynucleotide strands are produced by providing overlapping single-stranded segments of the plurality of polynucleotides and incubating under annealing conditions whereby the single-stranded segments from the different polynucleotides anneal to form the partially annealed polynucleotide strands.

61. The method of claim 59 wherein the overlapping single-stranded segments are random segments of the polynucleotides.

62. The method of claim 59 wherein the overlapping single-stranded segments are non-random segments of the polynucleotides.

63. The method of claim 59 wherein the plurality of overlapping single-stranded segments are produced by cleaving the population of polynucleotides to produce a population of overlapping double-stranded fragments, and denaturing the double-stranded fragments to produce the overlapping single-stranded segments.

64. The method of claim 59 wherein the overlapping single-stranded segments are produced on a DNA synthesizer.

65. The method of claim 13 wherein said population of related polynucleotides are species variants.

66. The method of claim 14 wherein said plurality of polynucleotide variants are species variants.

67. The method of claim 29 wherein said plurality of homologous polynucleotides are species variants.

68. The method of claim 30 or 38 wherein said plurality of polynucleotides are species variants.

69. The method of any one of claim 50, 55 or 60, wherein the overlapping single stranded segments are produced by PCR amplification.

* * * * *

SEQUENCE LISTING (1) GENERAL INFORMATION:

(iii) NUMBER OF SEQUENCES: 70

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single (D) TOPOLOGY: linear (ii) MOLECULE TYPE: DNA (xi) SEQUENCE DESCRIPTION: SEQ ID NO:1:

AAAGCGTCGA TTTTTGTGAT                                                         20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

ATGGGGTTCC GCGCACATTT                                                         20

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

TTAGGCACCC CAGGCTTT                                                           18

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

ATGTGCTGCA AGGCGATT                                                           18

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

AACGCCGCAT GCAAGCTTGG ATCCTTATT                                               29

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

AAAGCCCTCT AGATGATTAC GAATTCATAT                                    30

(2) INFORMATION FOR SEQ ID NO:7:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

TTCTATTGAC GGCCTGTCAG GCCTCATATA TACTTTAGAT TGATTT                  46

(2) INFORMATION FOR SEQ ID NO:8:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

TTGACGCACT GGCCATGGTG GCCAAAAATA AACAAATAGG GGTTCCGCGC ACATTT       56

(2) INFORMATION FOR SEQ ID NO:9:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

AACTGACCAC GGCCTGACAG GCCGGTCTGA CAGTTACCAA TGCTT                   45

(2) INFORMATION FOR SEQ ID NO:10:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

AACCTGTCCT GGCCACCATG GCCTAAATAC ATTCAAATAT GTAT                    44

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

AGTTGGGTGG ACGAGTGGGT TACATCGAAC T                                  31

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

AACCCACTCG TCCACCCAAC TGATCTTCAG CAT        33

(2) INFORMATION FOR SEQ ID NO:13:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

AGTAAAAGAT GCTGAAGATA AGTTGGGTGC ACGAGTGGGT T        41

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

ACTTATCTTC AGCATCTTTT ACTT        24

(2) INFORMATION FOR SEQ ID NO:15:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

AAGAGCAACT CAGTCGCCGC ATACACTATT CT        32

(2) INFORMATION FOR SEQ ID NO:16:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

ATGGCGGCGA CTGAGTTGCT CTTGCCCGGC GTCAAT        36

(2) INFORMATION FOR SEQ ID NO:17:

(i) SEQUENCE CHARACTERISTICS:

(A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

TATTCTCAGA ATGACTTGGT TAAGTACTCA CCAGTCACAG AA                              42

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

TTAACCAAGT CATTCTGAGA AT                                                   22

(2) INFORMATION FOR SEQ ID NO:19:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

AACGACGAGC GTGACACCAC GACGCCTGTA GCAATG                                    36

(2) INFORMATION FOR SEQ ID NO:20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

TCGTGGTGTC ACGCTCGTCG TT                                                   22

(2) INFORMATION FOR SEQ ID NO:21:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

TTGCTGATAA ATCTGGAGCC AGTGAGCGTG GGTCTCGCGG TA                              42

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

TGGCTCCAGA TTTATCAGCA A                                              21

(2) INFORMATION FOR SEQ ID NO:23:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:23:

ATGCTCACTG GCTCCAGATT TATCAGCAAT                                     30

(2) INFORMATION FOR SEQ ID NO:24:

(i) SEQUENCE CHARACTERISTICS:
            (A) LENGTH: 36 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:24:

TCTGGAGCCA GTGAGCATGG GTCTCGCGGT ATCATT                              36

(2) INFORMATION FOR SEQ ID NO:25:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:25:

AACCTGTCCT GGCCACCATG GCCTAAATAC AATCAAATAT GTATCCGCTT ATGAGACAAT     60

AACCCTGATA                                                           70

(2) INFORMATION FOR SEQ ID NO:26:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:26:

ATGATTACGC CAAGCTTT                                                  18

(2) INFORMATION FOR SEQ ID NO:27:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:27:

TTGTCGTCTT TCCAGACGTT                                              20

(2) INFORMATION FOR SEQ ID NO:28:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

TTCTGGCTAC ATCTTCACAA CTTATGATAT AGACTGGGTG AGGCAGACGC CTGAA        55

(2) INFORMATION FOR SEQ ID NO:29:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

ACAGGGACTT GAGTGGATTG GATGGATTTT TCCTGGAGAG GGTGGTACTG AATACAATGA   60

GAAGTTCAAG GGCAGGGCCA CACTGAGTGT A                                 91

(2) INFORMATION FOR SEQ ID NO:30:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

TGTCTATTTC TGTGCTAGAG GGGACTACTA TAGGCGCTAC TTTGACTTGT GGGGCCAAGG   60

GACCACGGTC A                                                       71

(2) INFORMATION FOR SEQ ID NO:31:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

AGAGGGTCAC CATGACCTGC AGTGCCAGCT CAGGTATACG TTACATATAT TGGTACCAAC   60

AGAAGCCTGG AT                                                      72

(2) INFORMATION FOR SEQ ID NO:32:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:32:

TCCCCCAGAC TCCTGATTTA TGACACATCC AACGTGGCTC CTGGAGTCCC TTTTCGCTTC    60

AGT    63

(2) INFORMATION FOR SEQ ID NO:33:

(i) SEQUENCE CHARACTERISTICS:
            (A) LENGTH: 68 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:33:

ATGCTGCCAC TTATTACTTG CCAGGAGTGG AGTGGTTATC CGTACACGTT CGGAGGGGGG    60

ACCAAGCT    68

(2) INFORMATION FOR SEQ ID NO:34:

(i) SEQUENCE CHARACTERISTICS:
            (A) LENGTH: 55 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:34:

TTCTGGCTAC ATCTTCACAG AATTCATCTA GATTTGGGTG AGGCAGACGC CTGAA    55

(2) INFORMATION FOR SEQ ID NO:35:

(i) SEQUENCE CHARACTERISTICS:
            (A) LENGTH: 91 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:35:

ACAGGGACTT GAGTGGATTG GAATCACAGT CAAGCTTATC CTTTATCTCA GGTCTCGAGT    60

TCCAAGTACT TAAAGGGCCA CACTGAGTGT A    91

(2) INFORMATION FOR SEQ ID NO:36:

(i) SEQUENCE CHARACTERISTICS:
            (A) LENGTH: 70 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:36:

TGTCTATTTC TGTGCTAGAT CTTGACTGCA GTCTTATACG AGGATCCATT GGGGCCAAGG    60

GACCAGGTCA    70

(2) INFORMATION FOR SEQ ID NO:37:

(i) SEQUENCE CHARACTERISTICS:

(A) LENGTH: 72 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

AGAGGGTCAC CATGACCTGC GGACGTCTTT AAGCGATCGG GCTGATGGCC TGGTACCAAC    60

AGAAGCCTGG AT    72

(2) INFORMATION FOR SEQ ID NO:38:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

TCCCCCAGAC TCCTGATTTA TTAAGGGAGA TCTAAACAGC TGTTGGTCCC TTTTCGCTTC    60

AGT    63

(2) INFORMATION FOR SEQ ID NO:39:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

ATGCTGCCAC TTATTACTGC TTCTGCGCGC TTAAAGGATA TCTTCATTTC GGAGGGGGA    60

CCAAGCT    67

(2) INFORMATION FOR SEQ ID NO:40:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

AGAATTCATC TAGATTTG    18

(2) INFORMATION FOR SEQ ID NO:41:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

GCTTATCCTT TATCTCAGGT C    21

(2) INFORMATION FOR SEQ ID NO:42:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:42:

ACTGCAGTCT TATACGAGGA T                                              21

(2) INFORMATION FOR SEQ ID NO:43:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:43:

GACGTCTTTA AGCGATCG                                                  18

(2) INFORMATION FOR SEQ ID NO:44:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:44:

TAAGGGAGAT CTAAACAG                                                  18

(2) INFORMATION FOR SEQ ID NO:45:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:45:

TCTGCGCGCT TAAAGGAT                                                  18

(2) INFORMATION FOR SEQ ID NO:46:

(i) SEQUENCE CHARACTERISTICS:
            (A) LENGTH: 46 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:46:

TTCTATTGAC GGCCTGTCAG GCCTCATATA TACTTTAGAT TGATTT                    46

(2) INFORMATION FOR SEQ ID NO:47:

(i) SEQUENCE CHARACTERISTICS:
            (A) LENGTH: 56 base pairs
            (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO:47:

TTGACGCACT GGCCATGGTG GCCAAAAATA AACAAATAGG GGTTCCGCGC ACATTT     56

(2) INFORMATION FOR SEQ ID NO:48:

(i) SEQUENCE CHARACTERISTICS:
            (A) LENGTH: 45 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:48:

AACTGACCAC GGCCTGACAG GCCGGTCTGA CAGTTACCAA TGCTT     45

(2) INFORMATION FOR SEQ ID NO:49:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:49:

AACCTGTCCT GGCCACCATG GCCTAAATAC ATTCAAATAT GTAT     44

(2) INFORMATION FOR SEQ ID NO:50:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:50:

TTCTTAGACG TCAGGTGGCA CTT     23

(2) INFORMATION FOR SEQ ID NO:51:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:51:

TTTTAAATCA ATCTAAAGTA T     21

(2) INFORMATION FOR SEQ ID NO:52:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:52:

TGCTCATCCA CGAGTGTGGA GAAGTGGTCC TGCAACTTTA T                          41

(2) INFORMATION FOR SEQ ID NO:53:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:53:

ACCACTTCTC CACACTCGTG GATGAGCACT TTTAAAGTT                              39

(2) INFORMATION FOR SEQ ID NO:54:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:54:

TGTCACTACC ACACTCGTGG ACTACCATGG CCTAAATACA TTCAAATATG TAT              53

(2) INFORMATION FOR SEQ ID NO:55:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:55:

TTAAGGGATT TTGGTCATGA GATT                                             24

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:56:

TAGCGGATCC TACCTGACGC                                                  20

(2) INFORMATION FOR SEQ ID NO:57:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:57:

GAAAATCTTC TCTCATCCG                                                   19

(2) INFORMATION FOR SEQ ID NO:58:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

```
GTCGACCTCG AGCCATGGCT AACTAATTAA GTAATTACTG CAGCGTCGTG ACTGGGAAAA        60

CCCTGGGGTT ACCCAACTTA A                                                 81
```

(2) INFORMATION FOR SEQ ID NO:59:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:59:

```
GTCGACCTGC AGGCATGCAA GCTTAGCACT TGCTGTAGTA CTGCAGCGTC GTGACTGGGA        60

AAACCCTGGG GTTACCCAAC TTAA                                              84
```

(2) INFORMATION FOR SEQ ID NO:60:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

```
TCGCCTTGCT GCGCATCCAC CTTTCGCTAG CTGGCGGAAT TCCGAAGAAG CGCG             54
```

(2) INFORMATION FOR SEQ ID NO:61:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:61:

```
TCGCCTTGCT GCGCATCCAC CTTTCGCTAG TTAACTAATT AACTAAGATA TCGCGCG          57
```

(2) INFORMATION FOR SEQ ID NO:62:

(i) SEQUENCE CHARACTERISTICS:
        (A) LENGTH: 462 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

```
ATGGTTCCGA TCCGTCAGCT GCACTACCGT CTGCGTGACG AACAGCAGAA AAGCCTGGTT        60
```

```
CTGTCCGACC CGTACGAACT GAAAGCTAGG TGATCTTCTC CATGAGCTTC GTACAAGGTG      120

AACCAAGCAA CGACAAAATC CCGGTGGCTT TGGGTCTGAA AGGTAAAAAC CTGTGACCCT      180

GCAACTCGAG AGCGTGGACC CAAAACAGTA CCCAAAGAAG AAGATGGAGA AGCGTTTCGT      240

CTTCAACAAG ATCGAAGTCA ACCGAACTGG TACATCAGCA CCTCCCAAGC AGAGCACAAG      300

CCTGTCTTCC TGGGTAACAA CTCCGGTCAG GATATCATCG ACTTCCTGCA CCTGAATGGC      360

CAGAACATCA ACCAACACCT GTCCTGTGTA ATGAAAGACG GCACTCCGAG CAAAGTGGAG      420

TTCGAGTCTG CTGAGTTCAC TATGGAATCT GTGTCTTCCT AA                         462
```

(2) INFORMATION FOR SEQ ID NO:63:

(i) SEQUENCE CHARACTERISTICS:
        (A) LENGTH: 465 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:63:

```
ATGGCACCGG TTAGATCTCT GAACTGCACC CTTCGCGACT CCCAACAGAA AAGCTTAGTA       60

ATGTCTGGTC CGTACGAGCT CAAAGCTAGG TTGTATTCAG CATGAGCTTC GTCCAAGGTG      120

AAGAGTCTAA CGACAAGATC CCAGTTGCAT TAGGCCTGAA AGAGAAGAAT CTGTGACTCT      180

GCAGCTTGAA TCCGTTGACC CGAAAAACTA TCCGAAGAAG AAAATGGAGA AGCGTTTCGT      240

ATTTAACAAG ATTGAGATTA ACCAAACTGG TACATCAGTA CTTCTCAAGC AGAGAATATG      300

CCTGTGTTCC TCGGCGGTAC CAAAGGCGGT CAGGATATCA CTGACTTCCT GCATCTGCAA      360

GGCCAGCACA TGGAACAACA CCTCAGCTGC GTACTGAAAG ACGATAAGCC TAACAAGCTG      420

GAATTCGAGT CTGCTCAGTT CACCATGCAG TTTGTCTCGA GCTAA                      465
```

(2) INFORMATION FOR SEQ ID NO:64:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:64:

```
Gly Gly Gly Gly Ser
1               5
```

(2) INFORMATION FOR SEQ ID NO:65:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:65:

```
NNKNNKNNKN NKNNKNNKNN KNNKNNKNNK                                        30
```

(2) INFORMATION FOR SEQ ID NO:66:

(i) SEQUENCE CHARACTERISTICS:

```
            (A) LENGTH: 30 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:66:

NNMNNMNNMN NMNNMNNMNN MNNMNNMNNM                                    30

(2) INFORMATION FOR SEQ ID NO:67:

(i) SEQUENCE CHARACTERISTICS:
            (A) LENGTH: 15 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:67:

Gly Gly Gly Gly Ser Gly Gly Gly Gly Ser Gly Gly Gly Gly Ser
1               5                   10                  15

(2) INFORMATION FOR SEQ ID NO:68:

(i) SEQUENCE CHARACTERISTICS:
            (A) LENGTH: 54 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:68:

ATGGTAGTCC ACGAGTGTGG TAGTGACAGG CCGGTCTGAC AGTTACCAAT GCTT         54

(2) INFORMATION FOR SEQ ID NO:69:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:69:

TAGCGGATCC TACCTACCTG ACGC                                          24

(2) INFORMATION FOR SEQ ID NO:70:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:70:

GAAAATCTTC TCTCATCC                                                 18
```